(12) United States Patent
Fu et al.

(10) Patent No.: US 9,546,355 B2
(45) Date of Patent: Jan. 17, 2017

(54) CONDITIONAL REPLICATING CYTOMEGALOVIRUS AS A VACCINE FOR CMV

(75) Inventors: Tong-Ming Fu, Ambler, PA (US); Dai Wang, Blue Bell, PA (US); Muneeswara Babu Medi, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/343,637

(22) PCT Filed: Sep. 4, 2012

(86) PCT No.: PCT/US2012/053599
§ 371 (c)(1),
(2), (4) Date: Mar. 7, 2014

(87) PCT Pub. No.: WO2013/036465
PCT Pub. Date: Mar. 14, 2013

(65) Prior Publication Data
US 2014/0220062 A1    Aug. 7, 2014

Related U.S. Application Data

(60) Provisional application No. 61/532,667, filed on Sep. 9, 2011.

(51) Int. Cl.
| | | |
|---|---|---|
| *C12N 7/00* | (2006.01) | |
| *A61K 39/12* | (2006.01) | |
| *A61K 39/00* | (2006.01) | |

(52) U.S. Cl.
CPC ............. *C12N 7/00* (2013.01); *A61K 39/12* (2013.01); *A61K 2039/5252* (2013.01); *A61K 2039/5254* (2013.01); *A61K 2039/55505* (2013.01); *A61K 2039/55577* (2013.01); *C12N 2710/16134* (2013.01)

(58) Field of Classification Search
None
See application file for complete search history.

(56) References Cited

U.S. PATENT DOCUMENTS

| | | | |
|---|---|---|---|
| 6,251,678 B1* | 6/2001 | Volkin et al. | 436/8 |
| 7,410,795 B2 | 8/2008 | Hermanson et al. | |
| 8,173,792 B2 | 5/2012 | Wandless et al. | |
| 2006/0110406 A1* | 5/2006 | Kemble et al. | 424/209.1 |
| 2009/0215169 A1* | 8/2009 | Wandless et al. | 435/325 |
| 2010/0034777 A1 | 2/2010 | Wandless et al. | |
| 2010/0285059 A1 | 11/2010 | Shenk et al. | |
| 2011/0200633 A1 | 8/2011 | Shenk et al. | |

FOREIGN PATENT DOCUMENTS

WO    WO2007146024    12/2007

OTHER PUBLICATIONS

Glass et al. Conditional and reversible disruption of essential herpesvirus proteins. Nat Methods. Aug. 2009;6(8):577-9. Epub Jul. 5, 2009.*
Straschewski et al. Protein pUL128 of human cytomegalovirus is necessary for monocyte infection and blocking of migration. J Virol. May 2011;85(10):5150-8. Epub Mar. 2, 2011.*
Spaderna et al. Deletion of gpUL132, a structural component of human cytomegalovirus, results in impaired virus replication in fibroblasts. J Virol. Sep. 2005;79(18):11837-47.*
GenBank: CAA35410.1. HCMVUL51 [Human herpesvirus 5]. Nov. 14, 2006.*
GenBank: AAA45980.1. major immediate-early protein [Human herpesvirus 5]. Aug. 2, 1993.*
GenBank: AAA31252.1. binding protein [Oryctolagus cuniculus]. Apr. 27, 1993.*
Jacobson et al. Safety and immunogenicity of Towne cytomegalovirus vaccine with or without adjuvant recombinant interleukin-12. Vaccine. Jun. 19, 2006;24(25):5311-9. Epub May 2, 2006.*
Wang et al. Human cytomegalovirus UL131 open reading frame is required for epithelial cell tropism. J Virol. Aug. 2005;79(16):10330-8.*
Nakashima et al. Conditional gene silencing of multiple genes with antisense RNAs and generation of a mutator strain of *Escherichia coli*. Nucleic Acids Research, 2009, vol. 37, No. 15 e103.*
Adler, et al., Human CMV vaccine trials: What if CMV caused a rash?, Journal of Clinical Virology, 2008, 231-236, 41.
Arvin, et al., Vaccine Development to Prevent Cytomegalovirus Disease: Report from the National Vaccine Advisory Committee, Clinical Infectious Diseases, 2004, 233-239, 39.
Chambers, et al., DNA Microarrays of the Complex Human Cytomegalovirus Genome: Profiling Kinetic Class with Drug Sensitivity of Viral Gene Expression, Journal of Virology, 1999, 5757-5766, 73(7).
Clackson, et al., Redesigning an FKBP—ligand interface to generate chemical dimerizers with novel specificity, Proc Natl Acad Sci USA, 1998, 10437-10442, 95.
Cui, et al., Cytomegalovirus vaccines fail to induce epithelial entry neutralizing antibodies comparable to natural infection, Vaccine, 2008, 5760-5766, 26.

(Continued)

*Primary Examiner* — Nick Zou
(74) *Attorney, Agent, or Firm* — Henry P. Wu; Gloria M. Fuentes

(57) ABSTRACT

The present invention relates to methods of inducing an immune response to cytomegalovirus (CMV) using a genetically modified CMV that is conditionally replication defective. The methods of the invention can be used to treat and/or prevent primary CMV infection, infection due to reactivation of a latent CMV and a super-infection of a different strain of CMV that had been previously encountered. The present invention also relates to a replication defective CMV which has been recombinantly altered to allow for external control of viral replication. Compositions comprising the replication defective CMV are also encompassed by the present invention.

12 Claims, 18 Drawing Sheets

(56) References Cited

OTHER PUBLICATIONS

Dargan, et al., Sequential mutations associated with adaptation of human cytomegalovirus to growth in cell culture, Journal of General Virology, 2010, 1535-1546, 91.

Distasi, et al., Inducible Apoptosis as a Safety Switch for Adoptive Cell Therapy, New England Journal of Medicine, 2011, 1673-1683, 365(18).

Elek, et al., Development of a vaccine against mental retardation caused by cytomegalovirus infection in utero, Lancet, 1974, 1-5, 1.

Fang, et al., Stable antibody expression at therapeutic levels using the 2A peptide, Nature Biotechnology, 2005, 584-590, 23(5).

Fouts, et al., Antibodies against the gH/gL/UL128/UL130/UL131 Complex Comprise the Majority of the Anti-Cytomegalovirus (Anti-CMV) Neutralizing Antibody Response in CMV Hyperimmune Globulin, Journal of Virology, 2012, 7444-7447, 86(13).

Freed, et al., Pentameric complex of viral glycoprotein H is the primary target for potent neutralization by a human cytomegalovirus vaccine, Proc. Natl. Acad. Sci. USA, 2013, E4997-E5005, 1.

Fu, et al., Restoration of viral epithelial tropism improves immunogenicity in rabbits and rhesus macaques for a whole virion vaccine of human cytomegalovirus, Vaccine, 2012, 7469-7474, 30.

Gatherer, et al., High-resolution human cytomegalovirus transcriptome, Proc Natl Acad Sci USA, 2011, 19755-19760, 108(49).

Genini, E. et al., Serum antibody response to the gH/gL/pUL128-131 five-protein complex of human cytomegalovirus (HCMV) in primary and reactivated HCMV infections, Journal of Clinical Virology, 2011, 113-118, 52.

Gerna, et al., Dendritic-cell infection by human cytomegalovirus is restricted to strains carrying functional UL131-128 genes and mediates efficient viral antigen presentation to CD8+ T cells, Journal of General Virology, 2005, 275-284, 86.

Gerna, et al., Human cytomegalovirus serum neutralizing antibodies block virus infection of endothelial/epithelial cells, but not fibroblasts, early during primary infection, Journal of General Virology, 2008, 853-865, 89.

Gerna, et al., Rescue of human cytomegalovirus strain AD169 tropism for both leukocytes and human endothelial cells, Journal of General Virology, 2003, 1431-1436, 84.

Gerna, et al., The attenuated Towne strain of human cytomegalovirus may revert to both endothelial cell tropism and leuko- (neutrophiland monocyte-) tropism in vitro, Journal of General Virology, 2002, 1993-2000, 83.

Glass, M. et al., Conditional and reversible disruption of essential herpesvirus proteins, Nature Methods, 2009, 577-580, 6(8).

Grimley, et al., Synthesis and analysis of stabilizing ligands for FKBP-derived destabilizing domains, Bioorganic & Medicinal Chemistry Letters, 2008, 759-761, 18.

Hahn, et al., Human Cytomegalovirus UL131-128 Genes Are Indispensable for Virus Growth in Endothelial Cells and Virus Transfer to Leukocytes, Journal of Virology, 2004, 10023-10033, 78(18).

Holt, et al., Design, Synthesis, and Kinetic Evaluation of High-Affinity FKBP Ligands and the X-ray Crystal Structures of Their Complexes with FKBP 12, J. Am. Chem. Soc., 1993, 9925-9938, 115.

Iwamoto, et al., A General Chemical Method to Regulate Protein Stability in the Mammalian Central Nervous System, Chemistry & Biology, 2010, 981-988, 17.

Macagno, A. et al., Isolation of Human Monoclonal Antibodies That Potently Neutralize Human Cytomegalovirus Infection by Targeting Different Epitopes on the gH/gL/UL128-131A Complex, Journal of Virology, 2010, 1005-1013, 84 (2).

Manley, K. et al., Human Cytomegalovirus Escapes a Naturally Occurring Neutralizing Antibody by Incorporating It into Assembling Virions, Cell Host and Microbe, 2011, 197-209, 10.

Miyazaki, et al., Destabilizing Domains Derived from the Human Estrogen Receptor, J. Am. Chem. Soc., 2012, 3942-3945, 134.

Mocarski, et al., Cytomegaloviruses, Fields Virology, 2007, 2701-2772.

Neff, et al., Clinical and laboratory studies of live cytomegalovirus vaccine Ad-169, Proc. Soc. Exp. Biol. Med., 1979, 32-37, 160.

Plachter, et al., Cell Types Involved in Replication and Distribution of Human Cytomegalovirus, Advances in Virus Research, 1996, 195-261, 46.

Plotkin, et al., Candidate Cytomegalovirus Strain for Human Vaccination, Infection and Immunity, 1975, 521-527, 12(3).

Revello, et al., Molecular Epidemiology of Primary Human Cytomegalovirus Infection in Pregnant Women and Their Families, Journal of Medical Virology, 2008, 1415-1425, 80.

Ryckman, et al., Characterization of the Human Cytomegalovirus gH/gL/UL128-131 Complex That Mediates Entry into Epithelial and Endothelial Cells, Journal of Virology, 2008, 60-70, 82(1).

Saccoccio, F. M. et al., Peptides from cytomegalovirus UL130 and UL131 proteins induce high titer antibodies that block viral entry into mucosal epithelial cells, Vaccine, 2011, 2705-2711, 29.

Sylwester, et al., Broadly targeted human cytomegalovirus specific CD4 and CD8 T cells dominate the memory compartments of exposed subjects, Journal of Experimental Medicine, 2005, 673-685, 202(5).

Tang, et al., A novel high-throughput neutralization assay for supporting clinical evaluations of human cytomegalovirus vaccines, Vaccine, 2011, 8350-8356, 29.

Vogel, et al., Improving Vaccine Performance with Adjuvants, Clinical Infectious Diseases, 2000, S266-S270, 30.

Wang, et al., Human Cytomegalovirus UL131 Open Reading Frame Is Required for Epithelial Cell Tropism, Journal of Virology, 2005, 10330-10338, 79(16).

Wang, et al., Human cytomegalovirus virion protein complex required for epithelial and endothelial cell tropism, Proc. Natl. Acad. Sci. USA, 2005, 18153-18158, 102(50).

Yang, et al., Investigating Protein-Ligand Interactions with a Mutant FKBP Possessing a Designed Specificity Pocket, Journal of Medicinal Chemistry, 2000, 1135-1142, 43.

Yu, et al., Functional map of human cytomegalovirus AD169 defined by global mutational analysis, Proc. Natl. Acad. Sci. USA, 2003, 12396-12401, 100(21).

Perng, Y-C et al., The Human Cytomegalovirus Gene UL79 Is Required for the Accumulation of Late Viral Transcripts, Journal of Virology, 2011, 4841-4852, 85(10).

Revello et al., Human Cytomegalovirus Tropism for Endothelial/Epithelial Cells: Scientific Background and Clinical Implications, Reviews in Medical Virology, 2010, 136-155, 20(3).

Dunn et al., "Functioning profile of a human cytomegalovirus genome"; Proc. Natl. Acad. Sci. USA, 2003, 14223-14228, 100(24).

* cited by examiner

```
                        SEQUENCE LISTING

<160> NUMBER OF SEQ ID NOS: 14

<210> SEQ ID NO 1
<211> LENGTH: 598
<212> TYPE: PRT
<213> ORGANISM: Artificial Sequence
<220> FEATURE:
<223> OTHER INFORMATION: IE 1/2/FKBP Fusion Protein

<400> SEQUENCE: 1

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Pro Glu Glu Ser Ser Ala
            100                 105                 110

Lys Arg Lys Met Asp Pro Asp Asn Pro Asp Glu Gly Pro Ser Ser Lys
        115                 120                 125

Val Pro Arg Pro Glu Thr Pro Val Thr Lys Ala Thr Thr Phe Leu Gln
    130                 135                 140

Thr Met Leu Arg Lys Glu Val Asn Ser Gln Leu Ser Leu Gly Asp Pro
145                 150                 155                 160

Leu Phe Pro Glu Leu Ala Glu Glu Ser Leu Lys Thr Phe Glu Gln Val
                165                 170                 175

Thr Glu Asp Cys Asn Glu Asn Pro Glu Lys Asp Val Leu Ala Glu Leu
            180                 185                 190

Val Lys Gln Ile Lys Val Arg Val Asp Met Val Arg His Arg Ile Lys
        195                 200                 205

Glu His Met Leu Lys Lys Tyr Thr Gln Thr Glu Glu Lys Phe Thr Gly
    210                 215                 220

Ala Phe Asn Met Met Gly Gly Cys Leu Gln Asn Ala Leu Asp Ile Leu
225                 230                 235                 240

Asp Lys Val His Glu Pro Phe Glu Glu Met Lys Cys Ile Gly Leu Thr
                245                 250                 255

Met Gln Ser Met Tyr Glu Asn Tyr Ile Val Pro Glu Asp Lys Arg Glu
            260                 265                 270

Met Trp Met Ala Cys Ile Lys Glu Leu His Asp Val Ser Lys Gly Ala
        275                 280                 285

Ala Asn Lys Leu Gly Gly Ala Leu Gln Ala Lys Ala Arg Ala Lys Lys
    290                 295                 300

Asp Glu Leu Arg Arg Lys Met Met Tyr Met Cys Tyr Arg Asn Ile Glu
305                 310                 315                 320

Phe Phe Thr Lys Asn Ser Ala Phe Pro Lys Thr Thr Asn Gly Cys Ser
                325                 330                 335

Gln Ala Met Ala Ala Leu Gln Asn Leu Pro Gln Cys Ser Pro Asp Glu
```

```
                    340                 345                 350
Ile Met Ala Tyr Ala Gln Lys Ile Phe Lys Ile Leu Asp Glu Glu Arg
                355                 360                 365

Asp Lys Val Leu Thr His Ile Asp His Ile Phe Met Asp Ile Leu Thr
            370                 375                 380

Thr Cys Val Glu Thr Met Cys Asn Glu Tyr Lys Val Thr Ser Asp Ala
385                 390                 395                 400

Cys Met Met Thr Met Tyr Gly Gly Ile Ser Leu Leu Ser Glu Phe Cys
                405                 410                 415

Arg Val Leu Cys Cys Tyr Val Leu Glu Glu Thr Ser Val Met Leu Ala
            420                 425                 430

Lys Arg Pro Leu Ile Thr Lys Pro Glu Val Ile Ser Val Met Lys Arg
        435                 440                 445

Arg Ile Glu Glu Ile Cys Met Lys Val Phe Ala Gln Tyr Ile Leu Gly
    450                 455                 460

Ala Asp Pro Leu Arg Val Cys Ser Pro Ser Val Asp Asp Leu Arg Ala
465                 470                 475                 480

Ile Ala Glu Glu Ser Asp Glu Glu Ala Ile Val Ala Tyr Thr Leu
                485                 490                 495

Ala Thr Ala Gly Val Ser Ser Ser Asp Ser Leu Val Ser Pro Pro Glu
            500                 505                 510

Ser Pro Val Pro Ala Thr Ile Pro Leu Ser Ser Val Ile Val Ala Glu
        515                 520                 525

Asn Ser Asp Gln Glu Glu Ser Glu Gln Ser Asp Glu Glu Glu Glu Glu
    530                 535                 540

Gly Ala Gln Glu Glu Arg Glu Asp Thr Val Ser Val Lys Ser Glu Pro
545                 550                 555                 560

Val Ser Glu Ile Glu Glu Val Ala Pro Glu Glu Glu Asp Gly Ala
                565                 570                 575

Glu Glu Pro Thr Ala Ser Gly Gly Lys Ser Thr His Pro Met Val Thr
            580                 585                 590

Arg Ser Lys Ala Asp Gln
        595
```

<210> SEQ ID NO 2
<211> LENGTH: 2081
<212> TYPE: DNA
<213> ORGANISM: Artificial Sequence
<220> FEATURE:
<223> OTHER INFORMATION: DNA Encoding IE 1/2/FKBP Fusion Protein

<400> SEQUENCE: 2

```
atgggagtgc aggtggaaac catctcccca ggagacgggc gcaccttccc caagcgcggc    60
cagacctgtg tggtgcacta caccgggatg cttgaagatg gaaagaaagt cgattcctcc   120
cgggacagaa acaagccctt taagtttatg ctaggcaagc aggaggtgat ccgaggctgg   180
gaagaagggg ttgcccagat gagtgtgggt cagagagcca actgactat atctccagat   240 tatgcctatg gtgccactgg gcacccaggc atcatcccac acatgccac tctcgtcttc   300 gatgtggagc ttctaaaacc ggaagagtcc tctgccaaga aaagatgga ccctgataat   360 cctgacgagg gccttcctc caaggtgcca cggtacgtgt cggggtttgt gccccccctt   420 ttttttaat aaaattgtat taatgttata tacatatctc ctgtatgtga cccatgtgct   480
tatgactcta tttctcatgt gtttaggccc gagacacccg tgaccaaggc cacgacgttc   540
ctgcagacta tgttgaggaa ggaggttaac agtcagctga gtctgggaga cccgctgttt   600
```

```
ccagagttgg ccgaagaatc cctcaaaact tttgaacaag tgaccgagga ttgcaacgag    660
aaccccgaga aagatgtcct ggcagaactc ggtaagtctg ttgacatgta tgtgatgtat    720
actaacctgc atgggacgtg gatttacttg tgtatgtcag atagagtaaa gattaactct    780
tgcatgtgag cggggcatcg agatagcgat aaatgagtca ggaggacgga tacttatatg    840
tgttgttatc ctcctctaca gtcaaacaga ttaaggttcg agtggacatg gtgcggcata    900
gaatcaagga gcacatgctg aaaaaatata cccagacgga agagaaattc actgcgccct    960
ttaatatgat gggaggatgt ttgcagaatg ccttagatat cttagataag gttcatgagc   1020
ctttcgagga gatgaagtgt attgggctaa ctatgcagag catgtatgag aactacattg   1080
tacctgagga taagcgggag atgtggatgg cttgtattaa ggagctgcat gatgtgagca   1140
agggcgccgc taacaagttg gggggtgcac tgcaggctaa gcccgtgct aaaaaggatg    1200 aacttaggag aaagatgatg tatatgtgct acaggaatat agagttcttt accaagaact   1260
cagccttccc taagaccacc aatggctgca gtcaggccat ggcggcactg cagaacttgc   1320
ctcagtgctc ccctgatgag attatggctt atgcccagaa atatttaag attttggatg     1380 aggagagaga caaggtgctc acgcacattg atcacatatt tatggatatc ctcactacat   1440
gtgtggaaac aatgtgtaat gagtacaagg tcactagtga cgcttgtatg atgaccatgt   1500 acggggcat ctctctctta agtgagttct gtcgggtgct gtgctgctat gtcttagagg      1560
agactagtgt gatgctggcc aagcggcctc tgataaccaa gcctgaggtt atcagtgtaa   1620
tgaagcgccg cattgaggag atctgcatga aggtctttgc ccagtacatt ctggggccg     1680 atcctctgag agtctgctct cctagtgtgg atgacctacg ggccatcgcc gaggagtcag   1740
atgaggaaga ggctattgta gcctacactt tggccaccgc tggtgtcagc tcctctgatt   1800
ctctggtgtc acccccagag tccctgtac ccgcgactat ccctctgtcc tcagtaattg     1860
tggctgagaa cagtgatcag gaagaaagtg agcagagtga tgaggaagag gaggagggtg   1920
ctcaggagga gcgggaggac actgtgtctg tcaagtctga gccagtgtct gagatagagg   1980
aagttgcccc agaggaagag gaggatggtg ctgaggaacc caccgcctct ggaggcaaga   2040
gcacccaccc tatggtgact agaagcaagg ctgaccagta a                       2081
```

<210> SEQ ID NO 3
<211> LENGTH: 264
<212> TYPE: PRT
<213> ORGANISM: Artificial Sequence
<220> FEATURE:
<223> OTHER INFORMATION: UL51/FKBP Fusion Protein

<400> SEQUENCE: 3

```
Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95
```

```
Thr Leu Val Phe Asp Val Glu Leu Leu Lys Pro Glu Ser Trp Ala Lys
            100                 105                 110
Gln Arg Val Pro Phe Leu Asp Asp Asp Gly Glu Glu Glu Asn Asp
        115                 120                 125
Val Gln Asp Asp Val Asp Ser Pro Val Pro Thr Arg Pro Leu Val Ile
130                 135                 140
Asp Glu Asp Ala Glu Pro Ala Ala Gly Thr Ser Gly Gly Leu Glu Gly
145                 150                 155                 160
Gly Gly Gly Asp Asp Glu Asp Gly Glu Asp Gly His Ala Leu Pro Asp
                165                 170                 175
Leu Asp Asp Asp Leu Leu Leu Gln Phe Glu Pro Met Leu Pro Arg Val
                180                 185                 190
Tyr Asp Leu Leu Leu Pro Ser Leu Asp Ala Arg Leu Asn Phe Val Asn
            195                 200                 205
Ala Gly Gln Lys Tyr Ala Ala Phe Leu Lys Tyr Val His Gly Asp Cys
        210                 215                 220
Ala Thr Cys Ser His Gly Glu Ile Leu Arg Glu Lys Thr Gln Leu Leu
225                 230                 235                 240
Thr Ala Ile Val Ser Lys Leu Met Asp Ile Asn Gly Ile Leu Glu Gly
                245                 250                 255
Lys Asp Glu Ser Ala Pro Gly Lys
            260

<210> SEQ ID NO 4
<211> LENGTH: 795
<212> TYPE: DNA
<213> ORGANISM: Artificial Sequence
<220> FEATURE:
<223> OTHER INFORMATION: DNA Encoding UL51/FKBP Fusion Protein

<400> SEQUENCE: 4
atgggagtgc aggtggaaac catctcccca ggagacgggc gcaccttccc caagcgcggc    60
cagacctgtg tggtgcacta caccgggatg cttgaagatg aaagaaagt cgattcctcc    120 cgggacagaa acaagccctt taagtttatg ctaggcaagc aggaggtgat ccgaggctgg    180
gaagaagggg ttgcccagat gagtgtgggt cagagagcca aactgactat atctccagat    240
tatgcctatg gtgccactgg gcacccaggc atcatcccac acatgccac tctcgtcttc    300 gatgtggagc ttctaaaacc ggaatcctgg ctaagcagc gggtgccgtt tctggacgat    360
gacgacggag aggaggaaaa cgacgtgcag gatgacgtgg attctccggt gccgacgcga    420
ccgctggtga tcgacgagga gcggagccc gcggctggta cgagcggtgg gctcgagggg    480
ggaggtggtg acgacgagga cggtgaagac ggacacgcgc tacccgatct tgacgacgat    540
ctgctattac agttcgagcc gatgctgccg cgcgtctacg atctgttgct gccctctctg    600
gacgcgcgct taaatttcgt gaacgcgggt cagaagtacg ccgccttcct caagtacgtg    660
cacggcgact gcgcgacctg cagtcacgga gagatcctcc gtgagaagac gcaactatta    720
acggcgatcg tcagcaagct catggacatt aacggaatcc tggagggaaa agacgagtcg    780
gcgccgggta ataa                                                     795

<210> SEQ ID NO 5
<211> LENGTH: 775
<212> TYPE: PRT
<213> ORGANISM: Artificial Sequence
<220> FEATURE:
<223> OTHER INFORMATION: UL52/FKBP Fusion Protein
```

<400> SEQUENCE: 5

```
Met Gly Val Gln Val Glu Thr Ile Ser Pro Gly Asp Gly Arg Thr Phe
1               5                   10                  15
Pro Lys Arg Gly Gln Thr Cys Val Val His Tyr Thr Gly Met Leu Glu
                20                  25                  30
Asp Gly Lys Lys Val Asp Ser Ser Arg Asp Arg Asn Lys Pro Phe Lys
            35                  40                  45
Phe Met Leu Gly Lys Gln Glu Val Ile Arg Gly Trp Glu Glu Gly Val
        50                  55                  60
Ala Gln Met Ser Val Gly Gln Arg Ala Lys Leu Thr Ile Ser Pro Asp
65                  70                  75                  80
Tyr Ala Tyr Gly Ala Thr Gly His Pro Gly Ile Ile Pro Pro His Ala
                85                  90                  95
Thr Leu Val Phe Asp Val Glu Leu Leu Lys Pro Glu Asn Pro Ser Thr
            100                 105                 110
His Val Ser Ser Asn Gly Pro Thr Thr Pro His Gly Pro His Ser Thr
        115                 120                 125
Thr Phe Leu Pro Pro Thr Ser Pro Ala Pro Ser Thr Ser Ser Val Ala
130                 135                 140
Ala Ala Thr Leu Cys Ser Pro Gln Arg Gln Ala Val Ser Arg Tyr Ser
145                 150                 155                 160
Gly Trp Ser Thr Glu Tyr Thr Gln Trp His Ser Asp Leu Thr Thr Glu
                165                 170                 175
Leu Leu Trp His Ala His Pro Arg Gln Val Pro Met Asp Glu Ala Leu
            180                 185                 190
Ala Ala Ala Ala Ala Ser Tyr Gln Val Asn Pro Gln His Pro Ala
        195                 200                 205
Asn Arg Tyr Arg His Tyr Glu Phe Gln Thr Leu Ser Leu Gly Thr Ser
210                 215                 220
Glu Val Asp Glu Leu Leu Asn Cys Cys Ala Glu Glu Thr Thr Cys Gly
225                 230                 235                 240
Gly Thr Gln Ser Thr Val Leu Thr Asn Ala Thr Asn Thr Thr Ser Cys
                245                 250                 255
Gly Gly Ala Val Ala Gly Ser Ser Asn Val Gly Pro Ala Gly Ala Ser
            260                 265                 270
Ala Ala Cys Asp Leu Asp Ala Glu Leu Ala Gly Leu Glu Thr Ser Ala
        275                 280                 285
Ala Asp Phe Glu Gln Leu Arg Arg Leu Cys Ala Pro Leu Ala Ile Asp
290                 295                 300
Thr Arg Cys Asn Leu Cys Ala Ile Ile Ser Ile Cys Leu Lys Gln Asp
305                 310                 315                 320
Cys Asp Gln Ser Trp Leu Leu Glu Tyr Ser Leu Leu Cys Phe Lys Cys
                325                 330                 335
Ser Tyr Ala Pro Arg Ala Ala Leu Ser Thr Leu Ile Ile Met Ser Glu
            340                 345                 350
Phe Thr His Leu Leu Gln Gln His Phe Ser Asp Leu Arg Ile Asp Asp
        355                 360                 365
Leu Phe Arg His His Val Leu Thr Val Phe Asp Phe His Leu His Phe
370                 375                 380
Phe Ile Asn Arg Cys Phe Glu Lys Gln Val Gly Asp Ala Val Asp Asn
385                 390                 395                 400
Glu Asn Val Thr Leu Asn His Leu Ala Val Val Arg Ala Met Val Met
                405                 410                 415
```

-continued

```
Gly Glu Asp Thr Val Pro Tyr Asn Lys Pro Arg Arg His Pro Gln Gln
            420                 425                 430
Lys Gln Lys Asn Asn Pro Tyr His Val Glu Val Pro Gln Glu Leu Ile
        435                 440                 445
Asp Asn Phe Leu Glu His Ser Ser Pro Ser Arg Asp Arg Phe Val Gln
450                 455                 460
Leu Leu Phe Tyr Met Trp Ala Gly Thr Gly Val Met Ser Thr Thr Pro
465                 470                 475                 480
Leu Thr Glu Leu Thr His Thr Lys Phe Ala Arg Leu Asp Ala Leu Ser
                485                 490                 495
Thr Ala Ser Glu Arg Glu Asp Ala Arg Met Met Ile Glu Glu Glu Glu
            500                 505                 510
Asp Glu Glu Gly Gly Glu Lys Gly Gly Asp Asp Pro Gly Arg His Asn
        515                 520                 525
Gly Gly Gly Thr Ser Gly Gly Phe Ser Glu Ser Thr Leu Lys Lys Asn
530                 535                 540
Val Gly Pro Ile Tyr Leu Cys Pro Val Pro Ala Phe Phe Thr Lys Asn
545                 550                 555                 560
Gln Thr Ser Thr Val Cys Leu Leu Cys Glu Leu Met Ala Cys Ser Tyr
                565                 570                 575
Tyr Asp Asn Val Val Leu Arg Glu Leu Tyr Arg Arg Val Val Ser Tyr
            580                 585                 590
Cys Gln Asn Asn Val Lys Met Val Asp Arg Ile Gln Leu Val Leu Ala
        595                 600                 605
Asp Leu Leu Arg Glu Cys Thr Ser Pro Leu Gly Ala Ala His Glu Asp
610                 615                 620
Val Ala Arg Cys Gly Leu Glu Ala Pro Thr Ser Pro Gly Gly Asp Ser
625                 630                 635                 640
Asp Tyr His Gly Leu Ser Gly Val Asp Gly Ala Leu Ala Arg Pro Asp
                645                 650                 655
Pro Val Phe Cys His Val Leu Arg Gln Ala Gly Val Thr Gly Ile Tyr
            660                 665                 670
Lys His Phe Phe Cys Asp Pro Gln Cys Ala Gly Asn Ile Arg Val Thr
        675                 680                 685
Asn Glu Ala Val Leu Phe Gly Arg Leu His Pro His Val Gln Glu
690                 695                 700
Val Lys Leu Ala Ile Cys His Asp Asn Tyr Tyr Ile Ser Arg Leu Pro
705                 710                 715                 720
Arg Arg Val Trp Leu Cys Ile Thr Leu Phe Lys Ala Phe Gln Ile Thr
                725                 730                 735
Lys Arg Thr Tyr Lys Gly Lys Val His Leu Ala Asp Phe Met Arg Asp
            740                 745                 750
Phe Thr Gln Leu Leu Glu Ser Cys Asp Ile Lys Leu Val Asp Pro Thr
        755                 760                 765
Tyr Val Ile Asp Lys Tyr Val
770                 775

<210> SEQ ID NO 6
<211> LENGTH: 2328
<212> TYPE: DNA
<213> ORGANISM: Artificial Sequence
<220> FEATURE:
<223> OTHER INFORMATION: DNA Encoding UL52/FKBP Fusion Protein

<400> SEQUENCE: 6
```

-continued

```
atgggagtgc aggtggaaac catctcccca ggagacgggc gcaccttccc caagcgcggc    60
cagacctgtg tggtgcacta caccgggatg cttgaagatg gaaagaaagt cgattcctcc   120
cgggacagaa acaagccctt taagtttatg ctaggcaagc aggaggtgat ccgaggctgg   180
gaagaagggg ttgcccagat gagtgtgggt cagagagcca aactgactat atctccagat   240
tatgcctatg gtgccactgg gcacccaggc atcatcccac acatgccac tctcgtcttc    300
gatgtggagc ttctaaaacc ggaaaatccg agtacccacg tgagcagtaa cggcccaacg   360
actccccctc acgggcccca caccacgttt cttcccccga ccagcccggc cccgtccacc   420
agctccgtcg ccgccgctac cttgtgcagt ccgcaacgac aggccgtttc gcgttacagc   480
ggctggagca ccgagtacac ccagtggcac tcggacttga caactgagct gctatggcac   540
gcgcacccgc gtcaagtacc tatggacgaa gcgctggccg ccgcggcggc cgcctcatac   600
caggtaaatc ctcaacaccc cgccaaccgt taccgtcatt acgaattcca gacgctcagc   660
ctcggcacct cggaggtaga cgaactgctc aactgttgtg cggaagaaac cacgtgcggc   720
ggcacgcaat ccaccgtact caccaatgcg accaacacca ctagctgcgg cggagccgtc   780
gccggcagta gcaacgtagg acccgccggc gcttcggccg cctgcgacct agatgcagaa   840
ctggccggcc tcgaaacctc ggcggccgac tttgaacaac tgcggcgact gtgcgcgccg   900
ctggccatcg acacgcgctg taacctatgc gccatcatca gcatctgcct caaacaggac   960
tgcgaccaga gctggctcct cgagtacagc ttgctgtgct tcaaatgcag ttacgcgccc  1020
cgtgcggcgc tcagcacgct catcatcatg tccgagttta cgcatctgct gcagcagcac  1080
ttttccgatc tgcgcatcga cgacctgttc cgacaccacg ttctcacggt cttcgatttc  1140
cacctgcact ttttcatcaa tcgttgcttt gaaaaacaag tgggcgacgc ggttgataac  1200
gagaatgtca ccctgaacca tctggccgtg gtgcgggcca tggtcatggg tgaagacacg  1260
gtgccttaca acaagcctcg cgccacccg caacagaagc aaaaaaacaa cccttatcac   1320
gtcgaagtgc cgcaagaact gatcgacaac tttctagaac acagctcacc tagccgcgac  1380
cgcttcgtgc agctgctttt ctatatgtgg gccggcaccg gcgtcatgag caccacgcca  1440
ctcacggaac tcacgcacac taagttcgcg cgactagacg cgttatccac ggcctcggaa  1500
agagaagacg caaggatgat gatagaagaa gaggaggatg aagaaggagg agaaaaagga  1560
ggagacgatc cgggccgtca aacggcggt ggcaccagcg gggggttcag cgagagcacg   1620
ctaaaaaaaa acgtgggtcc catttaccta tgtcccgtac ccgctttttt taccaagaac  1680
caaaccagta ccgtgtgtct gctgtgcgaa ctcatggcct gctcctatta cgataacgtc  1740
gtcctgcgcg agctgtaccg ccgcgtcgtc tcgtattgtc agaacaatgt gaagatggtg  1800
gaccgcattc agctggtatt ggccgatctg ttgcgcgaat gcacgtcgcc gctcggcgcg  1860
gcacacgagg acgtggcgcg ctgtggactc gaagcaccca cctcgcccgg aggcgactcg  1920
gactaccacg gcctgagcgg cgtcgacggc gcactggcgc gacccgaccc ggtattttgc  1980
cacgtcctgc gtcaggcagg cgtcacgggc atctacaagc acttttttctg cgacccgcag  2040
tgcgccggca catccgcgt caccaacgag gccgtgctct tcggacgcct gcaccccac    2100
cacgtccagg aggtgaaact ggccatctgt cacgacaatt actatataag tcgacttccg  2160
cgacgtgtgt ggctctgcat cacactcttc aaggcctttc agattacaaa acgcacctac  2220
aaaggcaaag tgcacctggc ggactttatg cgcgatttca cgcagctgtt ggagagttgc  2280
gacatcaagc tggtggaccc cacgtacgtg atagacaagt atgtctag               2328
```

<210> SEQ ID NO 7
<211> LENGTH: 402
<212> TYPE: PRT
<213> ORGANISM: Artificial Sequence
<220> FEATURE:
<223> OTHER INFORMATION: UL79/FKBP Fusion Protein

<400> SEQUENCE: 7

```
Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
                20                  25                  30

Asp Gly Lys Lys Val Asp Ser Ser Arg Asp Arg Asn Lys Pro Phe Lys
            35                  40                  45

Phe Met Leu Gly Lys Gln Glu Val Ile Arg Gly Trp Glu Glu Gly Val
        50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Pro Glu Met Ala Arg Asp
            100                 105                 110

Glu Glu Asn Pro Ala Val Pro Arg Val Arg Thr Gly Lys Phe Ser Phe
        115                 120                 125

Thr Cys Ala Asn His Leu Ile Leu Gln Ile Ser Glu Lys Met Ser Arg
130                 135                 140

Gly Gln Pro Leu Ser Ser Leu Arg Leu Glu Glu Leu Lys Ile Val Arg
145                 150                 155                 160

Leu Ile Cys Val Leu Leu Phe His Arg Gly Leu Glu Thr Leu Leu Leu
                165                 170                 175

Arg Glu Thr Met Asn Asn Leu Gly Val Ser Asp His Ala Val Leu Ser
            180                 185                 190

Arg Lys Thr Pro Gln Pro Tyr Trp Pro His Leu Tyr Arg Glu Leu Arg
        195                 200                 205

Gln Ala Phe Pro Gly Leu Asp Phe Glu Ala Ala Val Phe Asp Glu Thr
210                 215                 220

Arg Ala Ala Arg Leu Ser Gln Arg Leu Cys His Pro Arg Leu Ser Gly
225                 230                 235                 240

Gly Leu Leu Thr Arg Phe Val Gln Arg His Thr Gly Leu Pro Val Val
                245                 250                 255

Phe Pro Glu Asp Leu Ala Arg Asn Gly Asn Ile Leu Phe Ser Leu Gly
            260                 265                 270

Thr Leu Tyr Gly His Arg Leu Phe Arg Leu Ala Ala Phe Phe Thr Arg
        275                 280                 285

His Trp Gly Ala Glu Ala Tyr Glu Pro Leu Ile Arg Ile Ile Cys Gln
290                 295                 300

Lys Met Trp Tyr Phe Tyr Leu Ile Gly Thr Gly Lys Met Arg Ile Thr
305                 310                 315                 320

Pro Asp Ala Phe Glu Ile Gln Arg Ser Arg His Glu Thr Gly Ile Phe
                325                 330                 335

Thr Phe Ile Met Glu Asp Tyr Arg Thr Phe Ala Gly Thr Leu Ser Arg
            340                 345                 350

His Pro His Arg Pro His Pro Gln Gln Gln His His Pro Gly
        355                 360                 365
```

```
Pro Pro His Pro Pro Leu Ser His Pro Ala Ser Ser Cys Leu Ser Pro
    370                 375                 380

Glu Ala Val Leu Ala Ala Arg Ala Leu His Met Pro Thr Leu Ala Asn
385                 390                 395                 400

Asp Val

<210> SEQ ID NO 8
<211> LENGTH: 1209
<212> TYPE: DNA
<213> ORGANISM: Artificial Sequence
<220> FEATURE:
<223> OTHER INFORMATION: DNA Encoding UL79/FKBP Fusion Protein

<400> SEQUENCE: 8
atgggagtgc aggtggaaac catctcccca ggagacgggc gcaccttccc caagcgcggc        60
cagacctgtg tggtgcacta caccgggatg cttgaagatg gaaagaaagt cgattcctcc       120
cgggacagaa acaagccctt taagtttatg ctaggcaagc aggaggtgat ccgaggctgg       180
gaagaagggg ttgcccagat gagtgtgggt cagagagcca aactgactat atctccagat       240
tatgcctatg gtgccactgg gcacccaggc atcatcccac acatgccac tctcgtcttc        300 gatgtggagc ttctaaaacc ggaaatggcc cgcgacgaag agaaccccgc cgtcccgcgg       360
gtccgcacgg gcaaattctc ctttacttgc gccaatcatc taatattaca gattagcgag       420
aagatgtcgc gcggacagcc gctgagctcg ctgcgtttgg aagaactcaa gatcgtacgc       480
ctcatctgcg tcctcctctt tcaccgcggt ctcgaaacgc tgctactgcg cgaaaccatg       540
aacaacctgg gtgtctcgga ccacgccgtg cttagtcgca agacgccgca accctactgg       600
cctcatctgt accgcgaact cgccaggcc ttccggggc tggactttga ggcggccgtg        660
ttcgatgaaa cgcgcgccgc ccgtctcagc cagcgcctgt gtcacccgcg cttgagcggc       720
ggactgctga cgcgctttgt gcagcgccac accggcctgc cggtcgtttt ccccgaagac       780
ctggcgcgca acggcaacat cctcttctcc ctaggcacgc tctacggaca ccgcttgttt       840
cgtctggcgg ccttcttcac gcgccactgg ggtgccgaag cgtacgaacc cttgattcgc       900
atcatctgtc aaaaaatgtg gtactttat ctcatcggca ccggcaagat gcgcattacc       960
cccgacgcct tcgagatcca gcggagtcga cacgagacgg gcatttttac ttttattatg      1020
gaagattaca gaacgttcgc cggcacgctg tcccggcacc cgcaccgtcc gcacccacaa      1080
cagcagcagc accaccaccc cggtcccccc catcctcctc tttctcaccc tgcctcgtcc      1140
tgtctcagcc cagaggccgt actggccgcc cgcgcccttc atatgccgac gctggctaac      1200
gacgtgtga                                                              1209

<210> SEQ ID NO 9
<211> LENGTH: 693
<212> TYPE: PRT
<213> ORGANISM: Artificial Sequence
<220> FEATURE:
<223> OTHER INFORMATION: UL84/FKBP Fusion Protein

<400> SEQUENCE: 9

Met Pro Arg Val Asp Pro Asn Leu Arg Asn Arg Ala Arg Arg Pro Arg
1               5                   10                  15

Ala Arg Arg Gly Gly Gly Gly Val Gly Ser Asn Ser Ser Arg His
            20                  25                  30

Ser Gly Lys Cys Arg Arg Gln Arg Arg Ala Leu Ser Ala Pro Pro Leu
        35                  40                  45
```

```
Thr Phe Leu Ala Thr Thr Thr Thr Thr Met Met Gly Val Ala Ser
    50                  55                  60

Thr Asp Asp Ser Leu Leu Lys Thr Pro Asp Glu Leu Asp Lys
65              70              75                  80

Tyr Ser Gly Ser Pro Gln Thr Ile Leu Thr Leu Thr Asp Lys His Asp
                85              90              95

Ile Arg Gln Pro Arg Val His Arg Gly Thr Tyr His Leu Ile Gln Leu
            100             105                 110

His Leu Asp Leu Arg Pro Glu Glu Leu Arg Asp Pro Phe Gln Ile Leu
            115             120             125

Leu Ser Thr Pro Leu Gln Leu Gly Glu Ala Asn Asp Glu Ser Gln Thr
    130             135             140

Ala Pro Ala Thr Leu Gln Glu Glu Thr Ala Ala Ser His Glu Pro
145             150             155             160

Glu Lys Lys Lys Glu Lys Gln Glu Lys Lys Glu Asp Glu Asp Asp
                165             170             175

Arg Asn Asp Asp Arg Glu Arg Gly Ile Leu Cys Val Val Ser Asn Glu
            180             185             190

Asp Ser Asp Val Arg Pro Ala Phe Ser Leu Phe Pro Ala Arg Pro Gly
        195             200             205

Cys His Ile Leu Arg Ser Val Ile Asp Gln Gln Leu Thr Arg Met Ala
        210             215             220

Ile Val Arg Leu Ser Leu Asn Leu Phe Ala Leu Arg Ile Ile Thr Pro
225             230             235             240

Leu Leu Lys Arg Leu Pro Leu Arg Arg Lys Ala Ala His His Thr Ala
            245             250             255

Leu His Asp Cys Leu Ala Leu His Leu Pro Glu Leu Thr Phe Glu Pro
        260             265             270

Thr Leu Asp Ile Asn Asn Val Thr Glu Asn Ala Ala Ser Val Ala Asp
        275             280             285

Thr Ala Glu Ser Thr Asp Ala Asp Leu Thr Pro Thr Leu Thr Val Arg
    290             295             300

Val Arg His Ala Leu Cys Trp His Arg Val Glu Gly Gly Ile Ser Gly
305             310             315             320

Pro Arg Gly Leu Thr Ser Arg Ile Ser Ala Arg Leu Ser Glu Thr Thr
            325             330             335

Ala Lys Thr Leu Gly Pro Ser Val Phe Gly Arg Leu Glu Leu Asp Pro
            340             345             350

Asn Glu Ser Pro Pro Asp Leu Thr Leu Ser Ser Leu Thr Leu Tyr Gln
    355             360             365

Asp Gly Ile Leu Arg Phe Asn Val Thr Cys Asp Arg Thr Glu Ala Pro
    370             375             380

Ala Asp Pro Val Ala Phe Arg Leu Arg Leu Arg Arg Glu Thr Val Arg
385             390             395             400

Arg Pro Phe Phe Ser Asp Ala Pro Leu Pro Tyr Phe Val Pro Pro Arg
            405             410             415

Ser Gly Ala Ala Asp Glu Gly Leu Glu Val Arg Val Pro Tyr Glu Leu
            420             425             430

Thr Leu Lys Asn Ser His Thr Leu Arg Ile Tyr Arg Arg Phe Tyr Gly
            435             440             445

Pro Tyr Leu Gly Val Phe Val Pro His Asn Arg Gln Gly Leu Lys Met
    450             455             460

Pro Val Thr Val Trp Leu Pro Arg Ser Trp Leu Glu Leu Thr Val Leu
```

```
                465                 470                 475                 480
Val Ser Asp Glu Asn Gly Ala Thr Phe Pro Arg Asp Ala Leu Leu Gly
                    485                 490                 495

Arg Leu Tyr Phe Ile Ser Ser Lys His Thr Leu Asn Arg Gly Cys Leu
                500                 505                 510

Ser Ala Met Thr His Gln Val Lys Ser Thr Leu His Ser Arg Ser Thr
            515                 520                 525

Ser His Ser Pro Ser Gln Gln Leu Ser Val Leu Gly Ala Ser Ile
        530                 535                 540

Ala Leu Glu Asp Leu Leu Pro Met Arg Leu Ala Ser Pro Glu Thr Glu
545                 550                 555                 560

Pro Gln Asp Cys Lys Leu Thr Glu Asn Thr Thr Glu Lys Thr Ser Pro
                565                 570                 575

Val Thr Leu Ala Met Val Cys Gly Asp Leu Gly Val Gln Val Glu Thr
                580                 585                 590

Ile Ser Pro Gly Asp Gly Arg Thr Phe Pro Lys Arg Gly Gln Thr Cys
            595                 600                 605

Val Val His Tyr Thr Gly Met Leu Gly Asp Gly Lys Lys Val Asp Ser
        610                 615                 620

Ser Arg Asp Arg Asn Lys Pro Phe Lys Phe Met Leu Gly Lys Gln Glu
625                 630                 635                 640

Val Ile Arg Gly Trp Glu Glu Gly Val Ala Gln Met Ser Val Gly Gln
                645                 650                 655

Gly Ala Lys Leu Thr Ile Ser Pro Asp Tyr Ala Tyr Gly Ala Thr Gly
                660                 665                 670

His Pro Gly Ile Ile Pro Pro His Ala Thr Leu Val Phe Asp Val Glu
            675                 680                 685

Leu Leu Glu Leu Glu
        690

<210> SEQ ID NO 10
<211> LENGTH: 107
<212> TYPE: PRT
<213> ORGANISM: Artificial Sequence
<220> FEATURE:
<223> OTHER INFORMATION: FKBP

<400> SEQUENCE: 10

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Lys Glu
                100                 105

<210> SEQ ID NO 11
<211> LENGTH: 2082
<212> TYPE: DNA
```

<213> ORGANISM: Artificial Sequence
<220> FEATURE:
<223> OTHER INFORMATION: DNA Encoding UL84/FKBP Fusion Protein

<400> SEQUENCE: 11

```
atgccacgcg tcgacccccaa ccttcggaat cgggcccgcc ggccacgagc cagacgaggc      60
ggcggcggtg gcgttggcag caatagcagc cgacacagcg aaaatgccg  ccgccaacgc     120
cgagctctgt cggcgccgcc gctcactttc ctcgccacca ctaccaccac gaccatgatg     180
ggcgtcgcca gtaccgacga cgacagtctc ctcctgaaaa cgccggacga gctggacaag     240
tacagcggct cgccgcagac catcctcaca ctgacggata acacgacat  ccgtcagcct     300
cgggtgcacc gcggcaccta ccatctgatc cagttgcacc tcgacctccg acccgaagaa     360
ttgcgggatc ccttccagat tctgctctct acgccgctgc aattggggga agcgaacgac     420
gagtctcaaa ccgcccccgc gacgttgcaa gaagaagaaa cggcggcttc ccacgagccc     480
gagaaaaaa  aggaaaaaca agagaagaaa gaagaggacg aggatgaccg caacgacgat     540
cgtgaacgcg gcattctatg cgtggtctct aacgaggatt ctgacgtgcg cccggccttc     600
tctctctttc ccgcacgccc aggctgccat atcctgcgct cggtaattga ccaacaactg     660
acgcgcatgg ccatcgtgcg cctatcactc aatctcttcg cgctccgtat catcacgccg     720
ctgttgaaac ggctaccgct acgacgtaaa gccgcgcatc acacggcgtt acacgactgt     780
ctggcgctgc atctgccaga actcacgttc gagccgacgc tggatataaa caacgtaacg     840
gagaacgcgg cttccgtcgc tgataccgcg gaatcaacgg acgcggatct gacgcccacg     900
ctgacggtgc gcgtacgaca cgcgctgtgc tggcatcgag tggaaggcgg catctcgggg     960
ccgcgtggac tcaccagccg tatctcggcg cgcctctcgg aaaccacggc caagacattg    1020
ggaccctccg tctttggacg attggagcta gacccgaacg aatcaccgcc ggacctgacg    1080
ctgtcgtcac tcacgctata ccaagacggc atattacgtt caacgtgac ctgcgaccgc     1140
accgaggcgc cagccgaccc agtggcgttt cgcctgcggc tgcgacgcga aacggtgcga    1200
cgacccttct tttcggacgc gccactgcct tactttgtac cgccacgctc cggcgcggcg    1260
gacgagggac tggaggtgcg cgtcccttac gaattgacgc tgaagaactc gcacacgtta    1320
cgtatctacc gccgcttta  cgggccttat ctgggtgttt ttgtaccaca caaccgtcag    1380
ggactcaaaa tgcccgttac ggtctggcta ccgcgctcct ggttggaatt aaccgtactg    1440
gtgagcgacg agaacggcgc cacgttccca cgggacgcgc tcctggggcg cctctatttt    1500
atctcgtcaa agcatacgct gaatcggggt tgcctgtcag caatgacgca ccaagtcaaa    1560
tccacgctac actcgcggtc cacatcccat tcgccgtcgc aacagcagct ctcggtgctg    1620
ggcgcttcca tcgcgctgga ggacctgctg cccatgcgac tggcgtcccc ggagacggaa    1680
ccgcaagact gtaagcttac ggaaaatacg acagagaaga cgagtcctgt cactttagcc    1740
atggtctgcg cgatctcgg  agtgcaggtg gaaaccatct ccccaggaga cgggcgcacc    1800
ttccccaagc gcgccagac  ctgcgtgtg  cactacaccg gatgcttgg  agatggaaag    1860
aaagttgact cctcccggga cagaaacaag ccctttaagt ttatgctagg caagcaggag    1920
gtgatccgag ctgggaaga  aggggttgcc cagatgagtg tgggtcaggg agccaaactg    1980
actatatctc cagattatgc ctatggtgcc actgggcacc caggcatcat cccaccacat    2040
gccactctcg tcttcgatgt ggagcttcta gaactggaat aa                       2082
```

<210> SEQ ID NO 12
<211> LENGTH: 107

```
<212> TYPE: PRT
<213> ORGANISM: Artificial Sequence
<220> FEATURE:
<223> OTHER INFORMATION: FKBP (F36V, L106P)

<400> SEQUENCE: 12

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Pro Glu
            100                 105

<210> SEQ ID NO 13
<211> LENGTH: 321
<212> TYPE: DNA
<213> ORGANISM: Artificial Sequence
<220> FEATURE:
<223> OTHER INFORMATION: DNA Encoding FKBP (F36V, L106P)

<400> SEQUENCE: 13
ggagtgcagg tggaaaccat ctccccagga gacgggcgca ccttccccaa gcgcggccag      60
acctgtgtgg tgcactacac cgggatgctt gaagatggaa agaaagtcga ttcctcccgg     120
gacagaaaca agcccttta agtttatgcta ggcaagcagg aggtgatccg aggctgggaa     180
gaaggggttg cccagatgag tgtgggtcag agagccaaac tgactatatc tccagattat     240
gcctatggtg ccactgggca cccaggcatc atcccaccac atgccactct cgtcttcgat     300
gtggagcttc taaaaccgga a                                               321

<210> SEQ ID NO 14
<211> LENGTH: 230966
<212> TYPE: DNA
<213> ORGANISM: Artificial Sequence
<220> FEATURE:
<223> OTHER INFORMATION: rdCMV - Destabilized IE 1/2 and UL51

<400> SEQUENCE: 14
gggccgcgtg gtgggtcctc gaggggcggg ggggtgtttt tagcgggggg gtgaaacttg      60
gagttgcgtg tgtggacggc gactagttgc gtgtggtgcg gaggacggcg acggcgaata     120
aaagcgacgt gcggcgcgca cggcgaaaag aagacgcgtg tctgtgtctg tgtgattccc     180
cggggaaaag aggaagttcc cggggacgg cagcatgggt ccctgggac acacgaaaag      240 caacgcccgg gggcgaggga cgacggccct ggggaccgcg ggggaaataa cggccgcgag     300
gccacacact cgttcctgcg aagccgcaca ccccgaggcc gcgcacaccg ccgacacacc     360
ccgccaccac acccgccgg cacacccgcc acacgcccgc gacacacccg gcacgacaca     420
cccggcacac gcccgcgaca caccctgaca caccctgcca acacaccccc gacacaccca     480
acacacgccc gcgacacacc cggcacacac ccacccggcc gcgccccgac acacccaaaa     540
caccgccggt gcggggccgc gtggtgggtc ctcgagggag tgttgagggc cgtaagcgtg     600
```

```
ttgtgtccga cgctgcctgc gcactgccgg tgcgtgtcgt cccacggtat ttgttgtcgg    660
caccgggctt cgggacggtg tttcggcgcg ctgccggtgc gttccacggt ccttgcctgt    720
gtcgtttcgg cgctgcgctt gtcgggggtt ttcgagcgtt ctggccgccg gcgatgccgg    780
ggtgttgcgg agacggggggg tgtgcgggac ggtgttgggg ccggggacgg ggggttgcgct  840
ggggccgggg ctgttcgcgc cgcgtagggg aggttacgtt ggggacgggg acagtttgcg    900
gcgcggacca gggaacccac ctcacctatt taacctccac ccactacaac acacacatgc    960
cgcacaatca tgccagccac agacacaaac agcacccaca ccacgccgct tcacccagac   1020
gcccaacaca cgttacccct tacaccacagc aacacacaaac cgcatgtcca aacctcggac  1080
aaacacgccg acgaagaaca ccgcacacag atggagctcg acgccgcaga ctacgctgct   1140
tgcgcacagg cccgccaaca cctctacgat caaacacaac ccctactact cgcatacccc   1200
aacaccaacc cacaggacag cgctcatttt cccacagaga atcaacatca actcacgcat   1260
ccacttcaca acattggcga gggcgcagca ctcggctacc ccgtcccccg cgcggaaatc   1320
cgccgcggcg gtggcgactg ggccgacagc gcaagcgact ttgacgccga ctgctggtgc   1380
atgtggggac gcttcggaac catgggccgc caacctgtcg tcaccttact gttggcgcgc   1440
caacgcgacg gcctcgctga ctggaacgtc gtacgctgcc gcggcacagg cttttcgcgca  1500
cacgattccg aggacggcgt ctctgtctgg cgtcagcacc tggttttttt actcggaggc   1560
cacggccgcc gtgtacagtt agaacgtcca tccgcgggag aagcccaagc tcgaggcctc   1620
ttgccacgca tccggatcac ccccatctcc acatctccac gtcggaaacc gccgcacccc   1680
gccacatcca ccgcatcgca ccacccacat gcttcgcctc ggtcagatca cacgcttttt   1740
cctgtcccat ctacaccctc agccacggtt cacaatcccc gaaactacgc cgtccaactt   1800
cacgccgaaa cgacccgcac atggcgctgg gcacaacgcg gtgaacgtgg cgcgtggatg   1860
ccggccgaga catttacgtg tccaaaggat aaacgtccct ggtagacggg gtaggggat    1920
ctaccagccc agggatcgcg tctttcgccg ccacgctgct tcaccgatat ccaataaacc   1980
catcccctcg ccacgacgtc tccgcgtatc tttgtagcct caagaatccg tccccacgtc   2040
cacccatccc gagcactcca cacgccataa caaaccacgg acacgacaaa tgcatgcaaa   2100
cttctcattt attgtgtcta ctactctgtg ttgctacagg gagtgaagag ggtgaaggca   2160
aagaaaaaaa aaaggaacaa aataatagat tagcagaagg aataatccgt gcgaccgagc   2220
ttgtgcttct tttcttataa ggaggcaaat atactaggga aaacataaga ataggaagaa   2280
accgaggttt gggagaaaag ctgagataaa atagcgcatt ttccatacag aggttgttgt   2340
ttttgtggat cctaagaggt ttcaagtgcg aatctcaaag ttctcacgag aatattgtct   2400
tcaagtatcg acaactgtgg tccaagattt ttttttggtc tttttaggtt ctgcgaggga   2460
catcacgatg gatcgttgcg atgaagtcac gcgtacgcct ctggtgtggc gcggtgtcgt   2520
gacaggagag tgtgttttca gtgcagagct gtcttgattc ctatatccga gtatctgttt   2580
tctcgtaagg acggtaatct tctttggtgt aagtacatct aaaagctgca aactatattt   2640
taagggctgt ctctaggtgt actttgatgc tggagttttt cgctgtgttg atgtgaataa   2700
atctactact actattatat gcagaaagag tgattatgcc gagacaagat tgcattggct   2760
gaactgtttc aaaaacgcct acactctact tatccgtaaa cctaaggtaa tactatgtgt   2820
aagttgtttt tttttctttt tgtagtaaaa tggtgatacg tgcaattaaa actgtattcc   2880
atgtttccat cctttcattt caactttaaa ggcggctttg agagcgaaga agtgcgagga   2940
```

```
taaaaatgga tgactccttc gtgtccaggg agtcgactac tgcaacgctg attgattaaa      3000
agatggtctc cgatgatgat gttgttattg atcgaatcat ggtgcagaac ggcgacggag      3060
aggagcgtgt ccgccgccgg aaggtggtc tctttctctt ttcttttttc aagaaatctt       3120
ccatgtgttt atcgtagtga tcgaaatcga ctgatctcgg gttcttttg ttggtttctt       3180
ttcggttaat catgtattgt tttcttttt tacagaaaga actttttttt catgagcaat       3240
tcctcgcccg cgccggcat gccgaggtgg ggccactgcg atcagcggca tgccgacgcc       3300
gacccgggga tcttggattc accgttttct ctcttctctc tctacataca gaccgggtgg      3360
caggagcgg aaggaatcat cgtcgtcttt cattcttcga tgattatggt aatactaaat       3420
cttatctagg agcatataca tctaagattg gagtactagt agtcgtttgt ggtttctatt      3480
tttttttata tttatctatg acagttttc tgttttcgt tttgataata atataataaa        3540
aactcatgga cgtgaaatct ggcttggttg tggtgatttc attctcatta ttgttgtttt     3600
cttccgtct tgcggatgaa gatgttgcga tgcggttgtt gttggtgttg ctatacaccg       3660
agagagatga tcttttttgtt cttctggttc attctcctatg attgtttggc tgctgaccga   3720
cgcgtcagga tgtgcagggc atgcggggaa tcaggaccgg acacgggata atttcatcta     3780
cctatacgga gatcgcggtc ctcgccatga ggatcgcgac aggcgcgtcg aggggcagg      3840
aacacccttg cggattgaca ttcttggtgg tgtttcgttg ttgtcggtag ttgttgttga     3900
cgatgaggat aaataaaaat gaccttgttt ttgttctgtt ttctcttgtt gggaatcgtc     3960
gactttgaat tcttcgagtt atcggaaagc tgaggtaccc aaatgtctgt agctttttc      4020
tttttaccct cttgtttatc atctgcgatt cgtggtaggg aggagaggga aatgataatc    4080
cgagattaag gaaggagaa gataaaaaat aaaaaaaat aataaaacag aagccgaccg       4140
gccgccgacc cgttcccag gaccagccta cgaggaacgg ataacgcggt ggcgacggca     4200
gcggtggtgg cgctggggggt ggcggcagtg gtactgctga tggtagtcgg gacggaggag   4260
aggcgatgca tacatacacg cgtgcatgct gcatgggtgg atggtacggc cgggagacgc    4320
ggaagagaaa ctcacataaa aaggtgacaa aaagagcggt tgaaaaaaga aaacaagatt    4380
cgaccagaca gaagagaagg accggggctt ggcgacccct ccacgactgc tgttgtcatc   4440
tcggctcctc cgtcttctcc cggccacggg cggctaagtc accgccgttc tccccatccg   4500
tccgagcgcc gaccgaccag ccggccgatt cgcccgccgg ggcttctgga gaacgccggg   4560
gcagcagcga tctggggaag ctgctaaacc cctgcgtttt tatatggtag ctctgccgag   4620
cgcgggctga cgcgttgggt aagcggaaag acgtgtgtga cgaaaagggg tcccatggta   4680
tttcacgtga cgatgaggag atacggtttg gagcacatac ggtttagaaa aagggagttg   4740
tcgtgacaag ggctgaggga cctctgtctc catgtgtgta taaaagcaa ggcacgttca     4800
taatgtaaaa aagaacacgt tgtaaacaag ctattgctgt atcattcggc tgactatgct   4860
tcattcggac tgatttttctt ttcctaacgg cgtaacttaa agtgattaac gtatgatatt  4920
tgttccccag agttatacta tagtcatcat cctaaaattc agatataaat gaacacatgt   4980
cgtatgggat tattaagaaa ccgaaactct ccacagttca ccatcttctt cgtcattcaa   5040
ccgatgaccc actccgtaca acgaatcagt ctgctgcgtc atattgcaaa gcacaagcga   5100
cgtatgcgaa caacttgaaa cacaggctgt tgtattgacg accgttgtac cattattagt   5160
caccaccgtt atcccatgtt tcccacccga tggaaaaccg tcttctatca tcaactgtgg   5220
taagatttcg accctgcgag gtattcagtt tcctcatatc cataacctgg attttatcat   5280
taaacccccaa tattaaacac ttttttagta ccccccacccc accaaaaaat gtgactggac  5340
```

```
cggttcctag cagctctggg agccatgttc aggttgaacc acagctacag cgaaaccgag    5400
tccagtgacc ggtaaccacg tccagcccct gcgtatgtac cagtccaagc acgtccggtc    5460
attgttctac acaggaaatc taactaggtc aacgcaattt tattccaccg ttacgcagaa    5520
tactaacaaa aaaacacaca aatttaacga attacacgta gtttattaca tgaaaactgt    5580
aagaacacca attcactaag cgatacaaca tttagctgac ttccaagtgc cacacatcac    5640
cactgtattc atccatgttt tcaccgaacc aacgagacag atcgaagaag ccagaatctc    5700
ccgactttaa attacataaa tccaacgtat tatgaccaca gctcgacaca caaatagttg    5760
cgttactatt cacagtagca ttacctatac ccgtaacgtt gcacaaccac tgatcaccat    5820
tgttaccaaa aacggttttc cacttagttg tcaacggatc tttcctatgc gtaatggtaa    5880
aattactacc agtcgtcgct tttagctcat tacgagtatt atccgcatcc acatatatca    5940
acgtcatagc taggcacgct ataagtaccc cccccccaca atggaatgtt gccaaaccgg    6000
ttctttcccg ttatagccat agcgttccca ggcaaaagca aacgccaaac ctaatgcagt    6060
gaaaagcgct tgcagccaga accagcttat gtaccagcca caatcacatc cggttattgt    6120
ttccacagga aatcctacca ggcaaagccc cgcttgtttt gttcctatct tgtttagcaa    6180
ttcgtaaact gtcagcctag cgacgtccgt ttagatcaaa agtcacgtat atagcgacgc    6240
tgtttccatc cgtttcccg tcccgccgtt tccgaacaac ccacccgggt tcagacaacc    6300
gaccaccaac agaaatatac acacagacca ctgggagttc agttaaagat ttcatcaggt    6360
ttattttggc tgctgctagt cttttgcttc ttagaaaaaa aatacccata tagagaaata    6420
atgatagttt gacaacacat atggcaggga tttcttcttc atcaataaga tatgcaattc    6480
ccccagggag agactttcaa caattgaatt tacaaaaaca aaattacatc aggagaaaga    6540
gaggatacat taataaatat attatatctg gtgtatatac tgaatgctgc tggttcataa    6600
ggtaacgatg ctactttttt taattccaag atggttttc tttgttagtc ttttgttgac    6660
ttgctggttc ctaaaagttc gcaaaaacga ttgtgtgaag attttatgac gttggttgac    6720
tagttcatga gattctgctg tacgtgtgat ggttattcgc tggttcgttc taagatgagt    6780
atcgtactgt gtctgcgatg gtcgtctctt actggcattc tctcggctgc ctcttgcttt    6840
catgattgaa aaggaaaaaa ggactccgag ggcgcggtca tcttttactt ttcggttttc    6900
tcgttggcgg gtcagaggta gtcagatcat gagactgtcg tggtcgatga aactgtgtct    6960
gctcaagtga cgtccatttc ttgtacggag aaaaagtca tcgggataaa taaggctata    7020
caaggcgttg tcaagcgtgc ggctctaaac aaattaagcg atacaaaatt acagtaaatac    7080 gaataataaa ttaccccccct cccctgtgg tccccgaga cgagagccac ccatcgtgta    7140
ctctcgcacc acccacgacc acagagggag acgggacgaa gagacgacgc acagcgccat    7200
ctcctcctgg aggccggcga cgttaactgc tacagctgcg gcggcgaaga cagctgcgat    7260
ttgtcggccg acatgccgat ggtatgggcg cggcggcaa tggccgcggc agcggggagg    7320
agaggagaga gaagaggagc ggggcgtccg aaggcgagga tggcatggtc tcgccggagc    7380
gcccggcttt tatggaacac tcgcgtccgg ttgggtatca cccacaggaa gatgagtcac    7440
aacttccaaa ccatcttgag acccgagtaa cggtttacag gtcgcacgcc agtcagctaa    7500
aaacagcgga cagtcccacg ctgtttctgt tgtggctctc tccagttccc tcatcaccgt    7560
cccggtctcc gtcgtcatcg gaagaatacc acccgctctc atgcggcagt cgatcggcct    7620
cgacgaacga gacgcggcga cgcctctcca cggccgactg gttgtggtgg tgaaagaaga    7680
```

```
gcaccagcaa tcccaggagg agcaacaagc cctcacatgt ccaggaggtc ggggagaggg    7740
cctgtcggag atggccgtga ggcatcacgt acggcagctg aggagaaacg agaagaaag    7800 gaaaattacc gtcaggggcc ggggttctta ttagagaaac agcacgtagg tcaggatcca    7860
gatgctaatg gcaatcatga tgacgatgat catgcaggcc aagacgcggc gcaccaatgc    7920
cgaatccaat agccgccgtg cctccggttg gtggccggcg gcatctagag acatgatttg    7980
ggggggaccg gcggcgcaaa aagacaggga gatggacagt gtcacggtgt tttgttataa    8040
ttaggacatg gggaccggaa gccgagacag agtactacag ggtgttgaag ggtaacgtga    8100
gggagatcat gtcatgggcg ggctgaagac cgtgcgggga ggattgacgt gtgcggtgct    8160
tgtggaacac ggtgttttaa tatgtatccg cgtgtaatgc acgcggtgtg ctttctggca    8220
ctcagcttgg taagctatgt ggccgtctgc gccgaaacca agtcgccac caactgtctc    8280 gtgaaatcag aagataccca tttgacgtgc aagtgcagtc cgaataacac atcatctaat    8340
accggcaatg gcagcaagtg ccacgcgatg tgcaaatgcc ggatcacaga acccattacc    8400
atgctaggcg catactcggc ctggggcgcg ggctcgttcg tggctacgct gatagtcctg    8460
ctggtggtct tctttgtaat ttacgcgcgc gaggaggaga aaaacaacac gggcaccgag    8520
gtagatcaat gtctggccta tcggagcctg acacgcaaaa agctggaaca acacgcggct    8580
aaaaagcaga acatctacga acggattcca taccgaccct ccagacagaa agataactcc    8640
ccgttgatcg aaccgacggg cacagacgac gaagaggacg aggacgacaa cgtctgataa    8700
ggaaggcgag aacgtgtttt gcaccatgca gacctacagc accccctca cgcttgtcat    8760 agtcacgtcg ctgtttttgt tcacaactca gggaagttca tcgaacgccg tcgaaccaac    8820 caaaaaccc ctaaagctcg ccaactaccg tgccacctgc gaggaccgta cacgcacgct    8880
ggttaccagg cttaacacta gccatcacag cgtagtctgg cagcgttatg atatctacag    8940
cagatacatg cgtcgtatgc cgccacttg tatcattaca gacgcctata aagaaaccac    9000
gcgtcagggc ggtgcggcgt tcgcgtgcac gcgccaaaat ctgacgctgt acaatctcac    9060
ggttaaagat acgggagtct acctcctgca ggatcagtat accggcgatg tcgaggcttt    9120
ctacctcatc atccacccac gtagcttctg ccgagccttg gaaacgcgtc gatgctttta    9180
tccgggacca gggagagttg tggttacgga ttcccaagag gcagaccggg caattatctc    9240
ggatttaaaa cgccagtggt ccggcctctc actccattgc gcctgggttt cgggaatgat    9300
gatctttgtt ggcgcgctgg tcatctgctt cctgcgatcg caacgaatcg gggaacagga    9360
cgctgaacat ctgcggacgg acctagatac ggaacctttg ttgttgacgg tggacgggga    9420
tttacagtaa aagatgcgtg tcgcctgccg aagacctcac catctcacgt acaggcatac    9480
ggcgtataca atcataatat tctatattct gcatagagtt acatgcaaca gtactactac    9540
caatactgca tccatcacat cacccaacac tgcttctacc acctttgtga ccagcgtatt    9600
ttctactccg aataacaaca catcaacgac gccacacaca tctgtcacct cacaagcgtc    9660
aaccattggc aacatcacca acgttacctc cgacttgagt actttcacaa ccgtatattc    9720
tacattcaat acatcatatg ctaatatatc caatacggct gccactacag aattgatttc    9780
aacaaatacc aacactatat tatcttttac caacgtaaca gcaaacgcta catcatctta    9840
taacacaaca atcaccgtaa ctatcacgtc agatgaaact tcgcacaacg tatccactaa    9900
tactgcactt ataagcacgc catggcttac aaattgcagc gccacaacgt acaccacgta    9960
caaccgtact aactcttcca acgcttgtca cacagagaca acaatcatac gtttcaaaga    10020
aactaataca acaggaatag aagggagtaa tgtcaccata aaaggtaatt ctacgtggga    10080
```

```
ttgtctttca gtcgcctgga tacgacatta caatcgatcc acacacggac atcatctagg   10140
tcatcgtaag aacgcacata cccaatcttg gtattggtta cgcatcctta cctctcatac   10200
tgtatgtcat tctcaacatg aaagaccttc actgtaccat gacttatgtc gttcgtgcaa   10260
caacacagaa ctacatctgt acgatctaaa tatcaccaat tccggcaggt acagcagacg   10320
ttgttttaaa gaaaattact tcacaggaca tcacgaagat gaaaatttct acctattagt   10380
aacaccaaaa aatcatactg aagctattaa tgctactttc gtttgcccta gatacaacac   10440
cgatatcgaa aatgaagata gagagaaagg aagtcaacat actaacaata cacatcacca   10500
caaacgtaat ctctatcata gctcgcaaag aagccgcacc gtatggacca tcgtgttggt   10560
ttgtatggcc tgcatagttc tgttttttgc acgacgagcc tttaacaaaa agtaccatat   10620
gttgcaagac accgtcagtg aatcagaatt cattgttcga tatcacacag aacatgaaga   10680
ttgagctacg tttccgggca gacatcttat gaagctgaac aataaactaa acattctgt    10740
aaggctcagc gttcaaagga atattaatgc ccattgagcg agaactaata ttgcaatgga   10800
ctggcgattt acggttatgt ggacgatact aatatccgcg ttatcagaaa gctgcaatca   10860
aacctgttcc tgtcaatgtc cctgtagtac taccgttaac tattccacta gtactgagac   10920
agccacatca acatacagta caacagttat cagcaataaa agcacttcag aatctataaa   10980
ttgctctact gcaactgcac cagcaaccac cgtttctaca aaccgtcga aaacaaccac    11040
acagatatcc acaacgacaa atacaaacgt tgagactacc acatgtacca acaccaccac   11100
gaccgttact tgtgatggtt tcaattatac agtccataaa agatgcgacc gcagttacga   11160
ggtaatcaac gtaacaggat acgttggtgg caacataact ctaaaaaatg caatcagact   11220
gagaaatggc acaatgtaga ctggattcat tatgagtacc ccacgcataa aatgtgcgaa   11280
ttaggcaact atcaccaaac aacaccacgg cacgacatat gttttgactg caacgacacc   11340
tccctaacta tctacaactt aaccacaaga aacgctggaa aatataccag gcatcaccgt   11400
gataacggtc aagaagaaaa ttactacgta acggtgttaa ttggagacac aacgttatcc   11460
actcttggca catgccctgt aagatataaa gaatctagga acactgaaaa caccattgga   11520
agtaacatca taaaaaccat tgagaaagct aacattcccc tgggaattca tgctgtatgg   11580
gcaggcgtag tggtatcagt ggcgcttata gcgttgtaca tgggtagcca tcgcattccc   11640
aaaaaaccgc attacaccaa acttcccaaa tatgatccag atgaattttg gactaaggct   11700
taacatgcac atcaataaac ttttttttaac caataacatg tctctgtttt tttttgttaa   11760
caacctatga tataaagcgg tatattcaat cattactaaa caaaaaaaca tgggcatgca   11820
atgcaacact aaattgttat tgccagtcgc actaataccg gttgtaatca tcctaattgg   11880
tactctagtg cccatacttt tacatgaaca aaaaaaggcg ttttactggc gacttttttct  11940
gcaaagtcaa catgtagaag cacccattac agtaacgcag ggagacacag tctacctaga   12000
tgctagcaat aatccctgta attattccag cttttggtac cacggtaatt gcgaactttg   12060
tggatggaac ggatatctac gcaatgttac acattactac acaaacacat cgtgttcccc   12120
gcaattcatg tgcataaacg aaactaaagg tctgcagtta tataatgtaa cattaaacga   12180
ttcaggtgct tatactgaac acgttacgaa atgtgatctt tcatgtaaca ttactactta   12240
taacgaatat gaaatactca attacttcga taactgtaac tacaccataa atagcaccaa   12300
gcatattatc accgtggtgt cttcacgtca ttctaaacaa acaaattccc acgtatccac   12360
tcacgctggt tgggcagccg ccgtggtgac ggtaattatg atctacgttt tgatccactt   12420
```

-continued

| | |
|---|---|
| taacgttccg gcaactctga gacacaaact acgaactaga acaacgtaa atcgcatagc | 12480 |
| gtgattacaa agtatcgaca ctaatttatc caagataaaa tttgattact ccgtgcggtt | 12540 |
| ctcaaaaact gtaaggtccc gcttttctac tccatcatga aggatcgcaa tagaatactg | 12600 |
| ctatgtatca tctttatttg catcatgtgc ctcatttgta tttactttaa acgtcgttgt | 12660 |
| gttcttactc cgtctccaga caaagcggat ctgcgagtgg aatttccctc gttaccccg | 12720 |
| tgtatcggca tacaatgtgc tgcatgagaa cacgcgtgac acatagcgta cccctggacg | 12780 |
| gtacagttta tgataacgtc attcagggga agtatacatt actatcgacg tgttatcaca | 12840 |
| gaacacacag attttctgcg tgttttataa aagagcgtct cgaagcagct tgagccacac | 12900 |
| tacggtccag atgacgagcg taatcaaaaa tatgccgcgc agtagtcgaa agccgtactg | 12960 |
| agcgtgcgag gcgggtaggg tgccgaacga cggatatgcg tcgttgtcat cttcgactat | 13020 |
| aaggatcgcg accgagtctt cggccatggt aaacgtcacc ctgtgtggct ggtatgtagc | 13080 |
| gtatccggtt tggaattgtt ctgctccagc tcggggata gtgaggaatt ctcaagggat | 13140 |
| acgggaccca atgactggat aagagaaggg ttttccccg taagatgatc ctcgtatcac | 13200 |
| atgaggtctg gatatgtata aatgaagagt gaaataggca cagggaatca gatgccagcc | 13260 |
| tcgtgatgca gccgctggtt ctctcggcga agaaattgtc gtctctgttg gcttgcaaat | 13320 |
| acatcccacc ttaagcgatg agtccataaa gcaccgttgt ccgggtacgg tgaaagtgac | 13380 |
| tcggattgta gcacgtccct ttttttgtt tttgtatcgc ttatcgccac tgacagtgca | 13440 |
| atatttgat cgtgaggctg agtatggtta tgatgcttag aacgtggaga ttattaccaa | 13500 |
| tggtactact tgccgcgtac tgttattgtg ttttgggac ttgttcaatc ggcacgacga | 13560 |
| ctgctcccgt ggaatggaag tctcccgacc gtcagattcc taagaatatt acttgcgcta | 13620 |
| actactcagg gaccatcaac ggcaacgtta catttcgagg tcttcagaac aaaacggaag | 13680 |
| acttttttgca ctggttgtta gggtggggtc ataagtccat ctgttcgttc ttcccgaaac | 13740 |
| tccagggcaa ctataacgaa caacattaca gatatgaagt agcgaacctg acgtataact | 13800 |
| gcacctataa ccgcttgacg ttgctaaatc tgacgacgga aaacagcgga aagtactatt | 13860 |
| ttaaaaggga agatgcgaat ttcacctttt attactcttg ttacaacctg accgtgtcct | 13920 |
| aaagaacgca cgtgaagttc cacagagccg cgtggctgta gctattgtgt ttacgttgct | 13980 |
| tttgaaatgt taagcgtccc tacggcgcta acatgtttct aggctactct gactgtgtag | 14040 |
| atcccggcct tgctgtgtat cgtgtatcta gatcacgctt aaagctcgtg ttgtctttg | 14100 |
| tgtggttggt cggtttgcgt ctccatgatt gtgccgcgtt cgagtcctgc tgttacgaca | 14160 |
| tcaccgaggc ggagagtaac aaggctatat caagggacaa agcagcattc acctccagcg | 14220 |
| tgagcacccg tacaccgtcc ctggcgatcg cgcctcctcc tgatcgatcg atgctgttgt | 14280 |
| cgcgggagga agaactcgtt ccgtggagtc gtctcatcat cactaagcag ttctacggag | 14340 |
| gcctgatttt ccacaccacc tgggtcaccg gcttcgtctt actaggactt ttgacgcttt | 14400 |
| tcgccagcct gtttcgcgta ccgcaatcca tctgtcgttt ctgcatagac cgtctccggg | 14460 |
| acatcgcccg tcctctgaaa taccgctatc aacgtctcgt cgctaccgtg tagctagtta | 14520 |
| gccagctgtg tatagtttgt tgtgttttgc ttttgcatat ttgttttcag tcagagagtc | 14580 |
| tgaaacgggg tgggagggac ttttacgggt aatgcatgct aagatgaacg ggtgggctgg | 14640 |
| ggtgcgcttg gtaactcact gtttgaatac gcgctcacgc acatatgtag cactcaacat | 14700 |
| gttagctttt gcccgcacgc cccggggcgt gccgagctgc ctttttaata aagtctgggt | 14760 |
| ttccagatac gcgctggttc tgattttgat ggtttgtgcc tctgaaagct ctacgagctg | 14820 |

```
ggccgtgaca tccaatcgac tgcctaactg tagcacgata actacaacag cgggtcaaga   14880
cgctgaattg caccggtccgg caccgttaag ctgtaatgtg acccagtggg gacgttacga   14940
gaatggaagc acacccgtat tatggtgcac tttatgggga tcacgcacgc gagtctcatt   15000
aggacaccgt gtagcgtttg gctgttcttg gaaaacattt tttatttata acgttctga    15060 aagtagtggt ggcacttatt atcaaaaagg ttacaactgc accgacaaac atataacact   15120
atcttgtttc aacctaacgg tggttcctcg agcggttcaa agcacaacca ccgtaatgac   15180
acccacggtg gttacaaact ccacattcag tgtgtcactt gttgcgtcga gactgacgac   15240
aaattccagc gcgtttagac acgctagtta tcaacggcaa cagcgtgtcg gaaacgggac   15300
gttatccaag aacataacta acttggcatt cacctacggc agctggggcg tcgcgatgct   15360
gctgttcgcc gccgtgatgg tgctcgttga tttgggtttg cctcaatcgg cttggcgacg   15420
ctggcgaagc cacgtggacg atgaagaacg tggtttgtta atgtaggaaa taaaaggcac   15480
tgtttgagca tgactgtttc caaaccgtaa cgtggtaaat aaatcatggc ttccgacgtg   15540
agctcccatc ttctaacggt tacacaatcc cgttggacaa tacatcatat gtacaataaa   15600
ctgttgattt tggcgttgtt taccccgtg attctggaat ccatcatcta cgtgtctggg    15660
ccacagggag ggaacgttac cctggtatcc aacttcactt caaacatcag cgcacggtgg   15720
tttcgctggg acgcaacga tagtcatctc atttgctttt acaaacgtgg agagggtctt    15780
tctacgccct atgtgggttt aagcctaagt tgtgcggcta accagatcac tatcttcaac   15840
ctcacgttaa acgactccgg tcgttacgga gcagaaggtt ttacgagaag cggcgaaaat   15900
gaaacgttcc tgtggtataa tttgaccgtg aaaccgaaac ctttggaaac tactacagct   15960
agtaacgtaa caaccatcgt cacgacgaca ccaacggtga tcggcacgaa aagtaacgtt   16020
acggggaacg ccagtttagc accacaacta cgtgccgtcg ctggattctt aaatcagacg   16080
cctcgggaaa acaacacgca cctggccttg gtaggtgtta tcgtatttat agctctaata   16140
gttgtttgta ttatgggatg gtggaagttg ttatgtagta aaccaaagtt atagtgatgt   16200 gcttttatc agggagaagg ttttgtgcca acaatgacta accctgggct atatgcatcg    16260
gaaaattata acgaaaatta tgaacttacg gaagccgcca atacagcacg tacaaatagc   16320
agtgactggg taacgttagg aaccagtgcg tcgctgttga gaagcacgga gactgcggtt   16380
aaccctagca acgcgactac ggttactcca caacctgtgg aatacccagc tggggaagta   16440
caatatcaaa gaacgaaaac acattattct tggatgctaa ttattgccat aattctcatc   16500 attttttatta tcatctgtct gcgagcacct caaaaagtct acgatcgctg gaaagacaat   16560
aaacagtacg gacaagtatt tatgacggac acggagctgt gatgaactac aatgtataga   16620
tacacgtggc tgctttggtg gataacaata ttgcttcgta tacaacagtt ctatcaatgg   16680
tggaaaccag atacaacgtc atgcattcag aaaacgggat atgaaggtca aaacctcagt   16740
ctgcctccta gtaatgcatt atcatctaaa gactatactt tttcatggta taaagattca   16800
cttaaagccc ttaacatgtt atgttattat actgaaaaac ttgaagaaat agatagcaag   16860
ccagatacta tacgacgatg ttttttgaat catacattgt ttcttattaa tttaacaagt   16920
cactatagcg ggatttacta cttcgattct ctatacacat atggttgggt attacggaca   16980
cctctatgtt acaatgtcac tgtatattcc atatatcaaa cacacatcca cacaactata   17040
ttgctctatc cgcctacgtc cacatataat tcattaacta tatcatcatt tacctcaacc   17100
aacttaacac ataccgcggt ccactatgcc gccggtaacg ttgaagcaca acacgatact   17160
```

```
gccaccccac atacaatgtg gatcataccc ttagttatcg ttacaacaat tatcgtttta    17220
atttgtttca aatttcccca gaaagcttgg aataaattca cacaataccg atacaacagt    17280
atgctcaccg ccgcttaaag aatcaccgtc gagaaaacta aaacgtaaaa agaatggcca    17340
tgtacgttta tttttcagct cactgtttga ataccgtaaa cataatgacg tacatatacg    17400
tgattataca acaggtgttt gtgttatgcg gcgactgatt aaccatatcg tgaaccatga    17460
tcttttccga tggtccgtca tgaccgcaat gatattttac aggtattccg aaacctgtat    17520
ggaggtcact gtcagagtag gtgatccagt taccctcggt agtggacatg ttatcatcc     17580 aggacaaaaa gtacactggt ataaccagtc atgcgtcggc attagcaacg gcgaaaatac    17640
gcatcctatc tgcacctacg accctcctaa acctggtaga cgaaagacaa tgaaaaccac    17700
tccgttacca tcaccactgt tgtacgagtg tcacaattcc acattaagca ttcttcatgt    17760
aaacgtctca gatcccaaaa actattgcag gcgaaaatgt ccaccaaacg gtaactgtga    17820
atttcccaca tgttttacgt tatcactgat ttccagaacg acaaccacca gaaaccccgg    17880
acaaaaaact acgttgtcgc gattaaaaac cacgccaaat aaacatacgc agcacaaaag    17940
atccacgcga agaacgtcac ctagagatta caatgtaacg ggtctgccga aaggctttgc    18000
ggactcgttt accggtaacg tagaggcaca tagagccaaa gatgccgcac acagcgcatg    18060
gatcctcatt gtcatcatca ttatcatagt cgtcattta tttttcttca agattcctca    18120
aagactcaga gagaaatggg acaccagagg ataccttac aaaggaaccg acggcctgcc     18180
cactacggac tacttatcgt gagcggacgg atatctccgg tttcaaaccc actgtttgaa    18240
tatagggaca gtccctacgg aacctgagaa catgtggaaa tcacctgtgg tagaatgctg    18300
ctcaggtaca ttacctttca tcgtgaaaag gtactttacc tagcgatcgc atgcttcttt    18360
ggtatctaca tcagttttcca cgacgcatgc attctggtac ctgctaaagt aggtactaac    18420
gtcacattga acgcggtaca tgtgcatgac ggtgactatg tgtactggtc ttttggtgga    18480
ggtggagcta atagattaat gtgtcgctat acaccaaggc tagacgaaat tcacaaaaac    18540
accaatcgaa gttttcatg tcttacaaat cacagtctcc ttctcatcaa tgtaacggaa     18600
gaatatactg attactatcg caccatgacc acattcgtac atcagtccca taattggcac    18660
aaccacggca acaaatggac tttagacaca tgttattatg tatacgttac ccaaaacgga    18720
acacttccca ctaccaccac caaaaaaccc actacgacca cgagaacgac aactaccacc    18780
acaacaaaga aaacaaccac cacgagcacg acaacgacca ccactaccac caagaagacg    18840
acgacaagca ctacccatca tcgacactcc aatcccaaag aatccaccac ccctaaaacc    18900
cacgtagaac ttcacgtcgg tttaggagcc acagcagcgg aaacaccgtt acaaccaagc    18960
ccacagtacc aacacgtggc tacacacgcc ctctgggttt tagcggtcgt aatcgttatt    19020
atcatcatta tcattttcta ctttcgaata ccgcaaaagc tgtggctgct ctggcagcat    19080
gacaagcacg gcatcgtgct catccctcaa accgatctgt gagcaagtcg cgtaggaaat    19140
gattgcatga aatcactgtg aaacgccaac tccgtgccag ctggcgcggc ggacaggcct    19200
ttgacgtatt tgaagccagg cgcgctctcg ataccgaaag gatccgaggg ggctttccaa    19260
agccgacgtc cctgattccc ttcataaagc tgttgaccgg ccctagaaag accaagcagca    19320 tgctgtgggc ccactgcggt cgcttcttgc gttatcatct gctcccgctg ctgctgtgta    19380
gactgccatt cttactcctt ttccagcggc cgcagtgggc ccacggcttg gacattgtcg    19440
aggaggacga gtggctacgg gagatacaag gagcgacgta ccagctgtcc atagtgcgcc    19500
aagccatgca gcacgccgga ttccaagtca gagcagcgtc ggtcatgacg cggcgaaacg    19560
```

```
ccgttgacct ggaccgaccg ccgctttggt cgggatcgct cccgcatttg cccgtctacg   19620
atgtgcgttc cccgcggccg ttgagaccgc cgtcatcaca gcatcacgcc gtatcacccg   19680
aactgccgtc gcgagacggg atacgttggc agtaccaaga gctgcagtat ctggtggaag   19740
aacaacggcg gcgaaatcag tcgcgcaatg cgattccgag accctcgttc cccctccgg    19800 atccaccatc gcagccggca gaggatgcac gagacgcgga cgcagaacgt accgaatcac   19860
cacatagtgc agaaagcacc gtcaggcacg acgcgagtga gaacgcagtg cggcgacggc   19920
acgaaagacg gcgctataac gctctgacgg tccgcagccg ggactcgctg ctcctgacgc   19980
gaatacgctt ctccaaccaa cggtgtttcg gacgcgggcg tctgagacat cccgcgggaa   20040
gcggtcccaa caccggcgga ccgcgacccg gcggtgcggg actccgtcaa ctacgccaac   20100
aactgacggt ccgctggcag ctgttccgcc tacggtgcca cggttggaca cagcaggtct   20160
ctagccagat cagaacccgc tgggaggaaa gcaacgtcgt gagccagacg gccacgcgag   20220
tacgtacgtg gttcgtggaa agaaccacgt tttggcgtcg cacgtgggtt ccagacaga    20280 acccggcggc cgaagcgcaa gaactggccg tcataccgcc ggcacccacg gtgctccggc   20340
agaacgagga accacgtcaa cagcttacgg gagaggagag aagaaattca acgcacactc   20400
aacgtgaaga agtggaggac gtttcgagag agggcgcgag agaagggaat gatgggagcc   20460
gagcaagtgg aaacgacgag agaaggaata atgcggaag atatgatgat gatcatgagg    20520
ttcaagagcc gcaggtcact tatccagcgg gacaaggaga actgaatagg aggtcacagg   20580
aggagaacga ggaaggtgga ccgtgtgaat cgccgccaat gacgacaaat acgctgaccg   20640
tggcctgtcc gccccgagaa cccccgcatc gtgccctgtt tcgtctatgc ttaggactgt   20700
gggtctcgag ctacctggtt cgacggccca tgacgattta gaatacaccg agccattcct   20760
ttatttcccc ccatccccgg tcgcttatgc gtgttaaaca ctaccaataa agataatctg   20820
ccaatcgcac cttatatata atatgtggtc gcgtgtggtc tttttaagga gctctgaaac   20880
acagacaggt atgggcggtg gtcggctgcc gccgctgtgg ctgccgctac tgatcgcctg   20940
gagcgagtgg ggcaactgct gcctcgatgc gcctccggtg gtgcgttcgc cctgtctgca   21000
gccggtgcgc gaccgcaacc gcgagcggaa cccgggctca ccgcagttgc tgccttacgg   21060
cgaccgtctg gaggtggcct gcatcttccc cgcgcacgac tggccagagg tctctatccg   21120
agtccacctc tgctactggc ccgagatcgt gcgttcgctg gtggtggacg cacgcagcgg   21180
tcaggtgtta cacaacgacg ccagctgtta catcgccggc gggcgctggc gcttcgagga   21240
cggcggcgcg gcgcagcggc tgagcctctc gtttcggctc atcaccgaga ccgcgggcac   21300
ctacacctgc gtgctgggca acgagaccca cagcctggcg accgagacca cggcgctggt   21360
ggccgacgtg cacgacctgc gccactcgga ccgctcctgc gacctggctt tcggatcgcg   21420
ctcacagacg cggtacctgt ggacgcccga tccctccagg ttgcgcagta taaactgcgg   21480
ttgggagggt gaacgcacc gcgtagtcca ctacatcccc ggcacctcgg gtttgctgcc    21540
ctcgtgcgag gaggacgagc gcgaactgtg cgtgcccttc atcagccaga gcattgcgga   21600
caacaactgc agccgccggc atcgagttga cggcgctagg cggcgctatc atctacggag   21660
ggattactgg ctgacggatc cgaagatcgg gttgctggcc gcgggatcgg tggccctgac   21720
ctccctctgc cacctgctgt gctactggtg ttccgaatcg taccggcgtc tgaacaccga   21780
ggaggaaagc gaggcggcgg aggaaactgc cgcgggagaa gcctctgcgg tagcggcggc   21840
ggccgtctct gaggaagagc agcggcggga gtaaacgagg agagccatga agcggatgat   21900
```

```
tcgcagtcac ggcaggaaaa cggaatgtca gatgacgagc gccggcgagc gacgcggctc     21960
cgccgtcggt gcgcccatct gcggcagcgg tacccgacgc ggcagcggcg ccaacgaacg     22020
ccgcgactcc gacgtcggtc ccatcgccca cagtagcggt accagacgcg gttcggcgaa     22080
tgaaacgtcc gcctgtacgc ggaccgatca ccagaaggcg gacattgggc tgtggttcat     22140
gtttctggtt tttggactgt gttcgtggtt ggcgatgcgg tatcgcgcac aataaatttt     22200
gaatcgatgt caaggaacgc gtgttttgta ttttattggg aatattggcg gggataaacc     22260
tgtttcggat gtttacccct aatcttaccg gggacctcgt tgtcctctcc tccttcttcc     22320
tcggacaccg ggctccatgc tgacgtaggt accgactggg gtcaaaagcc tgggtactta     22380
tgaggagcgc gcacaaagga ccgttaggcg ccggcatgga gcgtcgccga ggtacggtac     22440
cgctgggatg ggtgtttttt gttctttgct tatctgcctc ttcctcgtgt gctgttgacc     22500
tgggtagcaa gtcctccaac tcgacctgcc gcttgaatgt gacggagttg gcctcgatcc     22560
atcctgggga aacgtggacg ttacacggga tgtgtatttc tatctgctac tacgagaatg     22620
tgaccgagga cgagatcatc ggcgtggctt ttacttggca gcataacgag tctgtggttg     22680
acctgtggtt gtaccagaac gacacggtga tccgcaattt cagcgacatc accactaaca     22740
tcttgcaaga cggactgaaa atgcgaaccg tccctgtgac taaactgtac accagccgca     22800
tggtcactaa tcttaccgtg ggccgctatg actgtttacg ctgcgagaac ggtacgacga     22860
aaataatcga gcgcctctac gtccgattgg gctcgctata tccgagaccg cccggatccg     22920
ggctcgccaa acacccctcc gtaagcgccg acgaggaact gtccgcgacc ttggcgagag     22980
acatcgtgtt ggtctcagcc atcactctgt tcttcttctt gttggcccta cggatccccc     23040
agcgactgtg tcagcggctg cgcattcgcc tgccgcatcg ataccagcgg ttacgcaccg     23100
aggactgaac ggataaccgc aaaggccacg tgcaacgttc acgctgctat aagaaggcca     23160 tgtccccgt ggacgggtct ctttgacacg agcgcggcac gccgttgcca cgagcatgga     23220
tcacgcgctc ttcacacact tcgtcggccg accccgtcac tgtcggttgg aaatgttgat     23280
tctggacgaa caggtgtcta agagatcctg ggacaccacg gtttaccaca ggcgccgcaa     23340
acatctacct cgacgtcgcg ctccgtgcgg ccccagagg cccgccgaga ttcccaaaag     23400
aagaaaaaag gcggccgtcc ttctattttg gcacgatttg tgctggctgt ttcgacgact     23460
tttctttcct cgggaggact cagagccact gatgtcggat ccggcacggt ctcccgaaga     23520
ggaggagtaa acaacacacg gctaagagga tacatcatca aagaagatag gaggggtcaa     23580
aacgcggact gaaagtatat aacgccgatc atgtccgagg aactgttaat aaaacgccat     23640
gatgacaatg tggtgtctga cgttgtttgt gctgtggatg ttgagagtgg tgggaatgca     23700
cgtgttgcgt tacgggtaca cggggatttt cgatgataca tcgcatatga cgttgaccgt     23760
tgtggggatt tttgacgggc aacactttt tacctatcac gttaattcca gcgataaagc     23820
gtcaagtcgg gccaacggta ccatttcttg gatggctaac gtctcggcgg cctaccccac     23880
ctacctggac ggggaaagag ccaaaggtga ccttattttt aaccaaaccg agcaaaacct     23940
gttagagctg gaaattgcgt tgggttaccg gtcacagagc gtgctgacgt ggacgcacga     24000
gtgtaatacc acgaaaaacg gtagttttgt agccggttac gagggatttg ggtgggacgg     24060 ggaaactta atggagctca aggataacct gacactatgg acgggcccca attacgaaat     24120
tagttggttg aagcaaaaca aaacgtacat cgacggtaaa attaaaaaca tcagcgaggg     24180
ggatactaca atacaaagga actatctcaa gggtaattgc actcaatggt ccgtcattta     24240
tagcgggttt caacccccg tcacccaccc agtggtaaag gcggtgtcc gaaaccagaa     24300
```

```
tgacaacaga gctgaagcat tctgtacatc ttacgggttc tttccagggg aaattaatat   24360
tacttttatt cattacggtg ataaggtgcc cgaggatagc gagcctcaat gcaatccgct   24420
acttcccacc ttggatggga cttctccatca gggatgttac gtagccatct tttgcaatca   24480
aaactacacc tgccgcgtta cacacggtaa ttggacggtg gaaatcccca tcagcgttac   24540
ctcacctgac gacagttcct cgggggaggt ccctgatcac ccgacagcta acaaacgcta   24600
taacaccatg accatcagca gtgtcctcct agccctgctt ttatgcgctt tgctattcgc   24660
gttcctgcac tactttacca ccttgaaaca ataccctacgt aacctggcct ttgcgtggcg   24720
ctatcgcaag gtccggtcgt catgaccagc aacgccctgt atgagctgtt tcgacgtagg   24780
ttaccgcgtg ccccgtcaa cacggtcatg tttctcacgc gacgcactcg tgatgggttc   24840
tgcggtcggt tgacgtccat cgccacgaat tcccactaca ctatgttcgt gttagatcac   24900
gggtccgtgc gcatcgagcg accgagtcag tcagaagtgg attgcgccag tttaatggaa   24960
acgctgaagc ggattcggtt acgaaattcg tgggtagcgt cagaagacga gctagatgtg   25020
agtcgcgggg acgcgtgaca caaaacgcgt tcaggattaa cgtaggtttt cgaaataacc   25080
tacgtccgtg agtgacgcgg tttcgtgttg aaacccgcgc cggttctcac ggtggtttat   25140
gatgaaaccg gcgttgggga tctacgcggg ttcctcattc aacctgcgaa aagaggaagt   25200
tgcggtaaaa ccacgtcaat aaagacgtca atgacacctc aatgttgcgt tggaacggtc   25260
tttatatata caaacgccgt tatgttcagt gtccggcaag atgctcggga tacgggctat   25320
gctggtgatg ctggattact actggataca gttgataaca aacaatgaca ctcgaagcaa   25380
caataccgat accatctttg tatctctcct taccggggcc aacggagtta ctcgcacagc   25440
catcgggggt ctgcattcaa actacaccaa cttaaccgag gcattcagat tcactccagc   25500
aaacacaaca actaactctt ccacggaggg taattggagc gtgactaacc taacggagag   25560
ttgcatcaac cgcggtgagt cctatctaac taccatctgg cttctgaact gcgctgacaa   25620
caatacttat tggtactctg gaaatgccta taaccataca attgacactt gtaaaaatac   25680
agtttcggga tatctcttct tcggcatgtg ccagctatgg aaagattggg ttactaatgc   25740
ttctcacgac actgtcagaa ttcagtcgtt gggaaatgaa atacgctgca tgctgctccc   25800
tagacagtat accctcaacg ccacggtgga atggtacaac aaatctgaag gtgacgtacc   25860
agaagaattt atggactatg ttatcctgac ccccttggca gtgcttacat gcggactgca   25920
ggaagcttat atactcgaca agggtcgtag atacatgtat ttgttttccg tgtcctgcgc   25980
gggaatcaca ggtaccgtat ctattatact cgtctcccta tcgctgctca tcctcatctg   26040
ttactatcgc tgtggccggc ttctgatatg cccacgcggc tttgaactct gccagaatt   26100 cactgaggaa gaggaggaaa aagaaaaatt gttaacgtac aaggacattg aagtccaggt   26160
gcctatccgc acgcggcggc tgctcgtccc ttggatccgg gagagcaaaa tgtgggtact   26220 accaccccg ctgcctccac gacctcccca cttaatagaa ttcccgccgt ctcctccgcc   26280
gtcgcctggg cccatgcaca tggtggtctg catgccagca tgacgactt tgaactttga   26340 gccccaagcg gtacggacta catatttcc ataaatctac actgaacttg agcacaaaaa   26400
tactgacaat ggactgaata tacagacttt tatatgatcc ttgtacagat gtaaataaaa   26460
tgtttttatt taaaactggt cccaatgttc ttcgggaatc atgggtggg gacggggac    26520 gcggtaagga gcaaaccggg gtacatgggg gggaacatcg tccagcagta gcaccagcgg   26580
attgggtagg ggttgctgcg gaggtcggtc gatgacgatg tcgatctcca tcggcagatc   26640
```

```
cggcaacatc tcttcgtctc cctcaccgac cagcactcgg cgctgttctg gatgtatatg    26700
attttggaaa agcctccgac gagctcgcgg cgcgtagaaa gccaagcggc gcaagggccg    26760
gcgagcccga aagtccatgc gcacagatgg catgagtcct tgagtgacgg tggtgagctg    26820
gggaacaggg ctacctccca tcgcgacggt gacagtggat ccatgagaga ggcgccgcac    26880
gctgcatggc taaataccgt gaatccctg acgtcgtctt tcgtcccgaa cgcgtcatgt    26940
tgggggcgag gcgtaaaccg tcgaggttga aaaaccgcgt atctgcgacc cgtccggact    27000
acgttgtttt tcagaagcgg ccacatgacc tcgagatgtc gtcacccaag gtatttaacg    27060
gcacacagcc agacgcgttc gtcagcagcg acgccgacaa gacctcagca tggctcggag    27120
gctatggatc ttgagcttac tagccgtgac cttgacggtg gctttggcgg caccttctca    27180
gaaatcgaag cgcaggtaaa cggaatctgg ggaattcaac acaggtaaga aatacaaaaa    27240
ataacgtgat tgtgaacgcg gttatcgtgt ttttgcagcg tgacggtgga acaacccagt    27300
accagcgctg atggtagtaa taccacccc agcaagaacg taactctcag tcagggggg    27360 tccaccaccg acggagacga agattactcc ggggagtatg acgttttgat tacagacgga    27420
gatggcagcg aacatcagca accacaaaag actgatgaac acaagaaaa tcaagccaaa    27480 gaaaatgaaa agaagattca gtaacagcag accccaaggg ttaacgatta tgttgactac    27540
cttgtttttt attaaaaagc tgtaaggttt tgctctaaaa acaccccgcc tccggtcttt    27600
tttcttttgt attcggcacg cgaaacacgg tttcttccca tagcctgtct aactagcctt    27660
cccgtgagag tttatgaaca tgtatctcac cagaatgcta gtttgtagag gctatgcggg    27720
atgctgcggc ggcgcgacct tccctctcca cccagccccg tcaaaacaca cgcgactcga    27780
gcggttcgta tgaaaaataa aaaacagctt tttatttaca ggaacgggga aaaaaaaggc    27840
acacggtccg tgggagacgc gggttcacgc gtcgtcaaaa agttggtggt ccactccgta    27900
aggacaggta ggcttattta gcttccgcat gctcctggtt ccgtaataaa tgccgttttc    27960
gtggcagcgt gtcatgccgc gagtcacaaa ctccatcaaa ctgtcggcca cgatgcaaac    28020
gtgctgattg ttggcagcaa agacgcgcat acagtcgtcc acgaagaggt tgatcacgtc    28080
gtaggggctc accaaccagc ctaaaggttc cacgtggtta ctgccgacca tgaccctcca    28140
gtcgttaatc tcgctccagt cgtacagccg aatcgtggag acgcgaatga cgctgtaatc    28200
acccatgacc atgagtcggc cgcgatacgt agcacgccac tgcgcgaacg cgtggatgtg    28260
catgcagccg gccagcgctc taagcgaggc ggtgtgcggc agctcctctg ggacggtgat    28320
gaagttgcag cgtcgcaaac cgatgttgag aaattcagtg atgctctcgg ccacaaaggt    28380
caacgagtca gagtagatgt ggtcggtcca caggtacatg gcgcccgagg cgcccaggta    28440
cagttcagac ggcacgttgt gatcgcccct tgtgtttaaga aagttgtagg tgcagatgct    28500
gccgacgaaa cgcagcggct cggggcagca gaggtagctg gccagacgct gtgcatcccg    28560
tccttcgtcg cgcaccaagc gccagcgacg ccggataacg aggcagcggt ctttgggcca    28620
gaccagggcc acgcgttgcc cgggtttcca cggtcgcgac gtcttaggag gcctccagcg    28680
gtcgagcaga ttgagaaaac agtccttgat taccgacatc gcggtcgcgc gtcggtggac    28740
aaaaagaaat cggccgatc cggaaaaaaa aaacgacggc aaaacaccgc cgtgctcgag    28800
cgaagggtgg cggagggcca aagaggcgg ccttgacggc gttggcagcg aaaaaattgg    28860
cacgcgagtc aaacgggaag tagcgtcggt gttttatgcc ccaagcagcg tcgtcgtcac    28920
tcgtggcgtc acagtcaacg gtgctgacgt ccttttgggg agtcgggcac gcgatcgtag    28980
atgccgttgt ggccgctgaa acgtcggttt tcaaacagca ggttaagtcc cagacacatg    29040
```

```
aacgtgttga gattatctcc cacccggatg tagcggtcgt cgcgcacgtc gcaggcgtag   29100
acggccccgg tataggcgac gacgatgggg ataaggtcga cgggccagcg caagtgagga   29160
aagggcgcgt tctcgccctt gaggctgacg gttcccaggc cgagaacgcg cattccgaaa   29220
gcggttttga tgttgcgcag caagtgaccg ccttccacgt tgttttcgaa acacctgagg   29280
ttgcatagac gcagttccgt tcccggcggg tacgtcaacg gcatgaactg cccgtggtgg   29340
cggatgatga atcgcgccat ggtatccaaa ccgaggctcc aggcgcgcaa cagcgggcga   29400
aagtagcgct taaccaacga cgaggtcagg tagcgcatgc agtgcagggt ctcgacggcg   29460
cgcagcccga cgcgcgcaaa ctccatgagg ttgcgggcca ggtagtagac ggcggtgtcc   29520
tcgcgtacat agcaaaaaac atagccctcg tccgagatga ggcacacagc ggtcttcttc   29580
tgctgatccg gcgacaacac gccctcgttc acgaagcgac ccacgaaggc caggcgcgtc   29640
tggcaacaca ggtagtgact ccaagccttc acgtcctccg gtttgaagtc ctcgtccgtc   29700
tcgatctcct gcagcactag gttccagccc ggcggccaga ccacgggcaa cacctggcct   29760
gcgttgatgc gcacgtaagc ttccagacag cccaggccga actcggccgt gagcgccagg   29820
ctagccagat cgctcatgtg acgcgccgag tcagtgggcg agcccggggg cccgtcgcac   29880
accacgctcc gtcttcttgt cctcaccgcg gccagcgtgg cgaggacact ttccgcgccc   29940
gaggctgtat cttcggtttg cccgccgag ccggccctca ctatataacg tcccgcccgg   30000
gtctcctcca tgtatgcagg taagcaactg agccgaacgc acctcagcag acgagaggat   30060
gtcgtcgcgg cgtcgcagct cgtcacgtcg ctctggcgaa ccctcgacgg tgatttatat   30120
cccctcgagc aacgaggaca cgccggcgga tgaggaggcg gaggacagcg ttttcacgag   30180
cacgcgggcg cgcagcgcca cggaagatct ggatcgcatg gaggccggtt tgtcgccta   30240
cagcgtctcc tcggacgctc cgtcgtcctt cgagctcgtg cgcgagaccg gcggcaccgg   30300
cgccgccaag aaaccgagcg aaaagaaacg atcgtcgtcg cgtcggcaac cgcagatcgc   30360
agcgggcgcg cctcggggct cgccggcgac acccaaggcc ggcaagtcgc ctaaagtctc   30420
gcgaccgcct agtgtgccct cgctgcccga gaacggcgcc ggcggcggtg gcgacgataa   30480
cagcagcagc ggcggtagca gcagtcgcac caccagtaac agtagcagaa gtaccagtcc   30540
cgtggcgcca ggtgagccgt ccgctgccga gggcgatgag ttttccttct gcgacacgcga  30600
catcgaagac tttgagcgcg aatgttaccg ggtcagcgtg gccgacaatc tgggcttcga   30660
gcccagcgtg gtcgcgccgc agcacgtcga gtatctcaaa ttcgtgctgc aagactttga   30720
cgtgcagcac ctccgccgcc tcaacgaatg catacccatg ccggccttcg cgctcaccag   30780
cctcgtcgac cccgtcttaa caacgtagc gcctggcgag cgcgatctca cgcgtcggat   30840
aatcacgcac gcggtgatca tcaactatta ctacgtggca caaagaaag cgcgccacat   30900
ggtggaggcc atacggacca ccgtgcgggg cgacacggta cgccgggtag ccgcgcaggt   30960
caacaaccag agccgttcgg ggcgtgcggc gcgctagcc cttcattttc tcacgtcacg   31020
aaaaggagtg acggacggcc agtacgccac gtctctgcgg cggctggacg aagagctgcg   31080
gcatcgcggc acgcccgaat cgccgcggct caccgaggtt taccagacgc tacgcgatta   31140
caacgtgctc ttctataccg cccactacac ctcgcgcggc gcgctctacc tctatcggca   31200
aaacctgcag cggctcaacg agaaccaccg gggcatgctc cggctgcttt cggtcgaaga   31260
gatatgcgaa gagcacacgc tcaacgatct ggcgttccta gtaggcgtcg agcttatgat   31320
cacgcacttt caacgcacca ttcgcgtgct gcgctgctat ctccagcacc agctgcagag   31380
```

| | |
|---|---|
| catctcggag ctgtgttacc tcatctatgt acaactgccg tcgttgcgcg aagactacgc | 31440 |
| gcagcttagt gacgtgatct actgggccgt cagtcaaaac tacgactacg cgctctacgc | 31500 |
| gagcacgccg gcgttgtttg acttttttacg cgtcgtgcgt cagcaggacg ccttcatttg | 31560 |
| caccgactac gtgtactgcg ccctgcgtct gctggcctgt cccgacagac ctattatcgg | 31620 |
| tgacaccggc ggcagcagta gctcccaacg cctcgtaggc gagtttatgg tgcgcgatcc | 31680 |
| gctgttgcgc gacccgcgcg ccacccacct gcgccagaaa ctcatcaccc gcgacatatg | 31740 |
| cgtggcgcgg ttgcaagcgc agccctcgag tcgacacatt ccggtcgaac acacgggtgt | 31800 |
| ctcctccgtc accctgctca aaatctttag ccaagtcccc cccgacgaac gcgaagaaga | 31860 |
| cacgttacgc gagatggctc ttaaagcgtt tatggaagcg aacggtaatc accccgaaca | 31920 |
| aatctgccga tccccaccac ccccgctgcc accgcgcgac tatcctcaac gcgacgagcg | 31980 |
| ggaccgtcac cgtcgcgacc gccgcgacag cggggaatac tgttgctgat ggtgggacga | 32040 |
| aacagcaggg cggaacagtt tatgatagaa agtcacagga agtatgtgt tgttttttt | 32100 |
| ttaatgtacc aagaataaaa agtgcgtcta cgaccaaagc ggtgtgtgga cgctcgtcct | 32160 |
| ctctgtcttc tccgggtttt tttttcacgt gttttttcct tcctatttg ttacggcaac | 32220 |
| agcgctgatg gcacgttgcc ggcttcgaac atcgcgtcgg tgatttcttg cttgcccggc | 32280 |
| gtcacacggt gacgtagcag cacgcggctc acgtagcagg ccgactcgcg gatgacctgg | 32340 |
| ccgtcggcgt cgcgtcgcag gcccgagcgg ttgccgtgac gcagtctgcc ctgcgcagcg | 32400 |
| cgctccacgt cttcaaagta gctgtgtagc aggccgcgct ccagcagctg cggcagcgag | 32460 |
| tcggcggcgc gcactacaaa gttctcacgg ctgatctcgt agcacagcac gctgccgtcg | 32520 |
| gccgccacgc cggccacgct gcggtcccaa ctgaaaaggt tggcgagtcc gatggtgccg | 32580 |
| atgacgcgca actgaccctg ggtcaccacc agcagcttcc agtattctac gtcgcgcggg | 32640 |
| gtgaggatgg tctcctccac gtcgcagaca acaacgtgt agccgcgcgg atagggcaga | 32700 |
| tccaggtggc gaccgcgctg gcggcgcata aaatcgtcta aattcaaacc gccgtcgggt | 32760 |
| gcgcgcctac tcgtcatcgc cgcgccttgt cggtcgatga ccccacggtg cttataacgc | 32820 |
| gccgccgcgg cttcatgtgg cgtgacctcc gacctcgtga ggccgaaaac ggcgtacatg | 32880 |
| aagacgctca aacttttgaa tgtgggcccg gtagcgcacc gagggccccg gggcggcgac | 32940 |
| gacggcgggc ccgagttcca gcggggcctt gcggcggcag cggttggcgt ggttgctcag | 33000 |
| ctcggcgtcc gagagcgccg agctgaactg cggcagccgc gtgcgatcct gcggcgcgtc | 33060 |
| cccgtgtcgc agcgagtgcc agagcaggcg ctggacgcgc gccgtctcgg gcgtcggcgg | 33120 |
| cgcgcgacag ccccggcgca gcttgaaaac gtgcaggcac agcagctcgc gcttgatgcg | 33180 |
| cagcgacacg ctgcggtagt cgggaatccg ctgcaccagc tcgagaaagt cgcagaaggt | 33240 |
| ctccacgaac gtgtcctcgg tgaagcgaat gcgcttcaga tcgtggacgt gtttgcgaaa | 33300 |
| ccgcgacagt tctcgacgtt gcacggggtt ctgagcgagt cccttgcgca gcagcgcagc | 33360 |
| ctcgccttta aacagcctga tgagccgctg cacgtccccg ctcaacatac gtatacacgc | 33420 |
| cgtgtactcg tgacgtatac tggcgcgcag cagccgaatg atacgcaggg ccagcacggc | 33480 |
| gttagaggcc aggtacatgg cgtagccgcg acgggttg gcacaggccc agcccgcggg | 33540 |
| gagcagaaag tagtcgtcga tcagcgtctg cgaccagtcg gcgaagccca ggtcacgtga | 33600 |
| tacgctgtcc tggacgcggg ccacgtcgcc ggccgtgagg tggcggatcg ccggcaggtg | 33660 |
| aaacgcgccc aggtgtcggt tgcgctccag cctcagctcg gcgtgctcca acgggaatg | 33720 |
| gtgggacgcc accgcggagg gcgacaaaga ggagtggtca ttgccgtcgt ggttaccgtc | 33780 |

```
gtggttaccg ccgttgtcgc gcccgtcgcc gcactcgcaa aaggccgcgt agaggtcctt   33840
caatgccgct tcggctcgcg ccataaacgt ggcgtggaaa aaacggcgg cgcggtgcgt    33900 ccggtacttg acgggcaacc cgcggcacag ggccgccggc aggcagcggc cgatgagttc   33960
gcgctcctcg ggctccagaa acaggcacag ggtgccgtcc aggcgcaggt acagctcctc   34020
ggtcatcgag catagctgcc gcaagtaatg ggtgcgcgtc ccaaaggtct tgtaatcgag   34080
caacgtgcac accacgtatt gccccgtggc cacggccaga gcgatgcgtt tggcggcacg   34140
actgatctct ggcaagtact gcgcctcgtg caccagacgg cggaaagcgc cggcgttgag   34200
ccagcgaaaa tgctgcggat cgggcggcaa gggcacgcct cgaagcgcgg cccagacagc   34260
gaggtccgac tcgagcgtca gaccgcggat gtcgtacttg ccgtgcgccg tagcgcaggc   34320
tgaatggacc agacagctgc ggcgaatgta caccatggcg tgcttgggat gtttgggcgc   34380
cggcgttttc ttttctgac cgccggcggc cgccagatcc tcgggcgtgc gacacaacag   34440
gccggcgcgc acagcctcct gtcgattacg aatcggcgtc aggtaggcgc gcaggaactg   34500
gtgacaaaac tcctcatcat cacgacagtc gtcgagatac tcgtacgtgg tgagcggatc   34560
gcgaaatagg cgctcgtcac cgtcgtcatg gtcttcttta gcctgctcct ccggctgctg   34620
ggttggcagt ggaggcggcg gctgatccac ggggttcatg actgagagga agaagaaggt   34680
ggcggcgaag cgacgcggag cgacggcggt aaagccagac accggctata tagctagtca   34740
tcacagtctc ctccttcacg acgccccgt gccgctcacg ctatccagca cgctacggcc    34800
cgaaaacacg tactcgctga cgtcgtacgc gggcgatgta tggctgctca ccggtttcgc   34860
ggcgacggtt gcgctcgagt ccaacggcga gaagcaaaaa cgccgtgggc aacgaaacca   34920
gaaggagccc tgacggataa aaccgcgcag cgtctcggcc aacttaacca gcatcgtacc   34980
gtacagcagt acgtgaatgc cgccatgcgc gtccataaat acggctttgt tcacgggttc   35040
catccatccg atgactacaa aatgggcctg ttctagcacg ccgatcacga aattgttggc   35100
ctcgtcggcc tcggccacgt tccacagagcc gaaagtgaaa gtacaagcgg gcgagccgcc   35160
caggcggatc ttgctaccgg cgtggagctg acatacgcgc agcagattgg cgcggtcgtg   35220
cagtatctgg gagagttcgt acatgcccgc aaaggtgtgc ttaaaccacg cgccctctac   35280
gatctcatcc acgtagtcgc gctcaaagaa gctgtacacg gcaaagaggc cgttctcaaa   35340
aaactcgccg aacgagagcc ccagcacgta caccttgtcc tcgccgggca ggtacgcaaa   35400
ggcgtgcccg tgcccggaga cccagatctc gggcgccgtg tttgcgtccg gcacgcattc   35460
gtacacactg acgaggccga taagtacaa gcggccagcc tggcgcaggc acgagaagcg    35520
ccggtaggtc ttgtgatcgc gcaccacccc aaagtactga gtgtcgccca gcatgatgcc   35580
gtgcagcggg ggccagcaca gcgggagcca acgacccgcc gtggcgcgca cgtagcgctg   35640
caggtgaacc ccgctcgcac gctcgcgcgg cttcgggcgc ttgtgggtcc aggcatcacg   35700
cagaccgcgc cagatgctgc tgaacttggg ctgcccgcgc agatagagcg acgagagcga   35760
gtcaaagtag cccacgacga gcctgtcggg agacacaaga gcgcgaaaat caaacctaga   35820
gcgacgacgg tgaaaaaacc gaccagaagc gcgtgtctca aacacgctac tttcggttat   35880
aaaaacaccg tcgccctatt tctgggcgcg tgtacactga tgactcacct acgctttttg   35940
aacggcagtc tcagctcggg attggcctcg tacagcgagc tgcggtccac ggggccgatg   36000
ctctcgtagc gaaagtcgtc gatgagcagc gccagcccca cgcgcacgaa gcccctgagg   36060
tcgcgcgcca gccgcaccaa cttatcctgc cccaccagcg ccgcgtacac ggtgcccgtg   36120
```

```
tcgccgcaga gaatccgcac gcggtgaaag aaggtcttgt cctcggcgcc ctcaatttcg    36180
cccagcggca tgacgggctc gcgcgtgtac aacgaacgtt gaaagcggcg cagcatcgag    36240
gccgagagcc ccagatcgcg cgccgtgcgc agcactaggg aatgcttctc gggccagatg    36300
agggtcagtt gcgcctcgcg gtgcgcctct acgtaggcgc aacgagcggc ggtgtcctcg    36360
caggccagca actcgcggaa agccagcagc gaacgtaggt agcggccgcg agcggaggcg    36420
cgcgagcggc ggcacagctc ggcccgatgg tcgggatgca ccaagggcac gttaggttgc    36480
agacgcgcgc agatggattc gtgcaccggg tcgcagcgga tcatgcsctt ggcaaaaaat    36540
ccggccagat ccgaggccaa ctcgtacagg cagtcctctt gcgcgtcgta ggcgaacacg    36600
gcgccgtacg cgtccacgaa cacctggtac cggcaggtgg cgtgcgagac cgtgccaatg    36660
agatgcagag ctcggaattc gccgaaaaag tcgttctggc agtgctccag atcgatctcg    36720
gtcagcgagt gcggcgaatg ctcgcccccg accacgtaga tgcactgcga gggccagccc    36780
agcgacacgc acgagccctc gaagcgccgc aagtaacgcc gcaggcsctc atagtcgcgt    36840
cgcacgcaca ggtcggccaa gtcgcgcgtg caaaagacct cgggtaccaa gcagcgtttg    36900
cgacgcggcc gacgcgcgtg cccaggcaga ggaggaaggc gcgacggcgg cgacgacgag    36960
gaggaagacg ccgtggccgc cgagcagccc ttgcgacggc cggacatgcc ggcagtccgc    37020
gacgatccac aggagacaaa aaagcagaag cagcagtagc ctcggcgacc cgctccaccc    37080
cgtcctccac acgctcagcc gcgactgaac gccggggcgc gccgctactt gggttttat    37140 agccatctgc cccccgtctc gggcacccgg gagcgatcta cggagacctg acagcagttg    37200
ggcaacacaa gatagggaaa tacaaagaca cttttaataa aaaacgagac tactttgtgt    37260
gtgtgctccg taaactgttt attctccccc tccgcttcgc tctggatggg ctccgggtcc    37320
gtcaacacgc gactcgcgcg gcaaaaggca cgctgttgac ggcgcgagag cccgtcgtga    37380
tagtccatca tgccccggag atcgtgcaca aagcagctgt cgccgcgcag aaaccgacgc    37440
agcgtctcca cgtgctgcag ctgccggcgc gtatcaggag ccgtcatcgc tgatgtcgtc    37500
atcgccctga caggcgcgta gatggcttcg cgagatcatg cgcgttttca accgccgtga    37560
cacatcaggt ccatcttgag ctggcgccgg gcctcgcgca ggtgttgcac gcgttgtgag    37620
cgggaggcga gttcggcttc ttgctcgaac tcctgctgct cactgtccga gagggtgcga    37680 taaaggcgg caaagtcctc caagtcggct acatgcgccc tgggtctgac gctccaaagc    37740
gtacgcagtc tgatgaagcg gacccatcga gcgtcacggc acgccgtctt gaacgcgggg    37800
cccgggaaga ggttcttctc cccggcgcgc tcgggccggc gaggccgacg cggtttatat    37860
acaccgtctc ggacggcggg acgccgagcc cgcgccgcgg ccgctcatcc ggagacggcg    37920
gaaaccgcga cgccggagga aacgggaccg gcaacgacg gcgtggcgg cgaccagatt    37980 atgggggaca aacccacgct tgtgaccctg ttgaccgtcg ccgtgtcgtc gccgccaccg    38040
tcgtcgccgc tgccgctcgt cagcttcacg gagctgttgt taccgccgcc gtccgtcgcc    38100
gccgctgcgg tggcggcgac agcgacgagc gaggtgggcg agaaaaccgc ggagcaagag    38160
gtagcggctg cggatccgga gaccgggaat gagagaagag aaaacaggga gaacgaagga    38220
ggggagacga ggacgacagg caccaccgcg gtcaaaaggt cgcacgacgg tatccctcgc    38280
caactggcag agcgcctgcg gctgtgccgc cacatggacc ccgagcagga ctatcgtctg    38340
ccggcgcagg acgtggtgac ctcgtggatc gaagcgctac gcgacgcgga ccgcgacaac    38400
tacggtcgct gcgtgcgcca cgccaagatt caccgttcgg cctcgcacct gacggcctac    38460
gagtcgtact tggtgtccat caccgagcag tacaacacgg cctcgaacgt gacggagaaa    38520
```

```
gcttcgtacg tgcagggctg catctttctc tcgtttcccg tcatttacaa caacacgcag   38580
ggctgcggct acaagtacga ctggtccaac gtggtgacgc ccaaggcggc gtacgccgag   38640
ctcttctttc tgctctgctc caccagcgag agctccgtgg tgctgcaacc gctcatcacc   38700
aagggcgggc tctgctcgtc catggcggtt tacgacgagg aaaccatgcg gcagtcgcag   38760
gcggtgcaga tcggtttttct gcacacacaa ctggtcatgg tgcccttcgt gccgcacgcc   38820
tgcccgcatt acgccgtgcc tttcacgacg ccgggaaagc cgggctgcgg cggtgctccg   38880
agcggcgttg cggggttgga ggaggcggcg ccctttggac gggtcagcgt cacgcggcat   38940
ggcgcgacgc tgctatgtcg cgtggaccat ctgacctgga tcagtaagcg cgtaaccacg   39000
tacggacaca aaaaaattac gcgctacctc gcgcagttcc gcggcacgat ggacgacgac   39060
gaggcagcgc tacccggcga ggacgaagcg tggatcgcgt ccaaaaacgt gcagtacgaa   39120
ttcatgggtc tcattttcac cgtcaacgtg gattcactat gcgtggacgc ggaacagcgc   39180
caactgctgg gcaccgtggc cacctccttc tgtcaccgcg tctcggacaa gatcacggcg   39240
cgcaacatgc cgcgcgcttt tccttctac ctgctgacga gcgcgcagcg cgggtacgac   39300
ctgcgattca gccgcaaccc gtcactcttt tttagcggcg acgcgctcaa ctgtccgctt   39360
ctcaatgagc ccaacgtgtt ttcgctcacg gtgcacgcgc cttacgatat ccacttcggg   39420
gtgcaaccgc ggcagacggt ggagttggac ttgcgctacg tgcagatcac agaccggtgt   39480
ttcttggtgg ccaacttgcc acacgaggac gccttttaca cggggctcag cgtgtggcgc   39540
ggcggcgagc cgctcaaagt cacgctgtgg acgcgcacgc gttccatcgt gatcccgcag   39600
ggcaccccca tcgccacgtt gtatcaaatt accgagggcg acggtaacgt gtactcgtac   39660
aaccaccaca cggtgtttcg gcagatgcac gccgccggaa caaccacgtt ctttctgggc   39720
gacatgcaat gcccgcgga caactttctc acgtctcccc atccctgacc ctccgtccgt   39780
cctcctttcc cgacacgtca ctatccgatg gttttcattaa aaagtacgtc tgcgtgtgtg   39840
tttcttaact attcctccgt gttcttaatc ttctcgatct tttggaggat gttctgcacg   39900
gcgtccgacg gcgttttggc gccccccatg ccggcagaac ccggttgcgg ccccgtaccg   39960
ctcttctggg gcgacgatag gtcgaaagcc accgttttca tgcccgtcgt gctcttgacg   40020
ggggaaccta cggcggcggt ccccgtcgag cggcgtgatt gcaaagccgc gctcgccccc   40080
ggtttcagga tggaggggga ggccacaggc ggcgcattcg atacgctgct tttggccgta   40140
gacgacggtg ggtaaacggt ggttaccgcg ggatacgtcg gcgtggtcga ggcggcccgg   40200
ctgctgccga acaggcgacc cggcgcgcta ccgctcacgg ggaccgaggg cggtcgacct   40260
accaccgcct tgccgcccaa agtaggtttc aaggaaggaa caccgacgcg gctgccccgg   40320
cctttcaccg gagacggggg ggcactcttg gccgggacg gagaggctga cgaaagcatg   40380
gacagcggcg atgtggcggg ggacacgaca tcatcctccg tgggcgacaa aacggacgcc   40440
gaggctgacg gctgtcgagc cgaagaagcg gaagaggttc ccgcgccaga agtcacgttc   40500
cttgatgacg tcgttttaga cgaagccggt tgaggttgca acagcgtggc gggtaccgtc   40560
gacggcgtgc ccgacacctg tttctctagc cttccctgaa ccggcgtcga cgtcaccgtc   40620
tgcgctcggg cggacgcgtg cggcgtcgcg actcgcttgc ccagcaccgg tttctggctc   40680
gtggatgtcg tcgtcattgg agacgataac ttagctttac gtattctgga cggcgtcgac   40740
tgctcgggcg tctgactggg aggcgaaatg acgtcgttgt tgtaatcgga cgacggtgtt   40800
gtgtgtccca ggctgacgac ggagccggtg tccgaggagt cgtcgtcttc ctcctcgctg   40860
```

```
tcttcgaccg gtgactctgc agtttggtcc cttaaagccc aaacctcatc agcggcgtcc    40920
cgagacgctg tttgtgtcac cgcggcgcgt ggagtcgacg gcctccgagg ggtggtggac    40980
acggtgtttt gagaagccgt ggaagtcgta ggcatcctga agggattgta agccaggtga    41040
ggattcttga gggcccacgc gcgttcgcgc ggccagttgg cggggttcat atccccgggc    41100
aacggcgccg tcggagccca gggcgagtta ccgttgaccg gggtttgggt acccgcgaag    41160
gtaggtgtcg gggccggagc gggggccgtg gaaggattga caggcgtcgg cgtgaggatg    41220
gcagcgccgg cgccagcagg aacgttaact ccggcgccga acgtcaacgt cggttgctcg    41280
aacttgtacg cggtggtgac gggcggtttg gcgctcgtct cggtatccgt gatgtccacc    41340
agcgtgtcgg tgaaacgcgg atcttgacgg ttgggggat  agccatccga gctgtcggaa    41400
tcctcgtcgc ccgagaaaag atcccctctg gtctccgtga gcggcctcac gtcccacgcg    41460
ctgtcccgac ggaccctccc cgggctggcc ttggtcacct gcggggagac gagactgaaa    41520
gccgcgtgac gctgttgttg ttgcgggatg ttcaagggac cgctggtcgg tttctgactg    41580
cccgaggata acaggccgct gaaaatgctg gaaacaccgc caccactagc ggcgcccttg    41640
ccgctagttc ccggttttctt gatgggcgta aagatgtttt tctcgtcatc atcatcgtcg    41700
tcgtcctcat cggcactgga gccaaagagc ctccgggagg cgctcggttt acgtgccggg    41760
ggcggtggtt gctgctgacg ttgctgcagg ttctgctgcc tctcctccca agccttcagc    41820
tgctgtttct cacgctgcac cacctcgtcg tccacccgtt tctgccgctc gcgacgcttt    41880
tcctcttcgt cgtaatagcc gacggccgcc gaacgggcag cgtgggcttc ggcggccggt    41940
gccagagaac catgggcctc gaagcggaac ggtttgtgtc ccttccaggg actggcgatc    42000
cagctccagc cgtccagcgg ctgcgtgggg acatgtttct tgggtaccga cgagaaggcc    42060
gaaccgccgc cgagcgagag gagattggcg tcatcgtcaa actccaacga cggcgagcgc    42120
gcgcccaaaa acgtgtgcgc cgactgtggg aagctgtcca cgtagatatc aaagtcctcg    42180
atgagcagct ccaacagcgt gtcggccgag tcgccgtttt ccacggcgtg cttgaggata    42240
ttgcgacagt agttggaatc aaaggaaagg cacatgcgca gctccttgac cagcagcttg    42300
cagcgctcct gaatgcgcgc cagacatttg cgctccagct cctcccaaga cctgcgcacg    42360
ttcatgatga cacggcccgt gtacacgagc ttgttgacgg cgttgaccag cgccgtgttg    42420
gcgtgccggt ccaggttaag gtcgagcggt tcacgcaga  acatgttacg gcgcacaccc    42480
tccaggtttt cttcaatgcg ctgcacctcc gtatccttga ggtgcacaaa ggcgatgggt    42540
tccgtctggc cgatggctgt gaccagcgtc tcgcgcaccg acatcttggc cagaatgacc    42600
gcgcttacga gcgcgcgttc cacgatctcg gcatcgtggc gcacgtccgt atcgaattcg    42660
gtacggtcta gcacagccag gtggtcacgc gccttaccac gatcaccgaa cgggtaagtg    42720
tagccgcgac gcgccacggc cacgcaacgc acctcgaact cctcgagcac tgaggagagg    42780
tcggggttgt gaaaacgcag ctcgcggtag tatcccaacc aaagcatgag ctcgttgaac    42840
agcaccgtac gccggtgcag gcgttttttcg ccacatttttt tcaggatctt ggggtgtgcc    42900
tcgagatcca cgtcgggctt ttgcgtgaga tggcgcagaa agttgaccag ggctaccaca    42960
tcgcgccgct gtagaccgat aaactgcaaa ctcatgctgg ctttttctcca gaacccgaaa    43020
gcgtcgtcgc cccggactgc gcccgcggtc tgctattcgc ccacgatgga caccatcatc    43080
cacaactcgg tgagcgcccc acctagaggg agggggggta gtttaatagc ggaggcggat    43140
acgcggtttt ctttttaagcg ccgctgactt gtttcttctg ttttttcgcc ccgtgtgctg    43200
ttccgcccag acccgcaaca acactcctcc gcacatcaat gacacttgca acatgacagg    43260
```

```
gccgctattc gccattcgaa ccaccgaagc cgtactcaac acattcatca tcttcgtggg    43320
cggtccactt aacgccatag tgttgatcac gcagctgctc acgaatcgcg tgcttggcta    43380
ttcgacgccc accatttaca tgaccaacct ctactctact aattttctca cgcttactgt    43440
gctacccttt atcgtactca gcaaccagtg gctgttgccg gccggcgtgg cctcgtgtaa    43500
atttctatcg gtgatctact actcaagctg cacagtgggc tttgccaccg tagctctgat    43560
cgccgccgat cgttatcgcg tccttcataa acgaacatac gcacgccaat cataccgttc    43620
aacctatatg attttgctat tgacatggct cgctggacta attttttccg tgcccgcagc    43680
tgtttacacc acggtggtga tgcatcacga tgccaacgat accaataata ctaatgggca    43740
cgccacctgt gtactgtact tcgtagctga agaagtgcac acagtgctgc tttcgtggaa    43800
agtgctgctg acgatggtat ggggtgccgc acccgtgata tgatgacgt ggttctacgc     43860 attcttctac tcaaccgtac agcgcacgtc acagaaacaa aggagtcgta ccttaacctt    43920
tgttagcgtg ctactcatct ccttcgtggc gctacaaact ccctacgtct ctctcatgat    43980
cttcaacagt tatgccacaa ccgcctggcc catgcagtgt gaacacctca cactgcgacg    44040
caccattggc acgctggcgc gtgtggtgcc ccacctacac tgcctcatta atcccatcct    44100
gtacgcgctg ctgggtcatg attttctgca acgcatgcgg cagtgtttcc gcggtcagtt    44160
gctggaccgc cgcgctttcc tgagatcgca gcagaatcag cgagctacag cggagacaaa    44220
tctagcggct ggcaacaatt cacaatcagt ggctacgtca ttagacacca atagcaaaaa    44280
ctacaatcag cacgccaaac gcagcgtgtc tttcaatttt cccagcggta cgtggaaagg    44340
cggccagaaa accgcgtcca acgacacatc cacaaaaatc ccccatcgac tctcacaatc    44400
gcatcataac ctcagcgggg tatgagcttt cctgttactt tattcagaaa gcaccagaac    44460
ccgtcgccat ttcccctcat atacggtaca cgtcccctg atctgtcatc acggtacaca     44520
gatttcgccc gactgcggac gccgacggcc aatcgcgtgg cgtaggagtg gcgcccggc     44580 ttcattataa cgccacgtcg gagcccctgc gcgccacaac gccgtccggc gcaacttctg    44640
tctcggcacg gtacgataaa acaacgtcc cccgtcgacg ttgttttctc cgagcggtga     44700
tcgttcccgt ccctctcctc cctccgcggc ccccacgggcg gcggcctgct cgcacggacc    44760
tatactatta ccgccccacc gccgtcgtcg tcatgaactt catcatcacc acccgagact    44820
tctccaacga cgattcagtc ctgcgagccg ccgagatgcg tgacaacgtg gcaggctcga    44880
tttccaaagc gtacaagggc acggtacgcg ccgaaggcaa gaagaagctg ctgctgaagc    44940
acttgcccgt gccgccggc ggctgctcgc gccgcaacag caacctcttc gttttctgca     45000
ccgagcgcga ctaccgcaag ttccaccagg gcatcgcaca gctcaagcgc gcgccggccg    45060
aactggaccc ccacgagatc cagcaagtca cggccagtat ccgctgccgc ctgcagccca    45120
gtctccgcga gccgcccacg ccggccgacg agctgcagac ggctgtgtcg cgcgtgtgcg    45180
cgctcttcaa ccagctggtt ttcacggccc agctgcgcca ctactgcgag caccaggaca    45240
aggtggtgag ctacgcgcgc gacgagctga ctaaacgctg cggcgaaaaa tcggcgctgg    45300
gcgtggaagt gcatcaactg gtagccctgc tgccacacga gcgccaccgc gaactgtgcc    45360
acgtcctcat cggcttgttg caccagacgc cgcacatgtg ggcgcgctcc atccgtctca    45420
tcggacacct gcgccactac ctgcagaaca gcttcctaca cctgttgatg aactcaggtt    45480
tggatatcgc acaagttttc gacggctgtt accacagcga ggcctaccgc atgctcttcc    45540
agatcggtca tacggactcg gtgtcggcgg ccctggaact ctcacacggc gcggcggccg    45600
```

```
ggccgcccga ggccgatgaa acaacgacg agggagagga ggacgacgac gagctccgtc    45660
acagcgaccc ggcgccgctt cacgagtcca agaagcccg caacgcccgt cgtcccgca     45720 cacgcgtgcc gcctcacgag caaaagcccg aagaaaacga ggaggaagaa gaggagctgt    45780
ttccctcctg caaggcaacc gcagcattcc tgcgggcaga accctccgtc tccaacgacg    45840
acggcaacgg cggcgaacgc tgcgacacgc tagcgaccgc cctgcggcat cgcgccgacg    45900
aagaagacgg acctctagcc agccagaccg ctgtgcgggt cgccgcgacc ccctcacctt    45960
cagtcacccc agcccttacc cccgtcacgt cccccataac cccgttgtgt atttaacgtc    46020
actggagaac aataaagcgt tgatttctca agttccgctc tggttttggt ttcgttttca    46080
aagggagccc catcatggcc caaggatcgc gagcccatc gggcccgcca ctgcccgttc     46140
tccccgtgga cgactggctc aactttcggg ttgatctatt tggggacgag caccggcgcc    46200
tgctgctcga aatgttgacc cagggctgct ccaactttgt ggggctgctc aactttggcg    46260
tgcccagccc cgtatacgcg ctggaggccc tggtggactt ccaggtgcgc aacgctttta    46320
tgaaggtaaa gcccgtggcc caggagatta tccgtatctg catactcgct aaccactacc    46380
gcaacagccg cgacgtgttg cgggacctgc gcacgcagct cgacgtgctg tactcggatc    46440
cgcttaagac gcggctgctt agagggctca tccggctctg ccgcgctgcg caaaccggcg    46500
tcaagcccga ggacatcagc gtgcacctag gcgccgacga tgtgacattc ggcgtgctaa    46560
aacgagcgct ggtccggctg caccgggtac gcgacgcgct ggggctgcgc gcgtctcccg    46620
aggccgaggc gcgctatccg cgcctcacca cctacaacct gctgttccac ccaccgccct    46680
tcaccacggt cgaggcggtg gatctgtgcg ccgagaacct gtccgacgta acacaacgtc    46740
gtaaccgacc gttgcgctgc ctcacctcca tcaaacgccc gggctcacgc accctggagg    46800
acgcgctaaa cgacatgtat ctgttgttga cgctgcgaca cttgcagctg cgacacgcgc    46860
tggagctaca aatgatgcag gactgggtgg tggaacgctg caaccggctt tgcgacgcgc    46920
tttacttttg ttacacgcaa gcccccgaga cgcggcagac tttcgtcacg ctggtgcgtg    46980
ggctggaact tgcgcggcaa cacagcagtc cggccttcca gccgatgctg tacaatctgt    47040
tgcagctact gacgcaactg cacgaggcca acgtgtacct ctgcccggga tatttacatt    47100
tcagcgcgta caagctgctg aaaaagatcc aatcggtctc ggacgcccgc gagcgcggcg    47160
agttcgggga cgaggacgaa gagcaggaga acgacggcga gccgcgcgag gcccagctcg    47220
atctcgaagc cgatcccacg gcgcgcgagg gcgagctctt tttcttctcc aagaacctgt    47280
acggcaacgg tgaggttttc cgcgtgccag aacagcccag ccgctacctg cgccgacgta    47340
tgttcgtgga acggcccgaa accctgcaga tcttttataa cttccacgaa ggcaagatca    47400
ccaccgagac gtatcacctc cagcgcatct atagcatgat gatcgagggc gcctctcggc    47460
agacgggcct gacacccaag cgcttcatgg aactcctcga cagagcgcct ctgggccagg    47520
agtcggaacc cgagatcaca gaacatcgcg atttatttgc cgatgttttt cgccgtcctg    47580
tgaccgacgc ggcttcttcg tcgtccgcgt cttcgtcgtc gtcctcagca tctccgaatt    47640
ctgtttcgct gccgtctgcc aggtcgtcat ccacacgaac caccacgccc gcgtccacgt    47700
acacctcggc cgggacttct tctaccacag gtctcttgct ctcttcttcc ttgtcggggt    47760
cgcacggcat tagctccgcg gacctggagc agccgccccg gcaacgacgc cgcatggtca    47820
gcgtgaccct ctttttcgcc tactcggtag cctacagcca ccaccgacgt caccgaaggc    47880
gacgcagccc gccacccgca ccccgagggc cggcccacac acgcttccag ggacccgaca    47940
gcatgccgag cactagctac ggcagcgacg tcgaagaccc gcgggacgat ctggccgaaa    48000
```

```
acctacggca tctctgaaag cggttttttcc tcttttttcta cgtgtctgtc tcaagatgag   48060
acgtcgatat caataaaaat accgtcgacg tggttttttt aacagtgtgg ttttctttat   48120
tgactagcga agtacacagt ttacgagtag aaaagacagg gaaaggttat ataaaatgct   48180
gtattatata caaaaacatg cacataaaca aacgggacca tcgtgctcat catcccctcc   48240
ttgatcagtt gttcatgtaa acgtgtggcg gggtgagggg cggcatgccg ttggcggcgc   48300
cgggaataat gtgccgtcga ccgacgtcgc acaccttgaa acgccgtcgg cgcacgcagc   48360
ggtcgcagga cgggatatcc cagaggaagc ccatgtaggt ctcggggtcc tcgtcgtgaa   48420
agcggtagga gagttcaaag tggtgcaacg agcccgtccg agctcgcagc ttctggcgaa   48480
caccctccac gtcatcggtg cacagcgaca gtgctgggct gtcacacagg gcctgaagct   48540
cctgcggcca caggtgcgtg gccaggggcg agtccgtcgt caccagtttg acgcagtgca   48600
tcaggttctc ggtgatggcg tcgtacaggc gactctcagc ctcctcgtgc gtcatcacgt   48660
ttcgaggcag cgacagctcg tcgtcgtcat cctcgtcaaa catgatcatg ggtcagggg   48720
tttttttggg atgttgacag gtgggtgtct tttccagacg cacgatggcc tcacgccggc   48780
cgctgaaacg gtggtttcgg tgtcccttct ttcccatgac gcaggtgaac ataaccacgt   48840
cctcggccaa acggtagacg gcgtccatgg cggggtcgta gccgtagacg acgccgaaag   48900
tgtccaccaa gacgtactgg cgtacgagga actctttgcg ttctggcacc tcgtggccca   48960
gcgcgcccaa caactggtgg taacaggtga tgcgcggcac ggtacggatc atgagctcca   49020
tggtctggat gctgccgccc gcgcggacga cgctgaagga tgtttccttg aacttcataa   49080
cctctgtgtt gtgggtccag aaggcgaaat gggtgtcggg acactcatcg aaagggtcgt   49140
cgatggtgta ggaagcgtag cctcgcttgg tcacctcggc cgacaggctc tccacgtcac   49200
cgcggtagag catgacggcg ttccagtagt cgtcgtactg caccatgggc cgctggtagt   49260
cgcgcatagt gtggaagtgg tcgcggtgac gaaagccgtt ccgcagaaag tccttcatgg   49320
tgggtgccag ctcgtagacg cagtcgcgca ggtcatcgta gcagtagatg ccgccgcgct   49380
gcccgatgag cacgatgagt tggtagcgca taaagcccgg accctcgacg aagccaaagg   49440
ggtgcaggta ctcctgacag cagacgtaag cacctggtag agaatagaaa aaatccacgc   49500
acgttgaaaa cacctggaaa gaacgtgccc gagcgaacgt cctctttcca ggtgtcttca   49560
acgacgtggg gcttaccttg cgaacagacg gtgcccatct tgcccacgaa gggccccagg   49620
gcgctgcgcg aacggagctg gatgaagcag cgttcgggcc aggccacgtg cagccgggtg   49680
ccgcattcct gctccagaaa gtcgttgaga ccgttaaagt ccccggctcg gatggcgatg   49740
cagccgtagg ccatcagcgt gtcccgtagg tcgtccatga cggactcctc taccttcgct   49800
cgccgacgct gcgcttctcc agccaccgct gcggtcgaca gactcctccg tccgccttcg   49860
gagaactacg gcgcggcggc acggcccttta tagacactat cagcgttgac gtcagacgat   49920
ccgatgaacg tcgttttttg tgctggaact ccctcgtcc cgacaaatgt agcggaaatc   49980
ttcaagcaaa tcgcgacgaa gtccgatgag gaggatgcaa aagaggctga gcaacgcgat   50040
gctgcccgcc gccacagtac atatgctcaa caacgcccag tgtcccaagg cgcgactttt   50100
ggctcggagg agagccgaac ggcggtttct ccacatgacg gacaacgtgg tccagtacgt   50160
ccatcctttg cattccggtg tccagacggg aagcgttgtc atgttatttc ccgtaactgt   50220
cacgttatgt tttgttttgt ttctcgtgag cttaacggtc ctcttgagaa atcgcgggca   50280
catgtcttgt agaaagatat aatcactttc cgcgtatttc gtcagtgttg acatcacggt   50340
```

```
ggtagtgttt tctgaagaag tagcgttgtc agtgacgttt gtttcttccc aacgtacgta    50400
tgattcgaac ggactcgtgt gcgctattgc ccgcaacacg tagctgtggc cggtgaagtt    50460
gagcgtcagt tgtcccacgg tcacgttcgt gtcattccta aaacatgcta cttctccgtg    50520
aacttccgtg acgtttatct cacgactctc gttcaagaca cgcaggggaa accagccttc    50580
caggtgatac tgaaaaccaa atttaagcat gacgctgtgc catttccgtc gtgattgatt    50640
aaacgttaca ttcaagggca gtctggcttc ggtcccgaga caggggccgt tgtagatttg    50700
cgtgtgattg cgtgtgcagt ttaggtggca gttcatgctc gtggtgttgg aagtgcgatt    50760
aacgtccgta ccgtggtacg tacatcggac cgaaacaccg tgtcccgtgc tccaaagcag    50820
cgtcaacaac agccacacag aaacctacgt ggagacgaca cgggactttt tattgacgga    50880
gactcacgtt tctaccctcc cctttcccgt aggtaaaaac ccacgtttat cacacacgtt    50940
gtttttacct gaaacccgcg cagcccgtgg acgcgacaaa aaaccgcggc actagaaaga    51000
aaatgaaaca agtatgttta ttaagcagca tgtggggcta ataggggga taactgaggt    51060 atagcaacta tgaaaaaata ctacaaaaaa aaaagctgaa catggtcatc tagcagcaaa    51120
gttctccttc tagaccacga ccaccatctg taccacgtcg ccctcccgg ccgtgtacac    51180 gacatccttc accacgaccg gcggcagcgg cggcgacgag acaactcgc tctcgacgga    51240 ggccgggacg acagaggacg gggggtggt ggcggcggag gacgaagggg tggcggcggc    51300
agcgggatct tcttccgaca cgggcaacgg caggctcggc ggcgcggaca gcacccgttg    51360
cgccggggcg tgagaaggct gagccccggt ggcctggatg tgggccaacg aattggctcg    51420
cagcgagtcg cgatccacga aggtcatagg aattttccct tcgcggatcc gccgctcaga    51480
ttccaggatg gcgcgcacgt agctgttcac cgacttggca aaagtgcgcg gccctccgt    51540 attcttgtcg cgacgcgctt ccagcacctg ctttcgtag tccagctggt ggaagaccat    51600
caccaggtcg tccatagtgt gcgcgtgctg acggacgtgg gagcgcacct ccaccgggaa    51660
caaagcgttc caatactcca gcacgatagc accgtgccag aactgcgcca tgctgggcgc    51720
caggaaaaac aggataccgg agtcgtaggc gaacacgtcc cacttgggcg tcatgaacaa    51780
caccagctga cgcgtgggcc gcaccgaagc ttcctcccag gcctcgatga ccccgaacat    51840
gatgagctcc tggtccaacg gggggcagtg tcgctccagc caactgatct tgctcaggtt    51900
catctgcaga aactcgtacg aagggtcgca gatgcacacg tagagacccg agtcgtgccg    51960
cagcctggct ccgcgcttca tcagtttcct caccgcgtag cgaagcgcca ccttgcccaa    52020
cgccgacgcc tggatcagtc cccccacgtc catctgcgtc tgtcgccact cggcctcgtc    52080
cagcaggctc atgatagcgg cagtgctatg cgtggtcgta gtcatccttt ctatccttct    52140
ctatgaatag cagcaatagc ggtaaagtcc cttcttatac tatcccggag tctgtggttt    52200
ttttgtttac ccctgcttac tggtgagact gctgggggcc gttgtgctgc agcatccgag    52260
ctcgttgccg ccgttgccac aggaaccggt gtctccgcag gcctttttg agggcttcgc    52320 aggcttctcg cgcaagtcct gagaggccct cggcgtcgat ggggttcacc tcgggcgtcc    52380
gagcctcgtt ttcttcttct tcatcctccc tttcctcctc cgtgtcctcc cgctctgtgt    52440
cctccgttac gctctcctcc ccggcctcgg ccaagagcgc ggccaccaag tccacggacc    52500
gctcggtctc cgagttctca ccgtcaatta cgccatgttg gcggcgtaac cggtgccgag    52560
aacgccgggt gagcgcacat gctttttct ttcttaacca aggcgggaga ggatcttcaa    52620
ggcgttttcg ctggatccag cggtagctaa agtaccaaaa ggccagcagg cccacgctac    52680
ctaacagatt cacgtagact ggagacataa ttaaagaaag aagtgaaacc cgcgtgtggg    52740
```

```
tctcacgtcg tcttgaaaca ccgtcttata tacatgaaga tgccggacat gacgcgccca   52800
agacacgtgg ggttttcccc ttaggcgacc cggtttctta agatgttttt catcttcgca   52860
cgcgatgtac tacatcaaag ggtcggctga ccgaccgcat tgacgcacag tttccgagta   52920
cgcgcgtctc ggagcacctg acggtgagcc acccaactca cgcggatagg ggacaacact   52980
gacgtgaggg gcgattcacg tcactgacgg gaataagacg ggtgagggat ttccacctt t   53040 ttcttaagtg tgactctctt tacggtaaat cgcacctgtg acctcttaac ccctcctccc   53100
tggtacccga taaccgtgaa aaacacacac cacacgtcac gacaccgatc gattttcttt   53160
attcttagtg tgatgatagg taagggcact cgtgaggatg tgcaattatc attatcaagc   53220 cttttttcaag gcgtagtgat gatcgttggg cagaaccccc aggctcctag cgatctggga   53280
atagaaggag gagaacgagc ccagggccag aatgcccaca gtgtacatgg cccaggtctc   53340
cagaccgaac gtggcgggtc gcagcttcag atggtaggcc acccgctccg agagttgtga   53400
atgctcgttc aggcaacagg actgcaggtg ggtgagccca aaagcgcttt cgtttacgcc   53460
gcgcacgtgc accgtctggg ccgggcaatc ctggtgttgc gcgcgaaagt ggtcctgaca   53520
ggaaattccg tctacgtggc ggcgcgtgtt gttacccact tcgatcaaca acgtgttatc   53580
ggcaggatga tgcgagaacg cgacgacggt gttgttggag gtctggcggc aacagtacac   53640
gtcgagcgtc atgagggcca tgtcgccttg gtggtacacg gcgtacgccc aaccctggaa   53700
cacgagcgga cataacggac cgtgagcgga cgtcacggcg gcggttgtta ccgtcgtctc   53760
ggcaggagaa cacaataaac tcctgatcct catacacagg agtccaaccg tcagaattaa   53820
agtccgcgga gccataaccg cgcaagtgaa gccgatacga gtgttgctga atttgttcat   53880
tctgccgact gttgctcacg agcgttcgga ggcggtgcca caggctgttg gccattaaaa   53940
agtcctggcc cgaatgacga caagacagag cccgaggcga agaaaaggc gcccgtcatg   54000 aagacgtagg caggggaatt cccatatttt tatggcttct tttaaaagtc tgtatccgac   54060
tccatccggc gcttttccca aaccgtggtc tcctcgtcgt ccgactcggt acccaggagg   54120
tggtaagtct tttgccgcac gtagaaagct ttcaacgtgg agcaaaagat gagaataaag   54180
accccgaaaa cgaaacaaac cacgccgatc atgccgatgc agacgttcat gtcgacgtag   54240
ccggcggtgc tgttggcggt gcggcaaaag agtgtcatgt cgtgcgtgca caaaaaacaa   54300
cacacaccac aggccaggtc gtagcgtagt tattattccg tagcagcaat gatggtacag   54360
tcaagcacat gctctatccc cgttaccccg atgatgcttg cgtccccgtt gttatattgg   54420
cactgtcccg gttaatcacc acggtgaaca ccacggccaa gaaaatgatc cctaatatag   54480
cgaccactaa gagagcaaaa gtccatttcc agccgttgtc aaagtacgcc cccgtggtgg   54540
gatgcatggt ggcgggcatt tccatcatgt ccatgtcgaa cgtgtgtcgc ggcgacggcg   54600
aactaaccag gcagtacggg ggtcgatagg gcggtgggct gcagtcgggt ggtggcggcg   54660
gtggcgtgga aaccgtcgtc gggcacagac ccatggcctg ctcgtaggtg gggggcgcgt   54720
cgtcgtgatc ccggtcgcgg agcatcggcg tgggctccat gtcggtggca gtgacggcga   54780
cggtggtaac tgtggtggag acggtaccga cggcgtccgc ggttcacctt cgagcaaaga   54840
gccccttctt tttgcgcaaa cgacggcaaa acagttctct gggacaaccg gtggcgcggt   54900
aagcgggtgc cacgctttca gggtgggtaa acagtcgcg ggcgaagcag tagttgttgc   54960
agaaccgcaa gaacccgacg cgaaagaagc ccaggagtcc gcgcgccaga aagtgcgcct   55020
gccgcgtctc gggatgcacg ccgaagacgg cgccgctctc gttcaccagt atggagatgt   55080
```

```
ccaggcgctg ctgcgactcc accggcacgg cccgcaccac aaatacctgc agcacgttca    55140
gcgagcacgt ctcttttaac cagttgccgt gggccggatc ctcgtaagtc tggctcccgt    55200
tcaagacgac cgtcgtcagc gcctcattac cgtctcgcca gctgaagatg gaaccctcgc    55260
gcttcatgca caggcgccac aaggccagca ggtcgcgcgc caacatgaac tcgcgaccca    55320
cgtcgccgcc ggtctcgaag cggacatagc ccagttcttc gcgcagcggc gcgtagttgc    55380
gcaggccctc ctgcacgaag ccgcggaaac cggaccgcga caccaggtac agcgattcca    55440
ccacgggcga gtagacgtag acgcgaccgc cttcgccgat gagtacgggt agcggtgggc    55500
ggccgatggc ttcgcaacga ctcacagtgc ccaccggcag caggaacttg tcgcagcaca    55560
ggaaggtctt ctccaaacct ttaatattga gatgtccaaa gtaaccaacg cgtaacaggt    55620
cgcagtaggt gaagaaccaa ccgttttggcc agctgagacg cagcaccgtg ccgctgacgc    55680
gacgaaccag cttctgcagg tccttgcgag cgtcggaggt gacagagcag cggaaggtct    55740
cgttaaccag ctcgacagcc agcgcgtcct ccagcgtgcg ttccttcatc tcgtcgttga    55800
tgctctgacg gcgccgccgg atttcgtcga acgggccgc ggaggcggcg accgacgcgg    55860
aggtcgtccg aacgccctct gtgacgctgc cgtccggcca gtcaagaaag ctaaggctgg    55920
cgctgcgccg cctaaagtgt ccgatccgcg cgggacgtcg ctgagggacg gtggctggtc    55980
tgctggggcg ggtacggccg cgggtgtccg cggacacgtt agttatacac ggaattgagt    56040
cacgtggcac gttgccagct gaaaccgccg tcgtctccgc cggcgttttc tccatcacgg    56100
gaccgcgccg tgcgcgcgtt cccaggcacg cggcccgcgc tctagccgca ctttttgcttc   56160
ttggtgttag ggacgaactc gaacgttaca gaatcctcgc tgtcgctctc ctctttcgcg    56220
tcgttgaagt aattgccgga gttgcgatcc aaaccgccgc ctcctcctcc tccgccgccg    56280
cccgatccac ctttggacgt caggtagctg gtgatcttgt gctgctcgta ttttctccttg   56340
gaggaaagac cgtggtcgtg atcaccgccg ccgccaccgc tgctcatttt ccgcgtaccg    56400
gaaccaccgc cgccaccgcg gtcgtgcttc ttgccgccac cgccgccacc tcctcccaga    56460
ccgccgagac ccatgggctc gttcatgaga tcgttatcca gacccgggcc gtcgtcatgc    56520
agaccgccgg cattggccag cgaagagagg ctgccgccac caccgccgcc gccacgcgac    56580
ttgccgctgt tcccgacgta attttttgtcg aagggatcgc cacgctggaa aggttcctcg   56640
gtgagaaaat tctccacggc gaacagaccg ttgcggctgg ccacgtacaa cagcgtgtcg    56700
tgctccgtaa ctatacgcaa cgtgcacggc agtttggtga cggcgcaatt gagcagcgtc    56760
tggtagaagt tcttcagctg cacgttgata cgcatgtttt tcacgccgtg gaaactgacg    56820
cggttattgg ctgtgaattc cagctcgctg ccgttggtca ggataaactt gatggccggt    56880
ggaccggcgt gcaccagaat ctgcacggtg cccgtagggc agggcgcttt tttaacgtta    56940
cgcttgacgc gggtatgcgg cccgatccac ttaagcaggt cggccaccac gccgaaatct    57000
agatccacgt gcacggccga attctcgctt tcgcgcacaa tgtcttggcc gtgcacgcag    57060
gccgagctga actccatatt gaaatcgggc gcgcacatgg agatcttggc cgacaggtcc    57120
gagatgtcct gcacgtagaa cttggtcagg tccttgctgg aagtcaggta catgaaatta    57180
cccagcagcg cgctggaatt gttaatggtc ttgggctgaa acgacttgtc agtgatgtag    57240
aggcatgagc tgttaaaagt gattttttgac acgcagtgac tgcgtaccgt ttgcaagata    57300
agcgacggcg tgggcaagaa ggtaaccgtg gtgttctcct tgagcgcacg gatcacagat    57360
cgcagctgct ggatagccgt cttgtacggc ttcagccgca gcgccagcgt cggcggctcc    57420
gagaggcgcg tcttgcgatc catcccggac agcgtgcaag tctcgactaa ggagcgggcg    57480
```

```
cgagcgagcg aaagttttat agagagcaca cacgacgacc gggaacgctg cgaagacgcc   57540
cggcgtctaa taatacagcc gcgccgagcc agcgggcccc cgactaagag gcacagtact   57600
tatatactcc gaccttaaag cgccagtggt accacttgag catcctggcc agaagcacgt   57660
cgggcgtcat ccccgagtca tagtagaaaa ccagggccac gcactggtcc acaaacacgc   57720
tcaggttcac ggccgccatt tccacgtcgt tttggatcgc cggtgccgcc tggaacagac   57780
actgcgtcgc cttgccctcc tcctggtgct gctccaacca cgcgtaattc accacgggca   57840
cgcgcagcgg cctccgcacc acggtgggga agtaacactc acggttgggc gggcacaatg   57900
accacaccgt ctcctcctcg aacacggtgc gcgcgaagc ccacactgac ggcgtcacgc    57960
cccacagatg cgccacctcg tcgtcgggac ccaccgccag aaactgacag ttgcgcaatc   58020
cgaactcgag catgtcggcg cgcagcgctt cccagcgcgc gctggcgatg gagagccgcg   58080
gcaaccgata caattcgaaa atgaatttgc cctcttgata gatggtgcgt tcgaaccact   58140
cgcagcgcgg caaacccgac ttgcacaaat cgacgctagc gcgcaccgcg gcaaagtaca   58200
tgtgctcaaa gatgcgctcg atcaagtccc aagaggcaaa gtacgtgaac cctaaccgca   58260
tgagcgccgt gtgcaagcca gccacgccga tgtgcagcgg acgcagtttt ccagcgcgc    58320 tctctaccca ccattcggac gccgacatta gcgcgtccaa gcgcgcgttg ccccaaacca   58380 ccgcctcgt caccaactcg cgcagcacgc tcaaatcaaa gtaacgtcgc gtgttcccca    58440
aaaccacgtc gggtagatgc agcttctgct cgtcgctacg cgcaaacacg cagcgagcca   58500
cgttcaccgt cagccgctgc accggcatgt cacactcgcc aaagtggcac gacgccatat   58560
cgggactcaa gcacggcggc aggcacacgc tgtcggccat aatcgagtac ttgactacgt   58620
gatggacaaa gaccaccgag gcacggccct tgagcgcgca cagcaacatc ttttttcagaa  58680 aatcgtccgt gttcacgacc accttggggc acgattgctc gcagcgcgaa tactctttct   58740
cgaaagccga ctcctgaccc aggtccgaga gccgccggga gacaggccgc ccaaacagcg   58800
agtagcgctg ctcacgcgca cggtagcgct tcattaacac gctaggcacg ttgaaagcgt   58860
agcaaacccc cgtcaactcc gacgtgcttt ctttgagaat aaagttaatc acgcggatag   58920
cggccacgtc ccacatgtcc acaaacacac gtaccacggg tcgatgcacc tccttctcgc   58980
gtatcaaatc gcagtatccc cccaggcaac gaatcacgct gttcacatcg gcgttaagtc   59040
gcgttacgtt caccgacaca gaaacgccgc aactcaaggt actcatccac ttgcacatgg   59100
ccgcccaact ggcgtcacgc gagaaagggt cggccgagat cagaaagtcg tactgcggca   59160
cgcgatcgaa acccacggta gacatggtga aggtggacag cgacagctgc ccatcgcgac   59220
agcgcttcaa caccgattcc aacacctcgc cctcgaaacg cgcatccaga tggaaacgat   59280
agatgcgcga gtgcctactg ttctcgatag cggccgtcaa cgccacggcg atgcgcaaaa   59340
acacgccgcc cgggctctcg tcctgtccgt gcagttggcg acacaccttα tccaaacaca   59400 aaatggccgt gtacaagccc cagcaaccgg ccaattccac aaaacgcgcc gtctcctcgg   59460
ccagcttggg tagatcctcc atgtgacgca gcacaaaacg gcgcaccgac tcatcgcaca   59520
gctccgaagc gtaacacagt ggcgtgcggc tttcacgcgc ccagttggct ttgaaataaa   59580
agcgacccaa cagcaggtcg caacgcgcg agtgacgaat cagacaggga ccgtggcgca    59640
taatgagctg aaatagcctg aaactgccca aaccggcact gtgccgcgac acggtgtcca   59700
tctcgcgcca cagcgcgttc ctgtcggacg gcagctcccg cgccggctcc tgtacgccgc   59760
aaaagcgaaa cttgccccag tagccgtgac aatgacactt tttgcccatc aacatgcgcg   59820
```

```
tagcttgtat cggcggcgat actttgcaga gcgaagcccc gaaatcgtcc tcctcctcga    59880
cactgtccag ctccatcctg gtcgcgccgg ccggattaaa ggtgctcaga ccgctactca    59940
cgcgtccacc gcgactgggc acggcgggac cgctgtcacg cgtcaacgac agcacagacg    60000
gcgtgccgtc gggagacggc gactcggggac gccaactgac gacgccgcca ccactcgtaa    60060
aacccgctac acatgctaca ccgctcgata cgttggtatt tccagcggac gcttccttgt    60120
cacccccggg cagcggcccc tcctcgagct cgctgtcatc tcccccgata gtatcagcgg    60180
cgacctctgc cgacgattcc tccgtctcgg tttccgcgct gcggcttgga atcctacctg    60240
gccggcaccg atgtgcgggc accgaggaca cccgctgttc ctcgtccgcg tcagccggat    60300
tcataagttt acgaggaaaa taacaaagaa atcaggtaga tttcaataaa gtgagtctag    60360
atggcgccga caactacggt ttataaagtc tgtgtgcgat gtgttttttt cttctgtgtc    60420
tcctccccgt atgctgtcag cgccgctcag acgaattctc gaaagtctcc caattcgacg    60480
ctaaagttgt ccaaacggac gacggacagt ttgagttctt tgtgtaccag gaacgaggtg    60540
tgaatgtcgt cagccaggca ccagcccagc ttttgtatga ccccggtaca cagagggatc    60600
tggcgcgggc gcgtgatgcg acggttgaca aagctacagc gctcgcgggc gaactttccg    60660
cgtgcaacgt cgaccaaggt ctgccagtgt gcgatgctgg aggtgagcac gtagatgccg    60720
ggacgtgttt cgggcccgtc atagtcatag acgatgatta aatacacgta ttgcagccgt    60780 cccgggtct cttcccacgt caggtacatg tctttcggta tcatcaacgc gaacacctcc    60840
gttttgagcg tgttgtaaag gtagccgcgc atgacgcagg tgagcaacga ggtgatgccc    60900
agcgagacgg tcttgacgca gcccagcgtc tcgaggcggc ggtgcagcag atgcgggccc    60960
aggtccagcc actgcagcgc ggcgcgcgcg gccgaggccg tgtacacgct ttcgagcagg    61020
cagcgcgtgc tggccgagac gttggaggcg cgaatgccta acaggtaaag gctaatgtag    61080
aggtgtcgcg gcgagtcgca acccgtctcc atgcggatga gcagcgcgcc cggctgcgcc    61140
tcgaactcta ccaggccctc gggcacgaag aaacgcgccg tgagcgcctg gtgatcggcg    61200
tggtagagat agcgaaccga tatagtattt acctcgcgtt tggctttgag cgccgtcact    61260
agttcattgt cctcgtcggc cgggtcgcgc ggccgtttgg ccaccgcgcg cgcgtccatg    61320
atggcgaggc gcacggtaga tttcaaaaag ttgatagagc agctgcgggc acgggccacg    61380
gacaaagcgg aggcgttaaa taccgtgagc caattggaga tcggcgcggt ggatgccag    61440 gacgtgaccg cgagcgccgt gcgcgccttc gtgggtgcgt tgccgagctc gggctaccac    61500
tttggcttcg tgcgtcagaa cgtggtctttt tacctcctaa gccacgccac ggtacagacg    61560
gcgcgcgacc cgctgtacgc cgccgagcag ttgcacgaac agctggaccg cttcctgcga    61620
caccagcacg acggcggcgg agacgaggac cggttgccgt tctaccacaa cggggccacg    61680
ctgacggctt tccagaagct gttgcagacc ctgcgcgaga tccagaccgt aatagccgaa    61740
cagagcggcg gcaccgcggc ggcggcggac ttgatcgcca gtaacaacgc gtcgaccgag    61800
cgccgcggca agaagggcgg ttcgagttcc gggggccagc agccgctggt ccgccgggtg    61860
atcacgcagc tggaaacggc tgccacggag gcgcggccct acgtcaattg tcgcgccgtg    61920
gccgaactcc tggacctgac ctaccagcgg ctcatctact gggcctgcac gctcatgccc    61980
tacgtgttgt ttcggcgcga caccgacacc gaactggaca cggtgcttct gatgcatttt    62040
ttttacacac actaccgttc ggttaacggc gatttggccg tggagtttca aaactacgtc    62100
aagaacagcg tgcggcacat gagctctttc gtcagttccg atatcgacgg cgaccagaag    62160
cccggtgccg aacacatgcg tgacgtcagc tacaagctgt tcgtgggtaa tctgcaagcg    62220
```

```
cgtgacgcca gcggcctcat gtttcccatc attagcacgc gcatctccac cgtgaacctt   62280
tacctgtcgc ccgaacgtat gtttttccac ccgggtctga tctcgcgtct gttgagtgag   62340
gaagtttcgc cgcgcgccaa cctagacgct tacgcgcgcg tgtgcgatcg cgtgctggaa   62400
gaccacttgc atacgccgcg acgcgtgcaa cggctactag atctgacgca gatggtaatg   62460
cgactggtgg aactgggttt caatcacgat acctgcgcgg cctacgcaca aatggcgctg   62520
atccagccgg ccagtcagaa gagctcgctc tttgtcagcg agattcgcga gaaactcata   62580
cagatcatct acaatttta cacgttttc atgtgcctct atgtgtacag ccccacgttc   62640
ctgttcgacc accggcggcg gttgattttg gagcagcatc gatccacgtt gatcggctcc   62700
aaggaggaac tacagcacgt ctggagcaac gtgacactga acgtcaatac gcactttgcg   62760
gttcagtaca cggaagaaga ctttgaggca catacgaagg gtgccacgga ggcggagcgc   62820
gagtacctgt atcgggacct gcacagcaag tggggcgtgc acctgtttac cttgcgtccg   62880
tctcgcggcg cggccggcgc ggcctcgcct ttgcctccgc ttgacggcgt cacacgctcc   62940
gacatcttac gcgaatgcgc gctcgttaat ctgaacgaag gccgcgtcaa ctacgcctcc   63000
ctgctagcct tcagccatca tcccgagttc cccagcatct tcgcgcagtt ggtggtggta   63060
actgagttct cggagatctt tggtatcccg cagggcctgt ttcaagccgt gggttcgccg   63120
cgtcttttcg cactcattca gctgtgccgt gtattgttgc ccgagcaggt gacgctgtac   63180
cagaacctgg tctccatcta caacctgacc accttcgtca agcacatcga cgccgcggtt   63240
tttaagacgg tacgcgattg cgtcttcgac atcgccacga ctctcgagca cctcagcggt   63300 gtaccccgtca cgcccaatgt ggacctgctg gccgagctca tggcgcgctc cgtagcgcat   63360
aacctgtaca ccaccgtcaa cccgctgatc gaggacgtga tgcgcagcag cgccggcagt   63420
ctgagaaact atctgcgaca tacgcgactc tgtttcggtc tggcgcgtgg ccgggcgcgc   63480
ctctcggagg acggcgtgac ggtgtacgtg gaggtacaag gtcaatacgg actacgcgta   63540
cccaccacgc gtttcgtaga acagttgcgc gagctggttc gccgcgatcg gctgttggcc   63600
gagaatctgc gcggcttgaa cgagcgcctg ctgagtgttc gcgtgcgcgt acgtcagatc   63660
agcagcgaca cagaggaagt aagccgacac gccaagggtc accgcacggt ggcccagatg   63720
agcaaggcgc tcaaaaagac ggcctccaaa atcaaagtgt tggaaacacg cgtgacattg   63780
gcgctcgagc aggcgcaacg ttccaatggc gccgtcgtta ccgcggtgca acgcgcgcta   63840
gccgtctttg acgtactaag tcgcgagaac ttggaacgcc gcggcgcaca gctctgtctg   63900
acggaagcga cgagcctact gcaccgacat cgcgcgctag cgccgatgac ctggcccgcg   63960
ggcacgggcg ttgcggcggc ggccgaagcg gatcgcgcct tacgcgagtt cttggaggcg   64020
ccctgggaat cggcgcccca accgccgcga ctccgcatga cgcccgacac cgatcacgaa   64080
gaatcaacgg caggcgcgac gtccgtaccg gaggtcctgg gtgcgcgcta cgaacccgca   64140
cacctggccg cgagcgacct attaaactgg tacatcgtcc ccgtaagcca ggcgcagcag   64200
gacatcttgt cttcgatcga cccgcccgcc ggctcgacat cggtgtccct gccgccggcc   64260
tcgccatgaa agtcacacag gccagctgcc accagggcga catcgctcgc tttggagcgc   64320
gagcgggcaa tcaatgcgtc tgcaacggca tcatgttcct acacgccttg cacctgggtg   64380
gaacgagcgc cgtcctgcag accgaggcgc tggacgccat catggaagag ggcgcgcgtc   64440
tggacgcgcg gctagagcgc gagttgcaaa agaagctgcc cgccggcggg cggctgccgg   64500
tctacagact gggcgacgaa gtgccgcgcc gcctggagtc gcggttcggc cggaccgtgc   64560
```

```
acgcgctctc gcggcccttc aacggcacca ccgagacgtg cgacctggac ggctacatgt    64620
gtccgggcat cttcgacttt ctgcggtacg cgcacgccaa accgcgtccc acctacgtac    64680
tcgtcaccgt caactcgttg gcgcgcgccg tggtcttcac cgaggaccac atgttggtct    64740
ttgatccgca cagctccgcg gaatgtcaca acgccgccgt gtatcactgc gagggtctcc    64800
atcaggtgct gatggtgctc acgggcttcg gcgtgcagct gtcgcccgct ttctactatg    64860
aggccctttt tctctacatg ctggatgtgg cgaccgtacc agaggctgag atcgccgcgc    64920
gtttggtctc cacctatcgc gaccgcgata tcgacctcac cggcgtcgtc cgagaaagcg    64980
cggacacggc agcgacaacg accaccgccg caccttcctt acctccgctg cccgaccccg    65040
tcgtcgaccc gggttgccct cctggcgtgg cgcccagcat tcccgtctac gatccctcgt    65100
cctcacccaa aaaaacaccc gagaaacgcc gcaaggacct cagcggtagc aaacacggag    65160
gcaaaaagaa accccgtcc acgacgtcca aaacactggc caccgcctcc tcctccccct    65220
cagcgatagc ggcggcctct tcttcgtccg cggtaccacc gtcctacagc tgcggcgaag    65280
gggccctgcc ggccctgggc cgctaccaac agctggtcga cgaggtagag caggagttga    65340
aggctctgac gctgccgccg ttgcctgcca acaccagcgc ctggacgttg cacgcggcgg    65400
gtaccgaaag cggcgctaac gcggcaacgg ccacggcgcc gtccttcgac gaagctttcc    65460
tcaccgatcg tctccagcag ctcatcatcc atgccgtcaa tcagcgctcg tgtctgcgtc    65520
gcccctgcgg tccgcaatcg gcggcgcagc aggcggtacg cgcctatctg ggcctatcca    65580
agaaactgga tgcctttctg ctcaactggc tgcaccacgg cctggatctg cagcgcatgc    65640
acgactacct gagccacaag accaccaaag gcacgtactc gacgctggat cgcgcactgc    65700
tggagaaaat gcaagtcgtc ttcgatccct acggacgtca gcacggcccg gcgctcatcg    65760
cctgggtgga ggagatgctg cgctacgtgg aaagcaagcc cactaacgaa ctgtctcaac    65820
gactgcaacg tttcgtaacc aagcgaccga tgcccgttag cgacagcttc gtctgcctgc    65880
gacccgtaga ctttcagcgt ctgacgcagg tcatcgaaca gcgacgtcgg gtgttgcaac    65940
gtcaacgcga ggaataccac ggcgtttacg agcacttggc cggcctcatc accagcatcg    66000
acattcacga cctagacgcc agcgatctga accgacgcga aattctgaaa gcgctgcagc    66060
cgttggacga caacgccaag caggaactct ttcgcctggg caacgccaaa atgctagagt    66120
tgcagatgga cctggaccgt ctgagcacgc agctgctgac gcgcgtgcac aatcacatcc    66180
ttaacggctt tttgccggta gaggacctga agcagatgga acgcgtcgtc gagcaggtac    66240
tgagactctt ttacgacctg cgcgacctga actgtgtga cggcagctac gaagagggat    66300
tcgtcgtcat acgcgaacaa ctgagctacc tcatgacggg cactgtgcgc gacaacgtac    66360
cgctactgca agagatcctg cagctgcgac acgcgtacca gcaagccacg cagcaaaacg    66420
agggtcgcct cacgcagatc cacgacctgc ttcatgtcat cgagacgctg gtgcgcgacc    66480
cgggcagccg cggctcggcg ctgacactgg ccttggtaca ggagcagcta gctcagctgg    66540
aagcgctagg cggcctgcag ctacccgaag tgcagcagcg cctacagaac gcgcaactcg    66600
cgctaagccg cctctacgaa gaggaagagg aaacgcagcg tttcctcgac ggactctcgt    66660
acgacgatcc gcccaacgaa cagaccatca agcgacaccc acaattacgc gagatgttac    66720
gtcgcgacga acagacgcgt ctgcgactca tcaacgccgt actgagcatg ttccacacat    66780
tagtgatgcg actggcgcgc gacgagtcgc cgcgaccgac gttttttgac gccgtcagtt    66840
tgttgttgca gcaactgcca cccgactcgc acgaacgtga ggatctgcgt gccgccaacg    66900
ccacgtacgc gcagatggtc aagaaactgg agcagatcga gaaagccggt accggcgcat    66960
```

```
ccgaaaaacg tttccaagcg ttacgggagt tggtttactt tttccgtaat catgaatatt    67020
tctttcaaca tatggtcgga cgactgggcg tcggacctca ggtaacggaa ctctacgagc    67080
gatatcaaca cgagatggaa gaacagcacc tggaacggct agaacgtgaa tggcaagaag    67140
aggccggcaa gctcacggta acttctgtgg aggacgtgca gcgtgtcttg cccgggcac     67200 cgagccatcg tgtcatgcat caaatgcaac aaacgttaac caccaagatg caagactttt    67260
tagacaagga gaaacgtaaa caggaagaac agcaacggca gctactggac ggctaccaaa    67320
aaaaggtgca gcaggatttg caacgcgtgg tggacgccgt taagggcgag atgctctcca    67380
ccatcccgca ccaaccactg gaggccacac tcgagctgct cttgggccta gatcaacgcg    67440
cccaaccgct actagacaag ttcaaccagg acttgctgtc ggcgctgcag cagctgagca    67500
aaaaactaga cgggcgaatc aacgagtgtc tgcacggcgt gctgacgggt gatgtagagc    67560
ggcgctgtca cccgcaccga gaagcggcta tgcaaaccca gcctcgctaa accacttgg    67620 accaaatttt gggtccgcaa cttctgatcc atgagacgca gcaggccctg caacacgccg    67680
tccatcaagc gcagttcatc gagaagtgtc aacagggcga tccaactaca gccatcacgg    67740
gcagcgagtt cgagggcgac tttgcacgct accgcagcag tcaacagaag atggaggaac    67800
aattacaaga gactagacaa cagatgaccg agactagcga gcggctagat cgctcgctgc    67860
gccaggatcc cgggagcagc tccgtcacgc gtgtacccga gaaacccttc aagggtcagg    67920
agctggcggg tcggatcacg cccccgcccg ccgacttcca gcagcccgtt ttcaaaacgc    67980
tgctagatca gcaggccgac gcggcccgga aagcgctcag cgacgaggcc gatctgctga    68040
atcagaaagt acagacgcag ttgcgacaac gcgacgagca gctgagcacg cgcagaacc     68100 tgtggactga tctggtcacg cgccacaaaa tgagcggcgg actggacgtg accacccccg    68160
acgccaaggc gctgatggaa aagccgctgg agacacttcg cgagctgttg ggcaaagcca    68220
cgcaacaact gccgtacctg tcggcggaac gcacagtgcg ctggatgctg gcctttctgg    68280
aggaagccct tgcgcaaatc accgcggacc ctacgcaccc gcatcacgga gcaggaccc     68340 actaccggaa cctgcaacag caagctgtcg agagcgccgt gacgctagcg catcaaatcg    68400
aacaaaacgc ggcctgtgaa aattttattg cacagcatca agaggcgact gccaacggcg    68460
cgtccacgcc gcgggtcgac atggtccagg cggtggaagc ggtctggcag cgactggaac    68520
ccggacgcgt agccggcggc gccgcgcgtc atcaaaaagt gcaggaactg ttgcagcgct    68580
tgggtcagac gctaggcgac ctagaactgc aggaaacgtt ggcgacggaa tactttgcgc    68640
tgttacacgg aatccagacc ttcagctacg ggctggactt cggtcgcag ttggaaaaga     68700 tccgcgatct gcggactcgt tttgcggaac tggccaagcg acgcggcacg cgtctctcca    68760
acgagggagt cctgcccaac ccccggaaac cgcaggcgac gacttcactg ggcgcctta    68820 cacgcgggtt gaacgcgctg gaacgacacg tccagctggg tcaccagtat ctgctcaaca    68880
agctcaacgc ctcatcgcta gtctataggc tggaagacat tcctagcgtg cttccggcaa    68940
cacacgagac cgaccccgcg ctgataatgc gcgaccgcct gcgtcgccta tgcttcgcgc    69000
gtcaccacga caccttcctt gaagtggtag acgtcttcgg catgcggcaa atcgtcacgc    69060
aggccggcga acccattcac ctggtcaccg attatggcaa cgtagccttt aagtacttgg    69120
cgctgcgaga cgatggtcgg cccctggcat ggcggcgccg ctgtagcggc ggaggactca    69180
agaacgtcgt caccacacgt tataaagcca tcacggtagc cgtggccgtc tgtcagacat    69240
tgcgcacttt ctggccacag atctcgcagt acgacctacg accctacctc acgcagcatc    69300
```

```
agagccacac gcaccccgcg gagactcaca cgttgcataa ccttaagctc ttttgttatc    69360
tggtgagcac cgcctggcac cagcgcatcg acacgcagca ggagctgacg gccgccgatc    69420
gcgtaggcag cggcgagggt ggtgacgtag gggaacagag accgggccgc ggtaccgtgc    69480
tgcgcctgag tctgcaagag ttttgtgtac tcatagcggc tctgtacccc gagtacatct    69540
acaccgtcct caaatacccg gtgcagatgt cactaccctc cctcacagct cacctacatc    69600
aggatgtgat acacgcggta gtcaataaca cacacaaaat gccccccgac cacctccccg    69660
aacaggtcaa ggccttctgt atcaccccca cccaatggcc cgccatgcag ctcaataaac    69720
tgttttggga aaataaactg gtacagcaac tgtgccaggt aggcccgcaa aaaagcacac    69780
cgcccttagg caagctatgg ctctacgcca tggccacgct ggtctttcca caagacatgc    69840
tgcagtgtct gtggctagaa ctgaaacccc agtacgccga gacatacgcc tcggtgtccg    69900
aattggtaca gacgttgttt cagattttca cgcaacaatg cgaaatggtg accgaggggt    69960
acacgcaacc gcagctcccc accggagagc cggtgcttca gatgatccgc gtgccacgtc    70020
aggacacaac caccacagac acaaacacga ccacggagcc gggacttta  gatgttttta    70080 ttcaaacaga aaccgcccta gactacgcgc tgggctcctg gcttttcggc atacccgtgt    70140
gtctcggcgt gcatgtagcc gacctgctga aaggccaacg tatactagta gcgcgccacc    70200
tcgaatacac gtcgcgagac cgcgacttcc tccgcatcca acgctcccgg gatctcaatc    70260
tcagtcaact gctccaggac acgtggaccg aaacgccgct ggagcactgc tggctacaag    70320
cccaaatcag acggctacgc gattacctgc gtttccccac ccgcttagag tttattcccc    70380
tagtcattta caacgcacag gaccacaccg tcgtacgcgt gctgcgaccg ccctccacgt    70440
tcgaacagga ccacagtcgg ctggtgttgg acgaggcctt ccccaccttc ccgctgtatg    70500
accaagatga taactcatcc gcggacaaca tcgctgcgtc tggcgccgct ccaacaccgc    70560
cggtaccttt caaccgcgtg ccagtcaata ttcagtttct gcgtgaaaac cgccaccca    70620 tcgcgcgagt tcagcagccg ccgcgccgac atcgtcatcg agcggccgcg gccgcagacg    70680
acgacggaca gatagatcac gtacaagacg atacatcaag gacagccgac tctgcattag    70740
tctctaccgc ctttggcggg tccgtctttc aagaaaaccg attgggagaa acaccactat    70800
gccgagatga acttgtggcc gtggcgcccg gcgccgccag caccagtttc gcctcgccgc    70860
ctatcacggt gcttacgcag aacgtcctca gtgtctaga aatactgcgg ctagtgcgat    70920
tggacctgcg acaactggcg caatccgtac aggacactat tcaacacatg cggtttctct    70980
atcttttgta accgacactg acagtagcgg gtaataaaaa caataggatt tttatcgttt    71040
ttttatgtta caaaacaacg tatcactttc acggtgattt attcttgcta ttccttttcc    71100
ccttgggctg tcagcgccgg gtgcgcgaca cggctaccat gcgcaacagg tccagcttaa    71160
aggcgcactt gtcattaaac aggctggaca tgcgcgtgta cttgctcagc atggtggcca    71220
acaccgggtg ggtggcctct gatatctcgg tcggcagctc caaaacgacg ttaacgacgt    71280
gacggtgttt ttcgtcccgc ttgttggcca ccgtgggtcc cggcgcggtg ttagacatgg    71340
ggcaggccgt gggggagga cgaagaggaa gccgctgcta aaccgccgcg cgcctgctgc    71400
acaatgtggc cgccgacgtg gcaggcggtc tgtttaacca gcgcgcagcc ccgacacagc    71460
ggggcgccgt cctcgctttc caaacagctg tcgcggtact cgcccgtctg acagcgcgcg    71520
cacagcaggc cgtgcccgtg cgaagtgagg cgcaggagac gcgggaccgt cacgtcgcgt    71580
accaccacag tggagtcgca ggtgcgtgcc gcgcagggca gaatgacgtc gaaagccagc    71640
cggtgatcgt acacggcaca agccgcgttg aggcccagca cggctttcca gcccacgcgt    71700
```

```
acgcagcgct gtccaaagag cgtctcggag acgagctcgt agacgcgctg ccgcaccacc    71760
cgctgactgc cgcagagcga gcagtgcacg agctcggcgt gcgtgttgaa gatgacgctc    71820
ttttcttgac ggtcccgata atagaacatc gagttgagcg gaaagttttg ctggcagtgt    71880
agcttttcct tacccaggtt gaggcagtgt ccgcactgcc gacagaccac ggccaccagc    71940
gagcgcgcgt ccagatggcg ctcgcacttg agtcgacaca gacaccagag cggcaggtcg    72000
atgacgctgc cgatgaggcc gccgcgcagc gcggcgctga gtgcaaagag gacgatcttg    72060
gtgggctcta cgtgacgcgc ctgctgtccg gcgcccgcgt gtcctaccgc cgcagctgcc    72120
gccgtcgagc ctcctccgcg cgtctcgtcg tgcagaccca gtgcccgcaa cggcaccagg    72180
tatcgcggac acgtgtcgca aaacgtctgc accgcttgtc gggccagtac gtagagcggg    72240
tttccgcagg gtaccttccc ggcgtaccgg cgcaaggctg cgatgaggcc ccgcaactgc    72300
ggcgaccgcg gctgccgttg gtgacaccac tggttacggt ggtatacggc caaatcagcg    72360
cgggcgtcga agcgcttggc gcgtagtaat gctaggcacg gcgagctggt ggggtgaagc    72420
acgggcagcc gaaggtccac cccgaaaagg aaacggtgaa ggtcacctag cagcgaggcg    72480
gtgacaccgt ccaacaacgc gtgcagccgc tcgggcgggt agagccgcag acggcgcagc    72540
aggtagtcgg tgtcgtagcg ttcgaaacgc agaaaggcca tcgtgcggac ggccacggtg    72600
tgcagacagt ccatgctgta gacgtaagcg agaaacacaa agtagggctt ggtcataacc    72660
atacgctgaa agagcgccgt caccgcctcc cgctcggctt gccgacacac cagccattcg    72720
cgcaggaagc gttggtagag acggtcgccc agctcgcgat tcagaaagcg cttatccgtc    72780
acgaagagat gaaggacgca agaacgtggc acgtgatgca ccagctgctg ctggaggacc    72840
gccgacgtct cgccgcaaa ctgcgccggt ggctgcgacg tttctaccgc cgcttcctcc    72900
ggctgcagcg caccgcggcc gatcaccagc tgcacatgga aatggtcctc gtgaacgcag    72960
aggggcgcga agagacggcg cagagcctgg tggaactcat cagtcgcggt gtgcggagcg    73020
tgtcggagac gacgactggc catgaccgcg ccacagcaga gccagcacca gcagaagagc    73080
cagcaccagc gggcccagag tcgcaaagcg cgcgggcagc cacggcccag actgcggtcg    73140
cgatggcccg gagcgcgctc gccaccacga tgacggtgcc caacgataac cagtccgctc    73200
caaggacggc gcgcacggcg gagacggcgg atgacggtga tgggtcgaca cccctcgccg    73260
acgactcacg tgctcctcca gaggccgacg cgcggaccct ccgacgtcct ggcccgccgc    73320
tgccgctgcc gccttccctt ctcccgccag agccagcaac tcctcctcct cttcatcagc    73380
gtctccctcg cttgcgcatc cgcatcgtcc catacaggcc tcacaacgac acagccgcca    73440
cgaccccgcc gccatgggtg gcggcggcgg ccgaggcccg gcagcggcgc cgccagcggc    73500
gaccatggtg ggagagcaac tcggatgacg aggaggagga gggggagatg cggtccgaga    73560
ggaccgcttt cccgccgttc gcgtaagcgc ggccgacatg cgggcgcgcc acagggacgg    73620
accgctgccg ctgtgactgc ttacggtgac gtggttccgg accgccaacg acgtcgacgc    73680
ggctttcttg gcgtacagct cgcgcagcag attctcgtac tcgccctcgt tttcgggtcc    73740
gaaggcgatg agctcgatgt tgaagaccga cgccgaattg gatttgcgca ccacgcactt    73800
cgtcagcact ccgtaggccg agggcttgat ctcctcgatg tccttgagcg tgacgatgag    73860
cgactcgttc accttaagca cattgaactc acctacgtgg cgcgccggcg aaacgagctt    73920
gacgggcgct cgtacaaaac agcagaggga gacggcgcag ccagtgtttt taaagataaa    73980
acaaggcacg tggtctgtgc ggctctccca gtagctgagt agatactcga cacaatagac    74040
```

| | |
|---|---|
| cgtgtctgtc ttgagcatgg cgtcgcacac cgagtaattg gggttttttac agatgaggcc | 74100 |
| ggcatcggtg acgcgcagct cgctgggacc caacttgagg atacgccgcg tggcctgcac | 74160 |
| cagatcctga tggagaacct tgttcatctc catcgcaccg acgccaccgc cgatttattt | 74220 |
| acccggcgcc gactcgtctt ttccctccag gattccgtta atgtccatga gcttgctgac | 74280 |
| gatcgccgtt aatagttgcg tcttctcacg gaggatctct ccgtgactgc aggtcgcgca | 74340 |
| gtcgccgtgc acgtacttga ggaaggcggc gtacttctga cccgcgttca cgaaatttaa | 74400 |
| gcgcgcgtcc agagagggca gcaacagatc gtagacgcgc ggcagcatcg gctcgaactg | 74460 |
| taatagcaga tcgtcgtcaa gatcgggtag cgcgtgtccg tcttcaccgt cctcgtcgtc | 74520 |
| accacctccc ccctcgagcc caccgctcgt accagccgcg ggctccgcgt cctcgtcgat | 74580 |
| caccagcggt cgcgtcggca ccggagaatc cacgtcatcc tgcacgtcgt tttcctcctc | 74640 |
| tccgtcgtca tcgtccagaa acggcacccg ctgcttagcc caggattccg gttttagaag | 74700 |
| ctccacatcg aagacgagag tggcatgtgg tgggatgatg cctgggtgcc cagtggcacc | 74760 |
| ataggcataa tctggagata tagtcagttt ggctctctga cccacactca tctgggcaac | 74820 |
| cccttcttcc cagcctcgga tcacctcctg cttgcctagc ataaacttaa agggcttgtt | 74880 |
| tctgtcccgg gaggaatcga cttttctttcc atcttcaagc atcccggtgt agtgcaccac | 74940 |
| acaggtctgg ccgcgcttgg ggaaggtgcg cccgtctcct ggggagatgg tttccacctg | 75000 |
| cactcccatt cttttttccg cgtcctcaat cagcggcgcc gatcgccatg aatccgagta | 75060 |
| cccacgtgag cagtaacggc ccaacgactc cccctcacgg gccccacacc acgtttcttc | 75120 |
| ccccgaccag cccggccccg tccaccagct ccgtcgccgc cgctaccttg tgcagtccgc | 75180 |
| aacgacaggc cgtttcgcgt tacagcggct ggagcaccga gtacacccag tggcactcgg | 75240 |
| acttgacaac tgagctgcta tggcacgcgc acccgcgtca agtacctatg gacgaagcgc | 75300 |
| tggccgccgc ggcggccgcc tcataccagg taaatcctca acaccccgcc aaccgttacc | 75360 |
| gtcattacga attccagacg ctcagcctcg gcacctcgga ggtagacgaa ctgctcaact | 75420 |
| gttgtgcgga agaaaccacg tgcggcggca cgcaatccac cgtactcacc aatgcgacca | 75480 |
| acaccactag ctgcggcgga gccgtcgccg gcagtagcaa cgtaggaccc gccggcgctt | 75540 |
| cggccgcctg cgacctagat gcagaactgg ccggcctcga aacctcggcg gccgactttg | 75600 |
| aacaactgcg gcgactgtgc gcgccgctgg ccatcgacac gcgctgtaac ctatgcgcca | 75660 |
| tcatcagcat ctgcctcaaa caggactgcg accagagctg gctcctcgag tacagcttgc | 75720 |
| tgtgcttcaa atgcagttac gcgccccgtg cggcgctcag cacgctcatc atcatgtccg | 75780 |
| agtttacgca tctgctgcag cagcactttt ccgatctgcg catcgacgac ctgttccgac | 75840 |
| accacgttct cacggtcttc gatttccacc tgcactttttt catcaatcgt tgctttgaaa | 75900 |
| aacaagtggg cgacgcggtt gataacgaga atgtcaccct gaaccatctg gccgtggtgc | 75960 |
| gggccatggt catgggtgaa gacacggtgc cttacaacaa gcctcggcgc cacccgcaac | 76020 |
| agaagcaaaa aaacaaccct tatcacgtcg aagtgccgca agaactgatc gacaactttc | 76080 |
| tagaacacag ctcacctagc cgcgaccgct tcgtgcagct gctttttctat atgtgggccg | 76140 |
| gcaccggcgt catgagcacc acgccactca cggaactcac gcacactaag ttcgcgcgac | 76200 |
| tagacgcgtt atccacggcc tcggaaagag aagacgcaag gatgatgata gaagaagagg | 76260 |
| aggatgaaga aggaggagaa aaaggaggag acgatccggg ccgtcacaac ggcggtggca | 76320 |
| ccagcggggg gttcagcgag agcacgctaa aaaaaaacgt gggtcccatt tacctatgtc | 76380 |
| ccgtacccgc ttttttttacc aagaaccaaa ccagtaccgt gtgtctgctg tgcgaactca | 76440 |

```
tggcctgctc ctattacgat aacgtcgtcc tgcgcgagct gtaccgccgc gtcgtctcgt    76500
attgtcagaa caatgtgaag atggtggacc gcattcagct ggtattggcc gatctgttgc    76560
gcgaatgcac gtcgccgctc ggcgcggcac acgaggacgt ggcgcgctgt ggactcgaag    76620
cacccacctc gcccggaggc gactcggact accacgcct  gagcggcgtc gacggcgcac    76680
tggcgcgacc cgacccggta ttttgccacg tcctgcgtca ggcaggcgtc acgggcatct    76740
acaagcactt tttctgcgac ccgcagtgcg ccggcaacat ccgcgtcacc aacgaggccg    76800
tgctcttcgg acgcctgcac ccccaccacg tccaggaggt gaaactggcc atctgtcacg    76860
acaattacta taagtcga  cttccgcgac gtgtgtggct ctgcatcaca ctcttcaagg    76920
cctttcagat tacaaaacgc acctacaaag gcaaagtgca cctggcggac tttatgcgcg    76980
atttcacgca gctgttggag agttgcgaca tcaagctggt ggaccccacg tacgtgatag    77040
acaagtatgt ctagcgtgag cggcgtgcgc acgccgcgcg aacgacgctc ggccttgcgc    77100
tccctgctcc gcaagcgccg ccaacgcgag ctggccagca aagtggcgtc gacggtgaac    77160
ggcgctacgt cggccaacaa ccacggcgaa ccgccgtcgc cggccgacgc gcgcccgcgc    77220
ctcacgctgc acgacctgca cgacatcttc cgcgagcacc ccgaactgga gctcaagtac    77280
cttaacatga tgaagatggc catcacgggc aaagagtcca tctgcttacc cttcaatttc    77340
cactcgcacc ggcagcacac ctgcctcgac atctcgccgt acggcaacga gcaggtctcg    77400
cgcatcgcct gcacctcgtg cgaggacaac cgcatcctgc ccaccgcctc cgacgccatg    77460
gtggccttca tcaatcagac gtccaacatc atgaaaaata gaaacttta ttacgggttc    77520
tgtaagagca gcgagctact caagctctcc accaaccagc cgcccatctt ccaaatttat    77580
tacctgctgc acgccgccaa ccacgacatc gtgccctta tgcacgccga ggacggccgg    77640
ttgcacatgc acgtcatctt cgaaaacccc gacgtgcaca tccctgcga  ctgcatcacg    77700
cagatgctca cggcggcgcg cgaagactac agcgtcacgc tcaacatcgt gcgcgaccac    77760
gtcgttatca gcgtgctgtg tcacgccgtc tcggccagca gcgtcaagat cgacgtgact    77820
attttgcaac gcaagattga cgagatggac attcccaacg acgtgagcga gtcctttgag    77880
cgctacaaag agctcattca ggagctgtgt cagtccagcg gcaacaacct atacgaggag    77940
gccacgtcgt cctacgcgat acggtctccc ttaaccgcgt cgccgttgca cgtagtttcc    78000
accaacggct gcggcccctc ctcctcgtcc cagtccacgc cgcctcatct ccacccgccg    78060
tcgcaggcga cgcagcccca ccactactct caccaccagt ctcagtctca gcagcatcat    78120
caccgtcccc agtcaccacc gccgccgctg tttctcaaca gcattcgtgc gccttgacac    78180
tgtacggcag aaaagccggc tccaagtgca agcgccgcgg cagcaccatg tgcaaaaact    78240
tgtccttgcg cgcggtttcg ccgccgggaa agacgggcga cagcacgtta gttacagcct    78300
tgagaacctg ctcaaagtac ttgtcggcgt gaatgggcac gccgtgctcg cgcacgtagc    78360
tcggatcttc ggctacctcg tagttgcaca cggccgacgg tggtttccgc gccctcttct    78420
ttgccggctc tcctcctctc ctgttgctct cctctacccc gccgccgtca gcgtcgtcgt    78480
ccgtgccatc aatcgcgtcc gaccgggaaa ccacgccggc ggttacagaa tcaccgttgt    78540
cggaggaacc ctgcggcgcc gtccggacac cgggcgccgt cagaacgtaa aagacccgat    78600
ccccgaccga gggtagctcc tcagaacggg ccgccaatcg cttaatgacg gcaatgtgcg    78660
gcaggttaga ttgacggtac agcgagatgt ccttagagag caccgacgaa agcaccaggt    78720
cctcgacacg cacacggtgc aggtacagat cgtcgcgggc ctgcaccaag cggcgtaaga    78780
```

```
tacgccagaa accgcgtggc acgccgtact tcttgacttc atcgagtgag aggcgcgaca   78840
ggcgcacggc tgcttccgag acctcgcgat cctcaaagag cagcgagagg acgtcacgcg   78900
tgacgcccct gacgaactcg caggccgtct tgcgcaccag atccacgccc ttcatgctca   78960
gacccgaggc gccctccact ttgccgatgt aacgtttctt gcagatcatc ataagagaga   79020
cgaagacctt ttcaaactcc agcttgacgg gctccacaaa aagacaggcc gtcacgtagt   79080
gcgccaggct gggcccacgc gccaccagag cctgcggcgt caggccacga aagcggacaa   79140
acacgctgtc cgtgtccccg tagatgaccc gcgcctccac ccgccgttcg ttcgagcccc   79200
ctgacgatgt ttcgagcccc tccggtaacg cgctgctctc ctccgaatcc ccctcccgcg   79260
ttcccactac atagtcttcc tgattaaaaa aattgtgcaa aaaacacggc tctgaaaagt   79320
tgtctttgat gaaccgcgcc gtgcgctcta gcatgtcgcg accgatgcgc gtgatgctgg   79380
cggcgatggg cagacacggc atcataccgt tgaccacgcc ggtaaaaccg tagaaagcgt   79440
tgcacgttac tttgagcgcc atctgttcct tgtcgagcag catacggcgc acagggtctt   79500
gacactcgcg catgcattcg cgcacggcac gccgctgcga aacccacttg ttgagcagtt   79560
ccgagagcac cgagacgcgc accgaagcac gcacaaagcg gtgggtcacg ccgttctcta   79620
gcgtgacgct gtatacgtcg gcggggtcca cagggtactc gccacccggc accagcaggg   79680
tggagtagca gaggttgtgg gccatgatga tggaagggta gaggctggca aagtcgaaca   79740
cggccacggg gtcgttgtag taacccacct cgggctcaaa caccgtggcg ccctggtacg   79800
aaaccgccgc agtaccgccg gcgccgtgat tgtcgttgga aacgccgacg ccgccactac   79860
tgccggagcg gacgctgaaa acgccgacgc tgctactact gttactgccg gagccgggtg   79920
aaacgccgtc ctgactggac ggcgcagatt gcaagggcgg cgacatctga aacatagccg   79980
ccacagaacc cgcgtcgccg ggcacagcgg cggtagagat gatagcagcg ttaggtgaca   80040
cagcaacgct attcgtttcg ggcaccgtcg tacctttgct gtagtggttg ggcaggataa   80100
aatcgcggca ggcgcactcg tccagcagcg aggtgtagat acggatctgc tgtccgtcaa   80160
agatgacacg ccgcaacgga atttttagcca gccgcgcgat ggccccggcc tcgtagtgaa   80220
aattaatggt gttgaacaga tcgcgcacca atacggcgtc ctgcagacag taacggccta   80280
cctgggcgcg gccctcggca ttagccacga aacaacgcgg gatgtccttg taagacaggt   80340
catccttgcg ttgccgcagg taaagctcgg ccatagtgtt gagcttatag ttgggcgagt   80400
tagtcttggc catgcataca gggtacatgt cgataaccac cgaacccgca atatacacct   80460
tggtggcggc cgtgctggcc ggattgttgt gagaagccga gggaaaagcg gcggcgtact   80520
gccgcttaaa acccacggcg gggctgtgta aaagaaacg gccgccctgc gccgtaggca   80580
acttgcagaa gcgctgcgag tccacccttat acaggtactc gagacgcgtg aggatgtact   80640
tcaagtcaaa agagttgatg ttgtaaccgg tcacaaaggc cggcgcgtac cgttgaaaga   80700
aaagcataaa gcccagcagc agctcgtatt cggaagggaa ctcgtagacg tccacgtctg   80760
ggcccacctg cccgcaggtg ccgatcgtaa agagatgaag acccgagtgc ccaaagatca   80820
cacccctccga agtgcagccc cgaccatcgt tcccgtttgg gatcccctga tccacggcgg   80880
tgtttccccc cgtctcgtag cacacgcacg agatctgaat gacaatgtca tcggacttct   80940
cggcgcaggg aaaaccaccc tcgccgctca tgcactcgat atcgaaggac aggcatcgat   81000
agcgcggcca cgagctgtcg tcgggcacag ccaccaggtc agagacatcg cagtctacct   81060
cgatatcaca agtcgacgcg cgaccctgct gccgccagtc gtaacgattc acggagcacc   81120
agccgaacgt ggtgatccgc cgatcgatga ccaaacgcgt cagcggatcc acacggacct   81180
```

```
cgtacacggg aaaaccctgc tccagcagat actcgccgat ttttctggcc atggtccagt    81240
tgctgataga cacacactgc aaatcgggca cgggtcgcgt cccgtaccca tagatggagg    81300
tcttggtggc cggcgtgaca gacacggcgt atggcgtccg cggttcgggc actagttcgc    81360
ccacgctggc aatgacctca cgcagcctat cggtgtcgct gtactcacag taaaagtagc    81420
tgcgctgccc gaaaacgttg acgcagatac tgtagccgtg ttctgtggcc ccgaagaaac    81480
gcaacacgtt ccccgaaggc accagatgct gacgatagcg cggcgacacg ttttcgggcg    81540
agtcgaagaa gagcacggcg tccgtctgat cgtaggtgtg aaaacgaata ggtcccacca    81600
cgcgacccac cagggtctcg cgccaaggac acggccaaac catgtcatga ctcaacaaat    81660
gtttaatctc tcgatagaac atgagaggca gccgtcccgt cttatgcttg atcaaccccg    81720
tctgaccgtc gaacatgaca cctcgcggca cgatctgcaa aaactgtttc tgtggcggcc    81780
gcttgcccga gccctgcgcg gagccgggct gcgaacgctg acgccggcca cccgcgaccg    81840
caccgccggt cacgccgccg ctcagatacg ggttgaaaaa catagcggac cgtgagaggc    81900
tgacagctta cgaagcaaaa tcacaaagaa aatacacatg cagcacctag atatccagtt    81960
taaccccgta tatcacaagt ctctgtgtca atatttttg tctagttttt ttttcctcct    82020
ggttcagacg ttctcttctt cgtcggagtc tttcaagtgt ctgtagccgt ttttgcgatg    82080
tcgcagccgg tctagcaggt taggcttctg tcccttgtcc tgcgtgccag tctgtccgtc    82140
caaagaatct gtaccgttct gctgcgctcg ctgctctgcg tccagacggg ccagggccag    82200
aagcatctgg taagcctgct cgttggtgta aggcggagcc gccgtggatg catcagacga    82260
cggtggtccc ggtcctttgc gaccagaatt ataaacactt tcctcgtagg aaggcggagc    82320
ctgtaacgac gtgtctttgg tgctgcccga cgtcacggtg gtcccgtcgg cggacaccag    82380
atagggaaag aggttctgca gcggctgcgt gcacagacgc cgctgtcgag tatagatcaa    82440
ataagtgata atgactacgg ctatggccac gaggatgatg gtgaaggctc cgaagggggtt    82500
tttgaggaag gtggcaacgc cttcgaccac ggaggccacc gcgccaccca cggccccaat    82560
ggctacgcca acggcctttc ccgcggcgcc caggccgctc atgaggtcgt ccagacccett    82620
gaggtagggc ggtagcgggt cgactacctt gtcctccacg tactttaccc gctgcttgta    82680
cgagttgaat tcgcgcatga tctcttcgag gtcaaaaacg ttgctggaac gcagctcttt    82740
ctgcgagtaa agttccagta ccctgaagtc ggtatttttcc agcgggtcga tatccagggc    82800
gatcatgctg tcgacggtgg agatactgct gaggtcaatc atgcgtttga agaggtagtc    82860
cacgtactcg taggccgagt tcccggcgat gaagatcttg aggctgggaa gctgacattc    82920
ctcagtgcgg tggttgccca acaggatttc gttgtcctcg cccagttgac cgtactgcac    82980
gtacgagctg ttggcgaaat taagatgac cacgggtcgt gagtagcagc gtcctggcga    83040
ttccttcacg ttcatatcac gcagcacctt gacgctggtt tggttgatgg tcacgcagct    83100
ggccaggccc aagacatcac ccatgaaacg cgcggcaatc ggtttgttgt aaatggccga    83160
gagaatggct gacgggttga tcttgctgag ttccttgaag acctctaggg tgcgccgttg    83220
atccacacac caggcttctg cgatttgcgc cagcgcccgg ttgatgtaac cgcgcaacgt    83280
gtcataggtg aactgcagct gggcgtagac cagattgtgc accgattcca tgctggacaa    83340
atgagttgta ttattgtcac tcgtacttct tctggtccta tgagtgatat tcagactgga    83400
tcgattggcc aaacgttcca attccaccaa agatttttgc ttgatgcctt gccagaacac    83460
caccagaccg ccgctggttt cgaagacgga cacgtttccg tatttttcat atgtttgatt    83520
```

```
gtatgaagta ttgaaaatct gctgtaactt atttatagcc tcatcacgta cgcagtccag   83580
cgcggagtcg gacatgttca cttcttgttt cttagacaga aaagttgcag tcattttggc   83640
agaagaaaag tggtacgagt cttcggcttc ggaacggata gtacgttccg aggcttccca   83700
gaaggtgagc tggcaggtga cattcttctc gtcctgtata tcccaagaga tcaccgagtc   83760
ggcacgttcg agaaaagcca ccaacctatg ggtttctggc gcagcgttgg gtcttccaaa   83820 gtcgaaacg atggtgtagt tcgggaaaat gaaaaacttg tcgcgtttt ctccaaagta    83880 gctggcattg cgattggttc cgttgtagaa aggagaaatg taaaccacat cacccgtgga   83940
agttgcaaaa aaatgataag gatacttgga gcgcgcagta gtgatggtca gcatacagtt   84000
cagattacag gtctcacgat agagccaggt gctgccgcgg ctgtgccact gatccttgac   84060
cgtcacgtaa cgggtactgt gggtgttgga ataatcgtcg ggaattaatt gcatggtttt   84120
gttttcataa ctgtccctat gatatgccac gaaaaccgtg cctcctataa cgcggctgta   84180
ggaactgtag cattgagcaa acttgttgat gtgatgaatc tcccacatag gaggcgccac   84240
gtattccgta ttgctgccca gcagataagt ggtgtagatg taagcgtagc tacgacgaaa   84300
cgtcaaaacc ttttggtaga cccgtacctt aaaggtgtgc gccacgatgt tgcgcttgta   84360
gaccaccatg atgccctcat ccaagtcttc attgataggc ttcatcgagg tgcagatgat   84420
attacgttca aagcgaataa gatccgtacc ctgggccata aacacacgc gatagggta    84480 cttggtagtg ttgactccca ccacatctcc gtacttgagg gtagtgttgt agatagtctc   84540
gttggctcta tgactgacgg cttcagaaga cgttacgtgt tgagaataga ctgaccgggt   84600
ttgagcagac gtcgtacgag aagtatggct tccattgtga gtagaagaag ttgcatggga   84660
agtactagaa gaggaaaccg cagcacccag acagacgata cacaggttaa cgcagactac   84720
caggcaccag atcctggatt ccatgttcgt cgcgggccaa atccagcagc gatgaggcgc   84780
gtcgtggtct cttgcgtgtc gcgcggaccc tccgggaaac acccgcagtc gaggaggagg   84840
gatacggact tggcagccaa ggtcggtccg gctccctgaa gacacccgag acggccgcg    84900 cggccgtcag ggtggagggc ttggccacgg gagctgttgg cacgtcgcca ctctcatccg   84960
gtctggacag atgcctgtag aggaggagat atagatcttt ggacttataa agacttcctt   85020
cgtgacgaag cagcagcggc cactctttgt tatacgtgag aatcacatct ctgtccgggt   85080
gcagttcgtc gcgcaggcac gcgatcgaga gttgtttccc gaaagtttca ttatatagtg   85140
cgacggagag cacgagctcc cgcacgtgca tccacatctc cttctgcagc acgtttaggt   85200
cctgacagtc cgaaaaattg aaaaaaccca tatacttcac caccatccac tcactgggat   85260
acacggtacc ttccgcgcat ttgaccaaat cgtccttgac gtggggtagt acgcccgcgt   85320
tgtcgcaggc ataggccatg tccacattgt gagagagggg ataacgatcg gtgcagtggg   85380
tgaagagggg cccgttacac aactcgtaga tctgctgacc cagtagcggg agggattcca   85440
caggcagact cttgtggatc aggttattga ccacatacag gtgctcatcg taggtgaact   85500
gatcacccac gtccaccacg tcttggtcct ggtggtattg gctgcggtac agaaacccat   85560
tcatgagctt agagataaag tccagacaca agggccccac tagattgaca tcgatgagct   85620
tgctagtcag acgctcctgc gttttgatgc aacggatcac cttgccatag cccacctccg   85680
agaccttctg caggtaggcg cgtttgcgca cgttcacctc gcgagtgacg ttgtggatgc   85740
gggagcgcgc gtccaccaag tcgagagcct cgtgttcgtc gcagttgcgc acccgtaagc   85800
cgttctcgct gccgtcgccg tcctgcccat tcacccctcc ccctaccact ttcttgcctc   85860
ctccacgagc ccggccgccg ccaccgttat tcctctgact gtgagtactg ctgttgctgc   85920
```

```
tgttgctggc cgtcatcaaa gtcgtacccg tccccgacat cgcctcccgt ccacgcaggt   85980
gaatagcctc gccctcgggg ccgtcgcccc ccgtgccatc tggcagcgga cgtcgaatct   86040
cctcgagaat atgcttgatt ttggtgtaca tctcgttgct ttcgtggagc ttgttgaaca   86100
ccgggttgtc ctcgaaagct tgaatgctga gggatgtgat gaggtcgatg atcctgttgg   86160
gggcggcaaa gaccgacccc acgaacatgc gctcctcccc gtccaacgcc ttttccccga   86220
gcacgaagat gtcctccacg tcctcccccgt acagatggcg actgatgccg ttcatgagcg   86280
cccggcacag ctggtgatac acatttagct gctggatggt gatgcccacc cgcttgacga   86340
taacctccga ggtacgggac cagtaggtaa atccgacaa ggaatatatt cgttccgta    86400
tatccgtaaa caggttgtac tccctcagcg cctcctccgc tcctggatg tagctgtggt    86460
aggccgatga agaagagaat aggcttttga gggccgaaag gactccagcc aagtggggga   86520
tgcgcgttgt caggtccagc aggtcctgct ccaccgtctg gatattcaca tcggactggc   86580
ttgacgacg gtggaccgct atatggttgc acagcaagcc ctgcagccgc ttgttcagcg    86640
agcggccctg attcgggatg atggtcagct cctcgtagca ttgggcgcat gtcgtccctt   86700
cgacgtacac ttcctgacgc gccaccggcg agatgccgca taggcgacgg aggagctcca   86760
gcaactgcgc gcagacctcc aggccggcct ccggcgccag gatcccgtac acgtagttca   86820
ttttgcacag gaagcgctcg atgtcgttga gtgtggccag actgacgctg aaacggacgt   86880
tgtccgtaaa ctggagctcc acggtgtgat ggcgatcgca gcgatccaaa cggaggacgg   86940
tacggtagaa ggccgcccgg tccggctggc gcgagtaggc catcagcgcc cgatccagca   87000
aagccgtatc ctcgtgcagc gccttcagca gcatctccag gtagagcgtc agcaacgaac   87060
tctgcgtacg attctgcgcc accacctccg ggtagatctt ccggtacaga tacactatag   87120
ccgccgcgtt tctcttgaac ggcgtggact ccgccagtaa cacgttcgga tcgcagtact   87180
ttagacactc cagctccatg gcgtattcgt tgcatttcga acacactacg catagtttct   87240
gtaacaaatt catctccatg actcgactcg ctcacgtacg agacgctgtc gtccggtctg   87300
gcgccggcca gagacatgga gtcggtgcac aaataactcg cgggccgctc gctatgccga   87360
ctgacgttga cgttaatata taacgacgtc gtcgacgacg cgggttctgc tcccgaagct   87420
gttgccgccg cttgcggcgc aacctcctcc accaccgccg ccgccggctc ctccgcctcg   87480
ggcgacgggg gctcggagat gaccggctgt gtctgacact cctcccctt ctcaggcggc    87540
ccgggcgccg acgcgaatgt cggagtttgc cagcgcggcg gcggtctctg tctctggtgc   87600
cgcggcgcta accttcgggg ctgttgctgc tgttgatgat gcgacgccgt ctgtcgccgc   87660
tgttgcggcg gtagctgata cggtgtcgcc tggtgctgct gtgtcggtgg ctgctgttgc   87720
tgctgttgtt gcggtctgaa aagcggccac ggggctgcg actgttgttg ctgttgttgc   87780
gatgctcgtg gctgcggcgg ccgttgtcgc ggcgtttgct ggcggttaca accggctgcg   87840
tttggccggc aataacccgc tgcccccgcc gccccgctg ctcccgccga cgccgccagc    87900
ctcgtcttcg ccggcgttca cgagaaagca gccacctccc gtctcgccgg gcacgccgaa   87960
gcaaatggag ttgcccgcga cggactcgcc gagaagaaga ccgccacccc cgacgccgga   88020
cgccgcgccc acgccactgg gcgcgaagag cgccgacagg tcgtgcacct ccccccggc    88080
ggcgtccgtt aatcgctggg cgtcggcgtc cagcacgcgt cgcaagttct ccagcgaaaa   88140
gtcctccacg ccctgctcct gcaacgcggc aaacttgtcc atcagcgacg cggccagcgc   88200
ctcgcagcca tccacgaaga agagcacatc gtcggacgcg gggatctcct cgcgcacgct   88260
```

```
cagaatctcg tacacggcca tcacttcggg gtcgcaatcc aagttctcgg cgtccagcgc  88320
cagcatgacg cggttttttta taagatccgc gtcaaaaagc acgttctcgc ggcgcgagcg  88380
tttgatgagc acgtcggcca gacgcgtagc caagaggtag cgctggcgca tgaaacgata  88440
atcttggccg ctcatagagc tcacgttaag gctgcgttcc acaccgttgc ccgaaaagta  88500
gccgatctgc ccaaactgat agatctcctt gctgttgttg atacccgcat atttttccac  88560
gctcacgggc acggtcacca aggaacgatg ctcaaaaacg ctccgtacca acgattcacg  88620
cgccacagtg gcggccatgg gcgccggcac gcctgcggtc ttcaagccct tgacatgcaa  88680
cgcaaattcg gcgggcgacg agaaccgcgg actagcacct aacacgtgag gaaactgcgc  88740
gtggttctgc gtcgttaagc gcgtcgtcaa cccgtgcagc gagccgatgt agtctttgaa  88800
gccataatag cagaggaatt tgttatggaa acggctttcc acgtaactca gcacacagtc  88860
tggcgccaca tccagcagat cgtgctcctg atagtcagcg gtcacagcca ccagaaattt  88920
gacgaaagca ttgaactcgc ccatgtcacc tatgggcaca ttcttgggca acgcgttgga  88980
acagaccttc tgccaaaact gtaagcaggg gagaccacat tcaggaaaga gtcgctcgtg  89040
atgtcgatac agcagaaatc ccaagcagcc cttagccgga ttacgacgcg gaacgtgatc  89100
gcggcgaaaa aacacgctac ccgcgttgcc cttgcccgcg cggtagatgg gtcggttttt  89160
cacccgcacc atgatcaacg tgggtaccga cagccgcgag agcttgatct ccatgggcac  89220
cacggcgtac gtgccctgcg cgtacagcct aaagtccagc aggcggtcgt gatccgaatt  89280
cttggacgac ttgatctgct tggtgaagag aaagcccttg cgcgacgacg tggtggagaa  89340
cgcgccgtga atggattgaa aatgctgcgt catccatttg gataccaagt tggtggtcaa  89400
cggattgtcc acaatgtatg aggtagcggt aataagcgcc acgttctgga tcacgtaaaa  89460
gacggatctg aaataggcgt aggctagcag cggctggaag gccacggcgt agggattcag  89520
atccaggttg aaggcctgcg tggcgcccgc cacctcgtcg cggctgctct tgaggcgcac  89580
ctccgaaacg aaacccaggg cctcgtcgtc cacaaacttg ttgagcgccg aaaagacggc  89640
cacaaagtcg cttttgccgt gcgcgctaaa ggtatcctcg cccgtcacgg ggtcgatgag  89700
ccgcatcttg cggcagtaat ccaagatgcg attgagccga taggtacggt ccacgctagc  89760
gcccaacatg cgaccgccgc gccccatcat tcccccggaa tccccaccac ccccaccacc  89820
acgaccgcca cccagaccgt cgctcgggcc cccgctcacg tctcgtccac cacccccgcc  89880
agcaccgccg cccggaaccc cgtcgtcacc tttgccgtcc aaaccccgt ccttggcgtc  89940 gacgttgtaa cgccgaccga agctgcccaa aatatccacg tcgttgagaa acgcgactg  90000 cacggtgatc acgcagggct ccttcttggg ctgcttgggc accacgggca gcgggtgcg  90060 cacccgcacg aaggccgtct gataacacgt gtggcaacaa gtaccccccac aggcctcgca  90120 cagccccgcg gcgcagccca ccaggtgatt cgtgagcgtc gacgaacccg acaagcccgt  90180
gttgtacacc gagacacgat tcagatacca gacgaagccc gaaactagct gcggacacgt  90240
gccacacacc aacgccaaat gctgcggccc atagcgttcg tccttgagcg gcgcgccctg  90300
aaacttgagc accttgcgcg cgtcgttgta gacgtcttcg caggccgccg acaacccgtt  90360
ggtgaactga atagccttga gcaacgtctc ctgactggcc gtaccgccgg cgctgggatg  90420
ccgcgccgac gactggagat acaccagcct gtgctggtag agcaccgaat tagcgctgaa  90480
gaccaaggcg gccacgtgcg tcgagagatg caacttgagc tcggtcagcg cgcggatcag  90540
atcgcggtga tcggttgcgt tggtcactaa aggccactcg gaaaagagca tagattcggc  90600
aggttggtaa gccgaatcga aaataccgaa ggcaaaactg aaggccaact cgcaaaccac  90660
```

```
cgcgtcactc agcatcagat gatccttttc cagactgctg agtcgctggc tcatgtaccc   90720
caagtagcgc ttatgtggcg ccagcttcac cgactgctga ctgtcgtgca caaactgccg   90780
caacgccgcc tcgatcagca cacgcggctc cgagaagcgc agcgattgac accatgacgt   90840
gtacacgtag tagaaaagcg tctcgcttac ggccggcacg tagagccctc gcgcctccac   90900
aaaagcgctg cgcgcatcca gcgagacctc gtcggcttcg gcgtcaagct gcaacgaatt   90960
aaagagcgta ggcgggtaca acggcacgcg caccgcctcg ccgccgtgca gtcgcaccgt   91020
ggtcgcctcc tccacgcatg gaatcagctg accggcaaag agaaactcct tcaagccgtt   91080
gcccaccacc acgtgcacag tcgtctcgga cgcctgacag cccaccgccg cgcacaacgc   91140
cgccagatcg gtaggcacgc gatccgcctc gggcatgtaa gcctccaacg cgtacttctg   91200 gcgggcgtc  tcgcacagcc gatgcacgtc tccgtgatcc tcggtaaaag ccacgatgcc   91260
ttgcgtatga tgaaagtaga gcgcaaaagg acagaaggac gtgactttcg tgagcacccc   91320
gccgtcgtaa caaagcacag gcgtgcgcac agagacgccg aaatccgcct ccaccgtgag   91380
ccccgccaac aaaggagcga tcaccacgct cgaggaacgg tcgcatagcg agagagtggc   91440
cagaatctcc tgcgtttctg cgttcaacct gctgaagtag agaaaagccg cgggccccac   91500
cggcgctagc gcggttagtt cctcgtggct catggtggat gaacggaaga caatggctac   91560
gccgccactg agtgaatttt ataccaagga aaagttcagc acgtcatgtt tgacgcacga   91620
cgtctgagac accaccgtgg ccaccactgc ggtctggctg cggttgcgga ccaccaaagg   91680
cgacaaccgc aacgatccca gcaattcgta agaaaagcta accgctacgg tcaggtagcc   91740
tctcgcagcc agaccgctag ccgacgcacc cgcccgcgaa aatagcgtga tgttcgggac   91800
ggctttgcgt caccgccaac taacgtcggt agtcgagcac gtcgtttatc ctcagcacac   91860
cgtccgatca caatccgttt tcccactcag tcgcacaagc agcacataaa aaccccacac   91920
agggcacgtg aaaacaccgt ccctagaaaa cggcgttttc tgtcctaccg tcacccgtat   91980
acacaggcaa atcccaatcc cgatccccga aaacaccgta cggtgtttgt gacctccaaa   92040
atcacatcag ctaacaaacc gtgaaaagtc acgtttcacg aacacggtgt ttttaaatca   92100
caaagaaccg cctgacggtt tacaagcaga aacaccgcac cacggtggta caagcgcgat   92160
gaatctggtc tcgcaacctc aatcgccgct atcaccaccg attttcgctg cgctccgccg   92220
acaaaacgcc gtacaagcta cacacccccaa aaacccgcgc gcctacgggc gccaaacctg   92280
tgtgttatct caacgtcaca acacgacaca aaccgcgtaa cgtggtttcc cgaacacgta   92340
cgcggcacag accccccgaca cgtactcgaa gaccttacag tttacgagtc aataaaacag   92400
gaaaagatcc gaactttaaa attgtgtgtt tttattttcc catccccctc ttttaccaa    92460 aaaacacatt tttcgtcttg taaaaagtaa ctttcgccca ttgccatgaa acaccgtgat   92520
ggggaacggt gttgtgtgtc gactgacgtc actacggcga tcagtatcga cgtcgtgtat   92580
acataacggt gcccggtgtt tttattcggg gcgttgtcgc gtcttgatgt aatgtaacct   92640
gaaaccgccg tgcccaagaa tgcggaagcc agcgtgtaat cataacgggg ttttgggtac   92700
aatctgacga catctggcgg cgagcgtaca ccatcgaatg tggcgatcgc cggctctacg   92760
tcacaatgac gcaaaacac actgtaaaac ccgcgtagac agctttcctg gtcaacgagc   92820
gccatctggt gtcggcataa gaacaggcat caaccccgtg gccggcgagg cggtgagcac   92880
ttttgttggt cacgtgacca tcagcgcagg aagcgaggcc cgtagaaccg cccaagaggc   92940
ggtgccagat gccaacgtca taatcacaag gtgatttgtt acgtcacgcg cgcgcacgca   93000
```

```
cgcgcgcggt agaatacagc gatccctagt gaagccacac ccattacgtg tagccatatc   93060
cgcttacgta tacagccaca cccctaggta cgccaccttc tctaccaatc acagaaacgg   93120
atatacaatg acccctccct agactccacc ccttgtacgg aaatttcaga taggtggaac   93180
ccgttagggt tccaccgtcc tcggtgtacg tacaggcttc tccgtctacc ggaaatatac   93240
acctgctgac gtagacgcta ctcccggata cgcgtcataa gctactggac cctaggggg    93300 agtgtctaca gggctacgtg cacgccccct tacctagggt atccgccccc ttcctctgtt   93360
ttggcctagt aaacttaacg ccgccgcttc tcacgtgacc cctgacaagc ctacgtcaca   93420
ctcgcgtgac cacacccact ccggatatac gtcatcctgt ggaattccgg acatacggtg   93480
acgtagcgag cgtagcgagc tacgtcacgt atgcgtgcgt catctccggc ggaaatcatc   93540
tctgatgacg tagcgagcga agcgagctac gtcatcagtc cgttttacgt ataccggatg   93600
ctaggcgacg ccccgtaggg gcggagccta gcttccaccc ctaggatgca taccctatat   93660
agcataattc ttctaacgaa acgttctacg aaaacggact ggcggaacgg gaaccaccgt   93720 aaccccccc cctcaccccc ccccttctcc tccggaaccg gggggggcaa attttttacca   93780 aatttgggca accatgattt ccaatgggac ggcgtttccg tgcgcatgcg cagtcggggc   93840 gagttttttgg ttgtcagggc gttgccacgc ggattatggg atggtgactc gagtgcgcat   93900
gcgccgggga tgccgcatgg aaaacctata tataaggagg ggtgaaccag gggcccggg    93960 gcgcatgcgc gggccagggc ccgcggggagg gtcgccctgc gcatgcgccg gtaaaattcc   94020
actgtgtgtg tcgtgcgcat gcgccagtat ttttccacta gaggcggtca gtgcgcatgc   94080
gtcggtaaaa ttccactaga tgtgcgccgt gcgcatgcgc cggtattttt ccactgggcg   94140
gccgcaccta gggagcgcga gccccgtgcc gggcatgggc cgcggcggtg gaaaattacc   94200
gctccgccca cctaggcggg gcatctgaaa acctataaaa cccggcgtgc ccgccgcccc   94260
ccggcgcagt ccgcggcagg gttccggccg tgctgcggtc cgcacgctgc gcccgctccc   94320
gcctgcctcc cgcccacccc cccacccctcc ccggccgagg cccggcgccg gtccgtccgc   94380
gggcccgtcc caccgccctg gagcaccatc cggggccgtg ggcgggcac cgggcgcggc    94440 ccgctccgga cctcggccgg gggtccctcc cctccccccg ctcgacccccc ccatccgacg   94500 gcccggccgg gctgggaccc ccgcaccggg gtccggttcc ccgtccgtgg cccggggga    94560 cccgagcggg ggcttccac cccacccccg ctcctcccccg ggctccggcc cgggatccct    94620
cgctgctccc ggcgacctcc gccggcttcc cggtccaccc gccgcggaat ggacgggacc   94680
cggggtccgc gcccttcccc tcccccacg ggggggctggg tcgcggaccc cggttcctag    94740
gctcgttccg cggtgggcga ccggggatcc cccacccagc tccccttccc ggcccgcctt   94800 gctggcttt gggcccctgc gggcttttt tttccggctg ggggtcgcgg cggtcggccg     94860
acgacgacgg taggtgggcc gggtggacgg tggtggggac gggcgacgcc ccggctcgac   94920
ggcaatcggt cccggaaggt tggggggctgg gggcccggtc aggagctccg ggagcggggt   94980
cgaccgcgac ggcttccggg tctcgcggcg gctccctctc ggcggctccg gttgggctcc   95040 cctccccct ctcgagggtc cggccgccag tcgtgaccgg gggtccctcg gcctagccgc    95100
cggctctcgg tccgccttat cctgggcgtt ggcctgtccc gtgacgctcc cctcccccgc   95160
tgctccccaa aaaactccg cccgaaccgt cgcggcttgc tggccctggg cgtggtcccc    95220
cactcccctc cccccatcgg ccgcccagcc gggggtcggcg cctcggaccc caccaggctg   95280
tggcgtgtgt gctggccgat gcggcggcga ggttgggtgt ggccggaagc gctcgggtc    95340 gacggtgggc cgccatgaca cctcaattgt cgtcagtacg cccctccaca atcaccgtcc   95400
```

-continued

```
ccacacgatg ggcccggcag gtcacccaac gttggttcag gcccagtcgg gttttttccc   95460
cggcacgaac gcacgtcccc gtgggctcca cgcgttttcc accctttcct ggaggggtcc   95520
ggaacaccgt gaatccacgg ggagggtccc ggcacgggcc gaggagacca cgaccgtccc   95580
acccggcgtg tcgactcgtc cgagacccgg aagggaaca ggccccacct tttttttcct   95640
tctccgattt tgccgtggaa aacccgtgaa ccgatacggg tgcagacggc cgaaaaaaat   95700
cgagacgaca atatgacggc agggcgcgat cttctccccc atccgacaaa accgtgtccc   95760
ttaaaattcc ccacctttct ctgttcaaat ggccccgaaa ctgtaaaaca ccgtttgacc   95820 gcacccaac cggcgccatc ttggtgacct tctcgacggt tctctcgctc gtcatgccgt    95880
tctgagctcc gacatggcgg acgagagaaa atggcgtcga gagcctagga gcgttttttgc  95940 tccaggcggg taaaaaaata gcacgataac ttttctgtgc tttttttttga dacgttttag  96000 aagagcttt ttctgctcag agcgaaaaaa tgatagccct gaaaatctcg acgagtctgg   96060
ccgagcggcg ccatcttgga ggaggggcga gtcgcgggca ccgcctcggt accccctggc   96120
cgaggcgagt ccgcggtcgc cgcctgttcc gtgatgctac ctagagggcg ctgtcgaggc    96180
gactcttcct gttttcgccc tgagggctaa cggtcgctga cgtcaaacca tctcgtgctc    96240
gctgagtcac atccggttgt tgacaagcga tggaggaccg cacccaaagt gcgccctcta    96300
gtcatcgcgc ctgaccccccc ttataaactg ctcgaagaaa agaaccaactt atgtgaaaaa   96360 atacagaatg atgacaagtt catccaacac aaccgctcaa caacgccata tctatcagtg    96420
tccaaaaact atcttctatc ctttgaaact ataaatgctg cctatataca tatttagtat    96480
ccaagactct taccacgtag acgaaaagaa gtgatacaat gatcttgacg tgtatcgtct     96540
atatcgtgct agatatattc agataagacg cgcaaaccat agatttctca tcagtatcat    96600
gaaagaccta tagctctata tacgaaccta gtcattttag gacagccgcc ggagaagccg   96660
acgagggatc gggcgggtgc agccagaacc tcacgcccga tcccgcctcc ggtaggcgat    96720
ttgcatctgt ttggtaaaaa gctcataagt ctgtatgtga cctatatata ttatacgcta    96780
tgtacaccga actgtcgctg ttgtataaga agaaaaaact ctccatattt atatcgtctg    96840
aatttttgct tgatagacac gtgtttggaa ctctgtcccc ccacgttttc actgtgtata    96900
acaaaaatat gtgtttctca aaagatcttg aggtgtttga aaacggggga aacctgcgtt    96960
tgggtgctct aagccccgga ctgggacgta gccggcgtcc ggcacctata ttttttctatt   97020 ttttttttaca aaatatatga tgaaccaaga ataaaactct agctctcgtc tatttttaat    97080
atgctctact tagaaccttt ttaatgacag aatgaactcc atgttatacg ctctttatat    97140
agtttctctg cactaacctt taaaaccgta tccttccctg ttgtacaaat catcttttga   97200
tacacaatga tgacctgata tccctccata tatatgatcg gatattattc cgttagactt     97260
gtcctccttt tttttcctca tctcctgtat ctggagatat atgttgacca ccaccgccat     97320
gaccaccaaa aagctagccg tcacgactag aaatgtgtag gattcggact ttccgttcga   97380
gaagaaaaag agaccgcgtc tctggacgct cttttttgtca gtctgaatcg acccgggata    97440
cgtaagagag cggccctaca tcggggggcg ctcgagaccg acgacgttcc atctgaccag    97500
aaaaaaaaag gcacccctcg gtggcgacct ctcaccatcg tttgcccgtc cgcccgtcct     97560
tcgtagccat catcatctca ggctctatcg gtaccatcgt tgtcatctga aaaaaaaact    97620
gcctcaccca cctgcgtaaa aacaccatct ttccggaggt gcggtaagac gggcaaatac   97680
ggtcgtgccg aggcaaaaaa aacgcaccat cgacaccaca ccctcatgag caccacctgt   97740
```

```
cggtgttggt cgtcctccat cgttctctac gaacatctcg acgcccgggt gacggacgac   97800
ggcaagacgt cccggagaag acggtgttct ctcgggcggt acgctctctg gatctataat   97860
atctatagta gctaaacgag actgtgagta cgacgaacca catcatcttt tttttatgtt   97920
gcttctttag aaaatgactt atgtcgacga cactcggcat cagccatctc gtgaaacacg   97980
ctcgcttttc gtctctccaa ggaacactgg gtccgctgaa agggaccgtg taccgaccaa   98040
agcaaaaaac acacgtag taacatgatc aaccacgtct gaatgacacg aaaacacaat   98100
cgtataacgc tctattcatg gaacgaactt ggaataaaaa aaccatcgca ggccagaggc   98160
taagccgaaa ccgtccgggg aagcgggcgc gagttttccg acttagcctt tggtgctcgt   98220
tgagcctctt tttttttct gattctctga agaatcaccg tcacagccct atgacgcgaa   98280
atcaattgct agaacataaa cgttctcaac aggtatgaaa tgaacaaact agatgatgct   98340
ataaccttat attgtgtgta tatagatagg tgtgaaattt gtaggataaa aagtgtcgtt   98400
gtatgatgca caacgatcgt gaaactggag actgtagctc tctaccgaat gcaaatacac   98460
aaatgacatc gattcccgtc cccacataaa gaaatgtgct ttactgtgaa agaatgaaga   98520
agattcttgt tcctcgtacg acggggccct cgctcgtcgt gcctcttccc ccctccggga   98580
gaggggacgt cggggccctc cgtcgcaccg ggccgaagcc agtgaaatgt ttactacact   98640
gtcatcagaa tatatgatgt atattatttc ctccaaactc ctcaccatag ccaccaattc   98700
gcatcactta agaaagtagt agcaaccgcg gcggcggcga ccggccggtc gtcgtctcct   98760
cgtcctcaaa tgttgtacat gtgcagaaaa atgtgtaaat acgtgttatt tatcccatgc   98820
gtcttgtaca tagatatatg tttttatata cgctatttat actttatata tccttttgca   98880
taaccataga cagtcaagga ttttaatgat ttgctcatcc gcctttgagc catcgcttag   98940
gagttagttc ctctatgttc tcggcccacc ttttcgacta cagtagcaaa cccttgtact   99000
accaccccga taaaaaccac atcatcatcg tcaccacgac ctggaaacga cacacgttcc   99060
cccccaatct tgggcatgtg tatatataaa aagaatggga gggagaggac gtggggctcg   99120
agaagaaata aacgccaagc tcgattcgaa ccaaaaaacc acatgtgtat tgtgctttgt   99180
tttttttttt acggtggggg aaaaggaggg ggccgtcatt aacggaaacc gtgtatgggg   99240
tccggacacg aacagtacac agcttatggg gaaaaaagct cacagagaga aaaaacacca   99300
agctcaggca cgcgtacatc attattatca tcatcggata tctccaccacg ggtcatagta   99360 gtaccaagga gtgtgtaaca ccattttttc ttttctttgt aacgggataa gggacagcaa   99420
tcatcacgca caacacccctt cactctcttt ttagtcatcc atatcatcgc tgtaacacag   99480
catgtcctcg taatcgggcg tctggcagcg cattaccacc gagtcgtctt cttgcggtac   99540
cggtggtggt ggtggtggcg gcggcggctg ctgctgctgg gttgccgtcg tactgtgatt   99600
accgttggcg gactgcaccg ggatgatggg ctgcttgtgg ggaacctggg gtggactgcc   99660
gccgtgagaa ggcgacggcg tcatcaagtt aagctcacca cggtgactcc ggacaccggc   99720
gaggggcgcc gggggactgg gagggaccgc ggtcgtcttg tagacgacgg tgtccccgtg   99780
tcgatccgtg gctcgtacca gatcttgact gctagcgtcg tcactgtctt cgtcctcttc   99840
cagctcgccc tcagagtagt gctgctgtgg ttgcgacggt ggctgggcgg gaggagcggc   99900
ggcgatcatt ggagagggat gtcgatgact cccttctctg tccttttttat cgtaggctgt   99960 cagcgttgct gggtccgtcc tgctttccat atttgcgtat tgctcatcgg tgggatgaat  100020
ttggtctcct ccccgctgtt gtccgccggc agtggcgtgg ttgctggcgg ttgtcgttgt  100080
cgtaccggca aagacggtga gatccaatag cgactgctcg tcgaagggac agtacgctat  100140
```

```
catgaaacga tagggtgcca acgcgcgttg gatgcgcagt tcgcacatct cgttctgaca    100200
ctcgtggcac tgcagggcgc ctaggatcag gtccgagaca gcgccgcagc ggtaggtacc    100260
catggcgttg ttagtatcga actggtcaaa aaattggggc gtaccggtga cttgcaacgc    100320
gcgacggcgt agcgagacgg ccacgcgcga gaaagagcac acataggcca tggcgcggtg    100380
catgggttgc gagaaggtct cgggcggacg cttctgcaga tcgcagacgt cgtcgcgtag    100440
ccaggcgctc atttgaccgg gcttcttgac tagccgtttg agcgtgctgc aatggtcgcg    100500
ccagccgtcc tggtggtcca ggatgcagcc caggtccagg ttgttgagtt tgttgaagag    100560
tagctgacgc atgccgccca ccgtctccag atagggatcg tgcgggttga cgggtagccc    100620
gtgcaggtgg tggtacttca tgtagctgag cgtttcgtcg atgatggcca gcaacgtgtg    100680
caagttggga gcgttgtaca cggcgaagat cttttccacc accagcttgc gcagcaacgg    100740
ttcctccagc caatcgaact gttgacgaat gtgcaacagg tagtcggtgt gcatgagctc    100800
gtcgtgtgac agcaggatgc gaccgcgcgg ctgatgatct tgcgggaagg cggtggggac    100860
cttgagatcg gcggggtagg gtgccagacg tagactctcg gccgtgtagc gctgaaggtc    100920
gtaaacgggc gaggtagaac tcggtgaggt acccgacgag gcggcgccgc gctgcagacg    100980
cgctcttttt ttcttttcga tcaaacggct gagttgctgt agttcgtcct cgtccatggc    101040
gtccagttcg tcgtcaataa gcgccagcat ctgttgttgt tgcggtccgg cggacgatcc    101100
gtgatgatta ttggctgagg aggggtgaga agaaccgaaa gtcgtaggac aactgggaac    101160
tcggcgacga agatgcgtcg aatcgccgcc gtgatggtgc ggttcgccgt catcgttgtc    101220
gtaagactta ccgtagtggg ggttaagggg caccgaggcg gacgcggcca cgcgtcgctt    101280
gaaagaggag gacgccctat gtccgccacg gaagcccgcg gtgcccatga tgatgtgtcc    101340
gccggtgccc ccgagtgcgt ggcgggagga gggtggaagg ggaggaggat agtggtccgg    101400
atcgccttcg gtatcatcgt ctttgctgta gcggggtcgt cgtgcgggga cgcagggtcg    101460
gtgatgatgc gaggcggcgc cgacggtatc ttccgcgaga tggtgttcgc tggcggctgc    101520
tccgttccgt gtcgacggcg aggttggact tcgctcgcgt cggaacttcc gtggcacggg    101580
ttcgtaatcc agacagaagc gccgtgcgcg acgggcgcgg cgttcgcgct cgctcaggga    101640
agataacgac ggagcgtcgt gacggccgcg tgagtgcagc tccatggccg ccgtcgctag    101700
gaaggtcacg ttcgggcacg ctgatgtata tatagatgag accgctgccg gggggcgggt    101760
caccggcgcc gtggaaagtg aggctcagac ggcggtcgcc ggcggcacgg gcgcgtcggg    101820
cggtctgatt ttgatggaaa tgtggacgtt ttttggcgttg gagtgacact ttttggtgaa    101880
acagcggctc cagaggctgg cccagagcgc gtagctgtgc tcggtgcgca ggtcgatgaa    101940
cacctgcacg gtctcttgcg ggttgcggtg cgtgtagttg agacagcgaa atcccgcgt    102000 gcgcgcgccg tcgcgccgct tgacggccac gcagcaggcg ccgtggggct gaaagaggag    102060
gacgtggggc gcggtaaact gctcgctgac gtgcggttcg tagtgttgcg tgaggtgctc    102120
gagcagcggc ggccacacgc gggtgacgac gagccgctgc aagtccgtgt cggaaatcgc    102180
agcggcagtg gcgccgtcgc caccgtacag gtgataggcg agcacctcgg tgagaccgcg    102240
gcgtcgataa cgcgtcacgt taagcgagcg cgtctcgata aagttggctt cggtcgaggg    102300
gcagattttg tcgcgtacgc tgagaatgac gcgtggcggc ggcgacaggg gcaacgcggg    102360
caggtcgtgc ggcgggtggt ggtgaagcag gttacgcaga tccagttggg cgcgcacaaa    102420
gcctagcggg tgttcgcggt aggcgtcggg cacgatgaac agcggcaaca gacggcgatg    102480
```

```
catgaaatag ccgtcgtctt ggtccatttt atacatgtag ggcagacgta cagagcgtcc   102540
atggtggtag atgcctgtgt ctaggctgct ctcgggatgc gagatggggt ccagcagcgt   102600
gtgcagttcg gcgtcgagac agacggcgtg attgagcacc tgcgccacgg cgcgtaaaac   102660
gctggggtgt acggcgacgg tgcaggcggg gaacggcgtg atgatgcgca gccccagttt   102720
gcccttgcag cggcagtaag ggggtgacgt gtcaacggag gacgttgttt tttggaaaac   102780
gccgttatcc gggacgttat ttttatcctc tttcccgtct tcgtcttcct ctgtgtcgcg   102840
ctcgtcccgg taatcgagat agtcgtcgtc atcgaaaggc gcgccggccg cgtccacggg   102900
cacgctgttg ggtgggcacg cgcttttgaa gaaatagacc gggtgccggt cggggtgcgt   102960
gtagccaaag aggctcgccc atacggtcat ccagacgcgt cgtagtccgc gacatagctc   103020
aaagacggtg tgtcgcgcca gaccggagac gccgtcgcgc agccgtaaat caaagtcggg   103080
cacaaaattg aagacgggca gacgttcgtt gaagacttcg tgtcgcgtgt agtagaactg   103140
tgtctcgggg ctggtgctgg ccacgtcgtc gtcgtgtagc cacacggtct cggtcagggc   103200
ctcgtccgag aaacggctgt cgggtacgtg acggagcagg tcacgcggaa agaggctgcg   103260
atgccaggtt tcggaggcca cggcgcagaa gacgtgctgg tcattgggca ggtgtacgcg   103320
gtagacgggc agcggtcgct ccagcagcgg tgccagcgcg ggctcgggta gcaggtagcg   103380
acgttgcgag taacgcgtta gcgtgccggt ggtgtaagtc tgggctgtgc gtagcgaggc   103440
gcatagacgt aacaagccgg acaggagcg ttccagcggg gagaagacag actcggaaag   103500
cgtgttgatg cgttcgagct ggcgcgccag ctgcgtggag gtgccgaaga gcccgccag    103560
gtgcgtgccg tcgatgcggc cgccgtagcc ggccagcccc aagccgtgcg ggctggtcgc   103620
cgagtggggg gattcgtcga gacgcagtag gtgcgtctcc acgtagtcgt gtagaaagtt   103680
gtcgagcgag aagtattttt gcatgacgtc cagcagctcg gtggaaagcc ggcggcccag   103740
aaaacccggt tcgcgcgtgc actgcgcttc gggcgccgcg tcagcgtcgt aagccaccac   103800
gcgccggtac tcgagcaacc gcgcgcgtgc cagcgccgtg cggtaggcca ggtagacgta   103860
gtgcacgcag accgtgtcgg gcagacgcgc acgttcgcgg aacgcgttga tctgcgtgtc   103920
cacctgctct agctcggtgt agtcgcggcg gttgcgcgcg acggcgtacg ccacgaaagc   103980
ggacacgcgc tgacggaagg gcgagcccag tagcagacgc gcgaactcgc ccatggaggc   104040
gtgcgtgggg atgatggtgc ccaggtcgcg cgtgcagaag ctgcgcacgt actcctccac   104100
ggtggagatg gtgctgtact ggccctcgaa taggtagtag gccatggtca gcagcacctg   104160
gccctcggtg tgcccgaaga cgctgatgaa ccacgagggc gaggtggggc agaggaagac   104220
ctggttgaga tgacgtagca cggccgcgtg gtgaaagtac accaggtgct tgaattcgcg   104280
cacctcgccg ccgtgttcgg gcgagagcac gggcgtgcgg aaaagatgcc ggtagagcgg   104340
ttgcgtctcg gcctcgtcca gactggcgat gagcgccgag aggggatgg gctggcgcgc    104400
ggccaggtag cgcgagagct gcagcgtttc gttgttcacg gcgaagacgg gcgccacccg   104460
ccgcgagtcc gagcactttt gcgtctgtag gcagaagtaa acacgtcgcg agacctggtg   104520
tttgaccagc aggggaaga cgcagtggtc cgtcggtgtc tgcgagagta cgttggcgac     104580
tatatgagca gaatcatact ctgttgcgaa cagaacgagc gtcatcgtcg cgccggcacg   104640
atgcagctgg cccagcgcct gtgcgagctg ctgatgtgcc gtcgcaaagc cgcgcctgtg   104700
gccgattacg tgctgctgca gcctagcgag gacgtggagc tgcgcgagct gcaggcgttt   104760
ctggacgaga actttaagca gctggagatc accccgccg acctgcgaac cttttctcgc    104820
gacacggacg tggtgaacca cctgctgaag ctgctgccgc tctataggca atgccagagc   104880
```

```
aagtgcgcgt tcctcaaggg ctatctctcg gagggctgtt tgcctcacac gcggccggcg   104940
gccgaggtgg agtgcaagaa atcgcagcgt atcctagagg ccctggacat tctcatcctc   105000
aaactggtgg tgggcgagtt tgccatgtcc gaggccgaca gcctggagat gttgctggac   105060
aagttctcca cggatcaggc ctcgctggtg gaggtgcagc gcgttatggg cctggtggac   105120
atggactgcg agaaaagcgc gtacatgctc gaggccggcg cggctgcgac ggttgcgcca   105180
ctgacgccac cggcggtcgt tcaggggaaa agcggcgtcc gcgaggacgg ggaaacggtt   105240
gccgccgtgt cggcctttgc ctgtccctcg gtttcggact cgctgatccc cgaggaaacg   105300
ggggtcacgc gtcctatgat gagtttggct cacattaaca ccgtctcctg tcctaccgtt   105360
atgaggttcg accagcggct gctggaagag ggcgacgagg aggatgaagt gaccgtgatg   105420
tcgccgtcac ccgagcccgt gcaacagcag ccgccggtcg agcccgtgca gcagcagccc   105480
cagggacgcg ggtctcaccg tcggcgctac aaggagtcgg cgccgcaaga cgcgctgcct   105540
acgaatcacg aacgcgagat tttggatctc atgcgacaca gccccgacgt gcctcggag    105600
gcggtgatgt caccgaccat ggtcaccata cctcctcccc agatacccct tgtgggttcc   105660
gcgcgtgaac tcaggggcgt gaagaaaaag aaacccacgg cggcggcctt gctgtcctcc   105720
gcgtgaacag cctggcacgt tttggaaaac gtacgtgatc acggacacga cgagtacggg   105780
gtttctcata gacgtacttt attaggtcag ggatgacggg gaggtttcgg ccgacgtca    105840
aaaataacgt cattcgtgtt gacagggctt tctgcgtcgg agctcttttc atcttcttct   105900
gtctcgtcga cgtcatcgtc taccggcgag ggtgtccgtt gcagcaacgc gtgctcgggc   105960
gtgtgggtga accgatgtc gggggtgggc ggcacgatca tctgtcctag ggggtgactg    106020
cccaccggca gataggtaaa gcggtgggtg gtaaaaaccg cttggctac ggtggtgtgt    106080
ggggagatgc agacggtggt gtgcgaagtg ttgaccaccg tcacgccggc cgcggtaccc   106140
gggagccaga tggtgggtcg gatgatgaga tccgattgac taaactgcg cacgcccact    106200
atgagggcgc agataccggg cgcgtgcacg taggccgcgt caaaatagac ggtttgcgtg   106260
tgacccggac cgatcaccag cgtctgacgg gtacgtaacg aaaagaaacg gtgttcgttg   106320
ggcggcggca agttcatgag ctgccagggt tctggtacaa acaggggaa aacgccgata    106380
tcgccttcga tggtgcccgg aaagatggac tgaaaagtgt cgttgaggtt gacgacatcc   106440
aactgcggga cttgcagcct ggattccagc agctcgggca tgcaaacgaa ttgcgcgtcc   106500
aggcatttgt aaaaggtaat gccgaaaaaa ccttcgggga tatagaggct gacgcccagc   106560
gaggtgggca ctttgcgctc gcgtgatagc caaatgatgt gtttattgta aaaggccagc   106620
tgcgtgtggc attgtttgac gatgaaactg gaaggcatcc acttgtaagg aactttgagc   106680
ggtgacggta atgcgacga cgcttcatcc tctcccggat gctgctcttt gtcgtatttc    106740
tcctcggtcg attggggcag cgtaaatgtg gtttgaaaat cgctatcgct agcgaaacgc   106800
acgcagtaac gcatgttgac ggatttctcg gctaggatga tggagcctga tgacgatgcg   106860
gactcttcct tcattattaa cgtaggggtc tcccagaatc gctgaaaacg ggagcgcggc   106920
agccgcgaca gtaccagttg agagtcgatt cggtcggtca acatcgtaag catcgtggcg   106980
gtggtgtgat ggagtggaac acactagtat taggtctttt agttttatcg gtagtggcag   107040
agagttctgg taacaattca tccacgtcaa cctctgcaac tacatcaaag tcttctgcta   107100
gcgtatcaac taccaaacta acaacagttg caacaacttc tgcaacaact acgacgacta   107160
cgaccttatc gacaactagc actaaactca gttctaccac ccacgatcct aatgtgatga   107220
```

```
gacgacatgc gaacgatgat ttttacaagg cgcattgcac atcgcatatg tatgagctct   107280
cactgtccag ctttgcggcc tggtggacta tgcttaatgc tctaattctc atgggagctt   107340
tttgtattgt actacgacat tgctgcttcc agaactttac tgcaaccacc accaaaggct   107400
attgagggtg gacagattta cagcccggcg gtgttccggc ggggtaaggt ttacatacgt   107460
gggtgaccgg aggctaaagt tacgaatctc atctagaaac agcagcgagt ctagatagtc   107520
ccacagggga tctataaatg ttctctgaaa ccccattgat ggtgacgtag gtgtagtttt   107580
gttactatcg gaagctgttt tgttttccac gaacatggtt tcgttgtaat ataaggagct   107640
catgtcgaga gtaccgtaaa tagtgtacgg cgtttcgtta cggattagta cgtgcgtgtt   107700
tttcataaat tctgacacgg cggttcggtt gcggcttggt tcacaaaaag gattttgccg   107760
gtaacgtaga gtggtataca cccacgttgc taggtcccct aactgtgtgg ccataatgga   107820
cttcataaag ctgctatcag gacgataagc aattgtagac gtggaaaccc gccttgcggc   107880
ggtagtaata ctataagtca cgttagtagt gacgttgaga gcggcagacg ttgtatagga   107940
aaagtatggc gtagtagtac tctgagtttt cttagctttt ttttcgaatt gttccttaac   108000
gggcgcttgt ttacgtttta gttttcgcat agtgtttttt aacttggtgc cgttaatata   108060
cttggggacg cgaaatagat tccggctcat ggcgttaacc aggtagaaac tgtgtgtaca   108120
gttgcgttgt gcgtaacgta aaagcagggc ggttaaacct agaaaataaa tcgtttgact   108180
atctacgtta accttagtcg gacccacgta caatttggtg ttccaacgcg gtacattgaa   108240
aaacatgggg ttgaacgtgg tgaaattacc gcaaccttgt tcgccagtat cattacgttt   108300
ggaaacgttt agcatttcgg aaagacaagt catggaaggc acagtaccac aaggtggggg   108360
tctgaatgtt atcgttttag ccgtatgatt gtactgtgag taaacgtatt ttgcgggttt   108420
tctaagctgg gtactataaa aatcaaacca cagataggtt atactataat tctgaatggg   108480
gcccgctaaa atgtagtatt gtggaaactc tgtcatgttc atagtgagat ttttaaccgg   108540
ttgtttactt acattgtatt ttgtagaaat agtcgtttct agttgtctca aaatttctaa   108600
cttaagctga tctaatttat atttgcctat cttagacagt accaagcccc tccaaggacg   108660
attataaagc gcttttgaca taactttaca gtttatgaaa gaaacaagca agaaagatat   108720
agatattaga aacaccatct tagggacgtc tctcaccatc atctcttttc tccccatgac   108780
agaggaggag accccgcacc gtccgtctgc cttgtggttt ggcttgcctg cgtgtactca   108840
ctgctgattc tggtcgtttt gctgctcatc taccgttgtt gcatcggctt ccaagacgac   108900
ctagtctccc gcaccttggc tgtgtaccaa gcttgtatcc agggcccgat atgtaaccag   108960
acccataaca gtacctcgta aataaagacg cacagacctc acgcatatag taccatcaca   109020
ccgtgtggcg tgtactttat tacaacgagc aagagtgccc ctaagtattg gggcccgtac   109080
cgttttagaa gattttgtgt gaatgtcttt aacttttctg tcccttttct cataaactgt   109140
caggttctac agtcagcatg tcttgagcat gcggtagagc agatagatgc cgatgatggc   109200
cgatagcgcg tagacggaca tcatgaggag acgactgtcg gtggcgtcca cgacgacgtc   109260
agttacttct aggaccgtac cgttttcaa agcatgagg tagtgagttc gcggagatga    109320
gaccaccact tcgttgtagg gatccagggc gaaaaggacg tcgtccgagt cgtgcatgta   109380
catgatgttg atgacgcctt gcgtgtcgtc gtattctagc agggcgcttt ggcaaaaggc   109440
gcagttttct agtgaaatgt tgagcgccgc tgtgatgctg tgtgtggtgt gcatgttgcg   109500
cgttagttcg catttagttt gactgtccgt ttgggtgatg atgaggctct ggcctacgac   109560
ggtggtggag acagggtagg agataccttt gatcaggtac tggtttgtta cgacataact   109620
```

```
gacgtgttcg gagacggtta gcgcggagaa ggattcgccg agcggcagac aaaacaggtc 109680
ggggaaggtt tccagcgtgc ttggttgcat ggtagatagg atggagaggg cggcgggaac 109740
ggtagcagga acgtggcat cggggaagag acgcgtgagg cgttcgagcg agtgatcgcg 109800
tcgcccgcta ctggaacagg gtgtgtacag gtcgctgagg tattcgtggt gcggatgagc 109860
tagcaactgc gtaaagtgtg atagctcggc caatgaacag aggcccgttt ctacgatgaa 109920
gatttcgcgt ctctccgtcg tatgtaccaa catggagtgg acgaggctgc ccatgaggta 109980
gagttcttgg cgcgcgaagg ctgaaagaaa agaggccagg tgcgttttgt gtaattgtag 110040
ggcaaagtcg gcgatctgtc gtagtgccca ctggggaatg agatgttgct gattctgttt 110100
agaaagtatg tagaccaggc gtacgaggct ggtgatgtcg gtgatctggt ccggcgtcca 110160
gagggctcgt ttggccaggt ccacggctgt gggatatagc agcaatgtgg tgcgtggtgg 110220
tgtttgtgag aggcaggtga tcataaattc ttgtatttgt aagagtgcgg cctggcggtc 110280
tagggctcgt gggatggaga tttcggtgcc ggcctcttct tgtcgggctg ccgcgaacag 110340
tgctaatgcg taggcgaagg ccatttctac cgtgcggcgg tccaacattt gacatcgacc 110400
gcttttgagt acgtctacag cgtaacggtg aaagctgtta cgtaacagtg cgctgaggtc 110460
caggtagttg aagtcgagtg cggcgtcgag aaagtccgag tctttgagat aggagtgacg 110520
gtttagttga gctttcttaa ctagtaccag gagctcgtgt ttttcagttt gtcgtagtat 110580
aaagttgtcg cgttgatagg gcgctttgaa gagtacgcgt ggaagatgac cgaagataag 110640
cagcatgggt gtgtcgtcgt ctatagatac cgtaactacg aagaagtcct cggtcagtgt 110700
gattttaacg taacgtagtt cgtccatgag gtaaaagccc tggtgcagac agggcgtaac 110760
ggtgctgaaa agcagatcgt gtccatcaaa gaggatacag gtctggttaa agtgtggccg 110820
atgtagtccc gaggtggtgt gcgatcccctt ccagtcgtgt ggagtggttt ggggtggcat 110880
ccaaacgtga ggtattgaca gatcaatggg cggtggcacg gtggtgggct gctgacccag 110940
gctgtcttgt gccttcagct gctgcgaaaa agatcggtag ctggccaggt ctttggatac 111000
caatgcgtag gtgttaagtc tctgttggta tctttctagg gtttcggtca gatctacctg 111060
gttcagaaac tgctccgcca gaggacccgc aaaaagacat cgaggcatat ggaatacata 111120
gtattgatta tagctttgga aaaagttgaa actgatggcg ttttccctga cgaccgtgct 111180 gttacgagg ctgctgttgt aggtgcactg ggtggtgttt tcacgcagga agcggatggg 111240
tctcccgtag gtgttgagta gtaggtgaaa tgcgtgaggg tccagcgctt cggatgcggc 111300
gtccgcgcca tatcgttgcg aaggtaggtg actgaggagg tagacggtga agacagtgag 111360
gtaggggggg aggccgggcc gcatagcgcg gctgcgccgc tgggttcagc ggcgtgatcc 111420
aggtggtggt tggcgttaca cccgagagaa ggagagaaag gatcccagga aggggcaccc 111480
gggtgtggcg ctacgggtta caaaagtcgc gtctctgtct atttaatacg atgtcattgg 111540
ccgctgcgaa ggaagaagag gggacacgcg ggtaagccat gccgtccggg cgtggggacg 111600
acgctgattc gacggggaac gctctgcgga gattgcctca cgtgcgtaag cggatcggta 111660
agcgtaagca cctggacatc taccgtcgcc tgttgcgggt cttcccctcg tttgtggccc 111720
tcaaccgcct gttgggaggc cttttcccac ccgagctgca aaagtaccgt cgccgtcttt 111780
tcatcgaagt acgattaagt cggcggattc ccgactgcgt gttggtgttt ttaccgccgg 111840
actctgggtc gcgcggcatc gtgtattgct acgtgattga gttcaaaact acgtactcag 111900
acgccgacga tcagtccgtg cggtggcacg ccacccacag cctgcagtac gccgagggcc 111960
```

```
tgcgccagct caagggcgcc ttggtggact ttgattttct gcgtctgccg cgcggtggcg    112020
gtcaagtctg gagcgtagtg cccagtctgg tttttttca gcaaaaggcc gatcgcccat    112080 cttttaccg ggcttttcgt tcgggccgtt tcgacttgtg taccgattct gtcctggact    112140
atctgggacg gcgtcaggat gagtctgttg cacaccttt ggcggctacc cgtcgccgtc    112200
ttcttcgaac cgcacgagga aaacgtgctg cgctgccccg agcgcgtgct tcggcggttg    112260
ctggaggacg cggcggtgac aatgcgcggc ggggctggc gcgaggacgt gctcatggac    112320
cgggtgcgca aacggtatct gcgtcaggag ctcagggatc tgggtcacag ggtgcagact    112380
tactgcgagc atctcgaagg gcgcgtgtcc gaggcgagg cgctgttgaa ccagcagtgc    112440
gagctcgacg aaggaccgtc gccgcggacg ctgctacaac caccgtgtcg tccgcgttct    112500
tcgtccccag ggaccggcgt ggcaggagct tctgccgtcc cacacggtct ttatagtcgg    112560
cacgatgcca tcacgggacc cgccgccgcc ccgtctgacg tggtcgcccc gtctgacgcg    112620
gtcgccgcgt cagcggccgc cggtgcttct tctacctggc tggcgcagtg cgccgagcgg    112680
ccgttgcccg ggaacgtacc tagctacttt ggaatcacgc agaacgatcc ctttatccgc    112740
tttcacaccg attttcgcgg cgaggtggtc aacaccatgt tcgagaatgc ctctacttgg    112800
actttctcct ttggtatctg gtactatcgg ctcaagcggg ggttgtacac gcaaccacgg    112860
tggaaacgag tgtaccatct ggcgcagatg acaacttttt ccatttcgca ggagctgctg    112920
ctcggcgtgg tcaacgcttt ggaaaacgtg acggtgtatc cgacgtacga ctgtgtactc    112980
tccgatttgg aagccgccgc ctgtctgctg gccgcctacg acatgcgct ttgggagggc    113040 cgcgatccgc cggactccgt ggcgacggtg ttgggtgagc tccctcagct gttgccgcgt    113100
ctggccgacg acgtgagtcg tgagattgcc gcttgggaag gccccgtcgc cgcgggtaac    113160
aactattacg cgtatcgcga ctcgcccgat ctacgctact acatgcccct aagcggtggt    113220
cgtcactatc acccgggcac ttttgatcgt cacgtgctgg tgcggctttt ccacaaacgc    113280
ggcgttattc agcatttgcc gggctacggg acgataacgg aggagctggt gcaagagcgt    113340
ctgtcgggcc aggtgcgcga cgacgtgctt tctctctgga gtcgacgtct gctggtcggc    113400
aagctgggtc gcgacgtgcc cgtctttgtg cacgaacagc aatatctgcg ttcgggcctg    113460
acctgcctgg ctggcctgct gttgttgtgg aaggtgacca acgcggatag cgtcttcgct    113520
ccgcgcacgg gcaaatttac gttggccgac ctgctgggtt cggatgccgt agccggcggc    113580
gggttgcccg gggggcgcgc gggcggcgaa gaggagggct acggggacg gcacgggcgg    113640 gtacgtaact ttgagtttct ggtacggtac tacatcgggc cgtggtacgc gcgcgacccc    113700
gcggtcacgc tgtcgcagct ctttcccggc ctggctctgt tggccgtgac cgagagcgtg    113760
cgcagcggct gggatccctc acgtcgcgag gacagcgccg gaggtggcga cggcggcggc    113820
gccgtgctca tgcagctcag caagagcaac cccgtggccg actacatgtt cgcgcagagc    113880
tccaaacagt acggcgattt acgtcgctta gaggtacacg atgccctgct ctttcactac    113940
gaacacgggc tagggcggct gttgtcagtg accctgccgc gtcaccgtgt gtccactctg    114000
ggctcgtccc tctttaacgt caacgatatt tacgaactgt tgtacttttt agtgttgggg    114060
tttcttccga gcgtggcggt gttgtaattt ccaccacgtg tcgctcgctg cataaagggc    114120
gaacgtcctc ggagagggta tattcgttcg gcgagagcgg gcggcggtgg tgggtatgtc    114180
cccttctgtg gaggagacta cctcagtcac cgagtccatc atgttcgcta ttgtgagttt    114240
caaacacatg ggcccgttcg aaggctactc tatgtcggcc gatcgcgccg cctcggatct    114300
actcatcggc atgttcggct ccgttagcct ggtcaacctg ctgactatca tcggttgcct    114360
```

```
ctgggtgttg cgtgttacgc ggccgcccgt gtccgtgatg atttttactt ggaatctggt    114420
acttagtcag ttttttttcca tcctggccac catgttgtcc aagggtatca tgctgcgtgg    114480
cgctctaaat ctcagcctct gtcgcttagt gctctttgtc gacgacgtgg gcctatattc    114540
gacggcgttg ttttttcctct ttctgatact ggatcgtctg tcggccatat cttacggccg    114600
tgatctctgg catcatgaga cgcgcgaaaa cgccggcgtg gcgctctacg cggtcgcctt    114660
tgcctgggtt ctttccatcg tagccgctgt gcccaccgcc gctacgggtt cactggacta    114720
ccgttggcta ggctgtcaga tccctataca gtatgccgcg gtggacctca ccatcaagat    114780
gtggtttttg ctgggggcgc ccatgatcgc cgtactggct aacgtggtag agttggccta    114840
cagcgatcgg cgcgaccacg tctggtccta cgtgggtcgt gtctgcacct tctacgtgac    114900
gtgtctcatg ctgtttgtgc cctactactg cttcagagtc ctacgcgtg tactgcagcc    114960 cgctagcgcg gccggcaccg gtttcggcat tatggattac gtggaattgg ctacgcgtac    115020
ccttctcacc atgcgtcttg gcattctgcc gctctttatc attgcgttct tctcccgcga    115080
gcccaccaag gatctggatg actcctttga ttatctggtc gagagatgtc agcaaagctg    115140
ccacggtcat ttcgtacgtc ggttggtgca ggcgttgaag cgggctatgt atagcgtgga    115200
gctggccgtg tgttacttttt ctacgtccgt ccgagacgtc gccgaggcgg tgaaaaagtc    115260
ctccagccgt tgttacgccg acgcgacgtc ggcggccgtt gtggtaacga caaccacgtc    115320
ggagaaagcc acgttggtgg agcacgcgga aggcatggct tccgaaatgt gtcctgggac    115380
tacgatcgat gtttcggccg aaagttcctc cgtcctctgc accgacggcg aaaacaccgt    115440
cgcgtcggac gcgacggtga cggcattatg agcggcggcg ctgtacggca gcggggagaa    115500
aagtggcaga taaatcacgt caggttcaca cgtcgttagc cagcgtcggc atatgaaggg    115560
cgcgggcggc cagtacggcc tctgggctga gacaggacga ggcagggtga gaaagaggag    115620
gatggggggg accggggtgg tggtgctgct gctgttgtgg gtgcggacgg tgcgggtgcc    115680
gggacagcgt gccggcgaac gttctgtaat cttccataat aaaagtaaaa atgcccgtct    115740
cgtgtcgact ccgctggatc tcgaaggcgt cggggggtaat gcgcatcttg ccggtgccga    115800
tgagataaaa gtaccacatt ttttgacaga tgatgcgaat caagggttcg tacgcttcgg    115860 cacccccagtg gcgcgtgaag aaggccgcca gacgaaacaa gcggtgtccg tagagcgtgc    115920
ctagggagaa gaggatgttg ccgttgcgcg ccaggtcttc ggggaaaacg accggcaggc    115980
cggtgtggcg ctgcacaaag cgcgtcagca gtccgccgct caagcgcggg tgacacaggc    116040
gctggctgag acgggcggcg cgcgtttcat cgaacacggc cgcctcaaag tccagccccg    116100
ggaaggcctg gcgcagttcg cggtacagat gaggccagta gggttgcggc gtcttgcgac    116160
taagcacggc gtggtccgag acacccaggt tgttcatggt ttcgcgcagt agcagcgttt    116220
cgagaccgcg gtgaaagagg aggacgcaga tgaggcgtac gatcttgagt tcttccaaac    116280
gcagcgagct cagcggctgt ccgcgcgaca tcttctcgct aatctgtaat attagatgat    116340
tggcgcaagt aaaggagaat tgcccgtgc ggacccgcgg gacggcgggg ttctcttcgt    116400
cgcgggccat catcgttcgc tcggtgagcg ggtagcgacg gtgacgacaa tgacgatgga    116460
cgagcagcag tcgcaggctg tggcgccggt ctacgtgggc ggcttctcg cccgctacga    116520 ccagtctccg gacgaggccg aattgctgtt gccgcgggac gtagtggagc actggttgca    116580
cgcgcagggc cagggacagc cttcgttgtc ggtcgcgctc ccgctcaaca tcaaccacga    116640
cgacacggcc gttgtaggac acgttgcggc gatgcagagc gtccgcgacg gtcttttttg    116700
```

```
cctgggctgc gtcacttcgc ccaggttttct ggagattgta cgccgcgctt cggaaaagtc   116760
cgagctggtt tcgcgcgggc ccgtcagtcc gctgcagcca gacaaggtgg tggagtttct   116820
cagcggcagc tacgccggcc tctcgctctc cagccggcgc tgcgacgacg tggaggccgc   116880
gacgtcgctt tcgggctcgg aaaccacgcc gttcaaacac gtggcttttgt gcagcgtggg   116940
tcggcgtcgc ggtacgttgg ccgtgtacgg gcgcgatccc gagtgggtca cacagcggtt   117000
tccagacctc acggcggccg accgtgacgg gctacgtgca cagtggcagc gctgcggcag   117060
cactgctgtc gacgcgtcgg gcgatccctt tcgctcagac agctacggcc tgttgggcaa   117120
cagcgtggac gcgctctaca tccgtgagcg actgcccaag ctgcgctacg acaagcaact   117180
agtcggcgtg acggagcgcg agtcatacgt caaggcgagc gtttcgcctg aggcggcgtg   117240
cgatattaaa gcggcgtccg ccgagcgttc gggcgacagc cgcagtcagg ccgccacgcc   117300
ggcggctggg gcgcgcgttc cctcttcgtc cccgtcgcct ccagtcgaac cgccatctcc   117360
tgtacagccg cctgcgcttc cagcgtcgcc gtccgttctt cccgcggaat caccgccgtc   117420
gctttctccc tcggagccgg cagaggcggc gtccatgtcg cacccctctga gtgctgcggt   117480
tcccgccgct acggctcctc caggtgctac cgtggcaggt gcgtcgccgg ctgtgtcgtc   117540
tctagcgtgg cctcacgacg gagtttattt acccaaagac gcttttttct cgctacttgg   117600
ggccagtcgc tcggcagtgc ccgtcatgta tcccggcgcc gtagcggccc ctccttctgc   117660
ttcgccagca ccgctgcctt tgccgtctta tcccgcgtcc tacggcgccc ccgtcgtggg   117720
ttacgaccag ttggcggcac gtcactttgc ggactacgtg gatccccatt atcccgggtg   117780
gggtcggcgt tacgagcccg cgccgtcttt gcatccgtct tatcccgtgc cgccgccacc   117840
atcaccggcc tattaccgtc ggcgcgactc tccgggcggt atggatgaac caccgtccgg   117900
atgggagcgt tacgacggtg gtcaccgtgg tcagtcgcag aagcagcacc gtcacggggg   117960
cagcggcgga cacaacaaac gccgtaagga aaccgcggcg gcgtcgtcgt cgtcctcgga   118020
cgaagacttg agtttcccag gcgaggccga gcacggccgg gcacgaaagc gtctaaaaag   118080
tcacgtcaat agcgacggtg gaagtggcgg gcacgcgggt tccaatcagc agcagcaaca   118140
acgttacgat gaactgcggg atgccattca cgagctgaaa cgcgatctgt ttgctgcgcg   118200
gcagagttct acgttacttt cggcggctct tccctctgcg gcctcttcct ccccaactac   118260
tactaccgtg tgtactccca ccggcgagct gacgagtggc ggaggagaaa cacccacggc   118320
acttctatcc ggaggtgcca aggtagctga gcgcgctcag gccggcgtgg tgaacgccag   118380
ttgccgcctc gctaccgcgt cgggttctga ggcggcaacg gccgggccct cgacggcagg   118440
ttcttcttcc tgcccggcta gtgtcgtgtt agccgccgct gctgcccaag ccgccgcagc   118500
ttcccagagc ccgcccaaag acatggtaga tctgaatcgg cggattttttg tggctgcgct   118560
caataagctc gagtaagaga gacgctatat ttagggcttc cctctctttt ttttctacac   118620
cgtgataccc taataaagca caccgcggtt attatcaacg tctctgtgtt tttattattt   118680
agaaataaat acaggaatg ggaaaaacac gcggggaaa aacaaagaag tctctctcta   118740
gatgcggggt cgactgcgtg gggtgctgga agtggaagcg gtgctgatgg gtgagggtcg   118800
tggcgcgggc acggaccgca acgtgctgct gatgtctgcc gcggtacgca cgtcgccgtc   118860
catgtcgctg cgcagataag aggtaggtcg tagtgcggcg tgctgcacgc tcaccgttaa   118920
tggtaccaag tcgtcaaggc tcgcaaagac gtgccacgag gggatgacga gcgtgagagc   118980
cccgttgtta ccgcttcgac gtctttgtcc ggtcaggatc agtgccgggg acagtccggc   119040
ttgggtgtcc gagtcctcgt cgccgctggc ttcctcgaag ccggcaaaca tggcttcgga   119100
```

```
caggggggtc ggcgtcggtg tggaggagag gtcatcttcg tcgtcctctt cctcttcttc   119160
ctcctcttcc tcggtgggtg gtaatccggg ggactgcggg agaaactcgg agacggcgcc   119220
gcgcatgacg ttgctccgtg gaaagagacc ggcgcgcagc tgcacctggg gacgcttgat   119280
tttgtccggt ttaccgggtg tgagagtcca aaacccacgg cggaaaaagt ggatgcggcc   119340
tagcggctgt cggtgttcca aatgaacggc ctgatcgccg gtcagcgtga cgcggagggt   119400
gattcgcaca cgatcgggta gcgggccggc ttctatggag acgcccggga tgttttccgg   119460
gaaaaagatg gtgtcgtgag tctgattggt ctcgaaagca ttctggatct gcacgatgta   119520
ctcgggatgt atgcgcgtca gcgtaaaact tttgggaatc aacagctgga agccgttgtc   119580
cggcaagcgt cgtaggtgcg ggtacggatt gtgtcgcgcc accacctcgg cgcgatgcgt   119640
gtaaaccgaa aagtgcagaa acacgctggt cggcgggtgc ggtgagtcgt gatgcagaaa   119700
cagcatgatc cattggcctc gttcgtccgt ctccgttttg tggatgtacg tgttagggtc   119760
cgaacaggcc agctgctcca gggcgtctac cagcgtcagc gggatggcgc cggcgcgaaa   119820
ggcgaactgg ctgacaaaga tctgccctgc ctccaaactg ctgtcggttc tgcggcgcca   119880
gttcggcgtt acggtcagtc gcacggccca gtggtgagcc gtgcggcgga tgatggcgcg   119940
cgcttccatt cgcggccgat tttcttcgcc gccgcgccgc tggctctgaa agaggtgcag   120000
tccgctaacg ggcacgcggt ccagcggcag cgcaaaggcc agtaccgaga ccgtgttgtt   120060
ttctgagcct ggcgtcaggc gtcgtgggcc aaagttgttg aggtccacca gcagtcggtc   120120
ctgttcgccc accacgcagc ggcccttgat gtttaagtcg gtcaggtcta cggtgtcgtg   120180
cggagatttg ttctcctgaa aacagcagag aaccgagggc cggctcacct ctatgttggt   120240
acgcaggtcc aggagtcgca gacgaccggc ttccagcgag ccgccttcca cgttggtgat   120300
gagccgaagc acctggcagt gcaggcgacc aaagcttccg ctggcggctt cggcctcgct   120360
gatcgcggcc gcttccgacg agggtccctc accgggcgag gacgatgcct gagacattgc   120420
gaaggcggga tgggggaggg gtcagggggat gcgcaaaggt gaacgggtct tcgtgggagg   120480
tcggaagggg ttccggcaac tgtcgcaaat atagcagcgg tgacaggtgt ggcggccaaa   120540
agttgcgtgt ctgagtggac gtgggttttt atagagtcgt cctaagcgcg tgcgcggcgg   120600
gtggctcaac ctcggtgctt tttgggcgtc gaggcgatgc atggcccggg caaggcgtct   120660
tgccggtggc ggcgacgttt gggttgcgca gcgggctgcc atacgccttc caattcggcg   120720
aagatgcggt agatgtcgtt ggcgtcccag aagaattcct ggtacttcag attctgaccc   120780
tgaaccgtag ccaccatggg caccaggttg cgggccagga tgccggcctg ccagggcggc   120840
caggtgaaca cggccggatt gtggatttcg ttgtcggaat cctcgtcggt gtcctcttcg   120900
ggcgcgacgg tggactcggc cttaaggcgg ccgcgtgtca taacgcccga cgtgcacgcc   120960
gtcgccgagg atgctgattt gcgtttgcgg cccgcggaag tggaggcgcc cgccatggcg   121020
ccgccgccgg tgacgcgggg cgtcttcgcg tcggtggtta cgagttcttc gtcggagtcc   121080
gatccgctgg tccagacgtc gtcgtcgccc tgggcggcac cctcgtcgtg ccggtcccag   121140
gtgtgtcggt actcaagctt gccctggatg cgatactggc tggtgaaggt ggggtgctcg   121200
ctgtactgag gcccgcgctg cagcagcaag tcgatatcga aaagaagag cgcagccacg   121260 ggatcgtact gacgcagttc cacggtctcg cgtatggctt gtacctccag gaagatctgc   121320
tgcccgttca tcaacaggtt acctgagatg ctcaggcccg ggatgctctt gggacacagc   121380
agcccaaaat gctcgtgtga ggtaaaagcc acatccagca tgatgtgcga gatcttgccc   121440
```

```
ggtttgatta tcatattttt gggacacaac accgtaaagc cgttgcgctc gtggggcgc   121500 atgaagggtt gcgggttgcg ggtcatcgtc aggtcctctt ccacgtcaga gcccagcgtg   121560
acgtgcataa agagcttgcc ggagggcacg tcctcgcaga aggactccag gtacaccttg   121620
acgtactggt cacctatcac ctgcatcttg gttgcgcgcg tgttctccat ggagcaaacc   121680
agctcgtgcg cgcacaccac gtgccgcagt gccacgtcct tggtgggaaa cacgaacgct   121740
gacgtgtagt agacgtcggg ctcttccac tggttctgct gacgcgtcca ggccagtccc   121800
gagaccgtga gacgcgcctg ccacatctgc ttgcccgacg cgtgaatcac agcgtcagct   121860
acgggcaggt gtcggtgttt gcgctcggcc gccgacgggt agtggtgcac gttgatgctg   121920
gggatgttca gcatcttgag cggcagcgcg tacacataga tcgacatggg ctcctggctg   121980
gggcagatgc ttcggcccgt ggggttgtgc acgttgaccg acacgttctc cacctcgctg   122040
cccgtaaagt acgtgtgctg cacctgcagc tgattgtcgc cgcggtggca tggcgtcgag   122100
tcgggcgtgt actgcgatac caagatcagc gagggctggc tcacgcgtac gtggataccc   122160
gtctgcagga gtcgcgtctc gtgcggcagc accggcgtat cgccgcgact aaacacggct   122220
ttcagcacgt gccccgaaat gggacccagt acggatatca tttcgggaca acggcgaccg   122280
cgcgactcca tgctgcctgc gcgtacgggt gtaggcgact gagcggcgcg ccctctgcgg   122340
ccgccgcctt acataggcag gcgaccaaac gcggaacccg aaataaaaac gttctacaca   122400
gagacaaccg cggattattg agtgtctttt tttattacaa aaaaagagg cgaagcccca   122460 ccgtcaccac accccatcac acaccaccac cgattttttt ttgttttaat cccgtatggc   122520
gcggacgcct agtgtccgtt tcccattatc agggtcctct gtttagagat cgccgcagac   122580
catggctaaa gtgacaggac tcgtcttctc tgtcgtattt tccgtaagct tacagtcttg   122640
cggttccgtc tccggggacg ccagtcgcat gggcagcagg tcctccagcg cgatggaagc   122700
gcccagcacc gagagctgct gttgcgacgg cgaatgggat gtggaccgcg agtgtagcgt   122760 ggattgact tggtgcgtca ttgctgacag gcaaccccga ttcagcgtat gctttgacga   122820
gataaaatag aggcgcccca ggagcgcgtc ccgtgggaac gtggcgccgt tctcgtcgct   122880
caccagtacg gttaattcca accaggagcg cggtagccag accgtaacgg gcattttgag   122940
tccctgacgg ttgtgtggta caaaaacacc cagataaggc ccgtaaaagc ggcggtagat   123000
acgtaacgtg tgcgagttct tcagcgtcaa ttcgtaaggg acgcgcacct ccagtccctc   123060
gtccgccgcg ccggagcgtg gcggtacaaa gtaaggcagt ggcgcgtccg aaaagaaggg   123120
tcgtcgcacc gtttcgcgtc gcagccgcag gcgaaacgcc actgggtcgg ctggcgcctc   123180
ggtgcggtcg caggtcacgt tgaaacgtaa tatgccgtct tggtatagcg tgagtgacga   123240
cagcgtcagg tccggcggtg attcgttcgg gtctagctcc aatcgtccaa agacggaggg   123300
tcccaatgtc ttggccgtgg tttccgagag gcgcgccgag atacggctgg tgagtccacg   123360
cggccccgag atgccgcctt ccactcgatg ccagcacagc gcgtgtcgta cgcgcaccgt   123420
cagcgtgggc gtcagatccg cgtccgttga ttccgcggta tcagcgacgg aagccgcgtt   123480
ctccgttacg ttgtttatat ccagcgtcgg ctcgaacgtg agttctggca gatgcagcgc   123540
cagacagtcg tgtaacgccg tgtgatgcgc ggctttacgt cgtagcggta gccgtttcaa   123600
cagcggcgtg atgatacgga gcgcgaagag attgagtgat aggcgcacga tggccatgcg   123660
cgtcagttgt tggtcaatta ccgagcgcag gatatggcag cctgggcgtg cgggaaagag   123720
agagaaggcc gggcgcacgt cagaatcctc gttagagacc acgcatagaa tgccgcgttc   123780
acgatcgtcg ttgcggtcat cctcgtcctc ttctttcttc tcttgttttt ccttttttt    123840
```

```
ctcgggctcg tgggaagccg ccgtttcttc ttcttgcaac gtcgcgggg cggtttgaga   123900 ctcgtcgttc gcttccccca attgcagcgg cgtagagagc agaatctgga agggatcccg   123960
caattcttcg ggtcggaggt cgaggtgcaa ctggatcaga tggtaggtgc cgcggtgcac   124020
ccgaggctga cggatgtcgt gtttatccgt cagtgtgagg atggtctgcg gcgagccgct   124080
gtacttgtcc agctcgtccg gcgttttcag gaggagactg tcgtcgtcgg tactggcgac   124140
gcccatcatg gtcgtggtgg tagtggtggc gaggaaagtg agcggcggcg ccgacagagc   124200
tcggcgttgg cggcggcatt ttccgctgtg tcggctgcta ttgctgccaa cgccaccgcc   124260
gccgcctcgt ctggctcgtg gccggcgggc ccgattccga aggttggggt cgacgcgtgg   124320
catgcttggt gtctgcgggc gcgagagggc cggctcagcc tttaaatatg caggtcgcgg   124380
atttgttatc gggtgaaacg tcacacaccg tgaagacgac ctgttcgcgg atgaggtcat   124440
ccagctgtcg cagcatgacg aaaagcgccg acagccgcgc gatctcgtcg tcgggcgaca   124500
cgtgctgcgg ccgcgcgggc gtgcgcggct cgccgacgct gcgctcgcgg tccagccgca   124560
tcagcagctc ctggcacttg acgagcagca tggagctgtc ctctagcgcc aacttgcgca   124620
cgtaggtcat ggtcagctcc gaggctaggt tggccaccat ggacatggag aggcaggcgg   124680
tcttcatgtc gatcagcagg tgctggtcga tgaccggatc ggggatggtg aaggtggcgt   124740
cgcgaaaagt aatggtctgc agctgctgca cggcagcctt tacctcctcg tacgaacggt   124800
cgagcgagaa gaggcccatg atgagtagtc gctggttgat ttccagcgcc agtggcatgg   124860
gtacgatcca gggcagcacc agctcccact ggcccagcgt cagcaggttc tcgcgcgcca   124920
gcggtccgtg gaagagcggc ggcagcacgc atagcgcgtc gcccttctcc caagtcacgg   124980
gtcccgtgtt gaggacggtg tagagcagtc cgtgcgtggg tacgtgtagg aggatctggt   125040
tgccttctac gcgccgcatc aacgtcagcg tcatattgcg cagcaggccg cgcagtcgta   125100
cgtagccgcg ggtgtgatct acgaactggt gtaggcccag ctggtagtgc ttgatgagat   125160
gtagacgttg cggaatgggc acaacggccg ctactagctt ggtcagtttg cctacgtcgg   125220
cgatgctgag cttgtggtcg aaagtgcaga agatgttggc ctccatgcc gccatagcgg   125280 cggtgaaatc ctggccgcga cggaggagag gcagagacga acaacgtctg caccgggcgc   125340
ggcgtcagag cgagcgtggc gcgtccgggc ccgcgtttgc gtctaggtga ctcgccgcta   125400
acctgcggtc gtcgccgtcc tcctcaccgg acggcctcac gagttaaata acatggattg   125460
ctgcagcggg atgatttcgc ctacgacgta gttaccaaag tgcgtttcgg acgtagcaaa   125520
agccccggcg ccaccccttga gtttggtctc catcagcgcc agcgtggtgg tgctgaggat   125580
cggtagcgct tcctgcgtca gacggcacgg gttttcgatg agttgttccg tgccttcgac   125640
gcagacgtac tgcgtgtccg tgtcgccgcg gatgcagtcc ttggcgcgta gcaggtactc   125700
gtcgatggtt ttgaagagcg ttttgttggc cgcgataatc tcttctgtgt taaagtactg   125760
cgcgcaaggg ctgtagaatt tggagttgta gcctagacgt tcgcgatgtc gggtgttgta   125820
gagtacgtcg ctcagacagc cggcttgcga ggcccagggg ttgtgtgtgg ccgcgaaagt   125880
ctgtgcgtcc gcttcgcgat ggtcgtagat ggccttggtg gcggcctccg tgtcgtacgg   125940
atcgacggcc agcatgcagg aggcacgccc gcgcgggttg ttggggatct aaagtaatt   126000 aacgtccatc gtcaccggcg taaggattag ttcgcacgcg gccttttgtc cgtgcaccgt   126060
ggcggcggca ttgcgctcgg acatgctgcc gaacgtcagc atagagatgg tctccgtgtc   126120
taacagttgc ggccgttcta cgccggccgc gtgccggatc cagcggtcca cctcgtcgtg   126180
```

```
ccggtacacg ttcataggga agacgcgaaa gaggtcctgc acgcggacgc ccatgtcggt   126240
tcgcacgcgg tttacgtagg ctacgcaggt atttgacgtg taacccagac ccatgtctac   126300
ggtgttaatg ttctgcgtga cgtggtacgt agtgctgatg tcgcgttcct ccttggtcac   126360
gatagggttg ttgatgataa ctgacgtgca tgatttgccg ctgtagagca gcatgtccac   126420
ctcgaaggtg tcggtgcgta cggccgtgag tgcgaatccc gggtggatgt gcgccttggt   126480
ctgcagcacc agtgaaactg gtgagatttt gtataacatg gcggccagcg tcatgactga   126540
gtgcaacacg ttgggacagg tggccgagta acgcgaaaag ggcgagcgca gccagttgtg   126600
gtactcgtgc gcgaaggctg tgggtagcgg gaaaccaccg tcgtgacggt gatagtgcgg   126660
gaactcggtc acgtagcgtt taatgtcgtc gctcaacgcc gcgcagatgg tggggtttga   126720
gtagaaacgg tggaaaggta cgggtaggct gtactcgatc aacgtcttag gcgccgtcac   126780
gacgcagcag ccgttgtaaa gcacgtgctg acgtgagata aagtccggca ggccctgacg   126840
ctgcgcgtgg tccagaggcg cgcgcacttc gagcaccttg acgtgctcgc ccacgaattg   126900
cacggccaaa aacagttcac gacaggcctg cagcagcggc gtatgtgcgt cggtggcgac   126960
gtcctccacc agctcggtca gcatctcgcc tacggcttga cgttgcgccg ctatcgagtc   127020 ttcggggtg acaccgcttg tgctctcttt cgacgtcgta cctgacgtgg agaccgcggt   127080
ggcggccggc atcaggagaa acgccggtcg gtaaagagg tctactagca gcgtcttgag   127140
gttgagtccc aggccgcagg cccggttgtt ggtcatggcg gcatgaggc agagataaaa   127200 gaccttttgt aacgtccatt cgtcgtcggt ggcacggtaa tcgtccacaa acagcggctc   127260
gtcggcatcc atgcgcccca aacgcggtac gtccgaaacg ccgtggtgtc gcgcctcgat   127320
gttggccggg ttcaacggtt gccggtcggc cactacctgt acgccttcca tgttacgcgg   127380
caggtgcgta acgaagggg gccacagccg gtggtcgtgc agcgcgttca cgtaagccga   127440
tagcggttcc tcagccagtt gaccgttgtt aagtcccggc agcgctgaga tgcgcgttac   127500
cagacgcagc acgcgaccca gattgcggta gtgaaagagc aactgcggtg gtagggcgcc   127560
atcagccagg tgttcggcga tcaacgtcac cagcgcgtag ctgtgcgcaa aaaccagcag   127620
ctgacgtgtg tgaaacatgt tgacgataca acgtgctacg aaagtgcgga ttagcaaaaa   127680
agcgtcgacg ttgccgtgta ccagcacgtc gaccaggtag caaagctcgg ggtaattggg   127740
gcttgtcacg gtggttttga aaagtcgcaa cgtctcttcg tagtcgggtg gtggccgcag   127800
tcgcatgtgt tccatgatct cccaggtgcg cagttcgtgg aaggggcccg gtgccagtcc   127860
atctggcaaa ttaccgatga cgatacgcgg tgtacacagc gccaccgttt cgctgttttc   127920
ctggcagtgc gtaaagtcga agaaggggtg cagctcggtg tagagcgtga tgttgcccac   127980
cttgtagaag tcggtgacca caaagtcctg cttcatttcg ttcaccgtgc gcgggacctc   128040
gcgtcgtacg cggtaaaaat gcggtatgcg gcgcgccgca ccgcccatgg gttcctgctg   128100
aaaacgacac tcgagcagtc gttgcatggc gggttccgag ggcggtccgc gttccgtgaa   128160
ggtctgtaga cagggcgcgg gctcgtgcag caccgggtgg cacagcgtct tgagcgcgtc   128220
cacaaagtct atttttgta cggcacggtc ccggtttagc aggtaggccg tggtgggcaa   128280
cgcgttgcga acggtgtcgt taagcttaac tttgctttcc accgtggtgt aaccgcgatc   128340
ctcgggcaga tacagcccta cggggaagaa aaacgtcagg tccacgttac gttctagcgg   128400
atctttggta tcggtgtttt tgtagacgcg ccgcaagttt tccataatca ccgttttttc   128460
gcccagtcga atcacgtcca tgctcagcgg cgttaagctg tgcgcccgg cctgcgaaag   128520 cgagtcgttg ggcaaatgcg gttggcccga agtcagatga gccttgtacg agttgaaatc   128580
```

```
ggccaggatc gagtgatagg atatggcagt gacggcattt tcgggactga gtacaaaatt   128640
gccgtaggtg gccggcgccg agaccgtttc tttggtgatg tggcttgaga gcagcgacat   128700
gatgatctgc ataacgttgg ccgtgcttac catcacgccg ctgatcttgg cccccgagct   128760
cgtggtgtac gtggtggggt tgtctaggat gctatcggtg gccgcttcgg ccagacgcgt   128820
gaggaacttg agcacatagt cgcgatcgcg cgtgcgattc agcaaaaaga gcgtggccag   128880
cattttggcc ttgaagctct gcaagatgtt gcttcgctgg atgcggttca gtgcctgtcg   128940
cgccagtgtg gcgttttcta ccagcgtctg caccacaaag tacggcggcg ccttgcgtag   129000
cagtgtctgt aaaaagctgt gaatcaagcc gcgctccatg gcgtcggccg tgtttttaag   129060
cgcgcgcagc accgtgtgca tggcttccac gttgaggatc ttgtccaaga tggtgccctc   129120
gaatgtctcg cgcagatacg tgaggcaggc tgcgctgagc tcgaagggga tggtgatggg   129180
ggatttttca ctgtatttgg tgaccataat ggtggtctga cgactagtgg gcaaaccggc   129240
gccgctggcc acacgcggca cctgcacgtg aacagcatt ttgcccgtag tcagtttatt   129300
gaggtcgtgg aacttgatgg cgtgcgccgc cgcggccaag ccgctggtca aaaataaac   129360
ccattccagg cgattgcaga aggtgccgaa gatggcttcg aagtgaatat tgtaacgctc   129420
ggggtcatcg ccgtagtaga tgcgtaaggc ctcaaacatc tcctcgccgg cgctggtctt   129480
gacgtgcgtc agaaagtcag tgggaatgcc tactttaggc aggagctcga gcgccgacca   129540
gttctccatc gcggcggcgg cgtgagcgcg aggcgtcgga gctcggggaa agcagcgcga   129600
cccggagaat ggccggcgct gcgccgcgcc gcctcggctg tgacgctcta atagtcgttg   129660
gcggctccgc tatgccgcgc cgggttttac acgtccccgt gcacgttcgc gcctgcaacc   129720
tcacccaaga gctatcgacg ggcgaggacg cccgcttttg tcgtccgcga cccgttaacg   129780
tcgaacgggt gcgcgctgtt tttgcggctc tctaccgtgc ctgtccgata cacgtgagga   129840
ccgagcccga gcgtgtcaag ctggtactgg gtcgtctgtt actgggaccc gtggccgtac   129900
cctgtttttg cgacggtgaa gtggagggcc acggtgaaca tctggtacct acgacgcagt   129960
tttgtcgcgg gccgctgctc tacgtgcacc gacgttgttg ttgcggatcc gtgaccgccg   130020
ggcgcgcgct gtcctaccac gttctcgaaa accacgtggc cacgcatgtg ctacgcggat   130080
tgctctcgct gacggaatgg aatcgagaat tgccgagcct cttttgcgac tgtcctggcg   130140
gcggtggcgc ctcgggaacc gaggaacgct acgctatggc ctgcctgccg cgcgacctca   130200
gcctgcacct ggacgactat ccttacctga tggtggaaat cggacgcgta ctcagtgtca   130260
gcgaggtaga cgactacgta accgccgtct ccggctacct gggcgaggcc gcggcgccgc   130320
gcatccaggt tcactacaag ctgctctttg gactcaacgt gcgtccgcaa gcgccgtgcg   130380
cgttggacgc tacacgcgac ttttttctgc tggagctgca aaagctttgg ctgggcgttg   130440
aatatcacca cgaagtcacg tcggagtttt tcggtcgcgt actggctcag ctgcatcgcg   130500
accgcgcccg cgtcatgatg gcgcttcgct gcccgagca gacggtgtgc cacctgagca   130560
ccttcgttct cagtcgcttc aagcgacagg tactgtactt caagctacag gtgagctacg   130620
gcaagtgccg gactggtcac gctgacagaa gtgggggagg ggggaacggt ggaaatcagg   130680
gacaccacaa cctactgtgt tatcgacgcc ttagcgtcac atttgccgac acagacacgg   130740
tgtggagaaa ccttttctac gtttattacg aactagctcg ggatctgggg tcccatggga   130800
cggaggaccg acccgtaagc cgcggttacg gtgtttcttg cgcttcgagg acgtcgcgac   130860
tgtcaccgtc agaatcgacg gtggtttcgg cgaacggaca cgcgctgtct tccaccgcgc   130920
```

```
tcccgacgac gagcgcgggt cacaagctgt cactgccgcg cgacccggcc gcagatcgcg   130980
ttcgacgtta cgtatgcatt atctcgcgtc tcatgtacgc tcggtacggg gagagatggc   131040
gtaaacactg tcaacggcgg tcggagacgg gagaaggagga ggaggaagag acgctggaat   131100
cgggggagac tgacgccacg ccgccatttg actttacggg gcagcagctg cgccgggcct   131160
atcaggaaca ccgacgtcgt aaacatctag ccgtgcagcg ttacgcgccg tgccgtcgta   131220
agctcatcgg cgggatggag tttgccgagg tgacgggcgt gagtctagac cgcatcgccg   131280
tcaacgcttt caacaccaac cgcgttatca atatgaaggc tgcgctctcg tccatcgccg   131340
cgtcgggtct cggcgtacgc gcgccgcggc ttcccaagaa catgacccac agttttgtga   131400
tgtacaagca cacctttaag gagcccgctt gcaccgtcag cacttttgtt tccaacgacg   131460
ccgtctacat caactcgctc aacgtcaata ttcgcggttc ctaccccgag tttctgtact   131520
cgctgggcgt gtaccggctg cacgttaata tcgatcactt ttttctgccg gccgtggtgt   131580
gcaacagcaa ctcctcgctg gacgtgcatg ggctggagga ccaggcggtg attcgctcgg   131640
agcgcagcaa ggtgtactgg accaccaact ttccgtgcat gatctcgcat actaacaacg   131700
tcaacgtggg ctggttcaaa gcggctacgg ccattgtgcc gcgcgtctcg ggcgccgacc   131760
tggaagccat tctgctcaaa gaactctcgt gcatcaagaa catgcgcgac gtgtgcatcg   131820
attacggtct gcaccgtgtt ttcacgcaac tagagctgcg caattcgtac cagatcccct   131880
tcctggccaa gcagttagtg ctgttttctgc gtgcttgcct gctcaagctg cacggtcgag   131940
agaagcggct gcagttggac cgcctagtat ttgaggcggc acagcggggt ctctttgact   132000
acagcaagaa cctcacggcg cacaccaaga tcaagcacac ttgtgcgctc atcggcagtc   132060
gtctagccaa caacgtgccc aagatcctgg cccggaacaa aaaagtcaaa ttggatcacc   132120 tgggccgaa cgccaacgtg ctgacggtgt gtcggcacgt ggaagcccac aagatccctc   132180
gcacgcgcct caaagtgtta gtcgaggtgc tgggcgcgtt gcagagtatc agcggtacgc   132240
cgcacacgcg cgaagtgatc caccagacgt tgtttcgatt gtgctcggcg gccgcagcca   132300
catcgggcct gtgttcatcc cctcccccat tgtgtgtgtc ctcatcttcc tccgtccctt   132360
ctgtcccaac ctccgtcagc gttgacggca gttctgaacc cacgtcgccg cgagcgcggt   132420
ttgcatcacg atgatggaag ccgcggccgc tgccgccgcg gcgtttcgtc cggaggagcg   132480
tccgacgccg ggttggcacg acgcggcgtt gttaatggac gacggtacgg tgcgcgagca   132540
cgcgtttcgc aacggaccgc tgtcgcaact gattcgccgt gtgttaccgc cgccgcccga   132600
cgccgaagac gacgtggttt ttgcttccga gctgtgtttt tattgcagcg gtcgttttaa   132660
ccgcaggtcg tccgtcttct ccatctattg gcagaagcat agcgatctgg tgtacgcgct   132720
tacgggcatt acccattgcg ccaagttggt ggtggaatgc ggtcagttgg ggagtagtag   132780
gctacggtgg cgcgacggtg atgcgagtgg tgaggagcgc cggggagacg acgacagcag   132840
ggacgagctg tacgacgtgc cgggcattta tatgattcgc gtcaacgacg gcggcagcac   132900
cggccccaga cacgttattt ggccgggtac cagcgtgctt tgggcgccgg acgttgtgat   132960
cactacggtg cagcgacgaa tctcggcggc gcgcgccctg tgaacacgt tccgccaata   133020 tttttttttg ctggaacggc gctcgcacga ggagctggtt ctttgtccgc ccagagatgga   133080 ggagcgtcta gcgccgctgt tgcagagtgc cacgcgcggt gattcggaca tgtttgacgg   133140
tgtggtggcc agcgcttatc accgtttgcg aatgagtaat attccgcgtt catccgcccg   133200
tctgctggaa cactgcgtgg ggctggcggg tgctaagaag ctgctcttgc tcgacgtgcc   133260
gcgtctggag aactatttc tttgtcaagt ctgtctttac gagctggacg aggacgagat   133320
```

```
gggcgaggag atgctgggca tgttggccgg aaagcccgag gatgccgccg tctcgggcgc  133380
aagcggcggt tttctgctac atcgcaagac gatgaagctg gccgcctgtc tgtgtttgtt  133440
gctcaattcg ctgcatttgc accaggaggc gctggaggcc ttggatcctc cgccgccgcg  133500
cgtcgaggag aacgaccttg tcaacgtggt gctgcgccgt tattatcgca gtcacggcgg  133560
cgtgcaggcg cggacgctgg cggcggcccg ggctttgtta gccgactacg ccgaaacgtt  133620
ttcgcccttg gggagtttta cgcgcctggg ttacgatcgt ctcgtttctg ccgatgccgg  133680
cgtcagtcgc cggcacctgg tggctctgct gcgtgcctag ctgaccctga acggatggc   133740
gtgtatatcg tcacacaggt aggtggccat gatgacggcg atgataagat cgtccgagat  133800
acgattctgg cgcttggccg agtaacgcgc cgtcgtgcct tcggccagcg tgacgcggtg  133860
caggttctga atctgctcca gaagatactc gatgggtcg  tggctcagct tgatggtgta  133920
ggagacgagc tcttgcgagg ctttgatgta gcccgagttg aaacgcgaga tgaactgttc  133980
cacgccagc  gccttgtcgc ggcccatgag gtagaagggc tgttcgatgt ggttctggtc  134040
gggcgtgtgg tagaagagca cgcggatgag cgtgctgctc tgcacgctct gtcggatgag  134100
gcaggcgatg cgcacggccg ccgcctggtt ggtgttgccc tccacggcga tgcgcagttc  134160
gtccaggtaa gggtgcaggc tcagcaccga gatgatcatg tgcgccgcgc actcggcgat  134220
ggctacctca gaactctcgg agaggtcgcg caaaaagaaa tgctctaggc cgtaaatgaa  134280
aaactggtgt cggtaggcgc ctacggccgc cacgcccgtg cccgaggcct tgcggttggt  134340
ggtgaaggcc gggtccagat acacgtaaag cgtcttgccg aaataatcgt aggcgttggt  134400
gttgagcgtg ctgtaacgca aaatatcgaa ctcttcgcgg ctctggtccg tgatgagcac  134460
ggtgttctgc gagattttat tggtaccgcc gatgatctcg tccatgaaag cgcccggcat  134520
aaacatgttg gccgtcttgc gcacttgcga gttgaggctg atgaaggtgg gcttgtgcag  134580
tcggtagcaa ggacacgccg tggcgtcgcc cttctccgtg aagctgtgca ggtgctcttc  134640
gcacacgtaa gagaccacgt tgagcatgtc aaagggcgca ttgttaaggc gcgtcaagaa  134700
acacgtggag tcactggtag tgttggtgga cgatatgaag atgatcttgg tggtattctg  134760
ggccaggaac cccagaatgg tgttgaaggc ctctttcttg atgaagtgcg cctcgtccac  134820
cagcagcaag tggaagtttt gtcctcggat gctctgtgta gagaggagac agaaaaggga  134880
ctcttatgat tacgcacgct cgactggaag cctacagagt cggggtgggg ccggacaggt  134940
gagccaggtg agccgccagg tgaggcggga tcgccgtgtg ccaaccgggc tgcgacctga  135000
aaaccggaac caatccgccg acaccggcgc gcgtgacgc  gcgcccataa aaacgaaagt  135060
gtcgtcgtcg cgacccgcca cagccgccat gaactcgttg ctggcggaac tcaaccgact  135120
aggggtcgcg cacgccacta cggaggatgt ttttatcttt gtcgaccgcc tctttcaaca  135180
cttttccttc cttttccagg ccgaggagtc aggcccgcgc cgcttggaac tggtcgcgtc  135240
cgtgttcgag cacctgacgg tggagtgcgt taacgacatc ctggacgcct gcagtcaccc  135300
ggacgtgaac gtcgcggaga caagcaacac ctgtcgtccc tgcccttctc ctgttccctc  135360
cgcccccaaa actgtcagcg gcgctcagac gtcatgtgcg acgcctcggg cgcctgtgac  135420
atgaggcacg tccagaacgc gtttaccgag gagatccagt tacactcgct ctacgcgtgc  135480
acgcgctgct ttcgcacgca cctgtgtgat ctgggcagcg gctgcgcgct cgtctccacg  135540
ctcgagggct ccgtctgcgt caagacgggc ctggtatacg aggctctcta tccggtggcg  135600
cgtagccacc tgttggaacc catcgaggag gccgcactgg acgacgtcaa catcatcagc  135660
```

```
gccgtgctca gcggcgtgta cagctacctc atgacgcacg ccggccgtta cgccgacgtg   135720
atccaggagg tggtcgagcg cgaccgcctc aaaaagcagg tggaggacag tatttacttc   135780
acctttaata aggttttccg ttctatgcat aacgtcaacc gtatttcggt gcccgtcatc   135840
agccaacttt ttattcagct tatcatcggt atctactcaa agcagaccaa gtacgacgcg   135900
tgtgtcatca aggttagtcg taagaagcgc gaggacgcgc ttctgaaaca gatgcgttcc   135960
gaatatggaa acgcacctgt attcggatct ggcgtttgaa gcgcggttcg ctgacgatga   136020
gcaattgcct ctacacttgg tgctcgacca ggaggtgttg agtaacgagg aggccgagac   136080
gctgcgctac gtctactatc gtaatgtaga cagcgctggc cgatccacgg gccgcgctcc   136140
aggcggagat gaggacgacg caccggcctc cgacgacgcc gaggacgccg tgggcggcga   136200
tcgcgctttt gaccgcgagc ggcggacttg cagcgggcc tgttttcgtg tactaccgcg    136260
cccactggag ttgctcgatt acctacgtca aagcggtctc actgtgacgt tagagaaaga   136320
gcagcgcgtg cgcatgttct atgccgtctt cactacgttg ggtctgcgct gccccgataa   136380
tcggctctca ggcgcgcaga cgctacacct gagactggtc tggcccgacg gcagctatcg   136440
tgactgggag tttttagcgc gtgacctgtt acgagaagaa atggaagcga ataagcgcga   136500
ccggcagcac cagttggcca cgaccacgaa tcaccgtcgg cggggcggac tgcgtaataa   136560
cttagacaat gggtcggatc gccgtttgcc cgaagcggct gtggcttctc tggagacggc   136620
cgtcagtact ccattttttg aaattccgaa cggagcagga acctcctccg cgaacggcga   136680
cggcagattc agtaacctgg agcagcgggt agcgcgtttg ttgcgcggcg acgaggaatt   136740
catctatcac gcgggtccat ggagccgcc ttccaagata cgcggtcatg agttggtgca     136800
gctgcgcctg gacgtaaatc cagacctcat gtacgccacc gatccgcacg accgcgacga   136860
ggtcgcgcgt acgacgagt ggaagggtgc cggtgtctcg cgtcttcgcg aggtctggga     136920
tgtgcagcat cgcgtgcgcc tccgtgtgct gtggtacgtc aattccttt ggcgcagtcg     136980 cgagctgagc tacgatgacc acgaagtcga actataccgg gcgttggacg cttatcgggc   137040
gcgcatcgcc gtcgagtacg tgctgattcg cgccgtgcgc gacgagatct acgctgtact   137100
acgacgggac ggcggcgcgt tgccacagcg tttcgcctgc cacgtgtcac ggaacatgtc   137160
ctggcgcgtt gtttgggaac tttgccgtca tgccttggcg ctctggatgg attgggcgga   137220
cgtgcgtagc tgtattatta aggcgctaac gcctcgtctg agccggggtg ccgccgctgc   137280
cgctcagcga gctcgtcgcc agcgcgagcg ctcggcgccc aaaccgcagg agctgctttt   137340
cgggccgcgg aacgagagcg gtccgcccgc cgaacagact tggtacgctg acgtggtgcg   137400
ctgcgttcgc gcgcaagtgg atttgggcgt ggaagtgcgc gcggcgcgtt gtcctcgcac   137460 cgggcttttgg atcgtccgtg atcgccgcgg acgcctgcga cgttggctct cgcagcccga   137520
ggtgtgcgtg ctgtacgtca cgccagactt ggactttac tgggtgctgc cgggcggctt    137580
tgccgtctct tcgcgcgtca ctcttcatgg cttggcgcag cgggctttgc gagaccgatt   137640 ccagaactt gaagcagttc ttgcaagagg aatgcatgtg gaagctggtc ggcaagagcc     137700
ggaaacaccg cgagtatcgg gccgtcgctt gccgttcgac gatctttagt ccggaggacg   137760
acagctcgtg tatcttatgc cagttgctgt tgctctaccg cgacggcgaa tggatcatct   137820 gttttgctg caacggccgt tatcaaggcc actatggcgt gaaccacgta catcggcgtc    137880
gtcgacgcat ctgtcatcta cctaccttgt accaactgag cttcggaggt cctttgggtc   137940
cagccagcat cgatttcttg ccaagcttta gccaggtgac cagcagtatg acgtgcgatg   138000
gtattacgcc cgacgtgatt tacgaggtct gcatgttggt gccccaggat gaagccaagc   138060
```

```
gtatcctggt caagggtcac ggtgccatgg acctgacctg tcagaaggca gtgacgctag 138120
gcggcgccgg cgcctggttg ctgccgcgtc ccgaaggcta cacgcttttc ttttacattc 138180
tgtgttacga cctgtttacc tcatgcggca atcggtgcga tatcccttcc atgacgcgcc 138240
tcatggcggc ggccacggcc tgcgggcagg cgggttgcag cttttgcacg gatcacgagg 138300
gacacgtaga tcccactggc aattacgtgg gttgcacccc cgatatgggc cgctgtcttt 138360
gttacgtgcc ctgtgggccc atgacgcagt cgctcatcca caacgaggaa cccgcgactt 138420
ttttctgtga gagcgatgac gccaagtacc tatgcgccgt aggttctaag accgcggcgc 138480
aggtcacact gggagacggc ctggattatc acatcggtgt taaggattct gagggccgat 138540
ggctgcccgt caagaccgat gtgtgggacc tggtcaaggt agaggaacct gtgtcacgta 138600
tgatagtgtg ttcctgtccg gtgcttaaga acctagtgca ctaacggggt ctgacagttc 138660
acggggagaa gaaacaagaa acaacaaaaa aaggaggac atggactcgc cacggtttgt 138720
ggcaaggcgt atgttatcat catggagcta ctcacgttgg tgttgtagca actggcaaaa 138780
agcgccgtgc tcttggcgcc gcggtggtcg atgctgatca cgttgtcctt gttctcgacc 138840
acgtagtcgc gcgcgaaggt gtggcggcag cggaactcga cctctttgag cacaaactgc 138900
gacacgtgct tttggtgcgc cacgtagccg atgctgatgc cgatcatgtg cttaagcaga 138960
aacgagataa tggggatgat gaaccaagtc ttgccgtgac gtcgcggcac caggaacacg 139020
gtggctttct gcttaaagat gtcgatggag gtctgcgaga ggaagtcgat ctggaaggcg 139080
tggatgaggt actgcagcac gcgattggcc agcacgggga tcttggtcac ggctataaaa 139140
aagatgacgt gtatcaataa attcttttga acggttcga gtcggatggc ttttgcgtcg 139200
ccctcgacgg cggtactgaa gccgccgtcg agccacttt taaagtcggt catgaagttg 139260
ttgatctgct gaaactgcgg atcgcggtag agctcggtca acgcgtccag cttctggtag 139320
gaggcgcgct gctcctcgga gcacgggcga aacgtcagtt tatcgagcgc gctcttgagg 139380
cgctcgtgaa acagcagctc gcgctggctt tcctcgggcg agttgtagtc gcggtggcgg 139440
ccgcagaagg ccatgagcgg caggaaggcc tcgttgcacg agtgggccag cccgagttcg 139500
gggtgcatca tctggtagcg cttgcggcac agcgtcgcca cattggtgaa ggccgtggag 139560
atgcaggagg tggggtggct cttgcgcttc tgcagctccg cgtagcgctc ctggatcttg 139620
gcggccgagt ctccgcgcaa catgatggcg gcggcggtgg tgcgagcgga ggttaggcgg 139680
cagcggcgag aggagaggaa aaagatggcg gccgcgagga cgacggagga tccacccgaa 139740
aaccacgttg ttgcggacgt ggctcgtggg acgggcgccg tcactcgttc gtcttcgtcg 139800
tccctagtgg tgtcgtcttc ctcggcgtca ggctcggacg aatcttcctc cgcctctcct 139860
ctcagtttcc ccgtctcctc ccctcaact gccgtcaggt ctccggggtc cgccggggtt 139920
tcaacgtccc tgtgctcggt ggaacggatg gtcgagctgt cggcgcagtc tccggccgcc 139980
gatttctcgg tctccgaggc ttggcgcttc gaggaggcca taaatatggc gctggtggcc 140040
tgcgaggccg tgtcaccta cgatcgcttt cgcctaattg aaacgcccga cgagaatttc 140100
ttgttggtca ccaacgtaat tccgcgcgaa tcggccgagg tgccggtgtt ggatagcagt 140160
agcagcggtg gcgatagcgg gccggaggac aaaaagaaaa acgtcgggaa taaaccgcg 140220
ggggaaaaga acggcggtgg gtctcggcc aaacgccgtc gtagacgacg cgctccgaaa 140280
aacgacgccg ccacgccgtc tttttctacgt cgacacgacg tgctgagcg tttcgcggcc 140340
gcggctaagc ctttgccgtc gctttgtgtg cgtgattatg cgttacgcaa tgctgaccgt 140400
```

```
gttacctacg acggcgaatt aatctacggc agttacctgt tgtatcgcaa ggctcacgtg 140460
gagctgtcac tctccagcaa caaggtgcaa cacgtggaag ccgtgctgcg acaggtgtac 140520
acgccgggct tgttagatca tcacaacgtg tgcgacgtgg aggccctgct gtggctgctg 140580
tactgtggac cgcgcagctt ttgcgcgcgt gacacttgtt tcggtcgcga aaagaacggt 140640
tgtcctttcc ccgcgttgtt gcccaaactc ttttacgaac ccgtgcggga ctatatgacc 140700
tacatgaatc tggctgagct gtacgtcttt gtttggtatc gcggctacga attccctgcg 140760
ccgacgccgc aggcgacgac ggcgggtggt ggtggtggta gtggtggcgg cggcggggcc 140820
ggcgcttgtg cggtcgagac gagcgcgtca gcaggccggg tcgatgacgc cggcgacgag 140880
gtgcatttgc ctttaaagcc cgtctcgctg gaccgtctca gagaggtgtt gcaggcggtg 140940
cgcggccgct tctcggggcg cgaggtgccc gcctggccgg cctcgtcgcg cacctgtttg 141000
ttgtgcgcgc tctacagtca gaaccgtctc tgtttagatc tcgcgcgtga cgaggcgcgg 141060
accgtgagtt atagccccat cgttatccaa gactgcgccg cggctgtcac cgacgtcact 141120
ttgagccaca tcttgcccgg ccagagcacc gtctcgcttt tccccgtcta ccacgtcggc 141180
aagttgctgg acgctctctc gctgaacgac gcgggtctca tcacgttgaa tctatgacgt 141240
cggtcaacaa acagctctta aaggacgtga tgcgcgtcga ccttgagcga cagcagcatc 141300
agtttctgcg gcgtacctac ggaccgcagc accggctcac cacgcagcag gctttgacgg 141360
tgatgcgtgt ggccgctcgg gaacagaccc gatacagtca gcgaacgacg cagtgcgtgg 141420
ccgcacacct gttggagcaa cgggcggccg tgcagcaaga gttgcaacgc gcccgacagc 141480
tgcaatccgg taacgtggac gacgcgctgg actctttaac cgagctgaag gacacggtag 141540
acgatgtgag agccaccttg gtggactcgg tttcggcgac gtgcgatttg gacctggagg 141600
tcgacgacgc cgtctaacag gtatagcaat ctccgtcacg cctctgttca gattttatta 141660
aaaaaaaaac acaacataac gacagtgtcg gtgtggtagc tagtgcagcc ttaggaacag 141720
ggaagactgt cgccactatg tcctccgcac ttcggtctcg ggctcgctcg gcctcgctcg 141780
gaacgacgac tcagggctgg gatccgccgc cattgcgtcg tcccagcagg gcgcgccggc 141840
gccagtggat gcgcgaagct gcgcaggccg ccgctcaagc cgcggtgcag gccgcgcagg 141900
ccgccgccgc tcaggtcgcc caggctcacg ttgatgaaaa cgaggtcgtg gatctgatgg 141960
ccgacgaggc cggcggcggc gtcaccactt tgaccaccct gagttccgtc agcacaacca 142020
ccgtgcttgg acacgcgact ttttccgcat gcgttcgaag tgacgtgatg cgtgacggag 142080
aaaaagagga cgcggcttcg gacaaggaga acctgcgtcg gcccgtagtg ccgtccacgt 142140
cgtctcgcgg cagcgccgcc agcggcgacg gttaccacgg cttgcgctgc cgcgaaactt 142200
cggccatgtg gtcgttcgag tacgatcgcg acggcgacgt gaccagcgta cgccgcgctc 142260
tcttcaccgg cggcagcgac ccctcggaca gcgtgagcgg cgtccgcggt ggacgcaaac 142320
gcccgttgcg tccgccgttg gtgtcgctgg cccgcacccc gctgtgccga cgtcgtgtgg 142380
gcggtgtgga cgcggtgctc gaagaaaacg acgtggagct gcgcgcggaa agtcaggaca 142440
gcgccgtggc atcgggcccg ggccgcattc gcagccgct cagcggtagt tccggggagg 142500
aatccgccac ggcggtggag gccgactcca cgtcacacga cgacgtgcat tgcacctgtt 142560
ccaacgacca gatcatcacc acgtccatcc gcggccttac gtgcgacccg cgtatgttct 142620
tgcgccttac gcatcccgag ctctgcgagc tctctatctc ctacctgctg gtctacgtgc 142680
ccaaagagga cgattttgc cacaagattt gttatgccgt ggacatgagc gacgagagct 142740
accgcctggg ccagggctcc ttcggcgagg tctggccgct cgatcgctat cgcgtggtca 142800
```

```
aggtggcgcg taagcacagc gagacggtgc tcacggtctg gatgtcgggc ctgatccgca 142860
cgcgcgccgc tggcgagcaa cagcagccgc cgtcgctggt gggcacgggc gtgcaccgcg 142920
gtctgctcac ggccacgggc tgctgtctgc tgcacaacgt cacggtacat cgacgtttcc 142980
acacagacat gtttcatcac gaccagtgga agctggcgtg catcgacagc taccgacgtg 143040
ccttttgcac gttggccgac gctatcaaat ttctcaatca ccagtgtcgt gtatgccact 143100
ttgacattac acccatgaac gtgctcatcg acgtgaaccc gcacaacccc agcgagatcg 143160
tgcgcgccgc gctgtgcgat tacagcctca gcgagcccta tccggattac aacgagcgct 143220
gtgtggccgt ctttcaggag acgggtacgg cgcgccgcat ccccaactgc tcgcaccgtc 143280
tgcgcgaatg ttaccaccct gctttccgac ccatgccgct gcagaagctg ctcatctgcg 143340
acccgcacgc gcgtttcccc gtagccggcc tacggcgtta ttgcatgtcg gagctgtcgg 143400
cgctgggtaa cgtgctgggc ttttgcctca tgcggctgtt ggaccggcgc ggtctggacg 143460
aggtgcgcat gggcacggag gcgttgctct ttaagcacgc cggcgcggcc tgccgcgcgt 143520
tggagaacgg taagctcacg cactgctccg acgcctgtct gctcattctg gcggcgcaaa 143580
tgagctacgg cgcctgtctc ctgggcgagc atggcgccgc gctggtgtcg cacacgctgc 143640
gctttgtgga ggccaagatg tcctcgtgtc gcgtacgcgc ctttcgccgc ttctaccacg 143700
aatgctcgca gaccatgctg cacgaatacg tcagaaagaa cgtggagcgt ctgttggcca 143760
cgagcgacgg gctgtattta tataacgcct ttcggcgcac caccagcata atctgcgagg 143820
aggaccttga cggtgactgc cgccaactgt tccccgagta accgggacgc ggaacgtgac 143880
ggttgctgag gggaaaggca acagagaagg tacaaaccca ccggcgggga aaataccgag 143940
gcgccgccat catcatgtgg ggcgtctcga gtttggacta cgacgacgat gaggagctca 144000
cccggctgct ggcggtttgg gacgatgagc ccctcagtct gtttctcatg aacacctttt 144060
tgctgcacca ggagggcttc cgtaatctgc cctttacggt gctgcgtctg tcttacgcct 144120
accgcatctt cgccaagatg ctgcgggccc acggtacgcc agtagccgag gactttatga 144180
cgcgcgtggc cgcgctggct cgcgacgagg gtctgcgcga cattttgggt cagcggcacg 144240
ccgccgaagc ttcgcgcgcc gagatcgccg aggcctggga gcgcgtggcc gagcggtgcg 144300
acgaccggca cggcggctcg gacgactacg tgtggctcag ccggttgctg gatttagcgc 144360
ccaactatcg gcaggtcgag ctcttccagt tgctggaaaa ggaatcgcgc ggacagtcgc 144420
gcaactcggt gtggcatctg ttgcgtatgg acacggtctc ggccaccaag ttctacgagg 144480
ccttcgtcag cggctgtctg ccgggcgccg cggcggcgga cggttcgggt ggcggcggct 144540
cgcactacac gggttcgcgc gccggcgtct cgccgggcat ccagttcggt atcaaacacg 144600
agggcttagt caaaacgctg gtggaatgtt acgtgatgca cggacgcgag ccggtgcgcg 144660
acggcctcgg tctgctcatc gaccccacgt cggggctgct gggcgcttcc atggacctgt 144720
gcttcggcgt gctcaagcag ggtagcggtc gcaccttgct ggtggaaccg tgtgcgcgcg 144780
tctacgagat caagtgccgc tacaaatatt tgcgcaaaaa ggaggacccc tttgtgcaga 144840
acgtgctgcg gaggcacgac gcggcggccg tggcctcgct gttgcagtca cacccggtgc 144900
cgggcgtgga gtttcgcggt gaacgcgaga ccccgtcggc acgcgagttt ctgctttcgc 144960
acgacgcggc gctcttcagg gccacgctca agcgcgcgcg cccgctcaag ccgcccgaac 145020
cgctgcgcga gtacctggcc gatctgctgt atctcaataa ggccgagtgt cggaagtga 145080 tcgtgtttga cgccaagcac ctgagtgacg acaacagcga cggggacgcc acgatcacta 145140
```

```
ttaacgcgag tctcggccta gccgcgggcg acggcgctgg cggcggcgct gatcaccacc   145200
tgcggggcag cccgggcgat cgccgccgc cgatacctttt cgaggacgaa aacacgcccg   145260
agctgctggg ccggctcaac gtgtacgagg tagcgcgctt ttcactgccg gcttttgtca   145320
atccgcgtca ccagtattac tttcagatgc tcattcagca gtacgtgctc agccaatact   145380
atataaagaa gcatccggac ccggagcgga tcgatttccg cgacctgcct accgtctacc   145440
tggtctcggc catcttccgc gagcgcgagg aaagcgaact gggctgcgag ttgctggccg   145500
gcggtcgcgt tttccactgc gaccacatcc cgctcctgct catcgtcacg cccgtggtct   145560
ttgaccctca gtttacgcgc catgccgtct ctaccgtgct agaccgttgg agtcgcgacc   145620
tgtcccgcaa gacgaaccta ccgatatggg tgccgaactc tgcaaacgaa tatgttgtga   145680
gttcggtacc acgccggtg agccctgaa agatgctctg ggtcgccagg tgtctctacg   145740
ctcctacgac aacatccctc cgacttcctc ctcggacgaa ggggaggacg atgacgacgg   145800
ggaggatgac gataacgagg agcggcaaca gaagctgcgg ctctgcggta gtggctgcgg   145860
gggaaacgac agtagtagcg gcagccaccg cgaggccacc cacgacggct ccaagaaaaa   145920
cgcggtgcgc tcgacgtttc gcgaggacaa ggctccgaaa ccgagcaagc agtcaaaaaa   145980 gaaaagaaa ccctcaaaac atcaccacca tcagcaaagc tccattatgc aggagacgga   146040
cgacctagac gaagaggaca cctcaattta cctgtccccg cccccggtcc ccccgtcca    146100 ggtggtggct aagcgactgc cgcggcccga cacacccagg actccgcgcc aaagaagat    146160 ttcacaacgt ccacccaccc ccgggacaaa aaagcccgcc gcctccttgc cctttttaact 146220 cataaacttt caggtctcgc gtacgattcg cgagtcggga atgggacacc cgtgggtgtt   146280
tctccgtgtg tatattattt ttttttttg tgtgtgtttg cgcccccgtg tgtctaatgt    146340
gctgtttgaa acacgtaaag tagctggtgg aagaacagat aaacctttaa taaaaaaaa    146400 agtatgtgct cccgacccac ggtctgcgtg tctctttttt atgtccatgt ctccaagtct   146460
ggtgcgggtg gcggcggggt taagcgtcct cgaagtcttc atcatcgtcg tgtcctctt    146520 cttcgcggag gcgacggctt ccaagctgt cgtggtgact gagcacagcg acttcttcgc    146580
cggaggctgt ggccagcgcc tggtacttga cactgccgct accgcgtccg cgaaagtagc   146640
ggacggcgcg acacgtcgta aacatggccc atatgaaaaa gagcatgccg aacgaccagc   146700
tgatgccggt gcggtattcg ttgctgagga aggtatcgta ctgcacgatg gggtagatga   146760
ggccgcagag tccaaagaag gcgcccaggt ggtagccgaa ttgcaccttg acgtattgaa   146820
aaaagacggc ctcgatcagt aaaaagtaga tgatggagat gatagcgtag accacgaaga   146880
cggctaacac catgtggcct gtacgcacga aaaagttgtt tccgaagccg tagcacaggg   146940
ccatggctac cacggtggtg ttgaaaccaa gcgctacctc taccaggttg acgatgagcg   147000
tgcggaactg caccgtacct ttgagcttgg ggtgcagacg cgagaagaaa aagagtgagc   147060
gtttgtagct gcggtactgc gtgaccatgc tcacgttgaa aatggtcagg cagaaaaagt   147120
gcacggcggc catgaaggcg atcatgctgg gcagccgaaa tgacatggtc agtgtgaata   147180
gttggaacgt gtccatgctg agaatgaaga ggaaggctgt gaggctgtcg cccatgtacg   147240
aaatgtcgcg tgtcgactgg tttaggctca tgcctttgtc cttgcgcatg ctgatcttga   147300
tccagcatac caggtagtag atggtcacgg ctaaaaagac gagctgcatg aacacggcgt   147360
agcacaccaa ctgcaccgag tctaagaaaa gcataggcgt gtgcaggtgc attacgttgt   147420
aggccgacat gttgagcctt tcaaagtcca cgacgtgata gtagacgcag gggtagccca   147480
ggtgcggaaa attgctcagc actagatgca cgctgacgtt gacaaaagtc agcaccatga   147540
```

```
aaacgataga agcgctccat gtccgtgtat tcaccttatc cacgtgcgag ggggccatgg   147600
cgatagcggc ggcccgctcg ctcgggaggc gatggggggcg cgccgatgac gacaggctcg   147660
cgggtcgtta aatactacga tgggagccgc cgcggctcac gacgcggttt gagcacgtcc   147720
gggcggtcgg tgaaaaaaga ccccgcgggc cttcgcgact ctcttctgtc cgaggatgac   147780
cgctcagccg ccgctgcacc accgccacca cccgtacacc ctgttcggga ccagctgtca   147840
tctcagctgg tacggccttc tagaggcctc ggtgcctatc gtacaatgtc tgttttttgga  147900
tctgggtggc ggccgtgccg agccgcggct tcacacgttc gtggtgcgcg gtgaccgtct   147960
accgccggct gaggtgcgtg ctgtgcatcg cgccagctac gctgcgctgg cctcggccgt   148020
gactacggac gccgatgagc gtcggcgcgg cctagagcag cgtagcgccg tgttggcgcg   148080
cgtgttgcta gaaggcagcg cgttaatccg cgtgttggcg cgcaccttca cgccggtgca   148140
gattcagacg gacgctagtg gcgtggagat tttggaggcc gcaccggcac tgggcgtgga   148200
aaccgcagcg ctgtcgaacg cgcttagtct tttccacgta gccaagctag tggtcatcgg   148260
ctcgtatccc gaagtgcacg agccgcgtgt ggtcacgcat accgcggaac gcgtctccga   148320
agagtatggc acccacgcgc acaaaaaatt gcgtcgcgcgt tactacgcct acgatttggc   148380
catgtcgttt cgcgtcggca ctcacaagta tgtgctggag cgcgacgacg aggccgtcct   148440
ggcacgcctc tttgaggtgc gcgaggtgtg ttttttgcgc acctgtctgc gtctggtcac   148500
gcctgtcggt ttcgtggccg tggcagtgac cgacgagcag tgttgtttat tgctgcagtc   148560
ggcctggact caccttttacg acgtgctttt ccgtggtttc gctgggcagc cgccgctacg   148620
cgactacctg gggccggacc tctttgagac gggcgccgcc cgttctttct ttttttcccgg   148680
tttcccgccc gtgccgtct acgcggtcca cggtctgcac acgttaatgc gcagacggc    148740
gttggacgcg gcggctgagg tgctctcgtg gtgcggcctg cccgacatcg tgggctcggc    148800
cggcaagctg gaggtggaac cctgcgcgct ctcgctcggc gtgcccgagg atgagtggca    148860
ggtcttcggt accgaggccg gcggcggcgc cgtgcgtctc aatgccacgg cttttcgcga    148920
gcgaccggcc ggcggcgatc gtcgctggct gttgccgccg ctgccacgtg acgacgcga    148980
cggtgaaaac aacgtcgtgg aagtcagcag cagcaccggc ggtgcgcacc cgccgagcga    149040
cgacgccact ttcaccgtgc acgttcgcga cgccacgcta catcgagtgc tcatcgtgga    149100
tttggtcgag cgcgtgctgg ccaagtgtgt acgcgcgcgc gacttcaatc cctacgtgcg    149160
ttatagtcat cgactccaca cttatgcggt ttgtgaaaag tttattgaga atctgcgttt    149220
tcgctcgcga cgcgctttct ggcagatcca gagtctgctg ggctacatct ccgagcacgt    149280
tacgtcagcc tgcgcttcgg ccggccttttt gtgggttctg tcgcgcggcc accgcgagtt    149340
ttatgtctac gacggctatt cgggtcacgg accgtctcg gccgaagtgt gcgtgcgac    149400
tgtggtcgac tgttattggc gcaaactttt tggcggcgac gatccgggtc ccacctgtcg    149460
tgttcaagag agcgcgcccg gcgtgctgtt ggtctgggc gacgagcggt tggtgggtcc    149520
cttcaacttc ttctacggca acggcggcgc cggtggtagt ccgctccacg ggtggtggg    149580
tggtttcgcg gcgggacatt gcggtggcgc ttgttgcgcg gctgcgtcg tcactcaccg    149640
ccattctagc ggcggcggtg gtagtggcgt gggcgacgcg gaccacgcga gtggcggcgg   149700
tctagatgcc gctgccggga gtggtcataa cggcggtagt gatcgggttt ctccctccac    149760
gccgcccgcg gcgttaggtg gctgttgctg cgcagccggt ggcgactggc tctcggccgt    149820
gggtcatgtc ctgggccggc tgccggcgct gttacgggag cgccgtgagcg tgtccgagct    149880
```

```
ggaagccgtg taccgcgaga tcctctttcg tttcgtggct cgccgcaacg acgtggactt    149940
ttggttactg cgcttccagc ccggtgaaaa cgaagtaagg ccgcacgctg gggtgattga    150000
ctgcgcgccc ttccacggcg tgtgggccga gcagggccag atcatcgtac agtcacgcga    150060
tacggcgttg gcggccgata tcggctacgg cgtctatgtg gacaaggcct ttgccatgct    150120
cacggcttgc gtggaggtct gggcgcgaga gttattgtcg tcctccaccg cttccaccac    150180
cgcttgttct tcttcttccg ttctctcctc cgccttgccg tccgtcactt cgtcctcttc    150240
gggcacggcg acggtgtctc ctccgtcttg ttcttcttcg tcggcgactt ggctcgagga    150300
gcgcgacgag tgggtgcgct cgctggcggt tgacgcgcaa cacgctgcta agcgggtggc    150360
ttccgagggc ctgcggtttt tccggctcaa cgcttaacga gtcacgtagg ggaactacgt    150420
gggtaagtga cgtggatact agtaaaaaaa gtgcgtcaaa gctcttagcg tgtgacgtgg    150480
atactagtaa aagggacgtc aaagctcact acgtgttgcg tgttttttttt ttttctatga    150540
tatgcgtgtc tagttcgctt ctcactcttc ctctcctcgt tcccagcgcg gcggcagctt    150600
gggggggtgag ggcaaattgg ggtagttggc gttgagcacg tctagcaggc ccaggcccac    150660
gggccaaccg tccacggtct tgcgctcggt cagcttgagg ctgaacgagt gtgcctcgtc    150720
ctgaccggta aggcggaaaa agaagcgtgc taccagctgc aggcaggtat gccgcgtctg    150780
ctggaagagc acgaaggtag cgggcacgta ctgcacaatg tgcggctctt tttcctcaaa    150840
gagcaggtag agcgcgctgc agatcagccg cctggcgctg tggtgcagca gccggccgaa    150900
gctttcgcgc acgttcaccg cgtccaggta ctggagcagg tcgtgcaggc acttgcgcgt    150960
taagttgcaa ttttccacgc acgaaataac ggtacagagc gcgaagtgca gcaggttgtc    151020
ggctttgacg atgccgcagc ggtgtttgag ccgcagatcc gagagcctca cctgcgtgac    151080
ggcgtcttcg gtctcgagca aaacacggcg ggagtagcct agaaaggccg aggtgcacag    151140
caactcgctg cggtactcgg ccatggagac cagcagcccg tgctccgtgt gcagccacag    151200
cttgtcgccg cgcaccgtaa agtcgagcac ttgcggctcc atgatcatca cattctgtct    151260
agtgaaatcc gtatggacct ccagcacgcc gcggatcatc agggcctcca tttcgaaatc    151320
ggccgacacg ctctgggccg cgccgctcct cgtctgccgt gatcaagcgg cgcggcgcgg    151380
accttttcaag tgttcctggg ccgccgctcg aggcagttcc cctttctggc actccgcccg    151440
ccgcttcgcg gctcatttgg cgccgacgcg ccttctcgcg gctgcaaatc agctccacgt    151500
atcggcaaaa cttgctgtcg tcgtaggcgg cggccacgat ctcgccgaag gagagctgca    151560
ggtaggcctc gggtacgggg tccagcgtgc ccagcgccag gatgtgacac agatagggca    151620
gggtcacgcg ctctaccgtg taattggagt agacgatggc ctcttcggcc ccttgatgcg    151680
tgaccagacg ccgtaggcga aggtacggaa aatactcgtt ttcccacaac tgcgtgagga    151740
agcgttccag cgactcggtg ccgggcacga actgcgagaa gaagctgttg gccaccaggc    151800
ggttgtcttc caccgccagc ggacggaagg gcgccgcgtc gcgcgccttg cgcacggcct    151860
ccaacacggg caggtggtag agttcggcgt cgcgcgcgcc caggctcatg gagtcctcgc    151920
gccgcgaggc gtagcgcgtg agcaggtcgc gcagttcgcg cacgcgattc tcccaggtct    151980
ggttaagcgt gcgcaggtcc tggatctcgt ccacctgcga ctggatctgc tcctccaggc    152040
acttgataac ctgcttctta aacaggtcgc ggatgtcccg ctcgggcgcc gccgggccgg    152100
gtggcggcgg cagcagcccg acgtggcccg cgggtcctcc caccacgcgc cgccgggtc    152160
ccaccacgcc gggtccgccc ggaccacgcg cgggtagtag acggttttgg tccaccagcg    152220
aggggggtcag gtcctgcaga aaggactcga cgctgtcctc gatgccgatg cgcgatttgc    152280
```

```
tgtccgagac gttaagcaaa aacttcataa tggactttt  ggcgtcgctg ccccggtcgt  152340
gctgctccat catctccacc agcttcttgc agttgagctc gtggcggctg gcggtcacca  152400
ctttcacagg aaaggtattg agcaactggc agatcttttg gtggcggcag agcccgtcgt  152460
agcgcagaat ctcctcgtgc aggtgtgcca ccggcgtggt gaacagcagc ttgtcgcgct  152520
cataagccag cggttcggcc gccacgtaca agcggatgtg cttgccgcgc agctgcgcct  152580
ccagccgctc cgagcgcacc ttcttgaaga cgcgtacctc gggcgcgttg gctacgcgca  152640
cggcgcccag gcgctcggcc acctgcagca gcagcgccag gttagcctgc agcaggtcct  152700
gcgccagcgg gtgtgtctcg gtggcccgct gcacggccgc gcgtacaaat tgcgcccgct  152760
cggccgcctc gctcggcttg gtcttcacgt ccagcagcgg taccagtccc accgttacgc  152820
accaatccac gtagagacca tagtcgtcgt tatcggcgta ctgatataaa atgtcggga   152880
gcgcgcccag cacgcccgtt tgcacgctct ggcgcaacga ggcgctccac accaacagat  152940
actgctccag gtcctcttcg tccagcgcgc ggtagggaaa tagcgccgcg tgcaacttcc  153000
actcctcggc cacgcgccgc accgtgatgg tgtcaaagag cgttttgcac actccgtaga  153060
gcagctgctt gcgcagcacg cacgggtcgc gcagcacctg gtgcatgctt ggccgcgac   153120
acgtccccag aaagccgtgc agcaaccgca ggaagctcat cgtctgcccc gtggggaaaa  153180
tgtcgatgac ggcctcgtca tccacgccgc ggcccacgcc caagtacgac gacgccttga  153240
tcctcaacct ctcgtcggcc gccaagatcg aacggatcgt cgacaaggtc aagtccctct  153300
cgcgcgagcg ctttgcgccc gaggattttt cgttccagtg gtttcgctcc atcagtcgcg  153360
ttgaacgaac gacagataac aacccctctg ccgcaactac cgccgcggca acgacgaccg  153420
ttcactcctc cgcctcctct tctgccgccg ctgccgcttc gtccgaggcc ggcggcacgc  153480
gcgtgccctg cgtcgaccgt tggcccttct ttcccttccg cgcgctgctc gtcaccggca  153540
cggcgggcgc cggcaagact tccagcatcc aggtgctggc ggccaatcta gattgcgtga  153600
tcaccggtac cacggtgatc gccgcgcaga acctcagcgc gatcctcaac cgcactcgct  153660
cggcgcaggt caagaccatc taccgcgtct tcggcttcgt cagcaagcac gtgccgctgg  153720
ctgacagcgc cgttagccac gagacgctgg aacgctaccg cgtgtgcgag ccgcacgagg  153780
agaccaccat ccagcgcctg cagatcaacg atctgctcgc ctactggccg gtcatcgccg  153840
acatcgtgga caaatgctta aatatgtggg agcgcaaggc cgcttcggcc tccgccgcgg  153900
ccgcagccgc cgcctgcgag gacctctcgg agctgtgcga gagcaatatc atcgtcatcg  153960
acgagtgcgg ccttatgctg cgctacatgc tgcaggtggt ggtgtttttt tactacttt   154020
acaacgccct gggcgacacg cgactttacc gcgaacgccg cgtgccctgc atcatctgcg  154080
tcggttcgcc cacgcagacc gaggcgctgg agagccgcta cgaccactac acgcaaaaca  154140
agagcgtgcg caagggcgtt gacgtgctct cggcgctgat tcagaacgag gtgctcatca  154200
actactgcga catcgccgac aactgggtca tgtttattca caacaagcgt tgcaccgacc  154260
tggactttgg cgacctgctc aagtacatgg agttcggtat cccgctcaag gaggagcacg  154320
tggcctacgt ggatcgcttc gtgcggccgc ccagctccat ccgcaacccc tcgtacgccg  154380
ccgagatgac gcggcttttt ctctcacacg tcgaggtgca ggcttacttc aagcggctgc  154440
acgagcagat ccgcctgagc gagcgccacc gtctctttga tctgcccgtc tactgcgtgg  154500
tcaacaaccg cgcgtaccag gagctctgcg agctggccga cccgctgggc gactcgccgc  154560
agcccgtcga gctctggttc cgccagaact tggcgcgcat cattaactac tcgcagtttg  154620
```

```
tcgaccacaa cctctccagc gagatcacca aggaggcgct gcgccccgcg gccgacgtcg   154680
ttgccaccaa caactcctcc gtccaggctc acggaggggg aggatctgta atcgggagca   154740
ccggcggcaa cgacgagacg gcgttttttcc aggacgatga taccaccact gcgcccgata  154800
gccgtgagac gctgctcacc ttgcgcatta cctacatcaa gggcagttcg gtgggagtca   154860
actctaaggt gcgggcctgt gttatcggat accagggcac ggtcgaacgt tcgtggaca    154920
tcttgcaaaa ggacacgttt atcgaacgca cgccctgcga gcaggcggcc tacgcctact   154980
cgttagtttc gggcctgctc ttctcggcca tgtactactt ctacgtgtcg ccctacacga   155040
ccgaggagat gttgcgtgag ctggcgcgcg ttgagctgcc cgacgtgagt tcgctctgcg   155100
ccgctgccgc cgccacggcc gccgctcccg cttggagcgg gggagagaat ccgataaata   155160
atcacgtcga cgcggattct tctcaggcg gccagagcgt gccggtatct caacggatgg    155220
aacatggcca agaggagacc cacgacatcc cctgcctgtc caaccaccat gacgactcgg   155280
acgccatcac ggacgccgaa ctcatggatc acaccagtct gtacgcggat cccttttttc   155340
tcaaatacgt caagccacct agcctggcgc tgctttcttt cgaggagacg gtgcacatgt   155400
acactacctt ccgcgacatt tttctcaagc gctaccagct catgcagcgt ctcacgggcg   155460
gtcgcttcgc cacgttgccg ctcgttacct acaatcgccg taacgtggtg ttcaaggcca   155520
actgtcagat cagctcgcag accggctcct tcgtgggcat gctttcgcat gtgtcgccgg   155580
cgcagacgta cacgctcgag ggctacacca gcgacaacgt gctcagtctg cccagtgacc   155640
gccaccgcat ccaccccgag gtggtgcagc gcggcctttc gcggctggtg ctacgcgatg   155700
cgcttgggtt cctctttgtg ctcgacgtta acgtttcgcg cttcgtcgag tcggcgcagg   155760
gcaagagtct gcacgtgtgc accaccgtgg actacggcct cacttcgcgc acggccatga   155820
ccatcgccaa gagtcagggc ctgtcgctcg agaaggtggc cgtggacttt ggggaccatc   155880
ccaagaacct caagatgagc cacatctacg tggccatgtc gcgagtcacg gaccccgaac   155940
acctcatgat gaacgttaac ccgttgcgac tgccctatga agaacacc gctatcaccc     156000
cctatatctg tcgcgcgctc aaagacaaac gcaccacgct tattttttga cacaacaccg   156060
tgtaaggaaa acgtgacttt attgagcagg gtaaaaacca cgtacaagaa ccacgttgtc   156120
tatccccaaa aaaacacaca ccgtcaggga acacatcgcc tatagatagc ggcactttac   156180
ataaaaccac cgtacctgca tcacggtggc tcgatacact ggaaattcaa taaaaaccac   156240
cgtgtctccg tgacggtact tatcgggtca gcgtcttttg agatttctgt tcgtaaactt   156300
atccgttttcc ccggtccgcg gtgtctcctc gcgaggctga cagtcgacgg gtggtacctg  156360
caagagaaga aacccgggtg ggagcgacgc cgtcgctggg tatcaacccc gcggctgacc   156420
gtcgtccggt aaaggaacaa cccgtcgtcg caagccgggt tcgaccaaga gaaaaaccc    156480
gggtgcgggg ggagacgggt cgtcctttgg ttgttcgcgg acggcgtaca tgccgcgtgg   156540
gtcagtcgac ggcgtcgctc cgtgcggtcg gtcatcattc tgcttcacat atatgggttg   156600
tttgtgtttt tttttataat gaatacgcac tgatcctatc cgtgactgcg cgtgtggcag   156660
agaggatgcc ttataacatg tattttgaaa aattgccaac agctataatt tctctcatgt   156720
agcagaatag agaccttttg tcgtcttttt gtttgtcatt acttgttttc cagggaatta   156780
gagagaggga accgcgcctc cggcggcggt gcccgcggac cccggcccct tctcgcgtgc   156840
gcggtgtgac tggttgagcg aatgagcagc taggcttggt ggtgctccgc gtgcggggga   156900
gaagacgatt aacaacaaaa aataagtgga agtggccggt gggtctttgt ccgcgtgcgc   156960
gcccatccgt cgccgggacc gagcagaaag tgatgtggtg gtacattgat tttttccttg   157020
```

```
acaggaaaga aaaaaaagag ttttgttttc ctatgtgaga ggagaaaggt atgtgaggag  157080
atgttcgatg atcgtatgtt acagttatgc tgtaaggaag cttttatcgt gcgtcctgtt  157140
tttcatttga tgtatatgac acaattgaaa cctatcgata ggcgtatatc gaggattcat  157200
caattcttag aatcgtcgtc ttttttggcta attggactttt gcccatgttg gttgtcattc  157260
gtggcctgag gtcatcgtcg tccacgacga cgtgtctata gcgtgcggtg tgatcattgt  157320
gtcgagccag agaaagcgcg cctcgcacga cgtttgcgga tcggctcgcg ggtgtgtgga  157380
attcctaaga acataatcag ctggtcgtct ttctttgatg tgttgttgtc gtcgaggtct  157440
tgcttcgttt tcttttttct ttttagtcga tggaactttt cttcggtacg ggttcttgtt  157500
atggaagctt gtgttttcga acatgaattc gaaaaaataa aaaggcctat cttcgtttca  157560
aaaaaaggac agatatcaat cttcttaact tatatcatgg taaattcaga atcctatggt  157620
gtcttattat ctctaaagta gtcaacatta tggtctaact tgtatttccc tgacgagata  157680
tatatgatcc ttataacctg gctactatca tgaacaacaa tatccttact tacagtcatc  157740
ttcgtgagtt aatgaagtat aatatcggtc atctatcaac ttatctgcta tgtaacgtac  157800
ccttttaggt attttgcgtt tcttaacgag tgtacccgcc tgtgtgaggc gaaactctga  157860
gaagtctacc gagtcgagtt acaagtcact aaaacactta cacgagttat ctatactaaa  157920
atcactatct atgttgtttg cttacctaat tattatccta catgacgaag ctacctccca  157980
acgtaaggta gggggagagg agacagaaca ataaaaagta actaatgttt cttagaactt  158040
acccgctaag gacttaccaa actatattca ccaaaaaaca acagctacgt gtttcatttg  158100
ttttaatcta ccgaagtaaa aaaaaaaaga tgattagcta tccagaacct acttacttct  158160
taatgtttta actaaggatg cctatgggat tggaaaaaaa atcacagcaa cttgctacta  158220
atcagttgac agcgaagaga ctcataacaa agatttctgg gtaatacggt tataataatg  158280
cttatggact aaaggatact tggaaaaaaa gaacgggcta tgactataga gattcgtcga  158340
gatatcaaac ttcaaatagg cggctatcat tcatggttgt ggtgactata tcgtggagaa  158400
aaaatgtgat cgttagttag ctaggtgaga cttacagcta tccatccgtc tagttttttcg  158460
ttgtaatgat gatagtacgt ctatggtggt gatcgatttt ggttaacaat ttgttcgttt  158520
aaaggcttaa tgtacttatg ctacatgatg tattattctt tgattcatcg ttcctcctaa  158580
gggggtgtat gtatgtatgt actagtcgta tagtgttcct aacatcatga ctattcagac  158640
tatggcttca tctatcgtgt ctaaagttca cttattctac tattactata tatatgcact  158700
actatgtaac taggatatgg tcctataagg tgtcttctat cacggtggct tgtttatcgc  158760
ttggcggtta cgagcaagag ttcatcacgg accagccgtg aggcagggca cacgcgggtc  158820
ggcggcgatg atgtcccccg cgaagggggac aacgaaaaca agaggccgcc ggccgcggcc  158880
acggatgcgt agcggttaca caatgtttgg ttgagcgttt tgtttcatcg tcgtggtggt  158940
tttgttgttc tctgtatata tcgtgtggtg gctttatcgt catcattatt atcatcattc  159000
ttgtttccat catcacgatg agttttctcc gttttcctct cctccagtgg tagtcgtgta  159060
tcatcatcaa tcatcgtagt gacgtcgttg ctgctgctgc tcttgccttc atggcggtat  159120
ttctcttcct cccccctaac cccatattaa ctcgtgagtg tgatggttag agtggctgct  159180
tgtttttttt ttcttttctc tttggaacaa caaaagagga taaagatggt cggtgaatgt  159240
attattatta tcatcattat gatacggtcg cggtcttctt ctccgatgac gaaacctgcg  159300
cacatcgaag aaaagacgag cgcgcgaacc gatagccgtc cgtctgggac gaaggagaag  159360
```

```
atgatgggga gaggaggaga gccccagaag ccagagcgag aagggagacg acagacatac   159420
gtcgtcaccg tcctctggag gaggcacggc ggcgctgttt gttgtttgga tgcttgatta   159480
tatcctgttc tatggggtag attattatca ataggcttgg ttttcaaagg tcagcctgtg   159540
tattgtcgtg tcttttttt tcgttctcat gatcgcggag accacacaga cgtgcgcgtc    159600
tcccaatggc taggcgttct ttttaggtag taatttttg atctttttt tttcttaaca     159660
agtctggctt gatttctttt atctatgatc gattcttctt tttctcgggg gttgcatctt   159720
ccgtgaaagt aaagtgacac tactctaaat ggtaaccata ttatctgttg attaggagaa   159780
aaaataattt tttcgcacga aatcgatcct aagtgaggtg atttacttgc tatcacacga   159840
aatgattatc ttttgctgct aacgtactga attttttaac agaattgctt ctccgtaact   159900
atttccgcag attcagacag attgtcaaaa agaatacgg cacagaaata gtgggtctgt    159960
ggcttttggt tcgtgtacat tcgcgtttgc gtgtcgagat ttctacggta tgtttattct   160020
tcctgcgatg atgtagggtc cttggtgtaa gtaggatttc gagtatctct cttagagcga   160080
acaaataat caaaaaacaa cagctaggaa atcgaggggt actctacgat aaagtgtctc     160140
tacaaagtga agaatgttac gttgtggtgg aataataaga ctcgcgtgat cgatgagtga   160200
tcgagagcgg ctcgaacctt cttttaagagc tttgtttagt gcaactttaa attacaagga   160260
gtagaaagct gaaatgaatc tatgaaggtg ctattctttg aatatcttac tttgtacgct   160320
tcacattcgt tatttggata gagagttgtc tagagaaaat ctgtgattct ctatgagtgt   160380
tattttatt atccttttgg ggactacgat ttttcttctt gttctacata ccactactac     160440
tcgtaatcac atacatggac gaaaaaaaaa ttcgtcaggc agtagatacc agattctccg   160500
acgttacggc gtcttttttt tcttttgaga gagtatctgc tgagattgtc cgtggtgtat   160560
ctagtcgcta ttttgttgt tactagtagt tttgcacaca gtttattcag tatagttttt     160620
cttcttgcca tgatcaatta agcccaccac ctttttttt agagaggagg aatttcgtct    160680
tgatctccag ccggagacaa cggcggtggt ggtggtggcg ggagagactt caaggcaatg   160740
aaaaaaaaaa tttcgttttg ccatcaagtg gtgacgataa cccgtcagat tgataattgg   160800
ttcctacaga aactattcta accgcggaag aagaaattg aaaaaaaaaa ttgacaaaaa     160860
catcataaca taaaggacca cctacctggg acgcgcagtt gggcggcgga ctgggacggc   160920
atgctgcggc gatgctgtcg gtgatggtct cttcctctct ggtcctgatc gtcttttttc   160980
taggcgcttc cgaggaggcg aagccggcga cgacgacgat aaagaataca aagccgcagt   161040
gtcgtccaga ggattacgcg accagattgc aagatctccg cgtcaccttt catcgagtaa   161100
aacctacgtt ggtaggtcac gtaggtacgg tttattgcga cggtctttct tttccgcgtg   161160
tcgggtgacg tagttttcct cttgtagcaa cgtgaggacg actactccgt gtggctcgac   161220
ggtacggtgg tcaaaggctg ttgggatgc agcgtcatgg actggttgtt gaggcggtat     161280
ctggagatcg tgtttcccgc aggcgaccac gtctatcccg gactcaagac ggaattgcat   161340
agtatgcgct cgacgctaga atccatctac aaagacatgc ggcaatgtgt aagtgtctct   161400
gtggcggcgc tgtccgcaca gaggtaacaa cgtgttcata gcacgctgtt ttacttttgt   161460
cgggctccca gcctctgtta ggttgcgag ataagtccgt gattagtcgg ctgtctcagg     161520
aggcggaaag gaaatcggat aacggcacgc ggaaaggtct cagcgagttg gacacgttgt   161580
ttagccgtct cgaagagtat ctgcactcga gaaagtagcg ttgcgatttg cagtccgctc   161640
cggtgtcgtt cacccagtta ctttaataaa cgtactgttt aaccacgttg cgtcgtgacg   161700
ttgtttgtgg gtgttgctag gcgggctgga aagatgatgt ataaatagag tctgcgacgg   161760
```

```
ggttcggcgc tctgccggct gcggcggcac tcgctccacg gcctccgacg agcgttgcgc   161820
tcgcgctttg cgccgccgcg tcatggatct ccctactacc gtcgtgcgaa aatactggac   161880
ttttgcgaat cctaatcgca tcctgcatca aagcgtcaat cagactttcg acgtgcgcca   161940
gttcgtcttc gataccgcgc gtctggtcaa ctgcgtggac ggcgatggca aggtgctgca   162000
cctcaacaag ggctggctct gcgctaccat tatgcagcac ggcgaggctt cggccggcgc   162060
caagacgcag cagggcttca tgtctattga cattacgggc gacggggagc tgcaggagca   162120
cctctttgta cgcggcggta tcgtcttcaa caaatccgtc tcctcggtgg tgggctccag   162180
cggacccaat gagagcgcgc tgctcaccat gatttccgag aacggtaatt tgcaagtgac   162240
ttacgtgcgg cattacctga aaaccacggc gaatcctcc agcggaggcg gtggttgcgg    162300
cgccgcgtct accgcttccg ccgtctgcgt gtcctcgctg ggtggcagcg gcgggactcg   162360
cgacggccct tctgcggagg aacagcaacg gcgaaggcag aacagcgtc acgaagaacg    162420
gcgcaaaaag tcgtcctcgt ctgccggtgg tggtggaggc ggcggcgctg gtggtggcgg   162480
tggcggcggc gggagcggcg gtcagcactc ctcggactcc gccaacggac tgctgcggga   162540
tccccggttg atgaaccggc agaaggagcg gcggccgcct ccctcctccg agaacgacgg   162600
tgagtcccgg ccctcctcgc gtcacggtgc tttccgagtg gactcgtgag cctcccgtag   162660
cgcacgagcg agcaggcgag cggtgttggt gcgctggtgg ttgtgtggat gataaccatg   162720
tgcttttcg tgcgctatgt gtcgtcccgt ctgtaggctc tcctcccctc cgggaggcga    162780
agagacaaaa gaccaccgca cagcacgaag gccatggcgg cggcggcaag aacgagacgg   162840
agcagcagtc cggtggtgct ggcggtggtg gtggcggcgg cagcggccgc atgtcgctgc   162900
cgctggacac gtctgaagcg gtggccttc tcaattactc gtcctcatcc tccgcggtct    162960
cttcttcctc caacaaccac caccaccatc atcaccacca taacgccgtg acggacgtgg   163020
ccgccggcac cgacggtgcg ttacttctac ccattgagcg cggagcggtg gtttcgtcgc   163080
cgtcgtcgac gtcgccgtcg tcacttcttt cgctccctcg acccagcagc gcccacagcg   163140
cgggcgagac ggtgcaggag tccgaggcgg cggcgacggc ggcggctgcg gggttaatga   163200
tgatgaggag gatgaggagg ctccggctg aggcggcgga ggcaccaccg cagtcggagg    163260
aggagaatga ttccaccact ccagtctcta actgccgtgt tcctccgaat tcgcaggaat   163320
ccgcggcgcc tcagcctcct cgcagtccgc gttttgatga cattatacag tcattgacca   163380
aaatgctcaa tgattgtaag gagaaaagat tgtgcgatct ccccctggtt tccagcagac   163440
tcttgccaga gacgtcgggc gggactgtcg tcgtcaacca cagcagcgtc gcgaggaccg   163500
ccgcagctgt ctccgcagcc ggcgttggcc ccccagcagc cgcatgtccg ccactcgtca   163560
ccaccggtgt tgtaccctca ggttccgtcg ccggtgtcgc gccgttgcc gccgcaatcg    163620
aaacaccagc tgctcctccc cggcccgtgt gtgaaatcaa gccctacgtg gtaaaccccg   163680
ttgtcgccac cgccgcggct gccagtaact cttcctcgtc ttcttcggct ccactgccgc   163740
cgccgccacc accgtcgggc ggacgtcggg gtcgggcccg gaacaatact cgaggaggcg   163800
gcggtggtgg cggtggtaga aacagccggc ggcaggctgc atcgtcgtcg tcctcctcct   163860
ctcgagatc gcgacggaga acaaccgcc acgaggacga ggaggacaac gaccctctgc    163920
tccggttgtc gcaagttgcc ggcaacggcc gccggcgagg gccctcgttc ctcgaggacg   163980
gactcgaaat tatcgatccc agcgaggagg ctgcgatcgc cgccgcctcg atcgcggcgt   164040
ttttcgacga ttaaaaaacc gagccgagac cggaaaaaat atgaaacagg acgcgcttgg   164100
```

```
acatttgggt ttccacccct tttggtgtgt gtctatatat attggtcact gattttttt  164160
acaataaaga gatagacatc acagttcacc accttgtctc cccggtgtgt ctattatcat 164220
caatcaccca cagagtcgcc agtccatggt ctctcggtaa tgcgtgtcca gatacgcgtt 164280
ggccagtata aaatggtcgt tgcccacgaa ggcgcgggtg tgttgcgcg cgacgggtg   164340
gcaggacttg agtaccaagt gccgccgtcg gtcgatcagg tactcgcagg tgtgcgcgtc 164400
ggcgccccac agcatgaaca ccagatgctc ccggcgctct gacagcctcc ggatcacatg 164460
gttactcagc gtctgccagc ctaagtgacg gtgagatcca ggctgtccgt gcaccacggt 164520
gaacacggtg ttgagcagca gcacgccgcg tcgcgcccag gcgtccaggc aacccgaggc 164580
cggacgctga aacccgtcca ccgtacgcgc cagttcgcga aacacgttgt tgagggaggg 164640
cggcggcggt cggcccgcca gcgtgccgaa ggccaggccg ctggcgctgc cgtcgcagta 164700
cgggtcctgg cccacgatca ccacgcgcac ctgctcgggc ggacacagat agctccagcg 164760
gtgtacgtgc tcgggtgccg ggtacaccat ctcgagttgc cgcgcgccct ccaccgccgc 164820
caccgtgtcg cgcagcagca ccgtgtcgtg gtcgggcaag ctgaggaagc ggatccagtc 164880
ggcgctcaga caaaacacgc gagcctgctc gtcggggtt aacagagagc ctttattatc  164940
agcaatgtta gcgagcatcc actgcttgag gccatagcg cgagtgagcc ggcaggttga   165000
cgcgcgtctg cttcagctcg ggcggcagtc cggcgtagta tttatctagg tggcgtagta 165060
gcggcgggtc cagctggtga cgcaggcaga attccttcac tgcgttgtac aggccgtaaa 165120
agagtgtgat gccctcgggc gcggcagcgg tgctcacggg cagacgcacg gcgcggttgg 165180
tacgcgtggc ttcgttgcgt atggccacca ccacgttaaa gagagacggt ggcaccagct 165240
cgaagcctaa cacgtgttcc gtgaagatgc tgcgcccgta tgacagtcgc gtgaggtcgt 165300
agccgcggca caggtcgtcc acgcacgtgt acacggccgg cgagccatcg ccgcactcgc 165360
tgtagccgcg catcaccgtc atccagcgcg gcgctgtgtc cgagctcaac agcgtcagca 165420
gggcccgcaa ttgatccgga ttgttgtaca gcagggccag agtgtccagg aaagcatcgt 165480
ccaacagcac ggagttggcg gcctccggcg taacgggacg gtaacgaata agttgcgata 165540
gcgggccatc gcgtctggta acattccacca acgggcgcag ccaactttca tacttgtcac 165600
cctgaaacac ctcacccaac aggcatcgac gcgttagttc ggggcactcc gcgggacttt 165660
tctcggcggc ggtaggagcg acgctgacgg cgactgagga aacaatgggc agcagaaggc 165720
aacaccacag cagtaccacc ggtccaggtg agaaagagaa gccgcaatcc gggcggcggc 165780
acatcaagtc tgcggcacga tgagagtgtg acggtaagga gccagttggc gccgaaagtt 165840
ggcgctcagg tcttcgatcc ctaaaacgtt atatattgca tccagcaggt gagccaggct 165900
aaacggattc acgtaccagg tttggttacc cgcgacgatg acggccagac cgtgggcgct 165960
acagttggag aggttcctgg gtacgaaggt aactgagtcg atgtcgcgcc acgggggaa   166020
tgagacagac gactggcgca cgctgtaatc acaactgtga ttgacgtgta gcgtgtaatt 166080
tcggttgcac tcagcctcga agtagagggg gaaccacagt tcgtcgtact cgtcgtcgtc 166140
ctccagttct ggctcttctt catccaccgc aatgtctacg ctgctctgag attcctcttc 166200
gtacaggatg attgacaggt tatggctaca caggtcctgg gcgggaggac gcgtgggagc 166260
gcgggtggtg gtaatgttt ccagatcgtc aaaagtcgga gtgtagtctg acgccgtgac  166320
gacaccgtcg acgagatgg tagaagttgc ggccggtgtc acggtggtaa gtatggatac   166380
agaaggggag ggggaagtag cgttcgtacc gatggttgtg gtattattat tccctgtgtt 166440
tcttgttcca gaaaccgttg acgttgagat gggaatcgac gtggtgctgg acgtcagatt 166500
```

```
gctgaccgag gaaaccgtgg tgggagtggt gacggtgtta ctcgtggttg aagtgacgtt  166560
aggggaggta gtagtggtac cggtggtggc gacggtagtg tttgtcgtgg cggcggcagc  166620
ggtggtactg gtaacggtgg tcgcgttggt ttccaccgct tcacacagta agcaaaagca  166680
cagggccggg aaaagcaacc agccccgcca tcgccgccgc cgcttcatga ggtgggcagg  166740
cgaaagctgg tgaattcgtt gtacagcggc aagtggggcg ccgcgatcga agggtacgtc  166800
aacaagctga cgttgatatt aaatacgtct ggctgctttt ctacgatgga agcgcacagg  166860
gttacggcgt caaacaggtc tttcttggtg gcgcccgaga cccacatctg gtatacaccc  166920
gtctcgtggt acgaagtaga gcgcggcacc accggacgga tgcagtccag aacgcggttg  166980
ggatcctggt gaaagaattt gaacgtggct acggcctgtg gcgtgtgcgg catcgtctgc  167040
gtgatgagct gctggcccgc taacacggtg acgttgtgca acttgagcag ggcactcttg  167100
agggcctgga aagcgttgcc gcacgaggcg ctgatctgca gctgcacggc cgtggagtcg  167160
tgcagccgca tgagacgtga tacctcttcg aagacgtact tgtatttgct ggcaaaaagt  167220
ggcgcgtacc gacagtcggc cggcaaaatg taggtggcgt taccgccgtt ggtggccacg  167280
gcgggcgcag cggccgcgga ggccggcgta acagcgtca gcggccggtg gtggctggta  167340
aggtcgatca tgggcggcgt ggtgaccgtg gcggtggcgg gcatgacggg gtttgcggcg  167400
acgggcactc cggccacagc ggcggccgcg gcggccacgg cggcacttgc cgagcccaca  167460
cccgccggca gtcctccgcc acccatgacg ccgccgggca gagcgtcgcc cagacagact  167520
tccgcagtgg cgggcgcgct ctcagcggtc agtacggttt gccgatcgac ctcgcgacga  167580
aagctggtga ggaactcact gtgatccatg gccgcagggc ccgagatccc gggattctgc  167640
gggtgctgac cgagtgcggg gcgagttata tggaagacga ttagcttgga gcggagtttt  167700
gcgtccctag ctgacctgcg gatcagcgac gtgccatagg gatagactgt gagcggcggc  167760
cgcaacggcg gggtcggccg ccgctcgtcg tcacggggcg gcgcgaggga ggaggaggtg  167820
gtgggtacga tcttgacgtg gttgacgtcc tgcccgtccg ggggaatacg caaaaaaccc  167880
cgtcgcggcg ctaccacgat ggtgcgatgg gtctttctct tgttggccgg ggccagggac  167940
ttgcagatgc gtgtggagcc gtagacgatc tggacgtggt cctgggagaa catgaccatc  168000
gccgccaacg ctcagcgggg ggacgtgttg ggaacacaga ggctgaggga aaactccgta  168060
gaagtcagcg aaataaagac aacacagcag ccactcctct cgtctcgggc cctaccactg  168120
cttgaagtag ggcaccgggt gtttctttt ctcaacgggc tcctccagtc tcttatagga  168180
ccagtcccgc cggcgcgcca gcatgtaggt cacgtacaaa agaataatca ccatgaacac  168240
caggaaagcc agcacgccgt aggccagcag ccggtcctcg aacagcgggt cgctcttgat  168300
aaacacgtag gtggtggtaa aacttcggcc cgcaatctga acgtggagac gcacgacagt  168360
atacgtgccg ttgaggtaga agacaaactc gcgtaaccgt tgtccgttat acgtcacgtt  168420
actaatattc cacggcggaa tgagctggtt gccctgatgc agatgcacgg tgctgttggg  168480
gtgatagagg ctgctaccgt tgagcaagca gtgttcgtgt tcctgaagca gcacgcggac  168540
ccgcatcgtg gtggcgttca ggcgagtccc gtacacggcg tagatgggat aggtgaaaag  168600
gtcccaagtg gcgttgtgat ggcggcccca gctgaagaaa gagcacgtgt actcagtggt  168660
ctcctgcggc ctgagtcccg agataagcag ctcttgagca gtagcgttgt aggagagatg  168720
tagttttcct gtggataaaa ttcataagtt gtttattttg ttggcaggtt ggcggggag  168780
gaaaaggggt tgaacagaaa ggtaggtgct acttaccttc attatcgggg gggaaggcgc  168840
```

```
taagatacccc cacctgagtg aagggaccct tgcagtctgt ccgtgcataa caagtaactg  168900
ataaaatgtc tggattttg gtgttattca acaggataac tttgcaggtg gcgtttagag  168960
acacttggtc gtggctgtag ctggcttcgc aattcacagt atacaggtgc ccctctttct  169020
gcgtcgtggc tatcacggaa gtggaggcgg acgaggtaga ggtttgtacc gtggtggtga  169080
cagcagaagt gacgttgtta gaggtactta ttgacgtagt agacgtgacg gtggtattac  169140
taggggaagt gacggcgctt gtggtgctac ttttcacccc cgggtgcatg tcgcccaaga  169200
gcgcaactac gagcgcgatc gccagtacgg aacacatgtt gccgtgtgac gagacggcgt  169260
gtggacgagc tatatgtggc aggaggtcgc gtcacctctt gtgacgccta aacgtccagc  169320
tccagataaa agaggcgtta ataatgaaga ccacaaaaac cacttgcgtc agtatgacaa  169380
tcataaaggc tcggtgattg ctacgcctaa agtacgcggg attatccacc agttcatcct  169440
gctgaacaaa gtggatgatt gacgtattgg tgttactatc cgtgttgttg accatggatt  169500
tgactaagaa agtcttggcg ccaaaagtcc cgttagagcc ccagcaggtg acgctgctat  169560
tcacataagt tcccggtgcc cccgctagca tgtatttcag ttggtgggta aattttttc  169620
tgtcgttatc catgtcattg ctgtagttga ccttgctggt gagaaagcgt gttttcaacg  169680
gggcacttat catcatccct gaggccaaaa agggcgaatt gcaagctgta gtgttacaaa  169740
aaatagtcaa gttagtgtca ttgtattgat aaatgtaagc catgcttact tcaggctcat  169800
accacccgat tccaatcgcg gccgccatcg ttaccacgtc ccatcttccc agacttacca  169860
ccgccaccac taacagcgtc accccgcac ggtacatagt taccctctcg acgtcgccgg  169920
ctgtcaatga cgtgcctgcg tcagtggcta tgatttatag cttttgggcc caaccgcaac  169980
ggatctgtcg taatctacct tccacagggc cgccgcgacg atgctgaacg acaggatcag  170040
acagacggcg tacaaaagtc ctaggtcggc gtcgacgcgg caggtgcgga tgtctcgcag  170100
ggtgggtaga tgggcgatgc acaactcttt ctcccccgc ccgtacatcc catcttgtat  170160
cagcagccgt agcgtggcat tgatggtcag cggggtaacc aaagaaatca catagggatg  170220
tgtacaggaa gtgcagtgac gggtatccgt gagatgtaag tcaccaccct cctcaccgtc  170280
atcatgaaag accaggactc gggtgagacg acccgatgaa tactggatct cccaccacag  170340
tctttggtcc aacaccgaga gggcgcaaga gattctaagt ctccctgggt tgggggagca  170400
gatgtaagtc ccgtatgtgc ctctcgccat cagggccata cacatgaggg ggagaaggac  170460
aattatccgg gaccacccgc accccacat cacgagacca gagacggaga tgtataaaaa  170520
aagctacttt tattaaacag cattctcacc acacgttaat actgtcacgg ggaatcacta  170580
tgtacaagag tccatgtctc tctttccagt ttttcactta ctgagacttg ttcctcaggt  170640
cctggatggc tgcctcgatg gccaggctca gggtgtccag gtcttcggga ggggtctcgg  170700
tgggctgctc aaactgcccc acggcgtagg ccttcgcggc cgtctcgtag ataggcagca  170760
tgaacccacc ctggttggtg gagaagatgc gcaccatgac ctgtttggga aacttttgca  170820
tcaggggcag gcacaggttg agagcgccca acaggtccac gggggtggca gcgtggatga  170880
tcatgttgcg gtaatcggag gaacgggggc ataattggtg ggtgtgcaat tctttgaggc  170940
tccacgcggc cttgacgcct tcgttacaag catcggctgt gcgctgcgcc acttcgggtg  171000
gatgtgtcac gggcatggtg tgctccatga ggaagggagt ggagagggcc aggttgcaca  171060
tggtgcccag gcgacaccgc accgcatcca cctcactctt cacctcatga ttgcgggtgt  171120
agataatctg gatgcccttg ttgttcacct gcatggtttt gcaggctttg atggcctcat  171180
ctaacacctg gtgcatactg ggaatcgtga agggcaggtt cttgtactca agagagcgat  171240
```

```
tggtgttgcg gaacatgcgg ctcacctcgt caatcttgac gcgacccgc cgagtctgca   171300 cgttgggtgt gcagaagggg gtgttcttat ctttcatgat attgcgcacc ttctcgttgt   171360
ccaactcgga gatgcgtttg ctcttcttct tgcggggtcc ggtgctcgcc ccgccgctgc   171420
tctgatggcc gcagctcagc agagaggagg aggccgcgcc accaaaaccg ccgcgcccat   171480
ggtggctcga ggtcacggat gctcctccgc cactgctgca tttcatctcc tcggactcac   171540
tctccgagtc cgaagccgaa ctgcaggagg aggaagacga agaggaacta tcttcatcgg   171600
gccggcccaa gggatcggga agaggagggt ggttcatctg ggagagcggg tgcgtgggag   171660
aggtcactcg cggcgtgccg ctgccggtgg aaggggaaga gcgggtagca ccgcgggttt   171720
cgacttcttc accctgttct tcctcgctat cagagatcac gatacagccg gcggtatcga   171780
taatcttgtt gcggtactgg atggtaaagt cgggctcggg cttgatgtct tcctgtttga   171840 tgagggcag catgataggc gcggaggca cgggcggttt aataatcacc ttgaaaggac   171900
gcgtggtttt gcgcggtttc ttacgcgggc tgagctcggg agtagcggat gccccgggga   171960
gaggagtgtt agtaaccgcg acgctggtgg gggtcggctt gttaagaggg gcgctgctaa   172020
cgctgcaaga gtgggttgtc agcgtggggc cggtgctact ggaatcgata ccggcatgat   172080
tgacagcctg ggcgaggatg tcacctgatg gtgataagaa gacacgggag acttagtacg   172140
gtttcacagg cgtgacacgt ttattgagta ggattacaga gtataacata gagtataata   172200
tagagtatac aatagtgacg tgggatccat aacagtaact gatatatata tacaatagtt   172260
tactggtcag ccttgcttct agtcaccata gggtgggtgc tcttgcctcc agaggcggtg   172320
ggttcctcag caccatcctc ctcttcctct ggggcaactt cctctatctc agacactggc   172380
tcagacttga cagacacagt gtcctcccgc tcctcctgag caccctcctc ctcttcctca   172440
tcactctgct cactttcttc ctgatcactg ttctcagcca caattactga ggacagaggg   172500
atagtcgcgg gtacagggga ctctgggggt gacaccagag aatcagagga gctgacacca   172560
gcggtggcca aagtgtaggc tacaatagcc tcttcctcat ctgactcctc ggcgatggcc   172620
cgtaggtcat ccacactagg agagcagact ctcagaggat cggccccag aatgtactgg   172680 gcaaagacct tcatgcagat ctcctcaatg cggcgcttca ttacactgat aacctcaggc   172740
ttggttatca gaggccgctt ggccagcatc acactagtct cctctaagac atagcagcac   172800
agcacccgac agaactcact taagagagag atgcccccgt acatggtcat catacaagcg   172860
tcactagtga ccttgtactc attacacatt gtttccacac atgtagtgag gatatccata   172920
aatatgtgat caatgtgcgt gagcaccttg tctctctcct catccaaaat cttaaatatt   172980
ttctgggcat aagccataat ctcatcaggg gagcactgag gcaagttctg cagtgccgcc   173040
atggcctgac tgcagccatt ggtggtctta ggaaggctg agttcttggt aaagaactct   173100
atattcctgt agcacatata catcatcttt ctcctaagtt catccttttt agcacgggcc   173160
ttagcctgca gtgcaccccc caacttgtta gcggcgccct tgctcacatc atgcagctcc   173220
ttaatacaag ccatccacat ctcccgctta tcctcaggta caatgtagtt ctcatacatg   173280
ctctgcatag ttagcccaat acacttcatc tcctcgaaag gctcatgaac cttatctaag   173340
atatctaagg cattctgcaa acatcctccc atcatattaa aggcgccagt gaatttctct   173400
tccgtctggg tatattttt cagcatgtgc tccttgattc tatgccgcac catgtccact   173460
cgaaccttaa tctgtttgac tgtagaggag gataacaaca catataagta tccgtcctcc   173520
tgactcattt atcgctatct cgatgccccg ctcacatgca agagttaatc tttactctat   173580
```

```
ctgacataca caagtaaatc cacgtcccat gcaggttagt atacatcaca tacatgtcaa   173640
cagacttacc gagttctgcc aggacatctt tctcggggtt ctcgttgcaa tcctcggtca   173700
cttgttcaaa agttttgagg gattcttcgg ccaactctgg aaacagcggg tctcccagac   173760
tcagctgact gttaacctcc ttcctcaaca tagtctgcag gaacgtcgtg gccttggtca   173820
cgggtgtctc gggcctaaac acatgagaaa tagagtcata agcacatggg tcacatacag   173880
gagatatgta tataacatta atacaatttt attaaaaaaa aaggggggc acaaaccccg     173940 acacgtaccg tggcaccttg gaggaagggc cctcgtcagg attatcaggg tccatctttc   174000
tcttggcaga ggactcttcc ggttttagaa gctccacatc gaagacgaga gtggcatgtg   174060
gtgggatgat gcctgggtgc ccagtggcac cataggcata atctggagat atagtcagtt   174120
tggctctctg acccacactc atctgggcaa ccccttcttc ccagcctcgg atcacctcct   174180
gcttgcctag cataaactta aagggcttgt ttctgtcccg ggaggaatcg actttctttc   174240
catcttcaag catcccggtg tagtgcacca cacaggtctg gccgcgcttg gggaaggtgc   174300
gcccgtctcc tggggagatg gtttccacct gcactcccat cgtgtcaagg acggtgactg   174360
cagaaaagac ccatggaaag gaacagtctg ttagtctgtc agctattatg tctggtggcg   174420
cgcgcggcag caacgagtac tgctcagact acactgccct ccaccgttaa cagcaccgca   174480
acgggagtta cctctgactc ttatcagaac acaacaactc agctgcctgc atcttcttct   174540
gccgctgcct taagtcttcc aaatgcgtca gcggtgcaag cccgctcccc gagctcattt   174600
tcagacacat accctaccgc cacggccttg tgcggcacac tggtggtggt gggcatcgtg   174660
ctgtgcctaa gtctggcctc cactgttagg agcaaggagc tgccgagcga ccatgagtcg   174720
ctggaggcat gggagcaggg ctcggatgta gaagctccgc cgctaccgga gaagagccca   174780
tgtccggaac acgtacccga gattcgcgtg gagatcccac gttatgttta ataaaaactg   174840
cgggcactgg ggacggtggt gttgtatatg tgaatttgta aataataaat gagacccat    174900 cctgtaaaaa tacagagtcc gtgtcagtct ctgaaggaca gtgtattggc atatagccaa   174960
taaagagagt tgtggcaaag agccatgtta tggattagta atggaaagta tcgtcaccaa   175020
taggggagtg tcaataatg gtcaataacc cacacctata ggctaagcta taccatcacc    175080
tataacatga ggaagcgggg gtgtatagac cccaagccaa aaacagtata gcatgcataa   175140
gaagccaagg gggtgggcct atagactcta taggcggtac ttacgtcact cttggcacgg   175200
ggaatccgcg ttccaatgca ccgttcccgg ccgcggaggc tggatcggtc ccggtgtctt   175260
ctatggaggt caaaacagcg tggatggcgt ctccaggcga tctgacggtt cactaaacga   175320
gctctgctta tatagacctc ccaccgtaca cgcctaccgc ccatttgcgt caatggggcg   175380
gagttgttac gacattttgg aaagtcccgt tgattttggt gccaaaacaa actcccattg   175440
acgtcaatgg ggtggagact tggaaatccc cgtgagtcaa accgctatcc acgcccattg   175500
atgtactgcc aaaaccgcat caccatggta atagcgatga ctaatacgta gatgtactgc   175560
caagtaggaa agtcccataa ggtcatgtac tgggcataat gccaggcggg ccatttaccg   175620
tcattgacgt caatagggggg cgtacttggc atatgataca cttgatgtac tgccaagtgg   175680
gcagtttacc gtaaatactc cacccattga cgtcaatgga aagtccctat ggcgttact    175740 atgggaacat acgtcattat tgacgtcaat gggcggggt cgttgggcgg tcagccaggc    175800
gggccattta ccgtaagtta tgtaacgcgg aactccatat atgggctatg aactaatgac   175860
cccgtaattg attactatta ataactagtc aataatcaat gtcaacatgg cggtaatgtt   175920
ggacatgagc caatataaat gtacatatta tgatatggat acaacgtatg caatggccaa   175980
```

-continued

```
tagccaatat tgatttatgc tatataacca atgaataata tggctaatgg ccaatattga 176040
ttcaatgtat agatcgatat gcattggcca tgtgccagct tgatgtcgcc tctatcggcg 176100
atatagcctc atatcgtctg tcacctatat cgaaactgcg atatttgcga cacacagaat 176160
cgcccaagtc accaaagtcg tctatcgcca tcccccgtaa acgatataag cgctatcgcc 176220
agatatcgcg tatgcccaaa aatcacttt ggaaaatgg cgatatcagt tacacagaaa 176280
ctcacatcgg cgacatttc aatatgccat attttcaaat atcgatttt ccaatatcgc 176340 catctctatc ggcgataaac accactatcg cgcgacatga atttagtcgg cgacagaaat 176400
ctcaaaacgc gtatttcgga caaacacaca ttttattatt cactgcagca tatagcccat 176460
tttagcgcgg cacacatcca gccgtttgtg tttttaacg ctctccaggt actgatccag 176520
gcccacgatc cgggttatct tgtcgtattc caggttgatc catcgatagg gaacgctgcc 176580
agcggcgccc agcaggtact gcgccttgtc gttcactttg ccgcagcgta ttcgcccgtc 176640
agcttcgagg tataacctac aacacggagg ggaaggggg gtacaaaacg tgaaattaga 176700 cttttttt aatgatgtt tgtccctctg tcttactttc ccataggctg taaggccctc 176760
gaggaagaga cttacggatt gtagttgcag ctcgtcagtt tgttgtgtac gacctggcgt 176820
gtcaatgaat gggtcatggt ggtgacgatc ccgcgaatct cagccgttt ctcgggactg 176880 tagcagactt cgccgtccgg acaccgcagc ctgtggattc atgaaaatct actctggcat 176940
tcccgaggat cgtcgatgga acatggctat cagaaacgtc gagagacaaa tccagacgca 177000
ccacagaacg cagacaatca taaaaatacg tacgcgacgg tgaagcgatt gcacattttg 177060
aaatcgtaac agcgttccgg cgggtggttg acgtttatga attcgcaaca ttcttctgcg 177120
cgcacccgcg gcacgcggct gtgacccaat agcagccaca acgtcgtcaa gaacggcgtc 177180
aggtctttgg gactcatgac gcgcggtttt caaaattccc tgcgcgcgcg acgggctcaa 177240
acgatgagat tgggatgggt acagaaggtg taagtctggt tattggcctc ggtgaacgtc 177300
aatcgcacct gaaaagacac gctgtagtcc cggaagacgt gggcccagct ctccagcttc 177360
atcacacaca tctgataacg cgtgccatcg ttgacgacga agcgtagcag cttggtctgc 177420
ttgggcacca tgtgcgctcc aaaaatcttg gcgtcttcca cgctgatctg cacgtttccg 177480
tcgctcggtt tcgaagccgt ttggggcatc cgttggagga tggtctggtt gcgaccgctc 177540
agataccaga tcacctttt cacccaggtg gagcttctct ccaccaaggt ctggccttcc 177600
cggttgtaca gcagatacag ggtctcgttg cgacactcgg gacccgttga tacctgctgg 177660
aaccccgaga attgcaaggg ggaccgtggg ggcgagggat agagaaaagg acagtaaaac 177720
gtcgccgcgt catgcggttt ggaatacgtc agtttagacc atggcgggga cggattctgg 177780
tttgccgtta gcgtcgacca cggagacgcc agacagggcg ttgcccaaac cgcgcacaga 177840
agcaggcagt gaaagtggtg acgaagcaga agccgcagca tattatttcc cgtgacgcag 177900
gctagttggc aaagagccgc acgctgaact cgaggctccg ggcgtgtggc gccagcgaac 177960
cggcggcgtt gaacgtggtc cttttgttgg tgccgccgcg acggttctga cgtctaaagt 178020
cgctgatgag caacgacacc tcggtcacgt tgattctgca agcacaggtt ccaaacgtca 178080
tttcataccc catgcggtta cttagccgtt accgttcgc ccttaccttc ccgttgtcat 178140
gcacctttag cgcgtaccct cacctcttga gcacgtcaaa gttgtccaag ccgtggctcg 178200
catcgtagtg gtagttcaac gtgaggtcca cgagctgttc cacatacttg taacgggttt 178260
ggtcgggcag cgcgcgagag cacgcgtccc agtaatgcgg tactcggtaa taatcgtttt 178320
```

```
tttccgcggt ttcccgctgg cactgaccca gcaccacggc gcacagacaa acagacagcc  178380
acacccgaca cagccgcatg ttgcagactg agaaagaaag ctttattatg agacatcata  178440
cacatagtat aggcgaggtg atggggcggg gaaagagttg gaaccgaaag acaaaaaaaa  178500
aagcctagtc gtactcggga tctctgagcg agacgggttg catggcaact ttcattagtt  178560
tgggaatctg ccagctggtg ctgttcgaag gttcttccat ttccgaggcg gtcagttcat  178620
cgtacaccga aacgtagtac ctgatggggt cctcctcatt gtccgagagg tgagattcga  178680
tggtcaaagg cgagcctctc ccataattgg gattcacgaa cgacgtgtcc aagttgccat  178740
cctttctgaa atagatgacg ttctcaggat catgtttcat cgcgctcgcgg gccgcggacg  178800 cctcctcctc ctcgtcccag tcccgagttt ccaaccgctg ataagggctc gaggaacaaa  178860
atccggcggg gatctgagaa cctcgtcggg aaccgctgcc aaacgggctg ctgccgccac  178920
tgtcgtccgt gtcgtccaac aggttgacgg cctcttcgtc ggcgaaacga aagcggcccg  178980
ggtgcttgca acacgaggag taaactaccg cgatcagtac cgctatgaag ctgaaaatgg  179040
aggtgcctgt cacgatgtag aagaggatag ccagcacttt catgatttcg tcattgcgcg  179100
cgtcgtgaac ggaagattcg cgggcagtgg tcatgttggt ttcggttgta ggttcgctac  179160
tcgtggtgct ctcgacggta tttctgctgc tggtgctagt agggacgttt gtgctgctgg  179220
tcatatttgt agcgtcgctg aagtcgatgt gaagcagcaa cccgaacgcg accaggacca  179280
ggaatgttgc gcgaaggaga ccccgcgggg ccggcattct tgagacgtgg cgacgtggat  179340
ttcttgttat gtccgcgaac gacgtgtaac gaggacgtgg tttccgcaag cctctaccga  179400
cgccgcgaca ccaggtaggt tatcaaaacg cgagcccata tcgccgccat cattgtaatc  179460
agcaatgtgt tgaggtactg cacgatgaat ctgtctagtg acaccagcca accctctgct  179520
tttgcgggca agcgcgcttt cggtgacagg gtgtatcgta cgtagccgcg ggtcaggcgc  179580
gcgttgtagc ggtacacgca gaaatctatc cacaggccaa cgcccggctg tagcttcgga  179640
tggtggataa tagcgcggtg acgtacgccg cgtggcttta gaatctccac ctgtaaggcc  179700
atctcctcca ggtagtgggt ctgactgcga cgcagcgtcc agttcatgta aaagtcggtc  179760
tcgccgtgtc cggccacgaa gaggctgctt actaatccag tctacattgt gccatttctc  179820
agtctgattg catttttttag agttatgttg ccaccaacgt atcctgttac gttgattacc  179880
tcgtaactgc ggtcgcatct tttatggact gtataattga aaccatcaca agtaacggtc  179940
gtggtggtgt tggtacatgt ggtagtctca acgtttgtat ttgtcgttgt ggatatctgt  180000
gtggttgttt tcgacggttt tgtagaaacg gtggttgctg gtgcagttgc agtagagcaa  180060
tttatagatt ctgaagtgct tttattgctg ataactgttg tactgtatgt tgatgtggct  180120
gtctcagtac tagtggaata gttaacggta gtactacagg gacattgaca ggaacaggtt  180180
tgattgcagc tttctgataa cgcggatatt agtatcgtcc acataaccgt aaatcgccag  180240
tccattgcaa tattagttct cgctcaatgg gcattaatat tcctttgaac gctgagcctt  180300
acagaatgtt ttagtttatt gttcagcttc ataagatgtc tgcccggaaa cgtagctcaa  180360
tcttcatgtt ctgtgtgata tcgaacaatg aattctgatt cactgacggt gtcttgcaac  180420
atatggtact ttttgttaaa ggctcgtcgt gcaaaaaaca gaactatgca ggccatacaa  180480
accaacacga tggtccatac ggtgcggctt ctttgcgagc tatgatagag attacgtttg  180540
tggtgatgtg tattgttagt atgttgactt cctttctctc tatcttcatt ttcgatatcg  180600
gtgttgtatc tagggcaaac gaaagtgcaca ttaatagctt cagtatgatt ttttggtgtt  180660
actaataggt agaaattttc atcttcgtga tgtcctgtga agtaattttc tttaaaacaa  180720
```

```
cgtctgctgt acctgccgga attggtgata tttagatcgt acagatgtag ttctgtgttg   180780
ttgcacgaac gacataagtc atggtacagt gaaggtcttt catgttgaga atgacataca   180840
gtatgagagg taaggatgcg taaccaatac caagattggg tatgtgcgtt cttacgatga   180900
cctagatgat gtccgtgtgt ggatcgattg taatgtcgta tccaggcgac tgaaagacaa   180960
tcccacgtag aattaccttt tatggtgaca ttactcccctt ctattcctgt tgtattagtt   181020
tctttgaaac gtatgattgt tgtctctgtg tgacaagcgt tggaagagtt agtacggttg   181080
tacgtggtgt acgttgtggc gctgcaattt gtaagccatg gcgtgcttat aagtgcagta   181140
ttagtggata cgttgtgcga agtttcatct gacgtgatag ttacggtgat tgttgtgtta   181200
taagatgatg tagcgtttgc tgttacgttg gtaaagata atatagtgtt ggtatttgtt   181260
gaaatcaatt ctgtagtggc agccgtattg gatatattag catatgatgt attgaatgta   181320
gaatatacgg ttgtgaaagt actcaagtcg gaggtaacgt tggtgatgtt gccaatggtt   181380
gacgcttgtg aggtgacaga tgtgtgtggc gtcgttgatg tgttgttatt cggagtagaa   181440
aatacgctgg tcacaaaggt ggtagaagca gtgttgggtg atgtgatgga tgcagtattg   181500
gtagtagtac tgttgcatgt aactctatgc agaatataga atattatgat tgtatacgcc   181560
gtatgcctgt acgtgagatg gtgaggtctt cggcaggcga cacgcatctt ttactgtaaa   181620
tccccgtcca ccgtcaacaa caaaggttcc gtatctaggt ccgtccgcag atgttcagcg   181680
tcctgttccc cgattcgttg cgatcgcagg aagcagatga ccagcgcgcc aacaaagatc   181740
atcattcccg aaacccaggc gcaatggagt gagaggccgg accactgcg ttttaaatcc   181800
gagataattg cccggtctgc ctcttgggaa tccgtaacca caactctccc tggtcccgga   181860
taaaagcatc gacgcgtttc caaggctcgg cagaagctac gtgggtggat gatgaggtag   181920
aaagcctcga catcgccggt atactgatcc tgcaggaggt agactcccgt atctttaacc   181980
gtgagattgt acagcgtcag attttggcgc gtgcacgcga acgccgcacc gccctgacgc   182040
gtggtttctt tataggcgtc tgtaatgata caaagtggcg gcatacgacg catgtatctg   182100
ctgtagatat cataacgctg ccagactacg ctgtgatggc tagtgttaag cctggtaacc   182160
agcgtgcgtg tacggtcctc gcaggtggca cggtagttgg cgagctttag gggttttttg   182220
gttggttcga cggcgttcga tgaacttccc tgagttgtga acaaaaacag cgacgtgact   182280
atgacaagcg tgaggggggt gctgtaggtc tgcatggtgc aaaacacgtt ctcgccttcc   182340
ttatcagacg ttgtcgtcct cgtcctcttc gtcgtctgtg cccgtcggtt cgatcaacgg   182400
ggagttatct ttctgtctgg agggtcggta tggaatccgt tcgtagatgt tctgctttt   182460
agccgcgtgt tgttccagct ttttgcgtgt caggctccga taggccagac attgatctac   182520
ctcggtgccc gtgttgtttt tctcctcctc gcgcgcgtaa attacaaaga agaccaccag   182580
caggactatc agcgtagcca cgaacgagcc cgcgcccccag gccgagtatg cgcctagcat   182640
ggtaatgggt tctgtgatcc ggcatttgca catcgcgtgg cacttgctgc cattgccggt   182700
attagatgat gtgttattcg gactgcactt gcacgtcaaa tgggtatttt ctgatttcac   182760
gagacagttg gtggcgactt tggtttcggc gcagacggcc acatagctta ccaagctgag   182820
tgccagaaag cacaccgcgt gcattacacg cggatacata ttaaaacacc gtgttccaca   182880
agcaccgcac acgtcaatcc tcccgcacg gtcttcagcc cgcccatgac atgatctccc   182940
tcacgttacc cttcaacacc ctgtagtact ctgtctcggc ttccggtccc catgtcctaa   183000
ttataacaaa acaccgtgac actgtccatc tccctgtctt tttgcgccgc cggtccccccc   183060
```

```
caaatcatgt ctctagatgc cgccggccac caaccggagg cacggcggct attggattcg 183120
gcattggtgc gccgcgtctt ggcctgcatg atcatcgtca tcatgattgc cattagcatc 183180
tggatcctga cctacgtgct gtttctctaa taagaacccc ggcccctgac ggtaattttc 183240
ctttcttctc cgtttctcct cagctgccgt acgtgatgcc tcacggccat ctccgacagg 183300
ccctctcccc gacctcctgg acatgtgagg gcttgttgct cctcctggga ttgctggtgc 183360
tcttctttca ccaccacaac cagtcggccg tggagaggcg tcgccgcgtc tcgttcgtcg 183420
aggccgatcg actgccgcat gagagcgggt ggtattcttc cgatgacgac ggagaccggg 183480
acggtgatga ggaaactgga gagagccaca acagaaacag cgtgggactg tccgctgttt 183540
ttagctgact ggcgtgcgac ctgtaaaccg ttactcgggt ctcaagatgg tttggaagtt 183600
gtgactcatc ttcctgtggg tgatacccaa ccggacgcga gtgttccata aaagccgggc 183660
gctccggcga gaccatgcca tcctcgcctt cggacgcccc gctcctcttc tctctcctct 183720
cctcccgct gccgcggcca ttgccgccgc cgcccatacc atcggcatgt cggccgacaa 183780
atcgcagctg tcttcgccgc cgcagctgta gcagttaacg tcgccggcct ccaggaggag 183840
atggcgctgt gcgtcgtctc ttcgtcccgt ctccctctgt ggtcgtgggt ggtgcgagag 183900
tacacgatgg gtggctctcg tctcggggga ccacaggggg aggggggtaa tttattattc 183960
gtattactgt aattttgtat cgcttaattt gtttagagcc gcacgcttga caacgccttg 184020
tatagcctta tttatcccga tgacttttt ctccgtacaa gaatggacg tcacttgagc 184080
agacacagtt tcatcgacca cgacagtctc atgatctgac tacctctgac ccgccaacga 184140
gaaaaccgaa aagtaaaaga tgaccgcgcc ctcggagtcc ttttttcctt ttcaatcatg 184200
aaagcaagag gcagccgaga gaatgccagt aagagacgac catcgcagac acagtacgat 184260
actcatctta gaacgaacca gcgaataacc atcacacgta cagcagaatc tcatgaacta 184320
gtcaaccaac gtcataaaat cttcacacaa tcgttttttgc gaacttttag gaaccagcaa 184380
gtcaacaaaa gactaacaaa gaaaaaccat cttggaatta aaaaagtag catcgttacc 184440
ttatgaacca gcagcattca gtatatacac cagatataat atatttatta atgtatcctc 184500
tctttctcct gatgtaattt tgttttttgta aattcaattg ttgaaagtct ctccctgggg 184560
gaattgcata tcttattgat gaagaagaaa tccctgccat atgtgttgtc aaactatcat 184620
tatttctcta tatgggtatt ttttttctaa gaagcaaaag actagcagca gccaaaataa 184680
acctgatgaa atctttaact gaactcccag tggtctgtgt gtatatttct gttggtggtc 184740
ggttgtctga acccgggtgg gttgttcgga acggcgggga cggggaaacg gatgaaaaca 184800
gcgtcgctat atacgtgact tttgatctaa acggacgtcg ctaggctgac agtttacgaa 184860
ttgctaaaca agataggaac aaaacaagcg gggctttgcc tggtaggatt tcctgtgaa 184920
acaataaccg gatgtgattg tggctggtac ataagctggt tctggctgca agcgcttttc 184980
actgcattag gttggcgtt tgcttttgcc tgggaacgct atggctataa cgggaaagaa 185040
ccggtttggc aacattccat tgtgggggg gggtacttat agcgtgccta gctatgacgt 185100
tgatatatgt ggatgcggat aatactcgta atgagctaaa agcgacgact ggtagtaatt 185160
ttaccattac gcataggaaa gatccgttga caactaagtg gaaaaccgtt tttggtaaca 185220
atggtgatca gtggttgtgc aacgttacgg gtataggtaa tgctactgtg aatagtaacg 185280
caactatttg tgtgtcgagc tgtggtcata atacgttgga tttatgtaat ttaaagtcgg 185340
gagattctgc cttcttcgat ctgtctcgtt ggttcggtga aaacatggat gaatacagtg 185400
gtgatgtgtg gcacttggaa gtcagctaaa tgttgtatcg cttagtgaat tggtgttctt 185460
```

```
acagttttca tgtaataaac tacgtgtaat tcgttaaatt tgtgtgtttt tttgttagta  185520
ttctgcgtaa cggtggaata aaattgcgtt gacctagtta gatttcctgt gtagaacaat  185580
gaccggacgt gcttggactg gtacatacgc aggggctgga cgtggttacc ggtcactgga  185640
ctcggtttcg ctgtagctgt ggttcaacct gaacatggct cccagagctg ctaggaaccg  185700
gtccagtcac attttttggt gggtggggggg tactaaaaaa gtgtttaata tttgggttta  185760
atgataaaat ccaggttatg gatatgagga aactgaatac ctcgcagggt cgaaatctta  185820
ccacagttga tgatagaaga cggttttcca tcgggtggga aacatgggat aacggtggtg  185880
actaataatg gtacaacggt cgtcaataca acagcctgtg tttcaagttg ttcgcatacg  185940
tcgcttgtgc tttgcaatat gacgcagcag actgattcgt tgtacggagt gggtcatcgg  186000
ttgaatgacg aagaagatgg tgaactgtgg agagtttcgg tttcttaata atcccatacg  186060
acatgtgttc atttatatct gaattttagg atgatgacta tagtataact ctggggaaca  186120
aatatcatac gttaatcact ttaagttacg ccgttaggaa aagaaaatca gtccgaatga  186180
agcatagtca gccgaatgat acagcaatag cttgtttaca acgtgttctt ttttacatta  186240
tgaacgtgcc ttgcttttta tacacacatg gagacagagg tccctcagcc cttgtcacga  186300
caactccctt tttctaaacc gtatgtgctc caaaccgtat ctcctcatcg tcacgtgaaa  186360
taccatggga ccccttttcg tcacacacgt ctttccgctt acccaacgcg tcagcccgcg  186420
ctcggcagag ctaccatata aaaacgcagg ggtttagcag cttccccaga tcgctgctgc  186480
cccggcgttc tccagaagcc ccggcgggcg aatcggccgg ctggtcggtc ggcgctcgga  186540
cggatgggga gaacggcggt gacttagccg cccgtggccg ggagaagacg gaggagccga  186600
gatgacaaca gcagtcgtgg aagggtcgcc aagcccccggt ccttctcttc tgtctggtcg  186660
aatcttgttt tcttttttca accgctcttt ttgtcacctt tttatgtgag tttctcttcc  186720
gcgtctcccg gccgtaccat ccacccatgc agcatgcacg cgtgtatgta tgcatcgcct  186780
ctcctccgtc ccgactacca tcagcagtac cactgccgcc accccagcg ccaccaccgc  186840
tgccgtcgcc accgcgttat ccgttcctcg taggctggtc ctggggaacg ggtcggcggc  186900
cggtcggctt ctgttttatt attttttttt attttttatc ttctcctttc cttaatctcg  186960
gattatcatt tccctctcct acctaccacg aatcgcagat gataaacaag agggtaaaaa  187020
gaaaaaagct acagacattt gggtacctca gctttccgat aactcgaaga attcaaagtc  187080
gacgattccc aacaagagaa aacagaacaa aaacaaggtc attttttattt atcctcatcg  187140
tcaacaacaa ctaccgacaa caacgaaaca ccaccaagaa tgtcaatccg caagggtgtt  187200
cctgccccct cgacgcgcct gtcgcgatcc tcatggcgag gaccgcgatc tccgtatagg  187260
tagatgaaat tatcccgtgt ccggtcctga ttccccgcat gccctgcaca tcctgacgcg  187320
tcggtcagca gccaaacaat cataggaaat gaaccagaag aacaaaaaga tcatctctct  187380
cggtgtatag caacaccaac aacaaccgca tcgcaacatc ttcatccgca agacggaaag  187440
aaaacaacaa taatgagaat gaaatcacca caaccaagcc agatttcacg tccatgagtt  187500
tttattatat tattatcaaa acgaaaaaca gaaaaactgt catagataaa tataaaaaaa  187560
aatagaaacc acaaacgact actagtactc caatcttaga tgtatatgct cctagataag  187620
atttagtatt accataatca tcgaagaatg aaagacgacg atgattcctt accgctcctg  187680
ccacccggtc tgtatgtaga gagagaagag agaaaacggt gaatccaaga tccccgggtc  187740
ggcgtcggca tgccgctgat cgcagtggcc ccacctcggc atgccggcgc cgggcgagga  187800
```

```
attgctcatg aaaaaagta tctttctgta aaaaaagaaa acaatacatg attaaccgaa  187860
aagaaaccaa caaaaagaac ccgagatcag tcgatttcga tcactacgat aaacacatgg  187920
aagatttctt gaaaaagaa aagagaaaga gaccaccttc ccggcggcgg acacgctcct  187980
ctccgtcgcc gttctgcacc atgattcgat caataacaac atcatcatcg gagaccatct  188040
tttaatcaat cagcgttgca gtagtcgact ccctggacac gaaggagtca tccattttta  188100
tcctcgcact tcttcgctct caaagccgcc tttaagttg aaatgaaagg atggaaacat  188160
ggaatacagt tttaattgca cgtatcacca ttttactaca aaaagaaaaa aaaacaactt  188220
acacatagta ttaccttagg tttacggata agtagagtgt aggcgttttt gaaacagttc  188280
agccaatgca atcttgtctc ggcataatca ctctttctgc atataatagt agtagtagat  188340
ttattcacat caacacagcg aaaaactcca gcatcaaagt acacctagag acagcccta   188400 aaatatagtt tgcagctttt agatgtactt acaccaaaga agattaccgt ccttacgaga  188460
aaacagatac tcggatatag gaatcaagac agctctgcac tgaaaacaca ctctcctgtc  188520
acgacaccgc gccacaccag aggcgtacgc gtgacttcat cgcaacgatc catcgtgatg  188580
tccctcgcag aacctaaaaa gaccaaaaaa aaatcttgga ccacagttgt cgatacttga  188640
agacaatatt ctcgtgagaa cttgagatt cgcacttgaa acctcttagg atccacaaaa  188700
acaacaacct ctgtatggaa aatgcgctat tttatctcag cttttctccc aaacctcggt  188760
ttcttcctat tcttatgttt tccctagtat atttgcctcc ttataagaaa agaagcacaa  188820
gctcggtcgc acggattatt ccttctgcta atctattatt ttgttccttt ttttttttctt  188880 tgccttcacc ctcttcactc cctgtagcaa cacagagtag tagacacaat aaatgagaag  188940
tttgcatgca tttgtcgtgt ccgtggtttg ttatggcgtg tggagtgctc gggatgggtg  189000
gacgtgggga cggattcttg aggctacaaa gatacgcgga gacgtcgtgg cgagggatg   189060 ggtttattgg atatcggtga agcagcgtgg cggcgaaaga cgcgatccct gggctggtag  189120 atcccctac cccgtctacc agggacgttt atcctttgga cacgtaaatg tctcggccgg  189180
catccacgcg ccacgttcac cgcgttgtgc ccagcgccat gtgcgggtcg tttcggcgtg  189240
aagttggacg gcgtagtttc ggggattgtg aaccgtggct gagggtgtag atgggacagg  189300
aaaaagcgtg tgatctgacc gaggcgaagc atgtgggtgg tgcgatgcgg tggatgtggc  189360
ggggtgcggc ggtttccgac gtggagatgt ggagatgggg gtgatccgga tgcgtggcaa  189420
gaggcctcga gcttgggctt ctcccgcgga tggacgttct aactgtacac ggcggccgtg  189480
gcctccgagt aaaaaaacca ggtgctgacg ccagacagag acgccgtcct cggaatcgtg  189540
tgcgcgaaag cctgtgccgc ggcagcgtac gacgttccag tcagcgaggc cgtcgcgttg  189600
gcgcgccaac agtaaggtga cgacaggttg gcggcccatg gttccgaagc gtccccacat  189660
gcaccagcag tcggcgtcaa agtcgcttgc gctgtcggcc cagtcgccac cgccgcggcg  189720
gatttccgcg cggggacgg ggtagccgag tgctgcgccc tcgccaatgt tgtgaagtgg  189780
atgcgtgagt tgatgttgat tctctgtggg aaaatgagcg ctgtcctgtg ggttggtgtt  189840
ggggtatgcg agtagtaggg gttgtgtttg atcgtagagg tgttggcggg cctgtgcgca  189900
agcagcgtag tctgcggcgt cgagctccat ctgtgtgcgg tgttcttcgt cggcgtgttt  189960
gtccgaggtt tggacatgcg gttgtgtgtt gctgtggtgt aagggtaacg tgtgttgggc  190020
gtctgggtga agcggcgtgg tgtgggtgct gtttgtgtct gtggctggca tgattgtgcg  190080
gcatgtgtgt gttgtagtgg gtggaggtta aataggtgag gtgggttccc tggtccgcgc  190140
cgcaaactgt ccccgtcccc aacgtaacct cccctacgcg gcgcgaacag ccccggcccc  190200
```

```
agcgcaaccc ccgtcccgg ccccaacacc gtcccgcaca cccccgtct ccgcaacacc   190260 ccggcatcgc cggcggccag aacgctcgaa aaccccgac aagcgcagcg ccgaaacgac   190320
acaggcaagg accgtggaac gcaccggcag cgcgccgaaa caccgtcccg aagcccggtg   190380
ccgacaacaa ataccgtggg acgacacgca ccggcagtgc gcaggcagcg tcggacacaa   190440
cacgcttacg gccctcaaca ctccctcgag gacccaccac gcggcccgc accggcggtg    190500 ttttgggtgt gtcggggcgc ggccgggtgg gtgtgtgccg ggtgtgtcgc gggcgtgtgt   190560
tgggtgtgtc gggggtgtgt tggcaggtg tgtcaggtg tgtcgcggc gtgtgccggg      190620 tgtgtcgtgc cgggtgtgtc gcgggcgtgt ggcgggtgtg ccggcggggt gtggtggcgg   190680
ggtgtgtcgg cggtgtgcgc ggcctcgggg tgtgcggctt cgcaggaacg agtgtgtggc   190740
ctcgcggccg ttatttcccc cgcggtcccc agggccgtcg tccctcgccc ccgggcgttg   190800
cttttcgtgt gtccccaggg acccatgctg ccgtcccccg ggaacttcct cttttccccg   190860
gggaatcaca cagacacaga cacgcgtctt cttttcgccg tgcgcgccgc acgtcgcttt   190920
tattcgccgt cgccgtcctc cgcaccacac gcaactagtc gccgtccaca cacgcaactc   190980
caagtttcac cccccgcta aaaacacccc ccgcccctc gaggacccac cacgcgggcc    191040
ggaatggatg tcgggcgtcc acctagatgg gtgcgcgccc gggaggcggc tgtgcgctcc   191100
agtggtacgc gcctgccgcg cgtcttcctt cgggtagctg cctttcccag tccacggcct   191160
tccagactgc gtggcgccaa ggcggcgcca gcacgcgccg tgcacgtcgc tgcctataaa   191220
agccagctgc gtgtcgcccg cggcacacgg gcgacgaagg cgtccgcgtg tctaaaccgc   191280
gtgctcgctg acgcgggttt gcttcctata tagtggacgt cggaggtgtc cggcgcccat   191340
ggcccagcgc aacggcatgt cgccgcgccc ccgcccctt ggtcgcggcc gcggggccgg     191400
agggccttcg ggggttggtt cctctcctcc ttcttcttgt gtgccgatgg gagcgccgtc    191460
aacagcgggc actggtgcga gtgctgcggc tacgacgacg cccgggccacg gcgtccaccg    191520 ggtagaaccc cgcgggccgc cgggcgcccc tccgagtagc ggcaacaata gcaacttttg   191580
gcacggcccg gagcgcctgt tgctgtctca gattccggtg gagcgccagg cgctgacgga    191640
gctggaatac caggccatgg gcgccgtgtg gcgcgcggcg tttttggcca acagcacggg    191700
ccgcgccatg cgcaagtggt cgcagcgcga cgcgggcacg ctgctgccgc tcggacggcc    191760
gtacggattc tacgcgcggg tgacgccgcg cagccagatg aacggcgtgg gcgcgacgga   191820
cctgcgtcaa ctgtcgccgc gggacgcgtg gatcgtactg gtggctaccg tggtgcacga   191880
ggtggacccc gcagccgacc cgacggtggg cgacaaggcc ggccatcccg agggtctgtg   191940
cgcgcaggac ggactgtacc tggcgctggg cgccgggttc cgcgtgttcg tgtacgacct   192000
ggcaaacaac acgctgatcc tagcggcgcg cgacgcggac gagtggtttc ggcacggcgc   192060
gggcgaggtg gtgcggctgt accgctgcaa ccggctgggc gtgggcaccc cgcgcgcgac   192120
gctgctgcct cagccggcgc tccgacagac gttgctgcgc ccgaggagg cgacggcgct    192180 cggacgggag ctgcgccggc ggtgggccgg cacgacggtg gcgctgcaga cgccgggcag   192240
gcgactgcag ccgatggtac tgctgggcgc gtggcaggag ctggcgcagt acgagccgtt   192300
cgcgtcggcg ccgcacccg cgtcgctgct gacggccgtg cgtcggcacc tgaaccagcg    192360
tctgtgctgc ggctggctgg cgctgggcgc ggtgctgccc gcgcggtggc tgggctgcgc   192420 ggcgggccg gcgacgggga cggcggcggg acgacgtcg ccgccagcgg cgagcggcac      192480
ggagacggag gccgccggcg gggacgcgcc gtgcgcgata gcgggagccg tggggtccgc   192540
```

```
tgtacctgtg cctccgcagc cgtacggcgc cgccggcggg ggcgcgattt gcgtgcctaa    192600
cgcggacgcg cacgcggtgg tcggggcgga cgcggcagca gcagcggcgc cgacggtgat    192660
ggtgggttcg acagcgatgg cgggtccggc ggcgtcgggg accgtgccgc gcgccatgct    192720
ggtggtgctg ctggacgagc tgggcgccgt gttcgggtac tgcccgctgg acgggcacgt    192780
gtaccgctg gcggcggagc tgtcgcactt tctgcgcgcg ggcgtgctgg gcgcgctggc    192840
gctgggacgc gagtcggcgc ccgccgccga ggccgcgcgg cggctgctgc ccgagctgga    192900
ccgcgagcag tgggagcggc cgcgctggga cgcgctgcac ctgcacccgc gcgccgcgct    192960
gtgggcgcgc gagccgcacg ggcagtggga gttcatgttt cgcgaacaac gcggtgaccc    193020
cataaatgat cccctcgcat ttcgtctttc ggacgctcga actctcggtc tcgacctcac    193080
caccgtcatg acagagcgtc aaagtcaatt gcccgaaaag tatatcggtt tctatcagat    193140
taggaaacct ccttggctca tggaacaacc tccaccccca tctcgccaaa ccaaaccgga    193200
cgctgcaacg atgcccccac cgctcagtgc tcaggcaagc gtcagctacg cgctccgata    193260
cgatgacgag tcctggcgcc cgctcagcac agttgacgac cacaaagcct ggttggatct    193320
cgacgaatca cattgggtcc tcggggacag ccgacccgac gatataaaac aacgcagact    193380
gctgaaggcc actcaacgac gaggcgccga aatcgacaga cccatgcctg tcgtgcctga    193440
agaatgttac gaccaacgct tcactaccga aggccaccag gtcatcccgt tgtgcgcgtc    193500
cgaacccgag gatgacgacg aagatcctac ctacgacgaa ttgccgtcgc gcccacccca    193560
gaaacataag ccgccagaca aacctccgcg cttatgcaaa acgggccccg gcccacctcc    193620
gctgccgcca aagcaacggc acggttccac cgacggaaaa gtttctgcgc cccgacagtc    193680
ggagcatcat aaaagacaga cccgaccgcc aaggccgcca ccgcccaaat tcggggatag    193740
aaccgcggcc catctctcgc aaaatatgcg ggacatgtac ctcgatatgt gtacatcttc    193800
gggccacagg ccacggccgc cagcacctcc gcggccgaaa aaatgtcaaa cacacgcccc    193860
tcaccacgtt catcattgaa agtctctcca gtccatatgt tgtcaggacg tgctgtcgtt    193920
ctccgcttgc tgcgaagccc gttcttccga gtcgtgtcgc tgcgtccagc gtcgcgccca    193980
agatgggaat ttgggtcttt tcacgcgtag cctcctccac cacggctgct gatcgccgtc    194040
actaaggacc gacacggagg atgacgagga gcttctcccc gactccgcgg tccgcgaccg    194100
gctacgtagc gcgtgtccct gccagtctcc gcagttacac cacacgtcgt gagcagcgtg    194160
cacctgctgc cgccactggg cctcggcgtg ctcaggccac ccgccggagc ccggtctgag    194220
ctccgacgca ggatgcgcgt actcaacgtg cgccttccag tccatacagc aacaccatag    194280
gtcgtgcgag tcgtcggcta cccgccgcca ggccagttcc cgcatgggaa ggctggacac    194340
gccgaccgag aggtcaccga gcccggacgc catctcttct tcctctccgt cgctgtcatt    194400
aagcagccag gtcacctcct ccgctccgcg gtccgccggt ctcgacggac cgcgccgccg    194460
tcggcaacac ggaaaacagc acgccagccc gagccgctaa ggccgcatgc ccctgccgcc    194520
caactgaaca cgcataccccc gctcaactgc gttttgccac ccctgtcagt gctctcgctc    194580
gagcaccacc ccgcatctcc caacctttt ccaataaacg aaaccgacat gacacacgta    194640
atgggtactc gtggctagat ttattgaaat aaaccgcgat cccgggcgtc tcagcacacg    194700
aaaaaccgca tccacatcat agacaagtta cagtccacag tcacatacac gataaacaat    194760
accaacaggg taatgtttat ggagtaaaac actattgtcc aggccacatg cgtgtatgac    194820
ttccgcacca tccgtactg catgttccac atgtacgcgc tagacgtgta atccactcgc    194880
agttcgggga cgcaacgcag ccagatcaca tccccttgca gtaccagacg cagggctagc    194940
```

```
gtctcgaaga tcggcatcac atctaagttc cgcacgttcc actttaacga ctccccggga   195000
acgaactcca cgtcgtcggc gtgtacgtac aggttctctc ccacgccgcc ataatcggcc   195060
ttcggatcga agacgaaccg actcatgttg cccacgatgc tcccccgagc aaacaacttg   195120
ccgttgtcaa tgtagcaccg gttgtcctcg atttgaaacc agggatgctt ggccgtggac   195180
ttccagggcc ggagcgcgtc ttccccggct ttagtgattc catcgggcag gcggatcaag   195240
ggacccatgg aggtccaaag acccacccag gctttccaga gattgttcat ggtgaaacag   195300
cgtgtggact gtacgctctt tcccaattta tatcccagag tagtgacgtg agcccagcca   195360
cctcccagat tcctgacgtt ttggttgtct ttcctgccaa ttcctcccgt aaacttatga   195420
ttatcctagc ccattcccga taaaaataca cggagacagt agatagagtt acgaataaac   195480
cggtttattt attcaagtgt ctcaggagat tattgaacga gcgtggatac cacgccgtcg   195540
tcagttcatg gtggcattga gcagccatag caccagagtc ccggcgcccg gtatcagaca   195600
cgctgaccta ccgggcgcct tcgagtccgt accccgcggc ctgggtgtta gagtccgtac   195660
cttgcagccc aggtaggttt caggtaccag ctggttcgta cctgttaaat aaatcgcaga   195720
cgggcgctca cccctacggt caggagcaca agaacaacca gagagaacag atatacgagc   195780
agggttctga acagcagacc ccaattgtcg tctctcatgc ttcgctgaag gtaccagttg   195840
atggtctgag agctatagtc catcctcacc tgaggaacac acgcggcata tttcttgggg   195900
tctccccacc tcgtagacaa cgtgatgtcc accatatcca cggtgtgcgt caccgggtgc   195960
ccaccgatgt tccactcgaa ataggctccg cgctcatcat ggtggtactg ctcaccggac   196020
acctgcagtc tgtccatgta agattgagag acgataccca cgttcacaaa gtgtttctcg   196080
gtgaagttgc ccgacatcct cccccttgaag tacagcatgc ccatatggaa ccagcattgg   196140
ttctcctcca ctcgaaagtg ggccgatctg atctccgata ccaccacatc caggggccgg   196200
ggcaccgagt ccgcgagtct caggaacaag acggccagga tcgcgagcac caacaccggc   196260
ttcatggctc cgaaggtccg ctgctcggct ccgctcaccg ctccggtctg gctgcagcag   196320
tgcttcgctg agaagtagcg tgtggactga acggtgtttt tgaatatata gcgtttcttg   196380
gtgacgttgt ttcccctacg tagtaggcaa ctacgtgcca aaagaggcgt tacggtactt   196440
tccgtactgg gatttccaaa ccgggacttt ccacacggcg gtttcaacac cgggactttt   196500
cacacggtga tttcggcacc gggactttcc gcacggcggt ttcgccaccg ctgacgttct   196560
catcgccgcc cacgtcaacg gtggcgacac cgtactttcc catgcggttt ataaacgtca   196620
agagtcacgt cagtcgccca cccccattac acggcgatat cccgataggg catgagggga   196680
cccgggtgtc gcgacatgtc gacgacaggt gcggattagt ggtcgtgtcg cgacatggac   196740
gtgcagggga atgtctgtcg cgatagagtt gatgtgacag cccgctacac ctctctgtcg   196800
cgacatgcat acacaacggg ccggcttgtc ggcgattgtc gcgacatatc gttatcagtt   196860
agcgaccgga gttgtctatc gcgacatatc gtcgactatc gcgacagaaa aaataccgtt   196920
cgtagagaat gccgtgttga aggaacgcgc ttttattgag acgataaaac agcatcagga   196980
gccacaacgt cgaatcccac gtccagtcga ttcgtatgtt atgctgcaca gcaatgctag   197040
aataacaacc agcagggtaa tcccgcaaca taaatacaaa gtcacagcga agaatccgtg   197100
tcgttctatc aagcgaaacg cgttccaaac ggccccgtca cagacgcagt tattcataag   197160
cgttaacaac cggtggctag gatgaatatc caaatcacag ggcagtagcc gacgactcg   197220 ttgacaggtc agcctaccct caaggttcct atcgttcgga cgggatttgt gcgttttagg   197280
```

```
cctctttttc gccgcctgca agcattggtg cgcaaagtcc tcacccagct gtttccagct   197340
atcatctgca tctgtgcagt cccctgtatc gttgtaacaa acgggtctgt gcgacttcgt   197400
tctcggaaca caagcttgtt gtcgcggaga cagagagaga agggttttcg ggtcacgcga   197460
agaccgctca ccggggggtcg gcaacgcaca catcaacaga aaaccgagac gaatcaagag   197520
atccatagtg aaggagtgat atcgacgtgc ttacgaaacg gcgattatat atgttctcaa   197580
caataccgcc ctacgttgta tgatgtaacg tgtgacgtga gtctgatcca acactgaacg   197640
cttcgtcgt gttttcatg cagctttac agaccatgac aagcctgacg agagcgttca   197700
tcggggcatg aagtacgcat tacacaaact ccatatattt gttacgatag aatacggaac   197760
ggaggaggct ttcgccacac ctatcctgaa agcgttgcat tctttatgat aggtgtgacg   197820
atgtctttac cattcccacg gctgctttgc gtgatgatga cattcatcat gtatttccat   197880
tcacacatac cttttgtgca tacggtttat atatgaccat ccacgcttat aacgaaccta   197940
acagtttatt agcccttgac aggataggtc aaaagattat atgtaggttt tccggtaaac   198000
cgaattgtga tatttctctg caggaaatag aacagcctgg tacctataaa acggacaatg   198060
cagtactgta gcagcgtaac caagtaggtc cacatgaaca cgtacaaaat tatggtaagc   198120
catcgttttt cataccacag cctgtagctg tcgtacatga atgaggacgg tcgaggaacc   198180
cagggtagtt gtaattgggg gcgacattcg tactgtccag aagacaattg cacgggtttc   198240
agtgagatga gtactttagc gatgtcggcg ggggcgctac gtttcaccgt gacggtgaga   198300
acttgaccgt cgtttgtat ttcatgaggc acgttataca agccactggt atcatgaagg   198360
atgacctctg atgcgatgtg aggattaaat tgtccctcaa accgccaaac gctggtcatg   198420
tttccaccgt caattacgca gctgacggtg tgagatacca cgatgttgga cttaggtttg   198480
ggggctaatt gccttttac aaattccctt ctgtattgca ggtcctgctg ccactgcttt   198540
tccgtgcgga aagtcgccat gtcttccaca cgtgtggcga cgatagacgc caccaaggta   198600
gctaccagaa gcagctggat ccgcatggca ttaccgtatg tcaattagaa agttgagcgg   198660
acacggttat cgttcctggc ggatataagt atataaacgc gagttagcct ttcccgtccg   198720
ttttgtacac ccgttcccca cacaaatgac gaatacgacc ttttttttta taaaaataaa   198780
ccacgtgtat tatataaaaa catttacata gaaaagagac acacggatca acataaggac   198840
ttttcacact tttggggtac acaggcgtgc caccgcagat agtaagcgct ggatacacgg   198900
tacacagtcc tggccagcac gtatcccaac agcagcacca tcgccataca gatggcgatc   198960
acgaccccga gctctaagtg tctgtattca tagtgtagtc gccgcaggtt atccactgaa   199020
ttcccgtaac tgaaataacg tatatggtac cgaggctggc accacatggg tttgcatttg   199080
gtgcacggca ccaaatgcag agtgagatgg tccaagtccg tgggcaccca ctggcgcaaa   199140
cggaatacgg cttcggtggt ctccacgagg cactccgggg cgtgcagacg gccccacttt   199200
cgtccgcgac ggcccgacca gccgacccga gccactatcc cttttctcggg ataagaacgta   199260
ccctgtacac gccacacagc gtccaacacg ccgtccttga cgacgcagct ggcctgatag   199320
ctggacacgt tgttaagcgg cggaaagcga aactgacgtg ccggcggagc cacatagttc   199380
ggttcaccgt gttgtcgcgg ttcgtcctcc ctatagtaat agtagtcgtc gtcctcatag   199440
gggttgccgg cgtgagccag cgttacccaa cagcagccca ggccgacgag gaggcgcagc   199500
caccgcctca tggcggcttc gccagtcaat cgtctttagc ctcttcttcc cgtgaggtcc   199560
ttccggtggc gcggtgccga cctcggaccc agggacgtat ccacctcagg tacacacagc   199620
aggctacctg gacaccgaag ctgaacaagg ctacgtgttt cacaaactgc accagtacca   199680
```

```
catagaggaa tgtcaggtag cgtctctccg caaacagccg ttccaagtct gagggcgtta  199740
cccgcagcgg caaccagggc agcctggacg ccggccggca atggagcacg ctccggttac  199800
aggcactgca ggggtaaacg gttaacatca cgtaagagag tcgtgcgtcc acctgtggga  199860
gctcagtttc gtaacgtaga gccccgtcat tttccagctg gggtgcgccg accttgaaat  199920
gggtcgcgct ccgctcgtta ccccaggtgc cgtaggctct cggggccgta tcggagaagt  199980
tgccacgcac aagccaggcg gccacgagta ccccgtgctg gacgtaacat tcggacacgg  200040
aactggagac acgtagccg  gacacgtccc caaacccgcg agggtactgg ggcagacgga  200100
cggacttgct atttgacaac ggacagatac gagacgacga ggacgcagac gactcgtcgc  200160
tggaccacga caaccggagc gactccttgg agcggctcga gagtacactt actgcgatca  200220
gacaccagtg ccagaagaag gaacaggtgg acggggacca caggatcata gccgccggca  200280
ccgcggccgg ccgcaggaag ccgcccggcg cgtcgtctgt gtgcgggagc cgaaacaccg  200340
tgcctcttta tatcgtcccg acgtgacgcg agtattacgt gtcaggggaa accccgtca   200400 cgacgaacgt gatttgtaag tgacgcgggg tgctgacggg gttcggcccg agaggtgacg  200460
gagcgcctca cgtcagtatg atgtccgatc cgcgtcagcc ccgacgtggt tgtggtcacc  200520
gaaacccacg tttatatgga cgttgagagc agcgcctgac cacatgattc atcataccat  200580
ttctcggaat cgggcccatg ccgggaaagc acattccttt tcagtaaaca acaatgacat  200640
cataacaaat cattttattc gcgaggtgga taataaccgc atatcaggag gagggatcgg  200700
gtgatgacgc aggccccgca gaacagtccg aaataaattt ttagtattgc cccatagtcg  200760
cctagatacc agaggtacgt taagttcatc aaaacgccca tcggcgtccc ggaatcgtat  200820
accgggcaca cgaagcgttc ataacaatcc cgggaggcga gtgttagggt agcagagtag  200880
tttcggggtc ggtttccttc cggcgacgac agttccgtgg gcagcagaat gtacagcgcc  200940
tcggtagctg tcgcggtgcc ttccacgagg atgggctgcc ggtgcctttc gtgattttcc  201000
ccgtcgtgta gccaagccga ggcccgcaaa gtcttaggcg aggggaattg tccatagagt  201060 ttaccgcac  ccttcagtac atggttctga ataacacagc cgcacgtgaa gtaggtaggt  201120
tctctcgtct cctccgtggc tgccgccacc actcccagcc accacaacag gcagatcgcc  201180
agagggttcc ggaggcttcc ccggcgtagc atggttttgg gttaaagcaa aaagtctggt  201240
gagtcgtttc cgagcgactc gagatgcact ccgcttcagt ctatatatca ccactggtcc  201300
gaaaacatcc agggaaaatg tcggtgcagc caacctttca catacagccc ccaaaacact  201360
tgaatcactg ccaccatcat cagcgtatac tgcgccgact taatcgtgag cgcgtagtac  201420
gccattagac ggcgatcttc gaacaatagt cgttcgatgt cctctaacga gctccacagg  201480
ggaacccaag gcacgaggca ccgggttcg  cactctacat aataagtttg gcattggtgg  201540 caggggaaa  agtagaacaa cacgagtttt gtgcgttggg gaacacgata gtcccggagc  201600
cagtagcgtt ttgcgacgag gctttcggag acgtcctcca ccggcgtcgg cactcgatcc  201660
gcgtagccct ccagcgtctg gtagtacacc cggggtgtcg gcgtgggcac ggacaggttc  201720
ccgcgcaggg tccacagagc ctccagtcga ccgcccgatc ggagcacgca gcgcgcctcg  201780
gaatactcta ctcggtactc cgaaacatcg gacagaggcg gtaacggctc cgtctccacc  201840
aagggcggag gttcatcgaa aagagtcaag gataattcag gcatactacc cgcgaccggg  201900
gcccagaggg ctagaataag cattacaagg ttcattctgt cttacaaggg aaggctgtta  201960
ccctgtctag actcaaaagc tgtaaggctg tcttatagca tgtagtcttg cacgtcacgg  202020
```

-continued

```
ggaacagggt ggtgatctag tgacgtcggg agaacacggt gttttagggt gcggggggaca 202080 aaggacagta cgacagatta ggtgatagaa acgttttttt ttatttatga aaaagccagt 202140
gtgccgtgcg gcctagggcc ccggcgtagt ttggatacca gatgggggcc gtcagggta  202200 ctaccacgag cagaaacata atgacttggt ccatgtatag cagcatagcg gtgcgcagca 202260
ggtcgccgtc cgtgtagcaa tttgacggtg agcgataaag caccgttaat gtgtcgcgga 202320
taagcacgat cttgaggccg tagatgaagc tcacagtcag tgctaaaatg atgcgttggt 202380
atggttccca ggactgcacg gcgatgaaga gccagagtat gggaagcatg aagcttagca 202440
aacagaggat ggctaaccgt cgttgcatgt tccaggccat gagccaggct aggcccgtac 202500
accagacgca gagcatggat gacaggacat aggcctggat taccacggtg cgatcgaaac 202560
acagcccgat ggtggacacg gatatcgtag tgagggtggt atataccatg accagcatca 202620
gggtcccggg tcggcgccga cgttccagcc agtacgcgtg gcaacgcaga gcgcagggta 202680
gcagtgtgct ccagaagggc aatgtatcgc gcaggtaggg ggccgtcacg cgccacggta 202740
tgagcatgaa aaggatggta gtggctatgg tggcgctggt ctggaacacg acagtgccgt 202800
agagacgtac catccagaga aagtgttgaa cgctccgcag ggtgtcttca tctttggtga 202860
ttacggtgac tcgacggatc ggcggtggtg acggcggcga cacgggtggg ggtttctctt 202920
tcttatggcc gagtggctcg ccttggtgaa actggatctg taccatgacg ggtgctcgac 202980
gaacagtcgt gggggcttta ggtacccggc aagttttata gagaaagggg gacgatgggt 203040
ggtggctacg agccaccgcc accttcgcaa tacgaggatc tgaaggcggc aaagacggtc 203100
gtccagggca ggcgccagag gttgggactg agcacgatca gcgtgatttt aaacatggtc 203160
accagtccta cgtagatcag cagcgagccg cgtaacgtct gagcagccgg cagttcgtcg 203220
cggatgtaac gcgtgccgta gaaagtcacg gtcatcataa ggaagacgat ggcgccgtag 203280
ccgtagagta gaatacgctg atgatggaac acggtctggt cgccgataac ccagagcgtg 203340
atgaaaaaaa cgctggtgag tacccgtgag catatgagct cccaacgctt agcgcgaaag 203400
ctgtccccaa ccatgacagc gccggtgcaa gctatccaca gcgtgaggac cagtgtgtag 203460
tcgatgagga tggcgggcag gtcggagcac caggtgtaga aaaccgtggt aacgagagg  203520 aggcctacgt agcccatggt caataccacg tcgtcggggt gccttttcgcc ctgtatcaag 203580 accaaacacc agagaaggga ggggggcaaaa accagcagca gaggggaaga ttcatgttga 203640
catatgttgt gggaatcggg gatacccagc caaatcattc cgcagaaagc cgtactgatg 203700
gcgatgtgaa agaccactag ggcgtagacc cggacgagga cagcaaaacg cgcagccac  203760 ataaggccgt ggtgcagctg caggagggaa gcccattgcg gcgaatgtag cgacggtagc 203820
ggcgggtcca tgaggcgggt gatgcgcccg agtgaacggg tgagcgtctc ggtggagtct 203880
tcttataaac cagcggagct caggcagcct tgctctggaa cgtcgcagtg gtggtgttga 203940
ggatgacgct gagcgtgccg ttgtcaatca ggtaatgatg ataggtgccg agcttggcca 204000
ggtagctgaa catttggtcc cagcgtgccg accacaccac gggcgtgagc atcaggagtg 204060
tggtgtgata gattagtgtt tcggtggcgt aaagtatcag cgagctgcgg atgacgtggc 204120
tcacgggcat tttggtggcg atgtagcgca cgtcttggaa aaggacgcc aggatgcagc  204180 ccacgaacac ggtgtagaga cacagcaaag tcttatgtaa ccaggtgtaa gtagaagcca 204240
ggacgctgac catcaccgtc aaaagtgtgg aggtaaaaag cgcgtcacgc cacacggagc 204300
tgagacggtc ctcccaagcc acgccgttgc aggccacgaa caacgtccac gttaggatga 204360
ggctagaaat gccgatgggc gctgtggcgc acaggttgag cccggcggtg gtgaacgaga 204420
```

```
gaagcgccac atacagcgca aacaccaggc cgttgctggg gtgtctgtga tcggtgagct 204480
ccagcgcgcc cagaaccaat actggtgtgc agctaagcaa tagcggcgag ggatcgtcgc 204540
tgcacttgta gcccagcgag gggtaaccca gccaaaccag cgcgctaatg agtacgctga 204600
aagcggtttc cagcgtcagc aatccgtaga cacgcatgac aatcgcggtc cgccgtagcc 204660
aacacacggc atcttcggaa actgtggacg ctgtttccga ataccgggag gagatcgtgc 204720
ttccctcttc caaggatcgg aaagtagcgt ccgtcgtttc ccgcggacgcg gcttccctgg 204780
tacgctccgt ttccgacgac gcggtttccc gctgcgtgga aactgtctcc atgtcgggac 204840
cgcagcgccc ggcggcgtat ccgcaaggtc tcgaagctac agcttgtcag aggaaaagta 204900
ggtttgcaaa aaggtgcgca gggtcatgat tctcagcacc atcagcagag tgaaaaccag 204960
actgagaaac accttgacgg ccgccaaaag cgcgcgttcc agcggcgtct cgtagcgtac 205020
agccagggcc gcttcgtgga aatgcgagac ggctagacag gtaatgagca cgctgaagga 205080
caagacgatc ttaaagcacc aggaccaacc acgcctcaag atgaccacca cgattgccgt 205140
gaaggtcaac gtgatcaaag catggacgac cacgatctga cggcggacgg tacgttcggg 205200
agccaacaac gctacgccgg tgcagctgag aaaggccagt aaggtgaaca acgcggccga 205260
gatgaccaac gtaccgtcca ggcagagaca tatcacgatc aacggcggca cgtgaagcag 205320
cgtgtaaaag agcagaacgc cgatattgct gggatgcgat gtttcgtaac agtgaatgaa 205380
gatcactgac gtgacgggta tgacaaagac gaggctgggc gaggactccg tgagacacag 205440
acgagaatgg tgaaaccacg tcgcgggcgc cgcgtagcag aaggcgctca acaacgcggt 205500
caagccggcc agctgccaac ccacggcgcc ataggtgtgc agcgccacgc ggcaacagtc 205560
gacccaagcc agactgcggg tcgccagccg ggtctcttgg atcccggggg gcacgtagat 205620
gaccgtgcca tcggtgggta cttgaaaccc ttttttctctt ctcatggtgc gctgcgttct 205680
ctggaaacgg ctgctctgtc cgaaaaccag ttccgaacga aaatctaggg cgagagggtg 205740
gacaacggcg tcgacgacga agcatgggac aggtcgttcg gcgttaacgt catcgcgtcg 205800
gacgacggta gttctaagag acgtagatcg ctcagcaggt cctgacagtt gcggattcgc 205860
aagatcagaa aaaaagggga aatgaacgta ataagagct gtagcgacgt atgcgccaca 205920
tcgcgtggca taagaacgtg acggacgaaa aggacctgct gcgaaaagtg accggcgaag 205980
ataaggccca ccgtgctgta gaagcccaaa agcagccgca ggggcaagt ccagggccgc 206040
gtgaagacga tgagaacgtt gaccagaaag accacgaccc agacgccgtt gatgagggta 206100
aattgatcgg acagggtgca gttgtcgcga cagatgaaga ctacttccgc gcagagcaag 206160
gtgatgacca acgtgagcac aaacgacgtc aacacctcgc ggggctcctg gcaggcacac 206220
gtgacaccta cgccgggat gtgcgccagg aggccgcga gtaatagcac cagctgtcgg 206280
aacggacgac ggcagcgcgg gtgccggttt cgctgagcga gaaccggtcg ctcatagcgg 206340
aaatacacga agagcgcgga ggccacaggc accaggagga gcacctcggg cgcccagaca 206400
acgtgacaag gaaagcccgg acgcgacttg agagtcgctg tagggaagac cagagagaag 206460
ctacccaaga cggccaccgc cgcggagatt tggaagagga gcaagccggc gattcggacg 206520
acaacctcga agcgatgcac ccagcccagc acggccacca cggccgcttc atcatagtcg 206580
tcgttgttgc cgctgtcgaa cagccgccga aacacgatct gtcgctgggt cgcggtggga 206640
aagcgcagac ccatgacagc cggaggctat atgaccgcgc gtctaagacg cgagatccgt 206700
gggggggactt ttagatgttt gggcggcccg cggttctaac aggcttgatt ggtggagacg 206760
```

-continued

```
gccggcgcgg cgggtggggg aaacgacgag ttttccgtt acgccatggt tcgcgtgagg  206820
tttctctgta cctcccgcaa aaggtcacag cccgaaatgg aggccgcgtt ggtggcccg   206880
gtggcgcgtg acgataacca ggtcatccaa gcgatgagtt tgtctaatga gtcctcggtg  206940
gtgaagagga tgagaatgag caggtacagg tacaccaggt tctcatagag acacaaggtg  207000
agcaggtcag cctcggacca cgcgatctca acaggcgcg tggtgtcaaa gaccgtgacg   207060
accagcatga agctgagcgc catggcgtaa tagcccaaaa aaagtttgtg ccccaacggt  207120
acgggctgca ggtaaagtgc gatcaagaac gcgataacgc cgatcacaaa cagcgtgacg  207180
atgacctgcc atcgacggtg attatggccg gctagacccg tgacgcagct gcagaggcta  207240
aaaagcacgc aagccaagag gcccgagaag gtcactagcg tagaggagga gcaggcgctg  207300
gccacgatca ccgaaagcgt cgtgagcacg ctataaatgg tgagcaggcc agggctcggt  207360
ggcgacgtga acgatccttc atcgcgttg ccgtgcagca gggccaaaca gatggtgggc   207420
accatcaaac ttaagggcgg cataaagccg gtgcaacaga aaagacggt gcctttaaga   207480
tgcggaaaag ccagcaccag gcccagacag agcaagaagg tgcaggtgcc ctgcacggcc  207540
acggtgctgt agacccgcat acaaagtaaa agcgacgta cgtcgttcgt cgacacggag   207600
gaaatcataa tgactccgcg cgagggtcgc gggggtgggg gcgcccaggc cgtcccggtg  207660
gcctctgagt tcggagacat gacggcggtg gcgatcaaaa ggcgcgtatg agaaaccgtt  207720
tatagagtgt aatagaatca ccgtcattcc cacacgcgt tccccataa agtcacgtaa    207780
cactcgagta agcgtgaaaa agctttattg ttgaataaaa aacacgagta caacaccgag  207840
ttgcggtgtc ctgtctgtct actgggtggg gaaggttcat cgtctgtctc tagagggaag  207900
gtggggaatg tctaagcgag cgggagcgtg tcatctcccc catcttttta caacaagctg  207960
aggagactca cgccgtcgat gcgtccgccg tgtttctcgg cgtactgctg cacccagacg  208020
tggccgctaa atatggcgac gctcatgttt aggagactca tgacgatggt gtacaacacg  208080
acgctgacac agacgctgtt tttagacaac gttccacgct ggtagatgag atccaggtc   208140
tcgtaaataa gcacggccga agcggcggtc accaccagga cgtagagtcc gctgtagatc  208200
ttgctgaccc acagcacggg cgaaaagtaa agcaataggt aaaagacgat gacgaccag   208260
ccgtagccaa tcccgatgac tttccagcgc gtgggattgt tgccggccag gtaggtgaga  208320
ccgctgcaga gaacgaaaaa gaccatcacc agggcaaacg acagaccgat gacgcgcctt  208380
tctccgcaaa agcccgtgca cacggtgatg ccggtgttga tcagcaagca cgccaccgtg  208440
agatgagcaa aattggtggt gtgtgggcga aactcggcga aaccgcgtag catagccagc  208500
gtggacacgg gtacgatgga ggatagggct ggcactatgc cgttggcgca ctgtccctgc  208560
acatcgggga aggcgagcca agccagcaag cagaccgtga gggtacaagc cagctgccac  208620
acgagcccgt gatagacctc catgagcagc ttaaagcgtt tcaaccattg gaagagctgc  208680
tgttcggcca ccagcgcgtg gctgcgatgg agcggcacga tggtgaccgt cggcgactca  208740
tggtgttcgg aaaccgaggc ggtgtcgccc atgctgccgc ttacgaccgc tgtcggtcta  208800
aggtaggcgt cgatgaaaca gtccgtctta tcagcacccg gttaccgcgg atttgattga  208860
cgtcacgagt gtggtcaaac cgtggcggca ccctgtatcc gacccgtcgt catgggctcc  208920
acaaccagag cctcagaaga tggtacatgc cgatgaataa agccacattt tcgacataga  208980
ggcgtagcga gggctgaaaa ctctccggga aagaactctg acaggtgatc agggacagat  209040
cgtgaattag catcagcgtc accgtcaaca gcgtcgtcgc gtgtaaaccg agaaagaacg  209100
gggccgcggc ccgcagcagc caaagtccca gcgccgtagc gcagagcaga gacaggaccg  209160
```

```
acggtagcca cagccgccgg agagacgcgc caggatcgca acccaaaagc gaggccccca  209220
ggcagctgag atctaccgcc agggcgagaa gagccgcgcc gacaaaggcc tgcggcgacg  209280
gctggcacat cagcaaggtc agaaaggcta gcgcgtgcgg caggcagtaa gccaacagga  209340
gtgggagttt gcggggacaa cggtcgatcg acggaccgcg tagcagcagg aacaggcagc  209400
cgacgggcac gacgaggctg agatgagaaa gcggcggtgg gtcgtcgtcc cgtccccgct  209460
cgcatagctc ggccaccggt ggcggcatga gccaccagct gagcacgctg agggcgacgg  209520 tgcggtaag  ctggaaggcg acgaggacgg aggcgcgcag ccataccgcc agcctctcta  209580 ggtagggac  tacctcctcg acggtccatt ctagcgggac gacatgaagc atggcgacaa  209640
gcgcggctgc tgtgaaaacg ggcacggttt tataggcatt aggacttccc cgtcgtactg  209700
gcggctgtca aagtcccgtt gtccaaaggc gcgccgtccg aaagactaat ccaacgggga  209760
cccgagagca tgagcaacaa cgtgagaaag atggccatgc tgtccaggta gagacagacg  209820
gcgtgacgga tgcattggtt aggtgggcag aaaaagatga ccataagact gtcgtaggcc  209880
agaataccca aaagaagct gatagagaag gcgcacaacg tcaccactat cttctgcagc  209940
caatcggcgt cgcttagcag agcgagcgtg aggaacgaaa gcagcattac cacgtagacg  210000
cagctgatgc atttccagcg acgtcggtca cggccaccta gaaacgccag ccccgtaaag  210060
gagataaaca acgccagggt catcacgtag gaacctacta gtacgcggct ttcagagcac  210120
atttggaaga tggccgccgt caggctgttg gccaacagat agatgaaaag caccgtggcg  210180
ttactagggt gttcgttgcc caacgtgtac gtgatgaaca tgcagacgat gggcacgagc  210240
acggtgagaa agaagctgta gttctcgacg caaaagttgc ggttttgtgg gaaccccaac  210300
caaaaaacgc ttcccaagcc gaagctgaaa gccagctgaa agatgaagat ggcgtacacg  210360
cgcagccata cggtgaactt tttgaaccac tcgagagcct ccatgcggga gagcagcagc  210420
gcgttagcct cctgcgcctg catggtggcg acggtctcgg cacaaagccg ctgcggcgca  210480
cctacccttc tcttatacac aagcgagcga gtggggcacg gtgacgtggt cacgccgcgg  210540
acacgtcgat taggagacga actggggcga cgccgctgct gtggcagcga ccgtcgtctg  210600
agcagtgtgg gcgctgccgg gctcggaggg catgaagtag agcacggaga caaagaggta  210660
catgaggtcc atgtacaagc agagcgcgcc cgggatataa ctctcatact cgatgtcgtg  210720
caggatgtcc tgcgtatcgc acaccaccga ggtcacgatg acggcaaac  cggctatcat  210780 caccaggatc tcacttaccg cctcgggaaa aagagaaaat acggcgaaca gtaagagaat  210840
cagcgtggat gcgcccgtca atagggaacg ctgtaattcc acgtcgcggg caaacagata  210900
cgtagcgagc gtgaggaaac aaaatagcgt cactgtggcc accatggcat aaatgactga  210960
acgatgacta agtggaagc  ctgacgccgt gacagccacg ctggtaagca acgtgtacgt  211020
cagtaagatc catacgtttt tgggaaagtt gggctcggcc caacgcaaca gacctaggca  211080
cacgatggag atcattaagc aagacagcgt cagacgcacg ctggaaaaga gctgctccaa  211140
ccggtgcggc aacaccagcc agcaaaaggc gcagacgctc ataaggatga ggcattgcac  211200
ccagataagg atgtagatgc gcagcaggaa gaccgaccgg gctatctgga cctgaccgcg  211260
gagcgacatg gcggcaacgc cggcggttat cgccgagatt cgtctaaata cacgaagcga  211320
actagaaaac gcacacacgt gatttgcaaa aagaaagcag ctgccggctt attattttat  211380
taaaaattta tctgtgcaga atcataagtt tatgatgaat aaaaacgggg aagggaatc  211440 tgcttttagg gacccgggtc tggtccgtcg tctcccatct ggtcgggttc ggggatgggg  211500
```

```
acctgtttca gcgtgtgtcc gcgggcgtgc atggcttttg ctcgccggcc gcgctgtaac   211560
caggcctctt tctctgtggt cggcgagtct tccgacgggt agggagcctg ggagtccatc   211620
gcttcaggcc caccgctcgt tccctcgacc gtcgtgtcgt cctcgttttc gctattacac   211680
ggggtttctg gagtatcgcc tatacggttg gcgattctcc gggggcggcc gctctcgtcc   211740
tcgtcgctgc tatcgccgcc cggtaattcg acgccgcatt cgttgtacgg aacgcggcac   211800
atgggcggcg gaaagaactt gggcatgcga aagcagcgtt gtccatccac ggtctgcgtg   211860
gtttcatcgt tatcctccca taatccccc tgtagcgccg gcagcgtttc gacgctgtga   211920
gaggggaagg cccagttctg gttgtcttgc agcgcgcccg tgggcagtag gtccgtgcgg   211980
ccccatgcgc tgctgttgtt gggtaccttg tcagtgccgc gagtaggtcg cagaaaccag   212040
tccagagcgc tctctagctg cgagcgtgtg atggtgccca gtgcgccgtg ccagcgcagc   212100
acgtctcttt tcagcgtgtg gtgacagacg ggcagctcct ccaaccgaca ctcgccgcgc   212160
aatccgcggt cgaagcggca gagaccacgc agtttaagca gaccgcactt gagaaacatg   212220
tgaaaattat cggcaatgcg atataggtcc gagtcctcga tcttgtgtag gtagaccacg   212280
ccaaacttgt cgagcagcac caggccgctg ggcacaaaag gcccgtaggc caggtaatag   212340
cccacgaggc cgacgacgta ccactcgcag cacaagcgtt gacgaataaa gttcagaaga   212400
tcgcgaaagt ccgcggccgg catgtggtca aaaggccggc aggcgcgcag gccctcgatg   212460
gagcccagca tgagcaacgg ctccacctcg gtgcgacccg gcgtgcggat gaccaggttg   212520
agaccgctca tttcgcgggc cgtcttggcc acggccgcag cgtcagtggg gtcggtgcag   212580
aggaattttt gcacatgata gcgcggttcg gtggtggcga acggcgtttg tgggtgccga   212640
tacacatatt cgcaccagag taggccgttc ttggaaaagg ctttgatatc actggccacc   212700
tcgtagagcc cgtcggtctc ccagtcgtag acgtagacgg tgccgtaatg acttagcatg   212760
agcacgcagg gcagttcctg cgcctgcttg gtgtttcgtg ttagatcgct gtcgggtgga   212820
cgcacggcta gtacaccgac ggcttccagg gtgtcatcgc agcagagata gtcggcggcc   212880
agagaacgtg cgtaaatctg cgggatggcg gcctgttcgc gcatcactag gaaccagttg   212940
gcggggttgc gcagtgctac ggtggttcct tggtggcgtt gcacgtaggt tctcagcgcc   213000
ggaggatcgt actggcgcag atagaggcct tgcagcatcg ataacgtctt ttgaaagacg   213060
gtgtttctaa attgaaaaac gccgtagtcg cagcggatag catcttcgca gcgctcgtcg   213120
cgctgtcgga gataggtgcc ccaggcttcg gcggcggctt tggtgagtag ggacatgccg   213180
gcggagccgt ctcgacagcg agtcggataa agccgcgctgc gcgaaagctt aatataggag   213240
cagcgtcaga cgaatcgcgg ctggtggccc gggggtggg acgcgccgcc tacacaaagt   213300
gctcccgaaa atcgaaactc ttgacccact ccggagacaa atccgtattc agattgatgc   213360
gtcgagcttc cacttcggct tccgaaacct cggcctccgt ccggtaggcg ttaacaatac   213420
gctgacccag gtgccaacgc tctttctctg ccaaacgccg ttgctcaaac cattcgtcta   213480
cgtccttgag gtcaaagaca gtgtcctcct caaggtcaaa gcctaggtct tcccactcgt   213540
cgtcatcgct ctcgtggccg gcggccatac gcgcggcaac cgcgtcttcc cctcctcttc   213600
tttcaacgtt gggtaccacg ttgttttctt cgggttccat aggttctgcg ccgctgtcgt   213660
catcatcctc tccctgctcc tcatcgtccg ccaaggcgtc gtggattacc tccaggttct   213720
gattgtcggg tacgacgtgg ttatcttcgt cgtcgtcgcg tggcatgggc ggcggccgac   213780
ggcggacgac cggcatggcg cggccgtcgt ttccttcgtc ttcctcttca ccgtctccca   213840
aggaacgcgg tcgacgacgt tccgcgaagt cgccgcggac cacgcgcgcc tgccaaatgg   213900
```

```
taaacgcgtc ccaaccgtcc cagttattga gcatttcggc gcgaaaacgg tcgcctcgac  213960
agagccagcg aaactgccgc gcgtagtcgc ggtctacgcc gctgtcgaac atggtaaagt  214020
gcagacgcgc cgcctcgccc atgtgtacgc agcctccgtt gcgttccagc ctggccgcgc  214080
gccgtagacc gtgttcgtag cggcgacgca cgtacacctt catgaggccg cgcgaaaaa   214140 gttcctctag gctgtcggcc agccggtaga tttcaccggc tagacgctgc aggggcggcg  214200
agcggtccag atgcgacttg acaatcacca cgtaaaaacg acagaaacgg tcgaagatga  214260
tgaggaagga cgtgtcaaaa aaaccaccgg cgcggtaaga gcccacggca cccagcaggt  214320
accagcggca acgcagttgc agcgtgacgt acatttcgca ctcggccaag cgggcggctg  214380
gcgctacctc gaagggccag cagtccgtca agcagccgaa actggtcagg agtttcaacg  214440
ttttggcatg gcgtccaggt gtatgaaagt tcacgtcgcg tccgtggtgt tcgccaacgc  214500
aggcggccaa cgcgtcggcg tcatgaccgt gacgcagcag catcgctacc acgtcgtgcg  214560
gtacccgcgt agcaaatggc gtctgtggct gacggtatac ggcttcggtg tacatcatac  214620
cgtaacgcgc cagctcgtcc agatgacgcg cgcacagcag cagaatctct tgcgagggtt  214680
cgtagatgta gaggcgcgta ccgccaccca tgcagagcac cagctccgtc tcttcgtagt  214740
gatcttccac catgatcacg cacttgccta gcacgataag gcgttcgggg caacaaatca  214800
cgtcgtccag cagctggtcg cgtagctccg gcatggtgct gccgggccgt acctgcagga  214860
accagttgtg cggaatgccg agcgacagca cctggtcgac gtggttacgg acccagtcgc  214920
gaagcacgtc ggcgctgtac tggcactcga agatgccctg aaagtcgccc atgacccgca  214980
gaaaagtttc gtagcgcgtg tggcaataga ggaattcatc gtttcgcgta aacgtgggag  215040
ctccgtcttc ccaacgtgta cgccacatgt caaaagaggc cgccagctag acaccccaga  215100
aaagaagcag agaaagagac ttctttgtgc gacacgtttt attctgcgtc ctccgctcga  215160
cgttcaaatc tggatgtact cgcgcacacc cgtcaggctc tttaagggaa aagggtccga  215220
gtacgtcact aaccgcgact gatgcaccag ggcggtaatc acccgctccg cgccctcgcg  215280
cgtcgacgaa cgcgtcgtca ccaggcaatg cagccgcggg cccgtatcgt cctgatgacc  215340
agcggcctcg cgctcggctg cttccacacc gacaatgtcg ggatccaaca cgtagctctg  215400
cgagttggtg tcgtagcggt gtagcaccaa cgtgttgggg tccagacgct cccacgcgcc  215460
ctcgtgcggg tcaaaacgct ccgttaaaca gagccagtca tactgctgct gcagaatacg  215520
ccgctcgcgc tcgcgtcgct catcgggcaa cgcggcgtct tcgttgaaga gaatgtcccg  215580
cttgtggtct acggcacgct cgtggtggtg cgggcacagg tgacggtgtt ccatacgcgt  215640
ctgacgttga cgctcgcgct caaaacgccg gtgtcgaaag accatttcca gcaacccat   215700 gcggaaaaac tccgtgatgg tgttggcaac gcgccgcaca tagtggttgg ggtcgtccat  215760
ctggatggcg tacacggcac cgaaccagtc cagcagtacc agcacttcgg ccacaaaact  215820 gcgtccggt cgcggacgtc ccgtcacgcc tagcacatac cacggcgtgg ccagattagc   215880
acggacagcc caccaccaac gacggctctc cacctcggtg agcgcacaaa agggccaaat  215940
gcggtgtaac tgctgtaccg ttttcatcaa ccgcataatc accgtaccgt aacccggtgt  216000
atgcaacttt acgtcgcaac ccaggattcg ttcggccgtg gcgtacgagc cctcgggcgt  216060
ggtgtcattg agaaacaaaa catgcatggt acgcgcgccc ttaggatatc gtcgcggaac  216120
gggtaccgtc attctccgca gagtggtgtg aatcacgtcg cgatacgcaa tctccgaacg  216180
tgacacaccg taacgtgcca gttcgtccag gttgtgcgat accaacacca tgtacttttc  216240
```

```
acgagtgtcg taggcgtaga cgcgagaaaa gcgacccata aaaaccacgt acggagtagc 216300
caccatgcca tcatggtgat cgcgacgtgg ctcgggcaac aaaataacag cgtatcccaa 216360
cggcgtcaac ggctcgcggc aacagatgag ctttgacgcc gcctgtttgg cggcggtaat 216420
gatcccgtcc tccgtacgta acatcacatg ccagcccttg gggggaccca aggacagaca 216480
gcgtccctcg ttacgatgaa cgtaacgcgt gatttccatt ggctccaggc aaaagaacag 216540
ttccttaaaa tcccgcaaca cttgtcggta taacgccatg ggatcctcgg ccgccacagg 216600
cagcgcgggg agctccggcg gcataactgc agcgccgtca gggccagaac ccgcagccgg 216660
atccatcatt gagcgacact ctcagccgga caaccggcgt cactgacaga agccgagcca 216720
aatacagaga aagcaacgct acaccgtcac cccgctccca agcgccgcgg aaagtgctcc 216780
gattttcac cgtcgttcgc gacgttgatt tgcctcggtc tgagaaccga cctagcgttc 216840
ggaccggtgc gcagaaacag ccggcggtcc gagccactga gcggttcaca gccccggccg 216900
ccgatagtta ccggagagac gttcgagctg caggtacatc agcgcttccc gcttcgccac 216960
cccgcgcccg ccccagttta tactctccga cgccccgtcc aacgcgcctg tggagggcca 217020
atcggaccgc gggagctctc caagtggatg acaggcacag ccgagtgccc gaccgtgaag 217080
agccctcatc cacctgaaca gaccgctaac cgaaggaccc cgagtcgcgt ccgtcggtcc 217140
cgacgtccgt cgccatctgg ctccctgctg ttggctacct ctcggatttc aaaaaagagc 217200
acgtgccgat gacggtgcac aggaaagagc caaagtgtca cggcgtcttt ttttatttgt 217260
attccttcc tgttttgtac tcgtaaactg ttgatgttgt ttttacatcc aaaagggcaa 217320
gtaagaaaca ggatgaggca tggtaggttt gggcgtgggg cggccctcca gcacggcggc 217380
ccgggccgcc cggcgggtga gcacccggcg ttgcgccgtg tctatcttgt gtttcttctg 217440
tgtcttttc ctatcttgtt ccgcgacggc ctctttcatc acgttcagca tgcgttcctc 217500
gacgccctcc agggatcctg gggaggaggg agtcctagtg aggcttccaa tgttgttttg 217560
tggattttcg gtttccttt cttggtcgtc atcgtcggac gtgtcgtctt cctcttgatc 217620
ctcttcttcg tccgagtagt agacgcatag tccttggttc atcaggctgg gattcatcag 217680
gttctgacgg ggaatccgct gttgtagacg tttaaccgcc cgttccaggc gagagctcat 217740
gccgcaccag acgctgtaac gccgcacggg cccgtagcgg gctgtttgtt cgcgtacatg 217800
atcgttgagc tcttgccaat attgtttggc acactccaga tcggaggttt gtggatagtc 217860
gggtcggatc cgcggatccc aactgacatc ggcggtgccg gagacttcgt ccagactgtt 217920
acgcatagag caccagtcgg gtcggacgat aaacctgtcc ttgcggatta accatttata 217980
acgtagttcg tgatggcgtg tagaggcccg tacacgctcc acggtcccaa agcggtccca 218040
gaagggaaag ttttcgtggg ggcagcgacc cggcacttcc agacgttcgg cgtcgtccac 218100
ggcgtagtga aaacgccggc cggcctggta aatttgagc agacccactg ttaacaacat 218160
atccacgctg tcagccaacc gccagatctc gcggcgagac acgtcaaaat agaaaaattc 218220
gcaggctcgg tcgaccagga tcacgaaatc ggcgtgaaag acgccggagg gtagcgattc 218280
gcccaccaca cccattatca tggtttcaca gcataagcgg tccacaaaga acttcaacag 218340
gtcgttgaat tgctccgtct ccatacagat gaagggccag acgcctttga ggttctcggc 218400
ctggccgcag agcagtagcg gacgtgtcat ctcgcccgga gtgcgcagag gcacgcattc 218460
gccgcgataa cgacaggtca cacgctgtag ttcgctgatg ctgttgtcgt gcaggcgaag 218520
gtcgcagata atatgatccg gttgcgtggt tagcagcggc gtgcgcattt gctcgccgta 218580
gatggcctcg cagtgcaaca gcccgtgtcg cgcaaaatcg tccaaactgt gcgccaggta 218640
```

```
gtaaagcacc ccgcgatcgc ggtctagaca ccacacggtt tcgtaacgtc ctaacaggag 218700
caccagacgg gcctggctag gtggctcaat ttcctctaca tacacgaaaa agtcgtcatc 218760
gtccgagtcc tcgtcctcag aagaggaccg cggcccgtgt actctgggca acacggtggt 218820
agagaactgc aggacgccca gagactcgag cgattcttcg cagcagatga gctgacccca 218880
gggcgtttcg ggcccgtcgg tgacagccgc gctgccaaag atgtcctcaa actctacaaa 218940
atctagacgc catccgggtg gcgctgaaat gggaaggcta atgttcatat cagcatagct 219000
acgaactaag tggcggatgt cctgccgcaa gtcttggcag agaatgagct ttcgtaaacc 219060
cttgagggtc ctccgaacaa cggccccaga cgcgtagcga taggactggc gcatggtgcc 219120
gcggcgtgga gcggcacttg gcagcctatt ttatggagtt tcttcagtga cgtggcttgt 219180
tcacgtcgtt cgtgggctgc ggttggcagc tccggtctgt aaaccacccg aaaagactga 219240
catcgacgtc aaagactcac gtaatttgga acatgtgcga ccgcaaagtg cgtcagaata 219300
gcacgtggct ttaggacata aaaagtaccg tgaggtctag acgtgggttt tgtgattgac 219360
acttacacca ggtaagccaa gggacggtga aactgtatgt gaggaatctg ggtgcttaga 219420
cgactaacgt gtaatgcttt ttacaggact gttcgacagg tgatagtacc tgtaaggtga 219480
tgaccacctc tacaaataat caaaccttaa cgcaggtgag caacatgaca aaccacacct 219540
taaacagcac cgaaatttat cagttgttcg agtacactcg gttggggta tggttgatgt 219600
gcatcgtggg cacgtttctg aacgtgctgg tgattaccac catcctgtac taccgtcgta 219660
agaaaaaatc tccgagcgat acctacatct gcaacctggc tgtagccgat ctgttgattg 219720
tcgtcggcct gccgtttttt ctagaatatg ccaagcatca ccctaaactc agccgagagg 219780
tggtttgttc gggactcaac gcttgtttct acatctgtct ttttgccggc gtttgttttc 219840
tcatcaacct gtcgatggat cgctactgcg tcatcgtttg gggtgtagaa ttgaaccgcg 219900
tgcgaaataa caagcgggcc acctgttggg tggtgatttt ttggatacta gccgtgctca 219960
tggggatgcc acattacctg atgtacagcc ataccaacaa cgagtgtgtt ggtgaattcg 220020
ctaacgagac gtcgggttgg ttccccgtgt ttttgaacac caaagttaac atttgcggct 220080
acctggcgcc catcgcgctg atggcgtaca cgtacaaccg tatggtgcgg tttatcatta 220140
actacgttgg taaatggcac atgcagacgc tccacgttct tttggttgtg gttgtgtctt 220200
ttgccagctt ttggttcct ttcaacctgg cgctattttt agaatccatc cgtcttctgg 220260
cgggagtgta caatgacaca cttcaaaacg ttattatctt ctgtctatac gtcggtcagt 220320
ttttggccta cgttcgcgct tgtctgaatc ctgggatcta catcctagta ggcactcaaa 220380
tgaggaagga catgtggaca accctaaggg tattcgcctg ttgctgcgtg aagcaggaga 220440
taccttacca ggacattgat attgagctac aaaaggacat acaagaagg gccaaacaca 220500
ccaaacgtac ccattatgac agaaaaaatg cacctatgga gtccggggag gaggaatttc 220560
tgttgtaatt cgatcctctc tcacgcgtcc gccgcacatc tattttgct aattgcacgt 220620
ttcttcgtgg tcacgtcggc tcgaagaggt tggtgtgaaa acgtcatctc gccgacgtgg 220680
tgaaccgctc atatagacca aaccggacgc tgcctcagtc tctcggtgcg tggaccagac 220740
ggcgtccatg caccgagggc agaactggtg ctatcatgac accgacgacg acgaccgcgg 220800
aactcacgac ggagtttgac tacgatgaag acgcgactcc ttgtgttttc accgacgtgc 220860
ttaatcagtc aaagccagtt acgttgtttc tgtacgcgcgt tgtctttctc ttcggttcca 220920
tcggcaactt cttggtgatc ttcaccatca cctggcgacg tcggattcaa tgctccggcg 220980
```

```
atgtttactt tatcaacctc gcggccgccg atttgctttt cgtttgtaca ctacctctgt 221040
ggatgcaata cctcctagat cacaactccc tagccagcgt gccgtgtacg ttactcactg 221100
cctgtttcta cgtggctatg tttgccagtt tgtgttttat cacggagatt gcactcgatc 221160
gctactacgc tattgtttac atgagatatc ggcctgtaaa acaggcctgc cttttcagta 221220
tttttttggtg gatctttgcc gtgatcatcg ccattccaca ctttatggtg gtgaccaaaa 221280
aagacaatca atgtatgacc gactacgact acttagaggt cagttacccg atcatcctca 221340
acgtagaact catgcttggt gctttcgtga tcccgctcag tgttatcagc tactgctact 221400
accgcatttc cagaatcgtt gcggtgtctc agtcgcgcca caaggtcgc attgtacggg 221460
tacttatagc ggtcgtgctt gtctttatca tcttttggct gccgtaccac ctaacgctgt 221520
ttgtggacac gttaaaactc ctcaaatgga tctccagcag ctgcgagttc gaaagatcgc 221580
tcaaacgtgc gctcatcttg accgagtcgc tcgccttttg tcactgttgt ctcaatccgc 221640
tgctgtacgt cttcgtgggc accaagtttc ggcaagaact acactgtctg ctggccgagt 221700
ttcgccagcg actcttttcc cgcgatgtat cctggtacca cagcatgagc ttttcgcgtc 221760
ggagctcgcc gagtcgaaga gagacatctt ccgacacgct gtccgacgag gtgtgtcgcg 221820
tctcacaaat tataccgtaa tataacttcg tatagcatac attatacgaa gttattaaaa 221880
aagcgctacc tcggcctttt catacaaacc ccgtgtccgc ccctcttttc cccgtgcccg 221940
atatacacga tattaaaccc acgaccattt ccgtgcgatt agcgaaccgg aaaagtttat 222000
ggggaaaaag acgtaggaaa ggatcatgta gaaaaacatg cggtgtttcc gatggtggct 222060
ctacagtggg tggtggtggc tcacgtttgg atgtgctcgg accgtgacgg tgggtttcgt 222120
cgcgcccacg gtccgggcac aatcaaccgt ggtccgctct gagccggctc cgccgtcgga 222180
aacccgacga gacaacaatg acacgtctta cttcagcagc acctctttcc attcttccgt 222240
gtcccctgcc acctcagtgg accgtcaatt tcgacggacc acgtacgacc gttgggacgg 222300
tcgacgttgg ctgcgcaccc gctacgggaa cgccagcgcc tgcgtgacgg gcacccaatg 222360
gagcaccaac ttttttttct ctcagtgtga gcactaccct agtttcgtga aactcaacgg 222420
ggtgcagcgc tggacacctg ttcggagacc tatgggcgag gttgcctact acggggggttg 222480
ttgtatggtg ggcggggggta atcgtgcgta cgtgatactc gtgagcggtt acgggaccgc 222540
cagctacgga aacgctttac gcgtgaattt tgggcgcggc aactgcacgg cgccgaaacg 222600
cacctaccct cggcgcttgg aactgcacga tggccgcaca gaccctagcc gttgcgatcc 222660
ctaccaagtg tatttctacg gtctgcagtg tcctgagcaa ctggttatca ccgcccacgg 222720
cggcgtgggt atgcgccgct gtcctaccgg ctctcgtccc accccgtccc ggccccaccg 222780
gcatgacttg gagaacgagc tacatggtct gtgtgtggat cttctggtgt gcgtcctttt 222840
attagctctg ctgctgttgg agctcgttcc catggaagcc gtgcgtcacc cgctgctttt 222900
ctggcgacgc gtggcgttat cgccgtccac ttccaaggtg gatcgcgccg tcaagctgtg 222960
tcttcggcgc atgtttggtc tgccgccgcc accgtcagtc gcaccacctg ggaaaagaa 223020
ggagctaccg gctcaggcgg ccttgtcgcc gccactgacc acctggtcac taccgccgtt 223080
tccgtccacg cggatacctg acagtccgcc gccaccgtac cagcttcgtc acgccacgtc 223140
actagtgacg gtacccacgc tgctgttata tacgtcatcc gacatcggtg acacagcttc 223200
agaaacaacg tgtgtggcgc acgctactta tggggaaccc ccggagcccg ctcgatcgac 223260
ggctacggtt caggaatgta ccgttcttac cgccccgaat tgcggcatcg tcaacaacga 223320
cggcgcggtc tctgaaggcc aagaccatgg agatgcggtt caccatagcc tggatgtggt 223380
```

```
ttcccagtgt gctgctgata ctggggttgt tgacacctcc gagtaacggg tgcaccgtcg 223440
atgttggacg aaacgtatcc attggagaac agtgccgcct tcgaaacggt gcgacgttct 223500
ccaagggaga catcgaaggt aacttcagtg ggcccgtcgt cgtggagttg gactacgaag 223560
atatcgatat tactggcgaa cggcagcgac ttcggttcca tctcagcgga ctcgggtgtc 223620
ctacaaagga aaatataaga aaagacaatg aaagcgacgt caacggtgga attcgctggg 223680
ctctatatat acaaaccggc gacgccaagt acggtattcg taaccagcat ttgagtatac 223740
ggttaatgta tcctggggaa aaaatacac aacagctgtt ggattctgat ttcagttgcg 223800
aacgtcaccg gagaccgtcc acgccgttgg gaaagaacgc cgaagtgcct cccgcgaccc 223860
gcacgtcttc tacatacagc gtcctcagcg cttttgtagt gtggatcgga tccggcctca 223920
atatcatctg gtggaccggc atcgtgcttc tggcggtgga cgctctcgga cttggcgagc 223980
gttggctgag gttagcactg tctcaccggg acaaacatca cgcatcgcga accgcggcgc 224040
tccagtgtca acgcgacatg ttacttcggc aacgtcgacg ggctcggcgg ctgcacgccg 224100
tttctgaagg caaactgcag gaagagaaga acgacagtc tgctctggtc tggaacgttg 224160
aggcgcgacc ctttccgtcc acacatcagc tgattgtgct gccccctcct gtagcgtcag 224220
ctcctcctgc ggttccctcg cagccccccg agtattcgtc tgtgtttccg cctgtataaa 224280
aataaagaga cgggaggctg atcgcggcct tcagcgtctc atttgtcttt actctcgagt 224340
gcggtcggtg tctcgtcggt gagacgaggc cgccgcccga caagttcgat ctcatgtcgc 224400
tcttggagcg cgaagagagt tggcgtcgcg tagtcgacta ctcgcacaac ctgtggtgta 224460
cgtgcggtaa ctggcagagc cacgttgaga ttcaggacga ggagccaaac tgcgagcagc 224520
cggagcccgc acactggctg gaatacgtgg cggtccagtg gcaggccggg gttcgcgatt 224580
ctcacgatcg ctggtgtctc tgcaacgcct ggcgtgatca cgccttgcgc ggccgttggg 224640
gtacggcgta ttcctcgggt tcctcggcct cttcctccgg tttcgtcgcg gagagcaagt 224700
tcacctggtg gaaacgactg cgccacagta cccggcgctg gttgtttcgc cgccggcgag 224760
ctcgatacac tccgtctaac tgtggggaaa gtagcactag cagcggccag agtagcggtg 224820
acgagagtaa ctgcagtcta cgcacccacg gcgtgtacac acggggtgaa caacactaat 224880
cgataagtcg cgtgtaggcg actggctaca tcaaccggat atctgcgggg atttaaaaag 224940
acgacccgtt gtcatccggc ttagaccaaa ccgtcctttt atcatcttcc gtcgccatgg 225000
ctatgtacac atccgaatcc gaacgcgact ggcgtcgtgt aatccacgac tcgcacggcc 225060
tgtggtgcga ctgcggcgac tggcgagagc acctctattg tgtgtacgac agccattttc 225120
agcgacgacc cacgacccga gccgaacgga gggccgccaa ttggcggcga cagatgcggc 225180
ggttacaccg tttgtggtgt ttttgtcagg actggaagtg tcacgcgtta tacgccgagt 225240
gggacggcaa agaatccgac gacgagtcgt cggcgtcttc ctcgggcgaa gcgccagagc 225300
aacaggtccc cgcttggaag accgtgcggg ccttctcgcg ggcctaccac caccgcatta 225360
accggggtct gcggggcacg ccccaccgc gcaacttgcc gggatacgag cacgcctccg 225420
agggctggcg gttttgcagt cgacgggaac ggcgagagga cgatcttcgc acgcgggctg 225480
agccggaccg cgtggtgttc cagttagggg gagtaccccc tcgccgtcac cgggaaactt 225540
acgtgtaaga acacggcgtg acaataaaca acatagcgta aatccccgtg tgatgtgtgt 225600
gattgacgtt cgggaaacat gtccccatca tcagcgtcac aattgacgtg ggttggtcac 225660
tgacgtgcag gatgttacgc gagtcagaga atcgcataag aacggagtgg tgagcgggtt 225720
```

```
cccacaggag tctctggcgc aaaagcacca tgagcctcag gttccccgag agggtgggtt   225780
acgagaaact gggataccgc ccgcatgcca aacgcgtgcg ggtgcatgac tcgttgggat   225840
tgacgcggtt tatcatgagg caactcatga tgtacccgct ggtgttgccg ttcactttc   225900 cgttttacgt gccgcggtcc tagcacgtca gtggtgacgc tgataattgc aacatggccc   225960
atgacgaacc cgcttgggac gaacgtcaat accacgtcaa accaccgtga cttggctgaa   226020
cgttgaaaca taaagccaaa gcgccgtcgg cacttggctt cagagcagcg cctcggggcg   226080
atgcgacggc gatgaactta gagcaactca tcaacgtcct tggtctgctc gtctggattg   226140
ccgctcgtgc tgtcagccgc gttggtccgc atggctccgg actcgtttat cgtgagcttc   226200
atgatttcta cgggtatctg cagctggacc ttctgggacc agtggtggcg gggaatcgct   226260
cagtccggac ctggagagag caggcggacc gagccagagg gaccttcgct tggcgttcag   226320
gccttaatac tagccgcatc ttacctgtcg gcagcatgta tcggggctcc gacgccttac   226380
ccgccggcct gtatcgtccc gaagaagagg tgttcctcct cttgaatcgc tgccatgggc   226440
cactgtcaac gccgaaaaat gcttgtctgg ctgaggttgg tgtcgctaat gccacttttt   226500
tgtctcgctt caatgtcggt gattttcacg gagcgtcatg ggaaaacggt accgctcccg   226560
atggagagcc cggggtatgc tgaaattcct cttaaaattt cgtaaacgac gtcgtccagt   226620
cgttgtgccg cgattcgtac ggttcatcgt ctacgtcgtt ttgttcaccg tcgctgtgca   226680
acgcgtgaaa caagagcgtg atgcgcacct tcggcggtat gaagaacgat tacgaaaaa    226740 ccgcgcacgg cgtcggcagt cttttccgtg acttggggcg atgggtccga gctgcggtat   226800
gggtcacggc ggcgtgtgtt ttattgacga agatgccgat gtgtgactaa aaacgtccca   226860
gccccagagc gatatgtttc aataaaaaaa atatgtagta tcatattatg cgtgtcctgg   226920
tttttcattt ttggatgtat gtatcgcata agggtggcg aggtgtgagg atgaaacata    226980
tgcagatacg cagtgttgtt atccgaacga aacccgtgta atgcgtacaa cggtacttca   227040
gtatgaaagt cccgtgtgtg ggggggggg gcaaatagtt gcgtttgccg ttgggcgtac    227100
gctacgtttg tatttctggc tataatatgt gcggtcatgt gtcgatgttc ctattgggaa   227160
gggtgtgact gtagggtgta taagtacgg tgggacgcag agggacattg atagaaacag    227220
gttgagcgct gtacgagttt cacacgctga atcggcgcca agaataaaac agtggttatt   227280
cgtaaaagta tggggggggg gggatgtttg tcgacggttg ttagatgcat tgcgtatctg   227340
tattagtagt tttgcaagcc gtggtgcgtg ttattgtgac gtagcaatta tcgtattgtg   227400
catgtgtcgt tcatcacaga gtttagtata ctaatatgaa gcgtcgcgag tattaaagca   227460
attggtgtct ctgtgctagt ctaacaacac ctgtgtaatg cgtacaacga gaaaaaagac   227520
gcgaaagcaa cgtgtatggg gggggggggg aataatattg ctaatcatgc gtcttgcagt   227580
acagatagcc gctgtatctt acgcgtattg tcgcaacagt tccacatcgg tgtaattgga   227640
tgtctggtac ttatcactgg cgtcgttata acattgtaaa acaagttttc gaaacataac   227700
gacagctgca aaagaaaacc agtttattga gcattgtaat ggtagtgtgt ggctatatta   227760
gaaaacgtga cgcgtcgcat gtcgcggcac aatctggcag cggggtcggg gtagggtacg   227820
gtgggaggca tgtacacaga tggaacaaaa gcagaagtaa cgtgagaagg agcatacagt   227880
ccagtatcca gcggttcctg agtagcacca cccatcaact gaatgccctc atgagtaaaa   227940
gtctgcgggc gacagccctt ggggaccgtt ggcatgggac gatcaatctc caaaccacag   228000
cgtaacaccg ttttcttcca acgtcgttga tagacgtcgt ttttacggtt actcccaaga   228060
acccagaaag tctcgtccaa gtcgtaccag gaatcttctc cggggagacg cgacggtttc   228120
```

```
caatcctcgt cgtctcgtct caaagcacgt cccaaactgg cttgaggagt caacggtggt  228180
tctgtgggtc gggtgtagcg cgagtgtttt cccttcatga gcgattcatc ctccttgcct  228240
ttaggctttt tggtcttttt gtgtatcatc tggccgccgg cctccataac caccgtggcc  228300
aagtccagtc ccagagcttg agcgtcggcg cggcgtcggg cgtcttgcag gtagtcttcc  228360
acatttgcac agatggccgg gtgtttggtg gctagggtga ggacctcagc ctcgccgcga  228420
cccggacgta gcaaaaaagc caactgcccg tgcggctcgc gcgcccacag cgcggcgcgc  228480
gggtgcaggt gcagcgcgtc ccagcgcggc cgctcccact gctcgcggtc cagctcgggc  228540
agcagccgcc gcgcggcctc ggcggcgggc gccgactcgc gtcccagcgc cagcgcgccc  228600
agcacgcccg cgcgcagaaa gtgcgacagc tccgccgcca gcgggtacac gtgcccgtcc  228660
agcgggcagt acccgaacac ggcgcccagc tcgtccagca gcaccaccag catggcgcgc  228720
ggcacggtcc ccgacgccgc cggacccgcc atcgctgtcg aacccaccat caccgtcggc  228780
gccgctgctg ctgccgcgtc cgccccgacc accgcgtgcg cgtccgcgtt aggcacgcaa  228840
atcgcgcccc cgccggcggc gccgtacggc tgcggaggca caggtacagc ggaccccacg  228900
gctcccgcta tcgcgcacgg cgcgtccccg ccggcggcct ccgtctccgt gccgctcgcc  228960
gctggcggcg acgtcgtccc cgccgccgtc cccgtcgccg gccccgccgc gcagcccagc  229020
caccgcgcgg gcagcaccgc gcccagcgcc agcagccgc agcacagacg ctggttcagg  229080
tgccgacgca cggccgtcag cagcgacgcg gggtgcggcg ccgacgcgaa cggctcgtac  229140
tgcgccagct cctgccacgc gcccagcagt accatcggct gcagtcgcct gcccggcgtc  229200
tgcagcgcca ccgtcgtgcc ggcccaccgc cggcgcagct cccgtccgag cgccgtcgcc  229260
tcctcggcgc gcagcaacgt ctgtcggagc gccggctgag gcagcagcgt cgcgcgcggg  229320
gtgcccacgc ccagccggtt gcagcggtac agccgcacca cctcgcccgc gccgtgccga  229380
aaccactcgt ccgcgtcgcg cgccgctagg atcagcgtgt tgtttgccag gtcgtacacg  229440
aacacgcgga acccggcgcc cagcgccagg tacagtccgt cctgcgcgca cagaccctcg  229500
ggatggccgg ccttgtcgcc caacgtcggg tcggctgcgg ggtccacctc gtgcaccacg  229560
gtagccacca gtacgatcca cgcgtcccgc ggcgacagtt gacgcaggtc cgtcgcgccc  229620
acgccgttca tctggctgcg cggcgtcacc cgcgcgtaga atccgtacgg ccgtccgagc  229680
ggcagcagcg tgcccgcgtc gcgctgcgac cacttgcgca tggcgcggcc cgtgctgttg  229740
gccaaaaacg ccgcgcgcca cacggcgccc atggcctggt attccagctc cgtcagcgcc  229800
tggcgctcca ccggaatctg agacagcaac aggcgctccg ggccgtgcca aaagttgcta  229860
ttgttgccgc tactcggagg ggcgcccggc ggcccgcggg gttctacccg gtggacgccg  229920
tggcccggct cgtcgtagc cgcagcactc gcaccagtgc ccgctgtgga cggcgctccc  229980
atcggcacac aagaagaagg aggagaggaa ccaaccccccg aaggccctcc ggccccgcgg  230040
ccgcgaccaa ggggcggggg gcgcggcgac atgccgttgc gctgggccat gggcgccgga  230100
cacctccgac gtccactata taggaagcaa acccgcgtca gcgagcacgc ggtttagaca  230160
cgcggacgcc ttcgtcgccc gtgtgccgcg ggcgacacgc agctggcttt tataggcagc  230220
gacgtgcacg gcgcgtgctg gcgccgcctt ggcgccacgc agtctggaag gccgtggact  230280
gggaaaggca gctacccgaa ggaagacgcg cggcaggcgc gtaccactgg agcgcacagc  230340
cgcctcccgg gcgcgcaccc atctaggtgg acgcccgaca tccattccgg gccgcgtggt  230400
gggtcctcga ggggcggggg ggtgttttta gcggggggggt gaaacttgga gttgcgtgtg  230460
```

```
tggacggcga ctagttgcgt gtggtgcgga ggacggcgac ggcgaataaa agcgacgtgc  230520
ggcgcgcacg gcgaaaagaa gacgcgtgtc tgtgtctgtg tgattccccg gggaaaagag  230580
gaagttcccg ggggacggca gcatgggtcc ctggggacac acgaaaagca acgcccgggg  230640
gcgagggacg acggccctgg ggaccgcggg ggaaataacg gccgcgaggc cacacactcg  230700
ttcctgcgaa gccgcacacc ccgaggccgc gcacaccgcc gacacacccc gccaccacac  230760
cccgccggca cacccgccac acgcccgcga cacaccggc acgacacacc cggcacacgc   230820
ccgcgacaca ccctgacaca ccctgccaac acaccccga cacacccaac acacgcccgc   230880
gacacacccg gcacacaccc acccggccgc gccccgacac acccaaaaca ccgccggtgc  230940
ggggccgcgt ggtgggtcct cgaggg                                       230966
```

CONDITIONAL REPLICATING CYTOMEGALOVIRUS AS A VACCINE FOR CMV

CROSS-REFERENCE TO RELATED APPLICATIONS

This application is a §371 National Stage Application of PCT/US2012/053599, international filing date of Sep. 4, 2012, which claims the benefit of U.S. Provisional Application Ser. No. 61/532,667, filed Sep. 9, 2011.

REFERENCE TO SEQUENCE LISTING SUBMITTED ELECTRONICALLY

The sequence listing of the present application is submitted electronically via EFS-Web as an ASCII formatted sequence listing with a file name "23109USPCT-SEQLIST-07MAR2014.TXT", creation date of Mar. 7, 2014, and a size of 339,186 KB. This sequence listing submitted EFS-Web is part of the specification and is herein incorporated by reference in its entirety.

FIELD OF INVENTION

The present invention relates to methods of inducing an immune response to cytomegalovirus (CMV) using a genetically modified CMV that is conditionally replication defective. The present invention also relates to a CMV which has been recombinantly altered to allow for external control of viral replication. Compositions comprising the replication defective CMV are also encompassed by the present invention.

BACKGROUND OF THE INVENTION

Cytomegalovirus (CMV), also known as human herpesvirus 5 (HHV-5), is a herpes virus classified as being a member of the beta subfamily of herpesviridae. According to the Centers for Disease Control and Prevention, CMV infection is found fairly ubiquitously in the human population, with an estimated 40-80% of the United States adult population having been infected. The virus is spread primarily through bodily fluids and is frequently passed from pregnant mothers to the fetus or newborn. In most individuals, CMV infection is latent, although virus activation can result in high fever, chills, fatigue, headaches, nausea, and splenomegaly.

Although most human CMV infections are asymptomatic, CMV infections in immunocompromised individuals, (such as HIV-positive patients, allogeneic transplant patients and cancer patients) or persons whose immune system has yet fully developed (such as newborns) can be particularly problematic (Mocarski et al., Cytomegalovirus, in Field Virology, 2701-2772, Editor: Knipes and Howley, 2007). CMV infection in such individuals can cause severe morbidity, including pneumonia, hepatitis, encephalitis, colitis, uveitis, retinitis, blindness, and neuropathy, among other deleterious conditions. In addition, CMV infection during pregnancy is a leading cause of birth defects (Adler, 2008 J. Clin Virol, 41:231; Arvin et al, 2004 Clin Infect Dis, 39:233; Revello et al, 2008 J Med Virol, 80:1415). CMV infects various cells in vivo, including monocytes, macrophages, dendritic cells, neutrophils, endothelial cells, epithelial cells, fibroblasts, neurons, smooth muscle cells, hepatocytes, and stromal cells (Plachter et al. 1996, Adv. Virus Res. 46:195). Although clinical CMV isolates replicate in a variety of cell types, laboratory strains AD169 (Elek & Stem, 1974, Lancet 1:1) and Towne (Plotkin et al., 1975, Infect. Immun. 12:521) replicate almost exclusively in fibroblasts (Hahn et al., 2004, J. Virol. 78:10023). The restriction in tropism, which results from serial passages and eventual adaptation of the virus in fibroblasts, is stipulated a marker of attenuation (Gerna et al., 2005, J. Gen. Virol. 86:275; Gerna et al, 2002, J. Gen Virol. 83:1993; Gerna et al, 2003, J. Gen Virol. 84:1431; Dargan et al, 2010, J. Gen Virol. 91:1535). Mutations causing the loss of epithelial cell, endothelial cell, leukocyte, and dendritic cell tropism in human CMV laboratory strains have been mapped to three open reading frames (ORFs): UL128, UL130, and UL131 (Hahn et al., 2004, J. Virol. 78:10023; Wang and Shenk, 2005 J. Virol. 79:10330; Wang and Shenk, 2005 Proc Natl Acad Sci USA. 102:18153). Biochemical and reconstitution studies show that UL128, UL130 and UL131 assemble onto a gH/gL scaffold to form a pentameric gH complex (Wang and Shenk, 2005 Proc Natl Acad Sci USA. 102:1815; Ryckman et al, 2008 J. Virol. 82:60). Restoration of this complex in virions restores the viral epithelial tropism in the laboratory strains (Wang and Shenk, 2005 J. Virol. 79:10330).

Loss of endothelial and epithelial tropism has been suspected as a deficiency in the previously evaluated as vaccines such as Towne (Gerna et al, 2002, J. Gen Virol. 83:1993; Gerna et al, 2003, J. Gen Virol. 84:1431). Neutralizing antibodies in sera from human subjects of natural CMV infection have more than 15-fold higher activity against viral epithelial entry than against fibroblast entry (Cui et al, 2008 Vaccine 26:5760). Humans with primary infection rapidly develop neutralizing antibodies to viral endothelial and epithelial entry but only slowly develop neutralizing antibodies to viral fibroblast entry (Gerna et al, 2008 J. Gen. Virol. 89:853). Furthermore, neutralizing activity against viral epithelial and endothelial entry is absent in the immune sera from human subjects who received Towne vaccine (Cui et al, 2008 Vaccine 26:5760). More recently, a panel of human monoclonal antibodies from four donors with HCMV infection was described, and the more potent neutralizing clones from the panel recognized the antigens of the pentameric gH complex (Macagno et al, 2010 J. Virol. 84:1005).

SUMMARY OF THE INVENTION

The present invention is directed to conditional replication defective CMV (rdCMV) and the use of rdCMV in compositions and methods of treating and/or decreasing the likelihood of an infection by CMV or pathology associated with such an infection in a patient. The rdCMV described herein comprises a nucleic acid encoding one or more fusion proteins that comprise an essential protein fused to a destabilizing protein. In the absence of a stabilizing agent, the fusion protein is degraded. Thus, the rdCMV can be grown in tissue culture under conditions that allow for replication (i.e., in the presence of the stabilizing agent) but replication is reduced, and preferably prevented, when administered to a patient (in the absence of the stabilizing agent).

One embodiment of the present invention is a conditional replication defective CMV. The rdCMV comprises a nucleic acid encoding one or more fusion proteins that comprise an essential protein fused to a destabilizing protein. The nucleic acids encoding the wild type essential protein are no longer present in the rdCMV and thus the fusion protein is required for viral replication. In preferred embodiments, the essential proteins are selected from the group consisting of IE1/2, UL51, UL52, UL79 and UL84 and the destabilizing protein is FKBP or a derivative thereof.

Another embodiment of the present invention is a composition comprising an isolated rdCMV and a pharmaceutically acceptable carrier. The composition can further comprise an adjuvant including, but no limited to ISCOMATRIX® adjuvant and aluminium phosphate adjuvant.

Another embodiment of the present invention is use of the rdCMV composition to induce an immune response against CMV in a patient. Patients can be treated prophylactically or therapeutically by administration of the rdCMV of the present invention. Prophylactic treatment provides sufficient protective immunity to reduce the likelihood or severity of a CMV infection, including primary infections, recurrent infections (i.e., those resulting from reactivation of latent CMV) and super-infections (i.e., those resulting from an infection with a different stain of CMV than previously experienced by the patient). In specific embodiments, females of childbearing age, especially early adolescent females, are vaccinated to decrease the likelihood of CMV infection (either primary, recurrent or super) during pregnancy and thus decrease the likelihood of transmission of CMV to the fetus. Therapeutic treatment can be performed to reduce the length/severity of a current CMV infection.

Another embodiment of the present invention is methods of making the rdCMV of the invention comprising propagating the rdCMV on epithelial cells, such as ARPE-19 cells (ATCC Accession No. CRL-2302), in the presence of Shield-1. In some embodiments, the rdCMV is propagated on epithelial cells on microcarriers or other high density cell culture systems.

DETAILED DESCRIPTION OF THE INVENTION

Figure 1A:
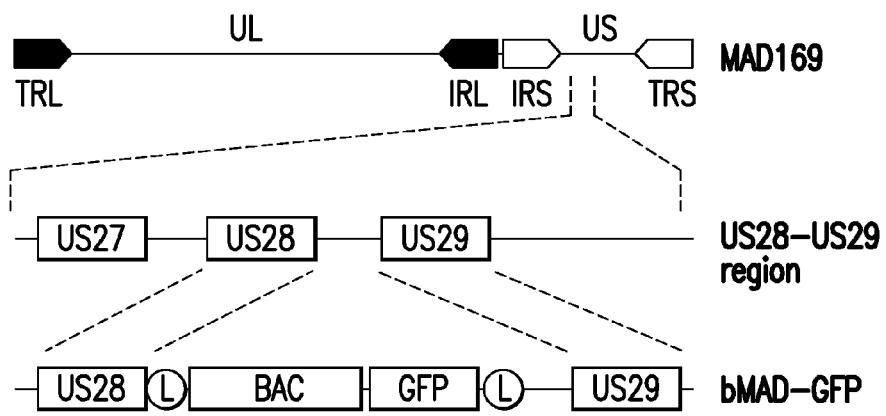
FIGS. 1A-1C shows a schematic diagram of the construction of a strain of CMV with restored expression of the pentameric gH complex. (A) Strategy for generation of self-excisable Bacterial Artificial Chromosome (BAC) to manipulate AD169 viral genome. (B) Repair of the frame shift mutation in UL131 to restore its expression. (C) Replacement of GFP with a cre recombinase gene to create a self excisable CMV BAC.

The present invention is directed to conditional replication defective CMV (rdCMV) and the use of rdCMV in compositions and methods of treating and/or decreasing the likelihood of an infection by CMV or a pathology associated with such an infection in a patient. The rdCMV described herein encodes one or more fusion proteins that comprise an essential protein fused to a destabilizing protein instead of the wild type essential protein. In the absence of a stabilizing agent, the fusion protein is degraded by host cell machinery. In the presence of a stabilizing agent, the fusion protein is stabilized and not degraded.

Suitable fusion proteins for use in the present invention retain sufficient essential protein activity to facilitate viral replication in a host cell in the presence of a stabilizing agent and cause a decrease (preferably greater than 50%, 75%, 90%. 95%, or 99% reduction) in CMV replication in the absence of a stabilizing agent. Preferably, the essential protein for use in the fusion protein encodes non-structural proteins and are thus not packaged into the rdCMV virions. Suitable essential proteins identified herein include the CMV proteins encoded by the essential genes IE1/2, UL51, UL52, UL79 and UL84.

An example of a destabilizing protein and stabilizing agent is described in US Patent Publication 2009/0215169 which discloses compositions, systems and methods for modulating the stability of proteins using a small-molecule. Briefly, a protein is fused to a stability-affecting protein, FKBP or a derivative thereof. An exogenously added, cell permeable small-molecule, Shield-1 (Shld-1), interacts with the FKBP or derivative thereof and stabilizes the fusion protein. In the absence of Shield-1, the FKBP or derivative thereof directs the fusion protein to be degraded by host cell machinery.

In an embodiment of the present invention, an essential CMV protein is fused to a FKBP or derivative thereof. In the presence of Shield-1, the fusion protein is stabilized. However, in the absence of Shield-1, the FKBP or derivative thereof directs the fusion protein to be degraded by host cell machinery.

In the absence of fusion protein, replication of rdCMV is reduced (preferably by greater than 50%, 75%, 90%. 95%, or 99% as compared to CMV not containing a destabilized essential protein) or prevented.

The recombinant virus to be used in the method of the invention also displays an immunogenic pentameric gH complex on its virion.

Embodiments also include the recombinant CMV or compositions thereof, described herein, or a vaccine comprising or consisting of said CMV or compositions (i) for use in, (ii) for use as a medicament for, or (iii) for use in the preparation of a medicament for: (a) therapy (e.g., of the human body); (b) medicine; (c) inhibition of CMV replication; (d) treatment or prophylaxis of infection by CMV or, (e) treatment, prophylaxis of, or delay in the onset or progression of CMV-associated disease(s). In these uses, the recombinant CMV, compositions thereof, and/or vaccines comprising or consisting of said CMV or compositions can optionally be employed in combination with one or more anti-viral agents (e.g., anti-viral compounds or anti-viral immunoglobulins; combination vaccines, described infra).

As used herein, the term "induce an immune response" refers to the ability of a conditional replication defective CMV to produce an immune response in a patient, preferably a mammal, more preferably a human, to which it is administered, wherein the response includes, but is not limited to, the production of elements (such as antibodies) which specifically bind, and preferably neutralize, CMV and/or cause T cell activation. A "protective immune response" is an immune response that reduces the likelihood that a patient will contract a CMV infection (including primary, recurrent and/or super-infection) and/or ameliorates at least one pathology associated with CMV infection and/or reduces the severity/length of CMV infection.

As used herein, the term "an immunologically effective amount" refers to the amount of an immunogen that can induce an immune response against CMV when administered to a patient that can protect the patient from a CMV infection (including primary, recurrent and/or super-infections) and/or ameliorate at least one pathology associated with CMV infection and/or reduce the severity/length of CMV infection in the patient. The amount should be sufficient to significantly reduce the likelihood or severity of a CMV infection. Animal models known in the art can be used to assess the protective effect of administration of immunogen. For example, immune sera or immune T cells from individuals administered the immunogen can be assayed for neutralizing capacity by antibodies or cytotoxic T cells or cytokine producing capacity by immune T cells. The assays commonly used for such evaluations include but not limited to viral neutralization assay, anti-viral antigen ELISA, interferon-gamma cytokine ELISA, interferon-gamma ELISPOT, intracellular multi-cytokine staining (ICS), and $^{51}$Chromimium release cytotoxicity assay. Animal challenge models can also be used to determine an immunologically effective amount of immunogen.

As used herein, the term "conditional replication defective virus" refers to virus particles that can replicate in a certain environments but not others. In preferred embodiments, a virus is made a conditional replication defective virus by destabilization of one or more proteins essential for viral replication. The nucleic acids encoding the wild type, non-destabilized essential proteins are no longer present in the conditional replication defective virus. Under conditions where the one or more essential proteins are destabilized, viral replication is decreased by preferably greater than 50%, 75%, 90%. 95%, 99%, or 100% as compared to a virus with no destabilized essential proteins. However, under conditions that stabilize the destabilized essential proteins, viral replication can occur at preferably at least 75%, 80%, 90%, 95%, 99% or 100% of the amount of replication of a CMV that does not contain a destabilized essential protein. In more preferred embodiments, one or more essential proteins are destabilized by fusion with a destabilizing protein such as FKBP or a derivative thereof. Such fusion proteins can be stabilized by the presence of a stabilizing agent such as Shield-1. As used herein, the term "rdCMV" refers to a conditional replication defective cytomegalovirus.

In preferred embodiments, the immune response induced by a replication defective virus as compared to its live virus counterpart is the same or substantially similar in degree and/or breadth. In other preferred embodiments, the morphology of a replication defective virus by electron microscopy analysis is indistinguishable or substantially similar to its live virus counterpart.

As used herein, the term "FKBP" refers to a destabilizing protein of SEQ ID NO:11. Fusion proteins containing FKBP are degraded by host cell machinery. As used herein, the term "FKBP derivative" refers to a FKBP protein or portion thereof that has been altered by one or more amino acid substitutions, deletions and/or additions. The FKBP derivatives retain substantially all of the destabilizing properties of FKBP when fused to a protein and also retain substantially all of the ability of FKBP to be stabilized by Shield-1. Preferred FKBP derivatives have one or more of the following substitutions at the denoted amino acid positions F15S, V24A, H25R, F36V, E60G, M66T, R71G, D100G, D100N, E102G, K105I and L106P. The FKBP derivative having the F36V and L106P substitutions (SEQ ID NO:12) is particularly preferred. In preferred embodiments, the nucleic acid that encodes the FKBP or FKBP derivative contains at least some codons that are not commonly used in humans for endogenous FKBP. This decreases the likelihood that the FKBP or FKBP derivative of the fusion protein will rearrange or recombine with its counterpart in human genome. The nucleic acid sequence of SEQ ID NO:13 encodes SEID NO:12 using such codons.

As used herein, the terms "Shield-1" or "Shld1" refer to a synthetic small molecule that binds to wild-type FKBP and derivatives thereof and acts as a stabilizing agent. Binding is about 1,000-fold tighter to the F36V derivative compared to wild-type FKBP (Clackson et al., 1998, PNAS 95:10437-42). Shield-1 can be synthesized (essentially as described in Holt et al., 1993, J. Am. Chem. Soc. 115:9925-38 and Yang et al., 2000, J. Med. Chem. 43:1135-42 and Grimley et al., 2008, Bioorganic & Medicinal Chemistry Letters 18:759) or is commercially available from Cheminpharma LLC (Farmington, Conn.) or Clontech Laboratories, INC. (Mountain View, Calif.). Salts of Shield-1 can also be used in the methods of the invention. Shield-1 has the following structure:

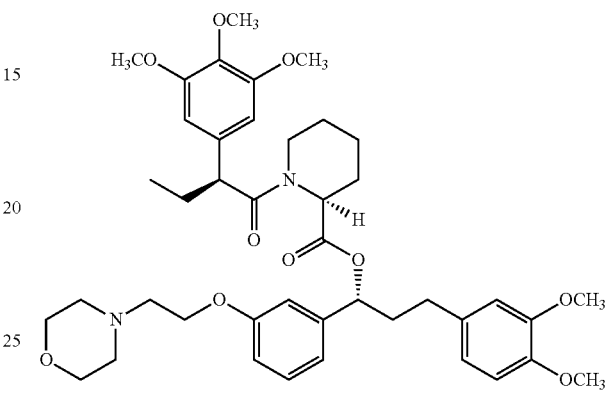

As used herein, the terms "fused" or "fusion protein" refer to two polypeptides arranged in-frame as part of the same contiguous sequence of amino acids. Fusion can be direct such there are no additional amino acid residues between the polypeptides or indirect such that there is a small amino acid linker to improve performance or add functionality. In preferred embodiments, the fusion is direct.

As used herein, the terms "pentameric gH complex" or "gH complex" refer to a complex of five viral proteins on the surface of the CMV virion. The complex is made up of proteins encoded by UL128, UL130, and UL131 assembled onto a gH/gL scaffold (Wang and Shenk, 2005 Proc Natl Acad Sci USA. 102:1815; Ryckman et al, 2008 J. Virol. 82:60). The sequences of the complex proteins from CMV strain AD169 are shown at GenBank Accession Nos. NP_783797.1 (UL128), NP_040067 (UL130), CAA35294.1 (UL131), NP_040009 (gH, also known as UL75) and NP_783793 (gL, also known as UL115). Some attenuated CMV strains have one or more mutations in UL131 such that the protein is not expressed and therefore the gH complex is not formed. In such cases, UL131 should be repaired (using methods such as those in Wang and Shenk, 2005 J. Virol. 79:10330) such that the gH complex is expressed in the rdCMV of the invention. The viruses of the present invention express the five viral proteins that make up the pentameric gH complex and assemble the pentameric gH complex on the viral envelope.

As used herein, the term "essential protein" refers to a viral protein that is needed for viral replication in vivo and in tissue culture. Examples of essential proteins in CMV include, but are not limited to, IE1/2, UL37×1, UL44, UL51, UL52, UL53, UL56, UL77, UL79, UL84, UL87 and UL105.

As used herein, the term "destabilized essential protein" refers to an essential protein that is expressed and performs its function in viral replication and is degraded in the absence of a stabilizing agent. In preferred embodiments, the essential protein is fused to a destabilizing protein such as FKBP or a derivative thereof. Under normal growth conditions (i.e., without a stabilizing agent present) the fusion protein is expressed but degraded by host cell machinery. The degradation does not allow the essential protein to function in viral replication thus the essential protein is functionally knocked out. Under conditions where a stabilizing agent such as Shield-1, is present the fusion protein is stabilized and can perform its function at a level that can sustain viral replication that is preferably at least 75%, 80%, 90%, 95%, 99% or 100% of the amount of replication of a CMV that does not contain a destabilized essential protein.

Replication Defective CMV

The methods of the present invention use a replication defective CMV (rdCMV) that expresses the pentameric gH complex. Any attenuated CMV virus that expresses the pentameric gH complex can be made replication defective according to the methods of the invention. In one embodiment, the attenuated CMV is AD169 that has restored gH complex expression due to a repair of a mutation in the UL131 gene (see Example 1).

Conditionally replication defective viruses are mutants in which one or more essential viral proteins have been replaced by a destabilized counterpart of the essential proteins. The destabilized counterpart is encoded by a nucleic acid that encodes a fusion protein between the essential protein and a destabilizing protein. The destabilized essential protein can only function to support viral replication when a stabilizing agent is present. In preferred embodiments, methods described in US Patent Publication 2009/0215169 are used to confer a conditionally replication defective phenotype to a pentameric gH complex expressing CMV. Briefly, one or more proteins essential for CMV replication are fused to a destabilizing protein, a FKBP or FKBP derivative. The nucleic acids encoding the wild type essential protein are no longer present in the rdCMV. In the presence of an exogenously added, cell permeable small-molecule stabilizing agent, Shield-1 (Shld-1), the fusion protein is stabilized and the essential protein can function to support viral replication. Replication of the rdCMV in the presence of the stabilizing agent is preferably at least 75%, 80%, 90%, 95%, 99% or 100% of the amount of replication of a CMV that does not contain a destabilizing fusion protein (e.g, the parental attenuated CMV used to construct the rdCMV). In the absence of Shield-1, the destabilizing protein of the fusion protein directs the fusion protein to be substantially degraded by host cell machinery. With no or minimal amounts of essential protein present, the CMV cannot replicate at an amount to produce or maintain a CMV infection in a patient. Replication of the rdCMV in the absence of the stabilizing agent does not take place or is reduced by preferably greater than 50%, 75%, 90%. 95%, or 99% as compared to a CMV that does not contain a destabilizing fusion protein (e.g, the parental attenuated CMV used to construct the rdCMV).

Using recombinant DNA methods well known in the art, the nucleic acid encoding an essential protein for CMV replication and/or establishment/maintenance of CMV infection is attached to a nucleic acid that encodes FKBP or a derivative thereof. The encoded fusion protein comprises the FKBP or FKBP derivative fused in-frame to the essential protein. The encoded fusion protein is stable in the presence of Shield-1. However, the encoded fusion protein is destabilized in the absence of Shield-1 and is targeted for destruction. In preferred embodiments, the FKBP is SEQ ID NO:10. In other preferred embodiments, the FKBP derivative is FKBP comprising one or more amino acid substitutions selected from the group consisting of: F15S, V24A, H25R, F36V, E60G, M66T, R71G, D100G, D100N, E102G, K105I and L106P. In a more preferred embodiment, the FKBP derivative comprises the F36V and/or the L106P substitutions (SEQ ID NO:12). In a more preferred embodiment, the FKBP derivative is encoded by SEQ ID NO:13.

The essential proteins targeted for destabilization by fusion with FKBP or a derivative thereof 1) are essential for viral replication; 2) can accommodate the fusion of the destabilizing protein without substantially disrupting function of the essential protein; and 3) can accommodate the insertion of a nucleic acid encoding the FKBP or derivative thereof at the 5' or 3' end of the viral ORF encoding the essential protein without substantially disrupting the ORFs of other surrounding viral genes. In preferred embodiments, the essential proteins targeted for destabilization by fusion with FBBP or derivative thereof encode non-structural proteins and, as such, have a decreased likelihood of being packaged into recombinant CMV virions. Table 1 shows CMV genes that meet the aforementioned criteria.

TABLE 1

Viral genes selected for construction of FKBP fusion

| Viral Gene | Function* | Kinetic phase | Fusion of FKBP | Sequence of Fusion Protein |
|---|---|---|---|---|
| IE1/2 (UL123/122) | viral transcriptional modulators | Immediate early | N-term | SEQ ID NOS: 1-2 |
| UL37 × 1 | Viral gene regulations | Immediate early | N-term | — |
| UL51 | DNA packaging | Late | N-term | SEQ ID NOS: 3-4 |
| UL52 | DNA packaging and cleavage | Late | N-term | SEQ ID NOS: 5-6 |
| UL53 | Capsid egress; nuclear egress | Early | C-term | — |
| UL77 | DNA packaging | Early | C-term | — |
| UL79 | Unknown | Late | N-term | SEQ ID NOS: 7-8 |
| UL84 | DNA replication | Early-Late | C-term | SEQ ID NOS: 9 and 11 |
| UL87 | Unknown | ? | N-term | — |

*according to Mocarski, Shenk and Pass, Cytomegalovirus, in Field Virology, 2701-2772, Editor: Knipes and Howley, 2007

The present invention encompasses rdCMV that comprise fusion proteins with an essential protein or derivative thereof fused to the destabilizing protein. Essential protein derivatives contain one or more amino acid substitutions, additions and/or deletions relative to the wild type essential protein yet can still provide the activity of the essential protein at least well enough to support viral replication in the presence of Shield-1. Examples of measuring virus activity are provided in the Examples infra. Methods known in the art can be used to determine the degree of difference between the CMV essential protein of interest and a derivative. In one embodiment, sequence identity is used to determine relatedness. Derivatives of the invention will be preferably at least 85% identical, at least 90% identical, at least 95% identical, at least 97% identical, at least 99% identical to the base sequence. The percent identity is defined as the number of identical residues divided by the total number of residues and multiplied by 100. If sequences in the alignment are of different lengths (due to gaps or extensions), the length of the longest sequence will be used in the calculation, representing the value for total length.

In some embodiments, the one or more viral proteins essential for viral replication targeted for destabilization are selected from the group consisting of IE1/2, UL51, UL52, UL84, UL79, UL87, UL37×1, UL77 and UL53 or derivatives thereof. In a specific embodiment, the one or more viral proteins essential for viral replication targeted for destabilization are selected from the group consisting of IE1/2, UL51, UL52, UL84, UL79, UL87. In a more specific embodiment, the one or more viral proteins essential for viral replication targeted for destabilization are selected from the group consisting of IE1/2, UL51, UL52, UL79 and UL84.

More than one essential protein can be destabilized by fusion to FKBP or derivative thereof. In some embodiments, the essential proteins function at different stages of CMV replication and/or infection (including but not limited to, immediate early, early or late stages). In preferred embodiments, the combination of viral proteins essential for viral replication targeted for destabilization are selected from the group consisting of IE1/2 and UL51, IE1/2 and UL52, IE1/2 and UL79, IE1/2 and UL84, UL84 and UL51 and UL84 and UL52. In a more preferred embodiment, IE1/2 and UL51 are targeted for destabilization in the same recombinant CMV. In a most preferred embodiment, the fusion protein comprising IE1/2 is SEQ ID NO:1 and the fusion protein comprising UL51 is SEQ ID NO:3. SEQ ID NOS:1 and 3 can be encoded by SEQ ID Nos:2 and 4, respectively. The genome of the rdCMV with the destabilized IE1/2 and UL51 is shown in SEQ ID NO:14.

The FKBP or derivative thereof can be fused to the essential protein either directly or indirectly. In preferred embodiments, the FKBP or derivative thereof is fused to the essential protein directly.

The FKBP or derivative thereof can be fused to the essential protein either at either the N- or C-terminus of the essential protein. In preferred embodiments, the FKBP is fused to the N-terminus of the essential protein.

More than one FKBP or derivative thereof can be fused to the essential protein. In embodiments where there is more than one FKBP or derivative there of fused to the essential protein, each of the individual FKBP or derivatives there of can be the same or different. In preferred embodiments, there is one FKBP or derivative thereof fused to the essential protein.

Additional Inactivation Methods

In some embodiments, the rdCMV described supra is inactivated further using a chemical or physical inactivation. Examples of such include heat treatment, incubation with formaldehyde, β-Propiolactone (BPL), or binary ethyleneimine (BEI), or gamma irradiation. Preferred methods do not disrupt or substantially disrupt the immunogenicity, including, but not limited to, the immunogenicity induced by the pentameric gH complex. As such, the immune response elicited by the CMV that has been further inactivated is preserved or substantially preserved as compared to rdCMV with no additional inactivation treatment. In preferred embodiments, the ability of the further inactivated CMV to induce neutralizing antibodies is comparable to those induced by rdCMV with no additional inactivation treatment. Inactivation regimen by any one or combination of the chemical or physical methods is determined empirically to ensure immunogenicity of CMV, including the pentameric gH complex.

Evaluation of Viral Replication

One skilled in the art can use viral replication assays to determine the utility of a particular essential protein fused to FKBP or derivative thereof. Because gene expression/encoded product function should not be substantially affected by the attachment of the FKBP or derivative thereof to the essential protein in the presence of Shield-1, the rdCMV should replicate at a rate that is comparable to the parental CMV in the presence of Shield-1 (preferably at least 75%, 80%, 90%, 95%, 99% or 100% of the parental virus levels). Replication of the rdCMV is substantially altered from the parental CMV in the absence of Shield-1 (reduced by preferably greater than 50%, 75%, 90%. 95%, 99% or 100% as compared to a CMV that does not contain a destabilizing fusion protein).

In preferred embodiments, the rdCMV in the presence of at least 2 µM Shield-1 replicates preferably at least 90%, more preferably at least 95%, most preferably at least 99%, of the amount that a non-rdCMV replicates.

In one embodiment, a composition comprising the rdCMV of the invention has a viral titer of at least $10^5$ pfu/ml, more preferably at least $10^7$ pfu/ml, in the presence of at least 2 µM Shield-1.

Conversely, rdCMV should not replicate substantially in the absence of Shield-1. The quality of a replication defective mechanism is judged by how stringent the control is under the conditions not permissive for viral replication, i.e., the infectious titers of progeny virions under these conditions. The rdCMV of the present invention cannot replicate substantially (either in cell culture or within a patient) without Shield-1 present. Its replication in ARPE-19 cells and other types of human primary cells is conditional, and a molar concentration of Shield-1 greater than 0.1 µM, preferable at least 2 µM, in the culture medium is required to sustain viral replication.

In one embodiment, a composition comprising the rdCMV of the invention has a viral titer of less than 2 pfu/ml, more preferably less than 1 pfu/ml, in the absence of Shield-1.

Methods to assess CMV replication can be used to assess rdCMV replication either in the absence or presence of Shield-1. However, in preferred embodiments, the TCID50 is used.

In another embodiment, rdCMV titers are determined by a 50% Tissue Culture Infective Dose (TCID50) assay. Briefly, this dilution assay quantifies the amount of virus required to kill 50% of infected hosts. Host cells (e.g., ARPE-19 cells) are plated and serial dilutions of the virus are added. After incubation, the percentage of cell death (i.e. infected cells) is observed and recorded for each virus dilution. Results are used to mathematically calculate the TCID50.

In another embodiment, the rdCMV titers are determined using a plaque assay. Viral plaque assays determine the number of plaque forming units (pfu) in a virus sample. Briefly, a confluent monolayer of host cells (e.g., ARPE-19 cells) is infected with the rdCMV at varying dilutions and covered with a semi-solid medium, such as agar or carboxymethyl cellulose, to prevent the virus infection from spreading indiscriminately. A viral plaque is formed when a virus infects a cell within the fixed cell monolayer. The virus infected cell will lyse and spread the infection to adjacent cells where the infection-to-lysis cycle is repeated. The infected cell area will create a plaque (an area of infection surrounded by uninfected cells) which can be seen visually or with an optical microscope. Plaques are counted and the results, in combination with the dilution factor used to prepare the plate, are used to calculate the number of plaque forming units per sample unit volume (pfu/mL). The pfu/mL result represents the number of infective particles within the sample and is based on the assumption that each plaque formed is representative of one infective virus particle.

In another embodiment, a hu-SCID mouse model is used to evaluate the ability of an rdCMV to replicate in vivo. Briefly, pieces of human fetal tissues (such as thymus and liver) are surgically implanted in kidney capsules of SCID mice. The rdCMV is inoculated 2-3 months later when the human tissues are vascularized. Viral titers are assessed 3-4 weeks after inoculation in plaque assays. The animal experiments can be performed in the absence or presence of Shield-1.

Evaluation of Immune Response

Administration of rdCMV of the invention to a patient elicits an immune response to CMV, preferably a protective immune response, that can treat and/or decrease the likelihood of an infection by CMV or pathology associated with such an infection in a patient. The immune response is, at least in part, to the pentameric gH complex.

The immune response elicited by the rdCMV can be assessed using methods known in the art.

Animal models known in the art can be used to assess the protective effect of administration of the rdCMV. In one embodiment, immune sera from individuals administered the rdCMV can be assayed for neutralizing capacity, including but not limited to, blockage of viral attachment or entry to a host cell. In other embodiments, T cells from individuals administered the rdCMV can be assayed for cytokine producing capacity including, but not limited to, interferon gamma, in the presence of an antigen of interest. Animal challenge models can also be used to determine an immunologically effective amount of immunogen.

Viral neutralization refers to viral specific antibodies capable of interrupting viral entry and/or replication in cultures. The common assay for measuring neutralizing activities is viral plaque reduction assay. The neutralization assays in this invention refer to serum titrations that can block virus entering cells. NT50 titers are defined as reciprocal serum dilutions to block 50% of input virus in viral neutralization assays. NT50 titers are obtained from nonlinear logistic four-parameter curve fitting.

Manufacture of Replication Defective CMV

The present invention encompasses methods of making the rdCMV. The rdCMV of the invention are propagated in the presence of a stabilizing agent such as Shield-1 on epithelial cells, preferably human epithelial cells, and more preferably human retinal pigmented epithelial cells. In additional embodiments, the human retinal pigmented epithelial cells are ARPE-19 cells deposited with the American Type Culture Collection (ATCC) as Accession No. CRL-2302. In some embodiments, Shield-1 is present at a concentration of at least 0.5 µM in the tissue culture media. In preferred embodiments, Shield-1 is present at a concentration of at least 2.0 µM in the tissue culture media.

In some embodiments, the cells used to propagate the rdCMV are grown on microcarriers. A microcarrier is a support matrix allowing for the growth of adherent cells in spinner flasks or bioreactors (such as rotating wall microgravity bioreactors and fluidized bed bioreactors). Microcarriers are typically 125-250 µM spheres with a density that allows them to be maintained in suspension with gentle stirring. Microcarriers can be made from a number of different materials including, but not limited to, DEAE-dextran, glass, polystyrene plastic, acrylamide, and collagen. The microcarriers can have different surface chemistries including, but not limited to, extracellular matrix proteins, recombinant proteins, peptides and charged molecules. Other high density cell culture systems, such as Corning HyperFlask® and HyperStack® systems can also be used.

The cell-free tissue culture media can be collected and rdCMV can be purified from it. CMV viral particles are about 200 nm in diameter and can be separated from other proteins present in the harvested media using techniques known in the art including, but not limited to ultracentrifugation through a density gradient or a 20% Sorbitol cushion. The protein mass of the vaccines can be determined by Bradford assay.

Shield-1 can be used to control replication of the rdCMV in conjunction with FKBP. After the desired amount of viral propagation in tissue culture cells is completed, the ability to replicate is no longer desirable. Shield-1 is withdrawn from the rdCMV to make the virus replication deficient (e.g., in order to be administered to a patient). In one embodiment, the rdCMV is purified from Shield-1 by washing one or more times. In another embodiment, the rdCMV is purified from Shield-1 through ultracentrifugation. In another embodiment, the rdCMV is purified from Shield-1 through diafiltrations. Diafiltrations is commonly used to purify viral particles. In one embodiment, filters are used with pore size of approximately 750 kilodalton which would only allow Shield-1 to pass through the pores.

After purification of rdCMV from Shield-1, there may a small amount be of residual Shield-1 remaining in the rdCMV composition. In one embodiment, the level of Shld-1 in the CMV composition after purification is at least 100-fold below the level needed to sustain replication in tissue culture. In another embodiment, the level of Shield-1 in the rdCMV composition after purification is 0.1 µM or less. In another embodiment, the level of Shield-1 in the rdCMV composition after purification is undetectable.

Determination of Shield-1 levels in a composition can be detected using a LC/MS (liquid chromatography-mass spectroscopy) or HPLC/MS (high performance liquid chromatography-mass spectroscopy) assays. These techniques combine the physical separation capabilities of LC or HPLC with the mass analysis capabilities of and can detect chemicals of interest in complex mixtures.

Adjuvants

Adjuvants are substances that can assist an immunogen in producing an immune response. Adjuvants can function by different mechanisms such as one or more of the following: increasing the antigen biologic or immunologic half-life; improving antigen delivery to antigen-presenting cells; improving antigen processing and presentation by antigen-presenting cells; achieving dose-sparing, and, inducing production of immunomodulatory cytokines (Vogel, 2000, Clin Infect Dis 30:S266). In some embodiments, the compositions of the invention comprise a rdCMV and an adjuvant.

A variety of different types of adjuvants can be employed to assist in the production of an immune response. Examples of particular adjuvants include aluminum hydroxide; aluminum phosphate, aluminum hydroxyphosphate, amorphous aluminum hydroxyphosphate sulfate adjuvant (AAHSA) or other salts of aluminum; calcium phosphate; DNA CpG motifs; monophosphoryl lipid A; cholera toxin; E. coli heat-labile toxin; pertussis toxin; muramyl dipeptide; Freund's incomplete adjuvant; MF59; SAF; immunostimulatory complexes; liposomes; biodegradable microspheres; saponins; nonionic block copolymers; muramyl peptide analogues; polyphosphazene; synthetic polynucleotides; IFN-γ; IL-2; IL-12; and ISCOMS. (Vogel, 2000, Clin Infect Dis 30:S266; Klein et al., 2000, J Pharm Sci 89:311; Rimmelzwaan et al., 2001, Vaccine 19:1180; Kersten, 2003, Vaccine 21:915; O'Hagen, 2001, Curr. Drug Target Infect. Disord. 1:273.)

In some embodiments, oil-based adjuvants including, but not limited to, incomplete Freund's adjuvant and MF59, are not used in the compositions of the invention.

In other embodiments, particulate adjuvants including, but not limited to, ISCOMATRIX® adjuvant and/or aluminium phosphate adjuvant are used in the compositions of the invention.

Pharmaceutical Compositions

A further feature of the invention is the use of a recombinant CMV described herein in a composition, preferably an immunogenic composition or vaccine, for treating patients with a CMV infection and/or reducing the likelihood of a CMV infection. Suitably, the composition comprises a pharmaceutically acceptable carrier.

A "pharmaceutically-acceptable carrier" is meant to mean a liquid filler, diluent or encapsulating substance that may be safely used in systemic administration. Depending upon the particular route of administration, a variety of pharmaceutically acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions including phosphate buffered saline, emulsifiers, isotonic saline, and pyrogen-free water. In particular, pharmaceutically acceptable carriers may contain different components such as a buffer, sterile water for injection, normal saline or phosphate-buffered saline, sucrose, histidine, salts and polysorbate. Terms such as "physiologically acceptable", "diluent" or "excipient" can be used interchangeably.

Procedures for vaccine formulations are disclosed, for example, in New Generation Vaccines (1997, Levine et al., Marcel Dekker, Inc. New York, Basel, Hong Kong), which is incorporated herein by reference.

Formulations

In some embodiments, the rdCMV of the invention is administered to a patient to elicit an immune response. It is desirable to minimize or avoid the loss of the rdCMV composition potency during storage of the immunogenic composition. The conditions to support such an aim include but not limited to (1) sustained stability in storage, (2) resistant to stressed freezing-thawing cycles, (3) stable at ambient temperatures for up to a week, (4) maintenance of immunogenicity, (5) compatible with adjuvanting strategy. Conditions that affect rdCMV stability include, but are not limited to, buffer pH, buffer ionic strength, presence/absence of particular excipients and temperature. The compositions comprise buffers to increase the stability of purified rdCMV viral particles suitable as vaccine composition.

The preservation of the integrity of viral particles can be assessed by immunogenicity assays in mice and/or viral entry assays. Viral entry events dependent on the integrity and functions of viral glycoproteins, including the pentameric gH complex. The pentameric gH complex also provides the substantial immunogenicity of rdCMV, thus the two properties are linked.

In some embodiments, the rdCMV is stored in buffer comprising 15-35 mM Histidine and 100-200 mM NaCl at a pH of between 5 and 7. In a more specific embodiment, the buffer comprises 25 mM Histidine and 150 mM NaCl at pH6.

In other embodiments, sugars can be added to provide further stability, such as polyols (including, but not limited to, mannitol and sorbitol); monosaccharides (including, but not limited to, glucose, mannose, galactose and fructose); disaccharides (including, but not limited to, lactose, maltose, maltose, sucrose, lactulose and trehalose) and trisaccharides (including, but not limited to, raffinose and melezitose). In a more specific embodiment, the sugar is sucrose. In an even more specific embodiment, the sucrose is between 5-15%.

In preferred embodiments, the rdCMV is stored in buffer comprising 25 mM Histidine, 150 mM NaCl, 9% Sucrose at pH 6.

Administration

A rdCMV described herein can be formulated and administered to a patient using the guidance provided herein along with techniques well known in the art. Guidelines for pharmaceutical administration in general are provided in, for example, Vaccines Eds. Plotkin and Orenstein, W.B. Sanders Company, 1999; *Remington's Pharmaceutical Sciences* $20^{th}$ *Edition*, Ed. Gennaro, Mack Publishing, 2000; and *Modern Pharmaceutics* $2^{nd}$ *Edition*, Eds. Banker and Rhodes, Marcel Dekker, Inc., 1990.

Vaccines can be administered by different routes such as subcutaneous, intramuscular, intravenous, mucosal, parenteral, transdermal or intradermal. Subcutaneous and intramuscular administration can be performed using, for example, needles or jet-injectors. In an embodiment, the vaccine of the invention is administered intramuscularly. Transdermal or intradermal delivery can be accomplished through intradermal syringe needle injection, or enabling devices such as micron-needles or micron array patches.

The compositions described herein may be administered in a manner compatible with the dosage formulation, and in such amount as is immunogenically-effective to treat and/or reduce the likelihood of CMV infection (including primary, recurrent and/or super). The dose administered to a patient, in the context of the present invention, should be sufficient to effect a beneficial response in a patient over time such as a reduction in the level of CMV infection, ameliorating the symptoms of disease associated with CMV infection and/or shortening the length and/or severity of CMV infection, or to reduce the likelihood of infection by CMV (including primary, recurrent and/or super).

Suitable dosing regimens may be readily determined by those of skill in the art and are preferably determined taking into account factors well known in the art including age, weight, sex and medical condition of the patient; the route of administration; the desired effect; and the particular composition employed. In determining the effective amount of the rdCMV to be administered in the treatment or prophylaxis against CMV, the physician may evaluate circulating plasma levels of virus, progression of disease, and/or the production of anti-CMV antibodies. The dose for a vaccine composition consists of the range of $10^3$ to $10^{12}$ plaque forming units (pfu). In different embodiments, the dosage range is from $10^4$ to $10^{10}$ pfu, $10^5$ to $10^9$ pfu, $10^6$ to $10^8$ pfu, or any dose within these stated ranges. When more than one vaccine is to be administered (i.e., in combination vaccines), the amount of each vaccine agent is within their described ranges.

The vaccine composition can be administered in a single dose or a multi-dose format. Vaccines can be prepared with adjuvant hours or days prior to administrations, subject to identification of stabilizing buffer(s) and suitable adjuvant composition. Vaccines can be administered in volumes commonly practiced, ranging from 0.1 mL to 0.5 mL.

The timing of doses depends upon factors well known in the art. After the initial administration one or more additional doses may be administered to maintain and/or boost antibody titers and T cell immunity. Additional boosts may be required to sustain the protective levels of immune responses, reflected in antibody titers and T cell immunity such as ELISPOT. The levels of such immune responses are subject of clinical investigations.

For combination vaccinations, each of the immunogens can be administered together in one composition or separately in different compositions. A rdCMV described herein is administered concurrently with one or more desired immunogens. The term "concurrently" is not limited to the administration of the therapeutic agents at exactly the same time, but rather it is meant that the rdCMV described herein and the other desired immunogen(s) are administered to a subject in a sequence and within a time interval such that the they can act together to provide an increased benefit than if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

Patient Population

A "patient" refers to a mammal capable of being infected with CMV. In a preferred embodiment, the patient is a human. A patient can be treated prophylactically or therapeutically. Prophylactic treatment provides sufficient protective immunity to reduce the likelihood or severity of a CMV infection, including primary infections, recurrent infections (i.e., those resulting from reactivation of latent CMV) and super-infections (i.e., those resulting from an infection with a different stain of CMV than previously experienced by the patient). Therapeutic treatment can be performed to reduce the severity of a CMV infection or decrease the likelihood/severity of a recurrent or super-infection.

Treatment can be performed using a pharmaceutical composition comprising a rdCMV as described herein. Pharmaceutical compositions can be administered to the general population, especially to those persons at an increased risk of CMV infection (either primary, recurrent or super) or for whom CMV infection would be particularly problematic (such as immunocompromised individuals, transplant patients or pregnant women). In one embodiment, females of childbearing age, especially early adolescent females, are vaccinated to decrease the likelihood of CMV infection (either primary, recurrent or super) during pregnancy.

Those in need of treatment include those already with an infection, as well as those prone to have an infection or in which a reduction in the likelihood of infection is desired. Treatment can ameliorate the symptoms of disease associated with CMV infection and/or shorten the length and/or severity of CMV infection, including infection due to reactivation of latent CMV.

Persons with an increased risk of CMV infection (either primary, recurrent or super) include patients with weakened immunity or patients facing therapy leading to a weakened immunity (e.g., undergoing chemotherapy or radiation therapy for cancer or taking immunosuppressive drugs). As used herein, "weakened immunity" refers to an immune system that is less capable of battling infections because of an immune response that is not properly functioning or is not functioning at the level of a normal healthy adult. Examples of patients with weakened immunity are patients that are infants, young children, elderly, pregnant or a patient with a disease that affects the function of the immune system such as HIV infection or AIDS.

EXAMPLES

Examples are provided below to further illustrate different features of the present invention. The examples also illustrate useful methodology for practicing the invention. These examples do not limit the claimed invention.

Example 1

Restoration of the Pentameric gH Complex

An infectious CMV bacterial artificial chromosome clone was constructed so that the encoded virion that expressed the pentameric gH complex consisting of UL128, UL130 and UL131 assembled onto a gH/gL scaffold.

CMV strain AD169 strain was originally isolated from the adenoids of a 7-year-old girl (Elek and Stem, 1974, Lancet, 1:1). The virus was passed 58 times in several types of human fibroblasts to attenuate the virus (Neff et al, 1979, Proc Soc Exp Biol Med, 160:32, with the last 5 passages in WI-38 human fibroblasts. This passaged variant of AD169 virus, referred in this study as Merck AD169 (MAD169), was used as the parental virus to construct the infectious BAC clone. Neither the parental virus AD169 nor the passaged variant virus MAD169 expressed UL131 or the pentameric gH complex.

The MAD169 was used as the parental virus to construct an infectious bacterial artificial chromosome (BAC) clone. A BAC vector is a molecular tool that allows the genetic manipulation of a large size DNA fragment, such as the CMV genome (~230 Kb), in *E. coli*. A BAC element along with a GFP marker gene was inserted immediately after the stop codon of US28 open reading frame (between US28 and US29 ORFs in the viral genome) with a LoxP site created at the both ends of the fragment (FIG. 1A). Briefly, a DNA fragment containing a GFP expression cassette flanked by two loxP sites and CMV US28-US29 sequences were synthesized and cloned into pBeloBAC11 vector. The BAC vector was linearized with restriction enzyme Pme I, and cotransfected into MRC-5 cells with MAD169 DNA extracted from purified virions. The recombinant variants, identified by green fluorescence expression, were plaque purified. After one round of amplification, the circular form of viral genome was extracted from the infected cells, and electroporated into *E. coli* DH10 cells. The bacterial colonies were screened by PCR for the presence of US28 and US29 regions. Candidate clones were further examined by EcoR I, EcoR V, Hind III, Spe I and Bam III restriction analyses. After screening, one clone, bMAD-GFP, showed identical restriction pattern with the parental MAD169 virus.

Figure 1B:
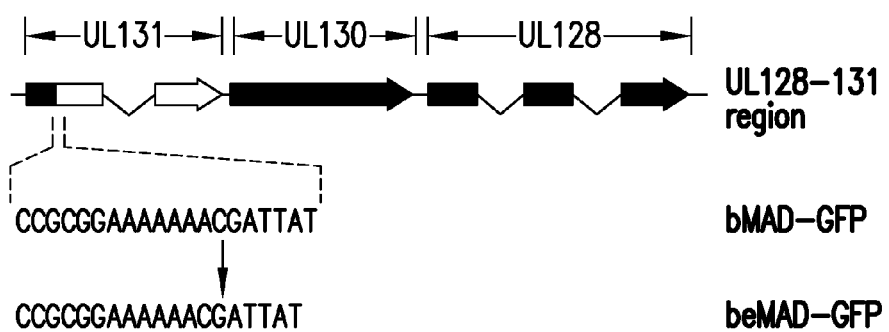
Figure 1C:
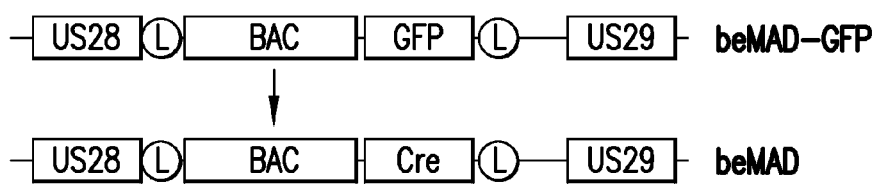
Figure 2A:
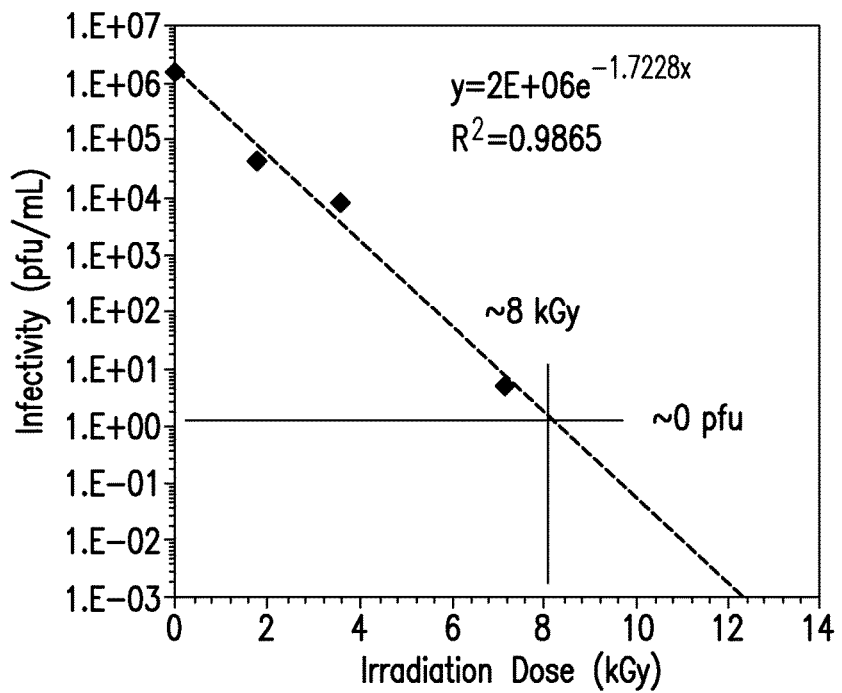
FIGS. 2A-2D show the effect of conventional inactivation methods on gH complex immunogenicity. γ-irradiation (A, B) and β-propiolactonE (BPL) (C, D) were used to inactivate gH complex expressing CMV. Inactivation kinetics were determined by plaque assay (A, C) while immunogenicity was determined by evaluating sera from mice administered the CMV for neutralizing activity against viral epithelial cell entry (B, D).
Figure 2B:
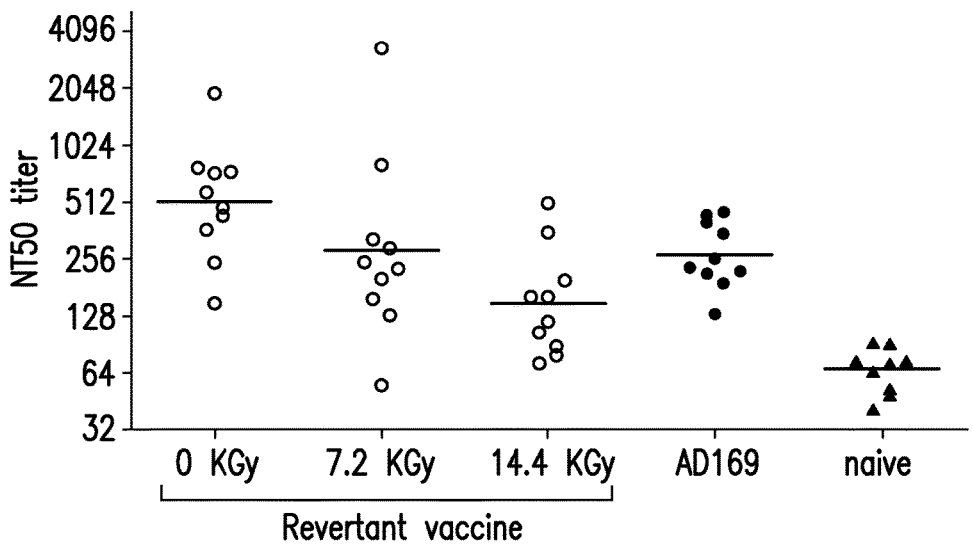
Figure 2C:
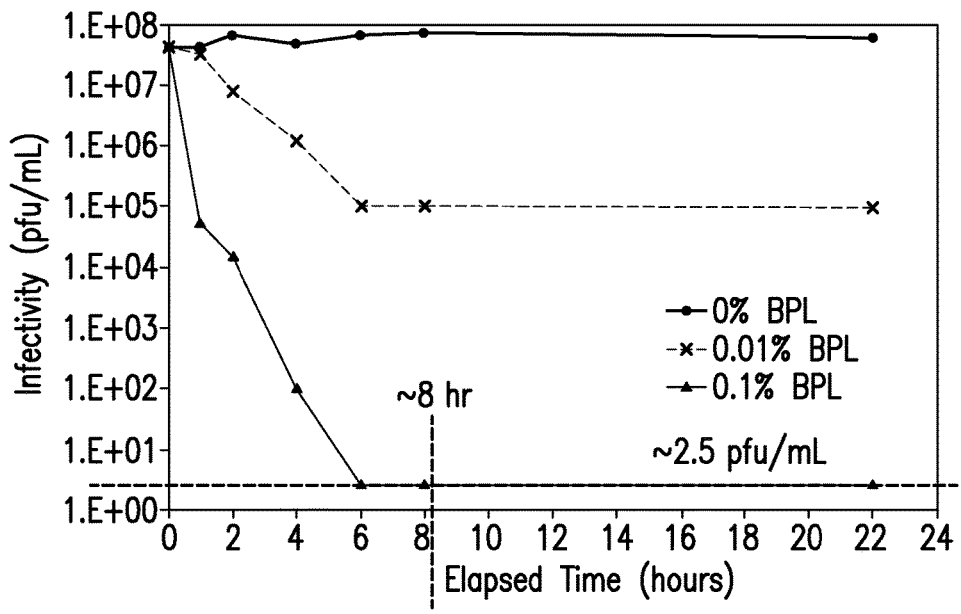
Figure 2D:
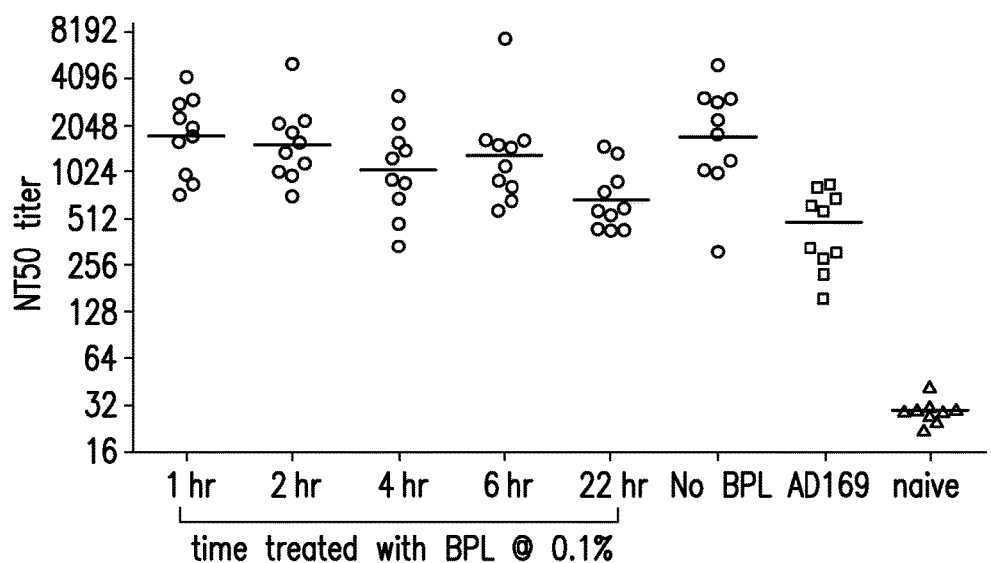

The frame-shift mutation in the first exon of UL131 underlying the epithelial tropism deficiency in MAD169 was repaired genetically in *E. coli* (FIG. 1B). Specifically, one adenine nucleotide (nt) from the 7 nt A-stretch in the UL131 gene was deleted (FIG. 1B). Deletion of 1 nt was sufficient to rescue the epithelial and endothelial cell tropism due to UL131, and thus the pentameric gH complex, now being expressed. Expression was confirmed by ELISA and western blot (data not shown). This clone was further modified by removing the BAC segment by LoxP/Cre recombination. The BAC DNA was transfected in ARPE-19 cells, human retinal pigmented epithelial cells (ATCC Accession No. CRL-2302), to recover the infectious virus (FIG. 1C). The resultant infectious virus, termed BAC-derived epithelial-tropic MAD169 virus (beMAD), differs from MAD169 only in two loci, (1) UL131 ORF where a single adenine nucleotide was deleted and (2) a 34 bp LoxP site inserted between US28 and US29 ORFs (see Table 2).

The genome of the BAC clone beMAD was completely sequenced. The overall genome structure of beMAD is identical to that reported in the ATCC AD169 variant (GenBank Accession No. X17403), which is comprised of two unique regions, unique long (UL) and unique short (US). Each unique regions are bracketed by two repeat sequences, terminal repeat long (TRL)-internal repeat long (IRL), terminal repeat short (TRS)-internal repeat short (IRS). The growth kinetics of the passaged variant MAD169 and the beMAD derived virus were indistinguishable in MRC-5 cells, a human fibroblast cell line (ATCC Accession No. CCL-171) (data not shown). Because the gH complex is not needed for growth on fibroblast cells, the differences in gH complex expression between the MAD169 and beMAD are not relevant.

TABLE 2

Molecular difference of CMV viruses

| Virus ID | Genetic composition | Proteins in virions |
|---|---|---|
| AD169 | ATCC laboratory strain containing frame-shift mutation in UL131 causing deficiency in epithelial tropism | |
| MAD169 | Contains frame-shift mutation in UL131 identical to ATCC AD169 | Identical to AD169 from ATCC |
| beMAD | Repaired frame-shift mutation in UL131; LoxP sequence (34 bp) between US28 and US29 ORFs | Identical to MAD169, with addition of the pentameric gH complex |

Example 2

Effect of Conventional Inactivation Methods on gH Complex

The effect of two conventional methods of viral inactivation, γ-irradiation and β-Propiolactone (BPL), were investigated on the CMV expressing gH.

The γ-irradiation was performed on lyophilized virions. Recombinant CMV vaccine at a concentration of 0.15 mg/mL in FINS (25 mM Histidine, 150 mM NaCl, 9% w/v Sucrose, pH 6.0) formulation was lyophilized using a conservative lyophilization cycle (−50° C. freezing and primary drying at −35° C. for ~30 hrs followed by secondary drying at 25° C. for 6 hrs) to obtain dry powder. The vaccine was lyophilized in a 3 mL glass vial with 0.5 ml filled in each vial. At the end of lyophilization, the vials were stoppered in a nitrogen environment and the samples were removed, labelled, crimped and stored at −70° C. until gamma irradiation. The vials were irradiated under a Co irradiator for the desired dosage of irradiation.

For BPL treatment, a BPL stock solution was added to the crude viral culture supernatant from growth on ARPE-19 cells to reach the final concentrations of 0.01% or 0.1% (v/v). The reaction was terminated with sodium thiosulfate at various time points. The BPL-treated gH expressing CMV were then purified by ultracentrifugation.

The inactivation kinetics for both methods were determined by plaque assay in ARPE-19 cells. Briefly, serial dilutions of viral samples in PBS were made and 0.1 mL was used to inoculate each well of a 6-well plate that had been seeded with ARPE-19 cells. The plates are incubated at 37° C. for 1 hr before addition of a 6 mL per well overlay medium containing 0.5% agarose. The plates are incubated for 18 days at 37° C. To visualize the plaques, about 0.5 mL MTT solution at 5 mg/mL (Thiazolyl blue tetrazolium bromide, Sigma M5655) was added to each well. The plates were incubated at 37° C. for 2-4 hr and the plaques were counted under lightbox. (FIGS. 2A and 2C).

Immunogenicity of the inactivated gH expressing CMV was assayed by determining the neutralizing antibody titers induced in mice. Briefly, female Balb/c mice (n=10) were immunized with 2.5 μg of CMV per dose at weeks 0 and 3. The sera was collected at week 4 and evaluated for neutralizing activity against viral epithelial entry. The neutralization titer (NT50) was defined as a reciprocal dilution of serum causing a 50% reduction in viral epithelial entry as compared to the negative control. The results from mouse immunogenicity studies showed that both conventional methods for inactivation had negative effects on neutralizing antibody titers induced by the gH expressing CMV (FIGS. 2B and 2D). The reduction of NT50 titers correlated with the duration of treatment by γ-irradiation or BPL. The prolonged treatments rendered the pentameric gH complex-expressing CMV more like the parental AD169 CMV in terms of immunogenicity in mice. Similar results were observed in rabbits and rhesus monkeys when vaccines inactivated with γ-irradiation or BPL were tested (data not shown). These observations showed that the pentameric gH complex is sensitive to both inactivation methods under the selected inactivation conditions.

Example 3

Construction and Screening of FKBP-Essential Protein Fusions

A CMV was constructed using the attenuated AD169 strain backbone that regains its epithelial tropism while being conditionally replication defective. Methods described in Example 1 were used to restore epithelial tropism.

The viral proteins to be fused to the FKBP derivative were selected based on two criteria. First, the proteins of interest were not detected in CMV virions by proteomics analysis (Varnum et al., 2004, J. Virol. 78:10960), thus, decreasing the likelihood that the FKBP fusion protein will be incorporated into virus. Second, the proteins of interest are essential for viral replication in tissue culture.

Using beMAD as the parental virus, the FKBP derivative (SEQ ID NO:12) was fused to 12 essential viral proteins individually, including IE1/2 (SEQ ID NO:1), pUL37×1, pUL44, pUL51 (SEQ ID NO:3), pUL52 (SEQ ID NO:5), pUL53, pUL56, pUL77, pUL79 (SEQ ID NO:7), pUL84 (SEQ ID NO:9), pUL87 and pUL105. A virus with two different essential proteins fused to FKBP was also constructed that fused each of IE1/2 and UL51 the FKBP derivative (the genome of the rdCMV with the destabilized IE1/2 and UL51 is shown in SEQ ID NO:14). After construction, all recombinant BAC DNAs were transfected into ARPE-19 cells, and cultured in the medium containing Shld-1.

The dependence of viral growth on Shld-1 was examined. The IE1/2, UL51, UL52, UL84, UL79 and UL87 fusion viruses were readily rescued in 2 μM Shld-1 in plaque assays (data not shown). The UL37×1, UL77 and UL53 viruses also produced plaques, but the plaques were small, and they grew significantly slower, comparing to the parental beMAD. Increasing the Shld-1 concentration to 10 μM did not significantly expedite the viral growth (data not shown). The UL56 and UL105 fusions were not recovered, suggesting that tagging of these proteins disrupts the function of these proteins, or expression of neighboring genes.

Varying concentrations of Shld-1 were used in additional experiments to further assess viral replication in the presence or absence of Shld-1. ARPE-19 cells were infected by the gH expressing CMV that also contained a FKBP derivative fused to an essential protein at MOI of 0.01 pfu/ml. After infection for 1 hour, the cells were washed twice with fresh medium to remove the Shld-1 from the inoculums. The inoculums were then added to ARPE-19 cells cultured in medium containing 0.05, 0.1, 0.5 or 2 µM of Shield-1. Seven days post infection, the cell-free progeny virus in the supernatant was collected and titrated on ARPE-19 cells supplemented with 2 mM of Shield-1. Virus titers were determined by a 50% Tissue Culture Infective Dose (TCID50) assay. Briefly, this dilution assay quantifies the amount of virus required to kill 50% of infected hosts. ARPE-19 cells were plated and serial dilutions of the virus were added. After incubation, the percentage of cell death (i.e. infected cells) was manually observed and recorded for each virus dilution. Results were used to mathematically calculate the TCID50.

Figure 3:
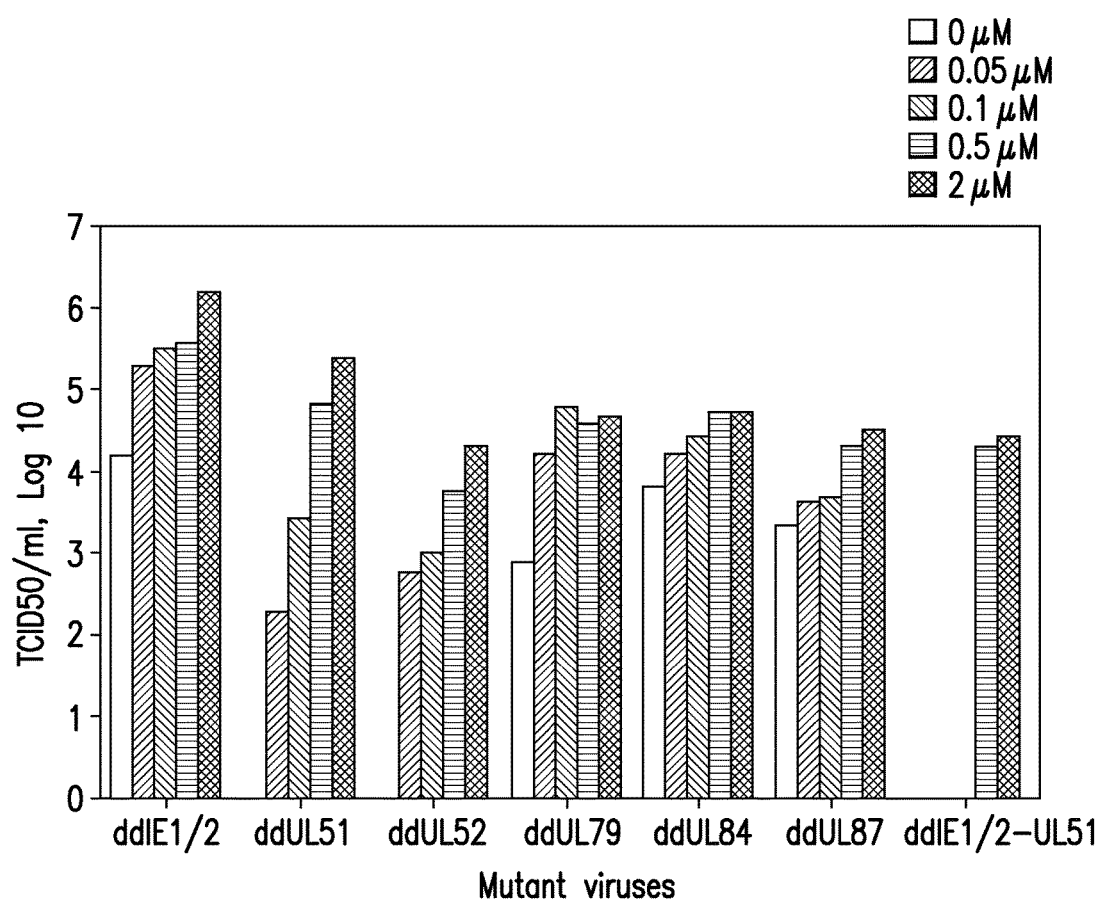
FIG. 3 shows the Shield 1 concentration dependent progeny virus production of gH complex expressing CMV with various essential proteins fused to a FKBP derivative. ARPE-19 cells were infected with the rdCMV viruses at a multiplicity of 0.01 PFU/cell for 1 h, washed twice with fresh medium, and incubated in the growth medium containing 0, 0.05, 0.1 0.5 or 2 µM of Shield-1. Seven days post infection, the cell free virus was collected, and virus titers were determined by TCID50 assay on ARPE-19 cells in the presence of 2 µM of Shield 1.
Figure 4A:
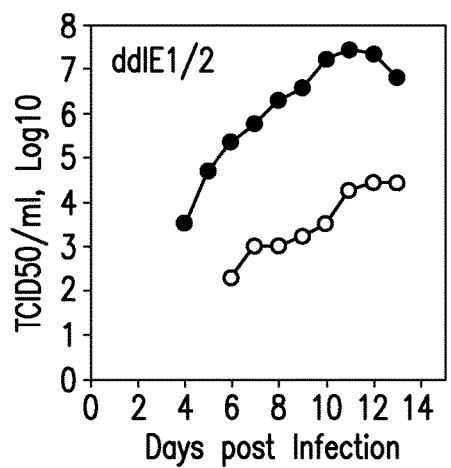
FIGS. 4A-4D show growth kinetics of rdCMV in ARPE-19 cells. Cells were infected with viruses containing (A) IE1/2, (B) UL51, (C) IE1/2-UL51 fusion proteins or the (D) parental beMAD virus at multiplicity of 0.01 PFU/cell. After one hour, the cells were washed twice with fresh medium, and incubated in the absence (open circle) or presence (closed circle) of 2 µM of Shield-1. Cell-free virus was collected at the indicated time points after infection, and infectious virus was quantified by TCID50 assay on ARPE-19 cells in the medium containing 2 µM of Shield-1.
Figure 4B:
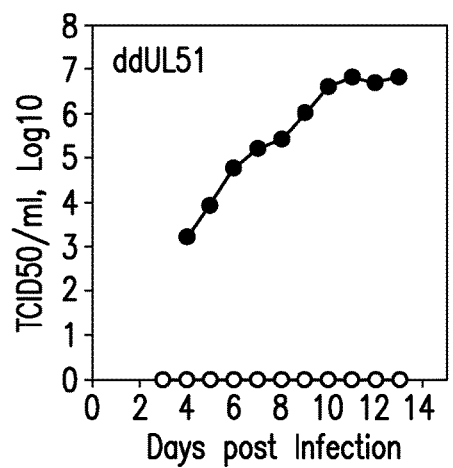
Figure 4C:
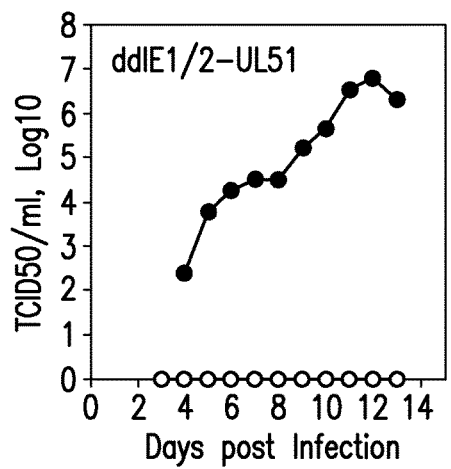
Figure 4D:
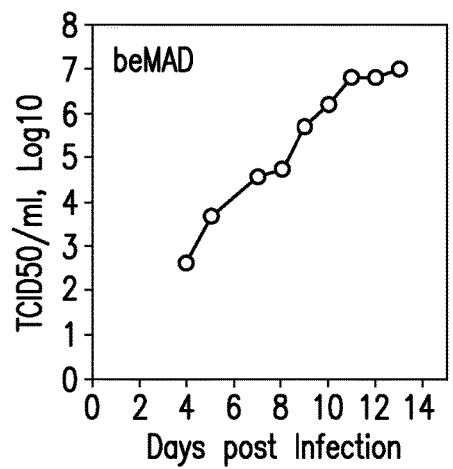

As shown in FIG. 3, efficient replication of all FKBP fusion containing CMV depended on Shield-1 concentration, albeit to varying degrees. Lower concentration of Shield-1 in general reduced the titer of progeny virus production. Among the viruses with a single fusion, only UL51 and UL52 absolutely required Shield-1 for replication. Other viruses with a single fusion, IE1/2, UL84, UL79, and UL87, could produce detectable progeny virus in the absence of Shield-1. The regulation was tightest when the FKBP derivative was fused to UL51 or UL52.

The growth kinetics of viruses with IE1/2, UL51, IE1/2-UL51 fusions were compared to the parental beMAD virus in the presence or absence of 2 µM of Shld-1. As shown in FIG. 4, in the presence of Shld-1, the single or double fusions had growth kinetics comparable to the parental beMAD. However, in the absence of Shld-1, only the IE1/2 could replicate, albeit at a lower and slower rate than the parental beMAD.

The tightness of the control of virus replication in the double fusion virus was also tested in different cell types (FIG. 5). These cells included human umbilical vein cells (HUVECs), MRC-5 fibroblasts, aortic smooth muscle cells (AoMCs), skeletal muscle cells (SKMCs) and CCF-STTG1 astrocytoma cells. The cells were infected by the IE1/2-UL51 fusion virus at MOI of 0.01 pfu/cell (except for CCF-STTG1 which was infected with a MOI of 5 pfu/cell), and then incubated in the medium in the presence or absence of Shield-1. All cell types were able to support lytic viral replication in the presence of Shield-1. No virus production was detected in the absence of Shield-1.

Example 4

Immunogenicity of the IE1/2-UL51 Double Fusion Virus in Animals

Figure 6A:
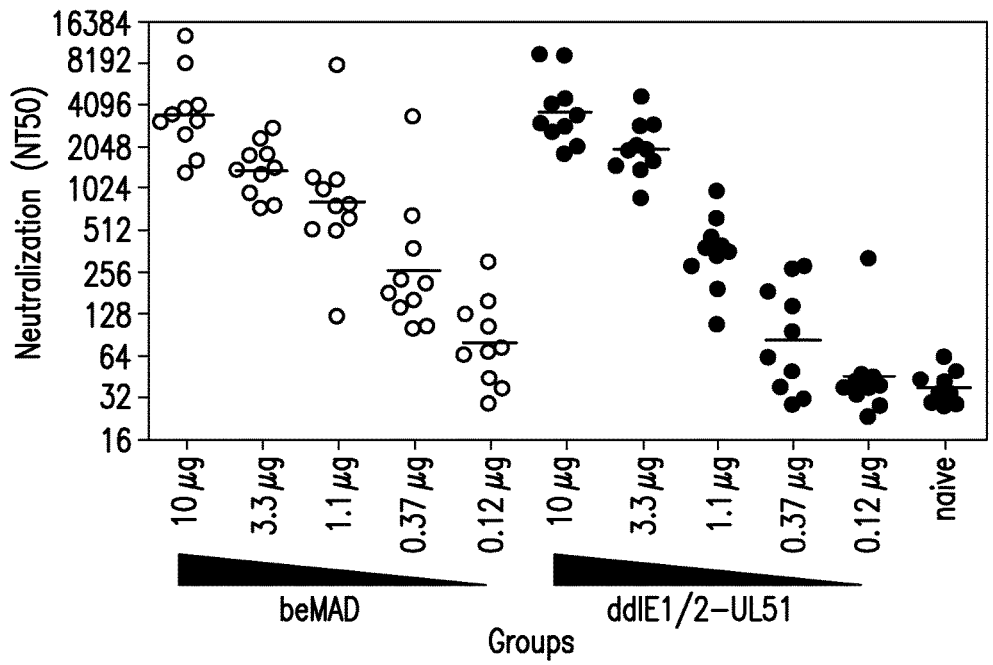
FIGS. 6A-6C Immunogenicity analysis of the IE1/2-UL51 rdCMV in mice, rabbits and rhesus macaques. (A) Mice were immunized at weeks 0 and 4 with beMAD (open circle) or the IE1/2-UL51 rdCMV (closed circle). (B) Rabbits were immunized at weeks 0, 3 and 8 with 10 µg beMAD or the indicated rdCMV. (C) Rhesus macaques were immunized at weeks 0 and 8 with 100 µg beMAD or the IE1/2-UL51rdCMV. In each case, serum samples were collected and analyzed by CMV micro-neutralization assay on ARPE-19 cells. Lines indicate the geometric mean titers of the neutralization (NT50) in each group.
Figure 6B:
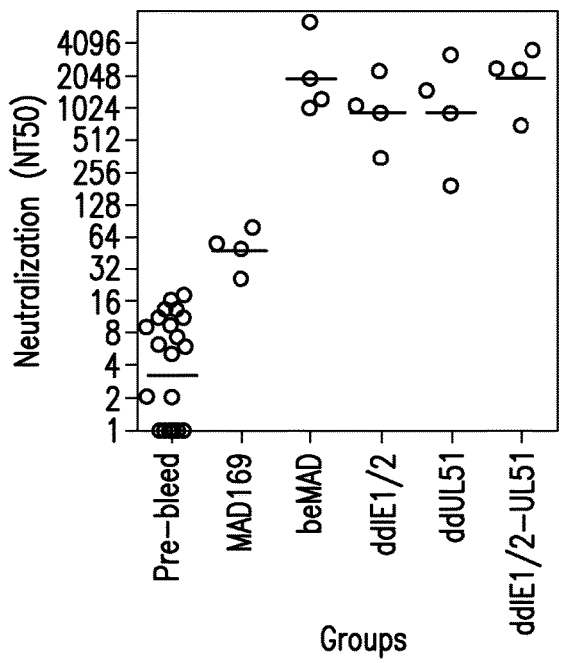
Figure 6C:
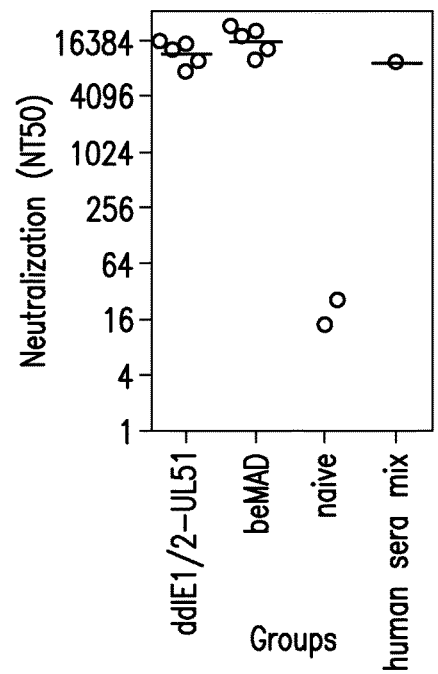

The immunogenicity of the IE1/2-UL51 double fusion virus was evaluated in mice, rabbits and rhesus monkeys. Dose dependent neutralizing response against the IE1/2-UL51 double fusion virus or the parental beMAD virus in mice was first compared (FIG. 6A). Six-week-old female BALB/c mice were immunized at weeks 0 and 4 with beMAD or the IE1/2-UL51 double fusion virus at doses ranging from 0.12 µg to 10 µg. Serum samples from week 6 were collected and analyzed by CMV micro-neutralization assay on ARPE-19 cells as described previously (Tang et al, Vaccine, "A novel throughput neutralization assay for supporting clinical evaluations of human cytomegalovirus vaccines" e-published Aug. 30, 2011 at doi:10.1016/j.vaccine.2011.08.086). The responses were compared at doses of 0.12, 0.37, 1.1, 3.3 and 10 µg. At the low dose range (0.12 to 1.1 µg), the beMAD was slightly more immunogenic with neutralizing antibodies consistently detected when dosage levels were above 0.37 µm. At the high dose range (3.3 and 10 µg), the neutralizing antibody titers induced by the two viruses were comparable.

Figure 5A:
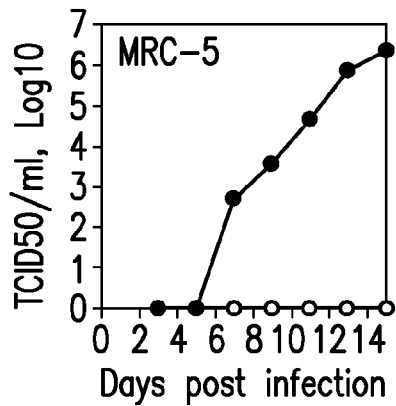
FIGS. 5A-5E Growth kinetics of the IE1/2-UL51 rdCMV in different cell types. (A) MRC-5 (B) HUVEC (C) AoSMC (D) SKMC (E) CCF-STTG1 cells were infected with the rdCMV virus and incubated for one hour. The cells were washed twice with fresh medium, and then incubated in the absence (open circle) or presence (closed circle) of 2 µM of Shield-1. Cell-free virus was collected at the indicated time points after infection, and infectious virus was quantified by TCID50 assay on ARPE-19 cells in the medium containing 2 µM of Shield-1.
Figure 5B:
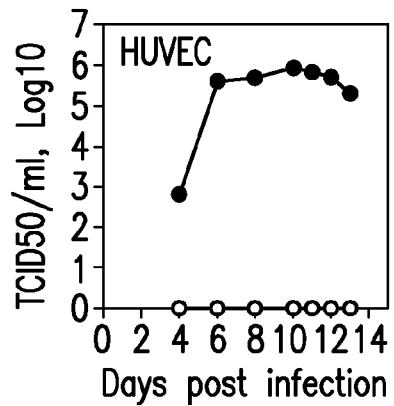

Next, the immunogenicity of different viruses in rabbits at dose of 10 us was compared. Female NZW rabbits were immunized at weeks 0, 3 and 8 with 10 µg of beMAD or the indicated fusion viruses. Week 10 sera were collected and analyzed by CMV micro-neutralization assay on ARPE-19 cells (FIG. 5B). The beMAD, single fusion viruses IE1/2 or UL51 and the double fusion virus IE1/2-UL51 could induce significantly higher titers of neutralizing antibodies than MAD169, a virus similar to AD169 and lacking the pentameric gH complex. This confirmed that expression of the gH complex by the virus significantly increased the immunogenicity of recombinant CMV.

Figure 5C:
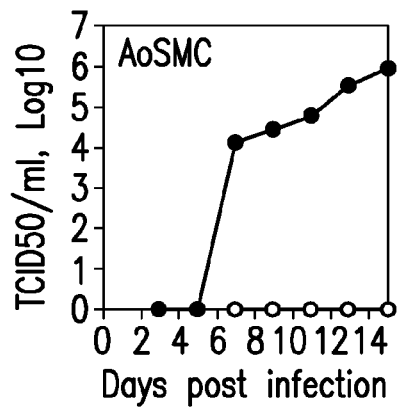
Figure 5D:
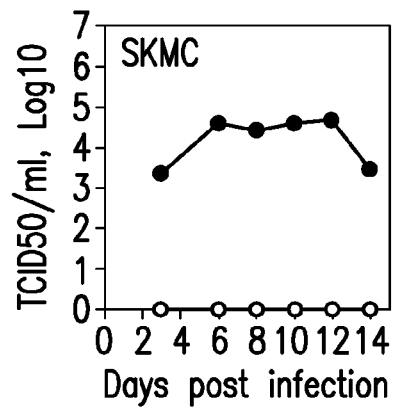
Figure 5E:
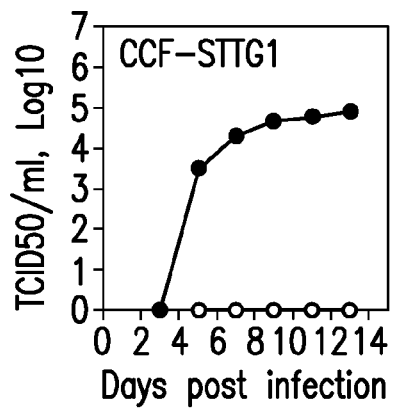

Next, the immunogenicity of 100 µg of the double fusion IE1/2-UL51 virus or the parental beMAD virus was tested in rhesus macaques. Week 12 sera was collected and analyzed by CMV micro-neutralization assay on ARPE-19 cells. The GMT NT50 titers at week 12 (post dose 3) were 11500 or 15600, respectively. These titers were comparable to the NT50 titers seen in naturally infected individuals (FIG. 5C).

Figure 7:
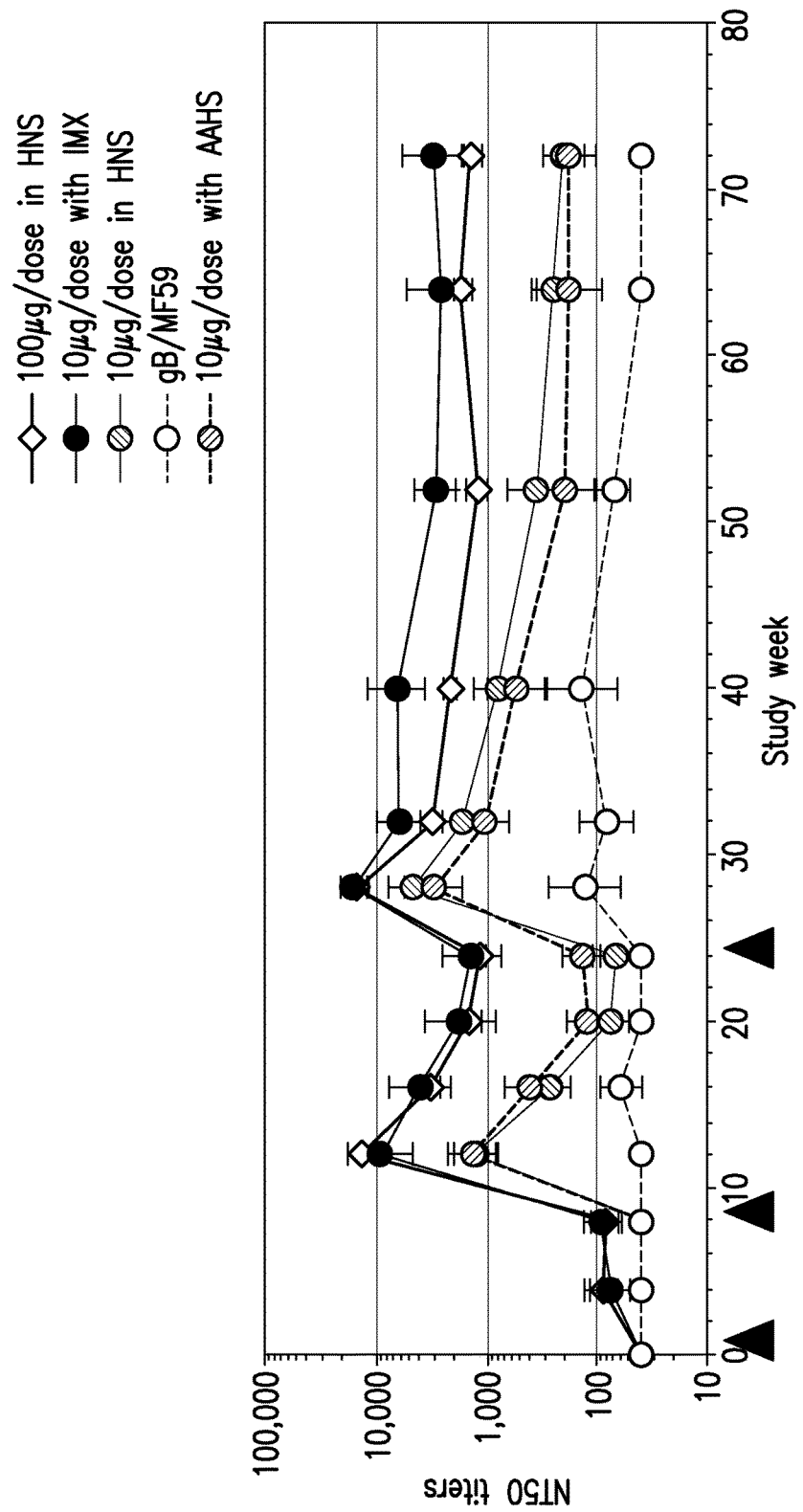
FIG. 7 shows longitudinal neutralizing titers in rhesus macaques vaccinated with the double fusion virus IE1/2-UL51. Groups of rhesus monkeys (n=5) were vaccinated with the indicated vaccine dose or formulations at week 0, 8, and 24 (shown as red triangles), while one group received gb/mf59 (30 mg/dose) at week 0, 4 and 24. The immune sera were collected at indicated time points and evaluated in a viral neutralization assay. The GMT of NT50 titers is plotted longitudinally with the standard error for the group. AAHS: amorphous aluminum hydroxylphosphate sulfate; IMX: ISCOMATRIX; HNS: base buffer.

The longevity of the double fusion virus IE1/2-UL51 CMV vaccine-induced immune response was demonstrated in rhesus macaques. Animals were vaccinated with either 10 µm/dose or 100 µg/dose double fusion virus IE1/2-UL51 (based on total protein mass). Formulations of 10 µg/dose vaccine with amorphous aluminum hydroxylphosphate sulfate (AAHS) or ISCOMATRIX® adjuvant were also included. Vaccines were administered at weeks 0, 8, and 24 in rhesus macaques (n=5). For comparison, a control group received recombinant gB at 30 µg/dose formulated with MF59 adjuvant at weeks 0, 4 and 24. Geometric means for reciprocal NT50 titers (GMT) for all groups are presented longitudinally (FIG. 7). Prior to vaccination, there was no detectable neutralizing antibody titer >40 for any of the monkeys. Minimal neutralizing activity was detected after the first dose at week 4 for all groups with the neutralizing antibody titers peaking around week 12 and week 28 (four weeks after the second and the third vaccination, respectively). The peak GMT at week 28 for the 100 µg/dose group was 14,500 (about 3-fold higher than the titer of 4,660 for the 10 µg/dose group). ISCOMATRIX® adjuvant, but not AAHS, provided adjuvanting benefit when compared with the 10 µg/dose group. The GMT at week 28 for the ISCO-MATRIX® group measured 15,800 whereas the AAHS group was 3,000 and the 10 µg/dose group was 4,660. Minimal neutralizing activity was detected for the control (gB/MF59) group, with the peak GMT never exceeding 200. At study week 72, close to 1 year after completion of the vaccination regimen at weeks 0, 8 and 24, the GMT for the 100 µg/dose group and the ISCOMATRIX® formulation group were maintained at 1400 and 3000, respectively. At this time, the GMT for the 10 µg/dose group and the AAHS group was around 200.

Peripheral blood mononuclear cells (PBMC) from rhesus macaques were collected at week 28 (4 weeks postdose 3) of the vaccination regimen and were evaluated in the IFN-γ ELISPOT assay. Monkeys were vaccinated with either 100 µg/dose (FIG. 8A) or 10 µg/dose (FIGS. 8B-8D) of the double fusion virus IE1/2-UL51. Additionally, the 10 µg/dose was formulated either with no adjuvant (FIG. 8B) or with AAHS (FIG. 8C) or ISCOMATRIX® (FIG. 8D) adjuvant. The antigens of pooled overlapping peptides representing five HCMV antigens were used to stimulate IFN-γ production ex-vivo. The HCMV antigens used were IE1 and IE2 (both viral regulatory proteins) and pp65, gB and pp150 (predominant viral structural antigens). Quality of the T-cell responses was assessed by the magnitude (geometric means) of ELISPOT responses as well as the responder rate to viral antigens. Prior to vaccination, there was no antigen-specific ELISPOT titer in any monkey (data not shown).

Figure 8A:
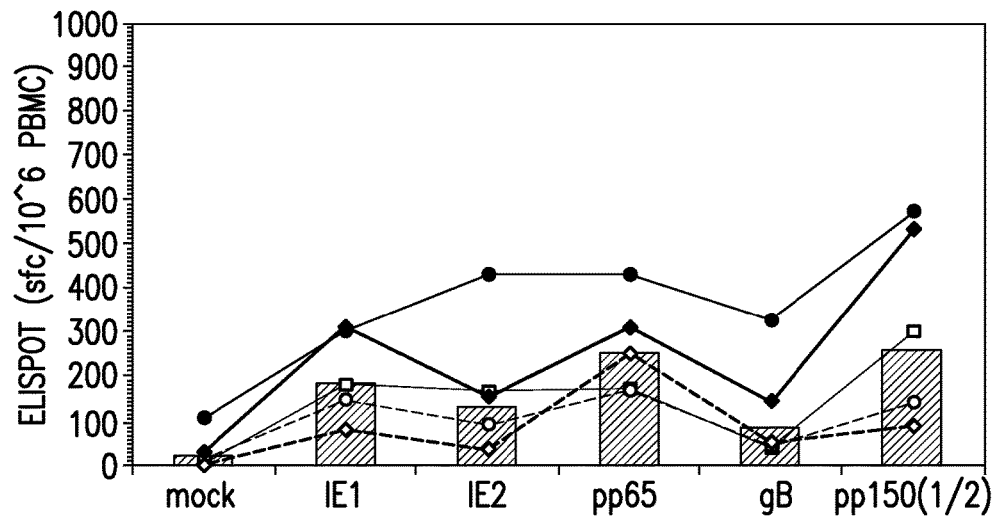
FIGS. 8A-8D show IFN-γ ELISPOT in rhesus macaques with the double fusion virus IE1/2-UL51 vaccination with either a 100 µg (A) or 10 µg (B-D) per dose. Either no adjuvant (A-B), AAHS(C) or ISCOMATRIX (D) were used. PBMC were stimulated with peptide pools representing HCMV antigens. Gray bars representing GMT for each antigen of the group (n=5). Responder rate for each antigen is shown at the top of each antigen within the panels.
Figure 8B:
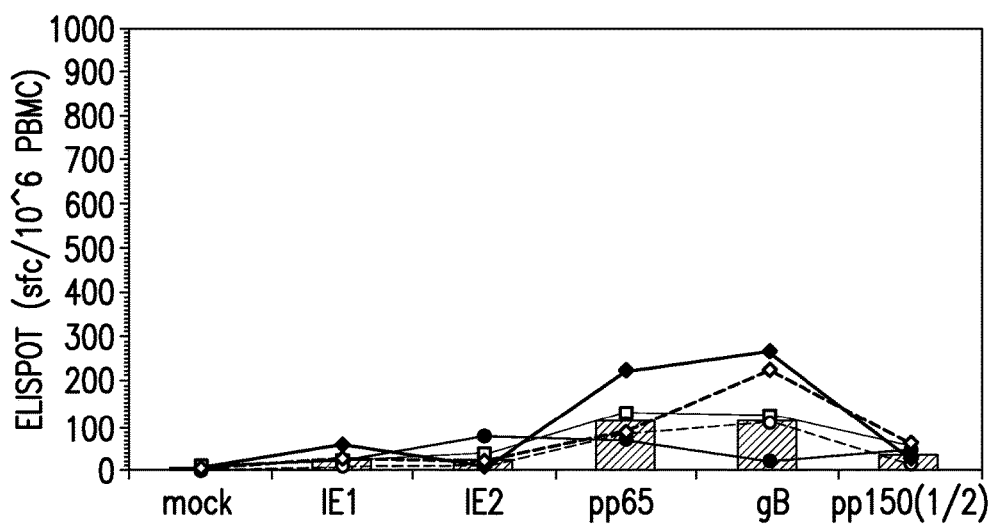
Figure 8C:
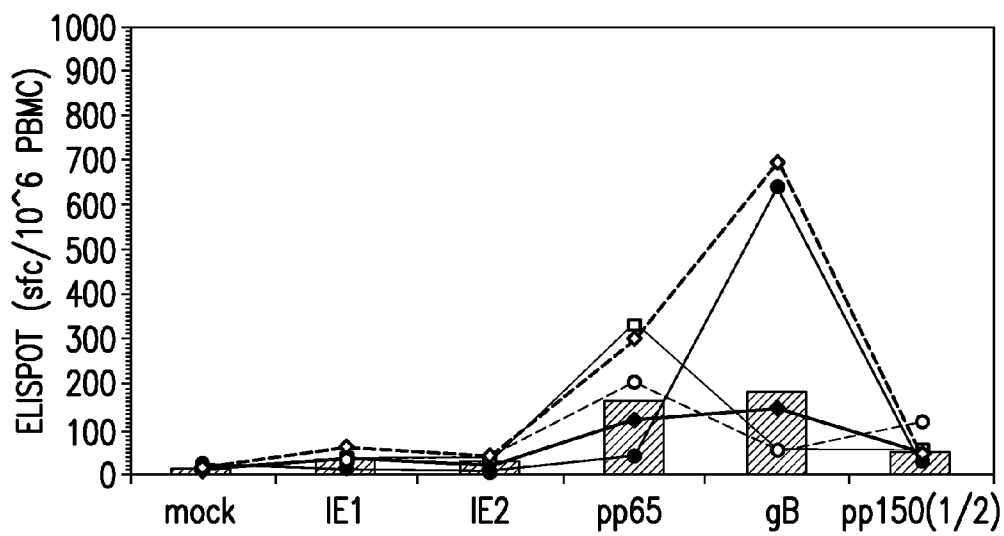

At week 28, the geometric means for ELISPOT responses to the five HCMV antigens (i.e., IE1, IE2, pp65, gB and pp150) were 186, 132, 253, 87, 257 spot-forming cells (SFC)/$10^6$ PBMC for the 100 µg/dose group versus 21, 24, 107, 111, 33 SFC/$10^6$ PBMC for the µg/dose group, respectively (FIGS. 8A and 8B). A responder in each group (n=5) was scored based on cutoff criteria of more than 55 SFC/$10^6$ PBMC and more than 3-fold rise in antigen-specific response over dimethyl sulfoxide (DMSO) response. The number of responders to the five HCMV antigens (i.e., IE1, IE2, pp65, gB and pp150) were 4, 4, 5, 1, 3 for the 100 µg/dose group versus 1, 1, 5, 4, 0 for the 10 µg/dose group.

Figure 8D:
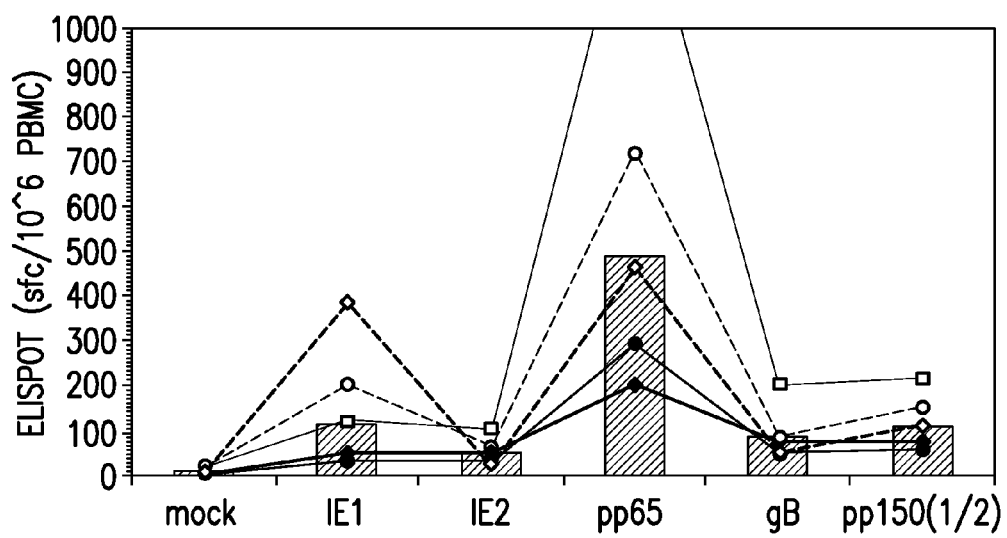

The effect of ISCOMATRIX® adjuvant on T-cell responses to a 10 µg/dose of the double fusion virus IE1/2-UL51 is shown in FIG. 8D. Geometric means of ELISPOT responses to the five HCMV antigens (i.e., IE1, IE2, pp65, gB and pp150) were 114, 53, 491, 85, 113 SFC/$10^6$ PBMC, respectively, and the number of responders in the group (n=5) are 3, 2, 5, 3, 3, respectively. The magnitude and breadth of the T-cells responses in the group with ISCO-MATRIX® adjuvant were similar to those in the 100 µg/dose group.

Figure 9A:
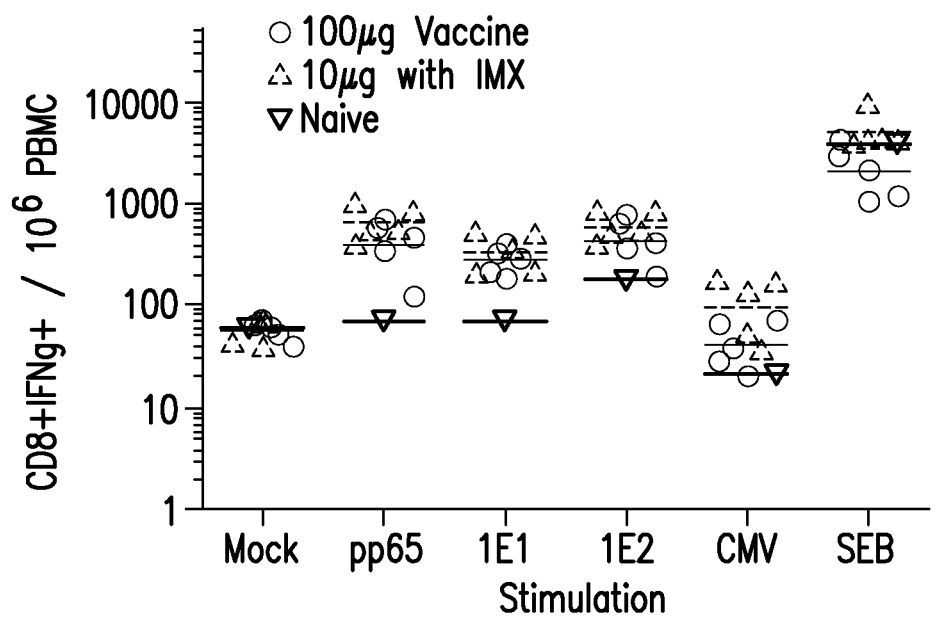
FIGS. 9A-9B show vaccination of the double fusion virus IE1/2-UL51 is able to induce T-cell responses of both CD8+ (A) and CD4+ (B) phenotypes in rhesus macaques. PBMC were collected from monkeys given either a 100 µg or 10 µg dose of vaccine with ISCOMATRIX® as adjuvant. PBMCs were stimulated with peptide pools representing HCMV antigens, followed by staining for IFN-γ and CD4+/CD8+ surface T-cell markers. The data are presented as number of CD4+/CD8+ positive, IFN-γ positive cells per million PBMC. The lines represent the geometric means (GMT) of the group receiving the same vaccine (n=5). The numbers at the bottom of the graphs represent the GMT of both vaccinated groups (n=10). CMV: purified virus; SEB: mitogen used as positive control agent; IMX: ISCOMATRIX.
Figure 9B:
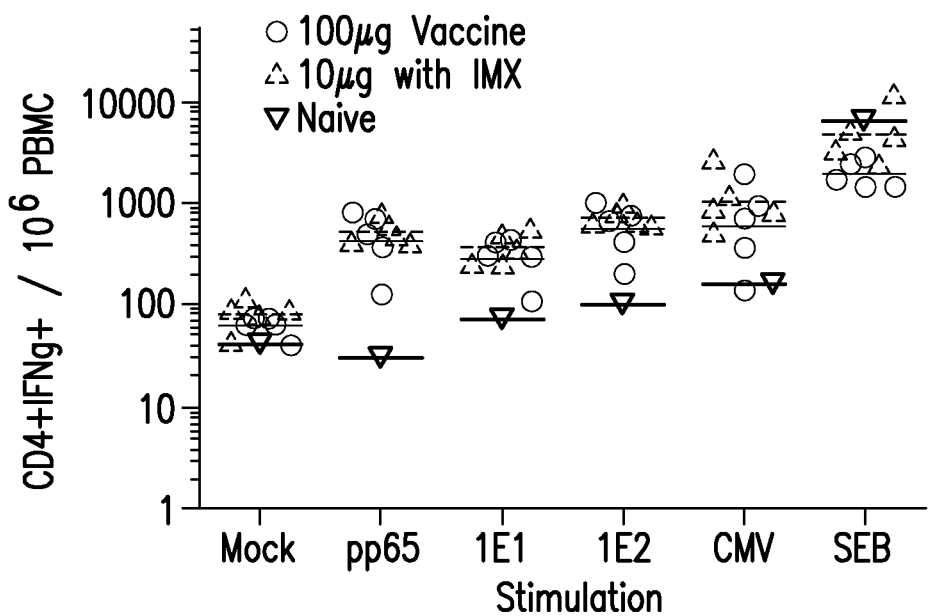

The PBMC from animals vaccinated with either a 10 µg/dose or 100 µg/dose double fusion virus IE1/2-UL51 (based on total protein mass) with ISCOMATRIX® were further analyzed in intracellular cytokine staining after being stimulated with HCMV antigens (pp65, IE1, IE2 or whole HCMV virion). The negative control was one naïve monkey not vaccinated with double fusion virus IE1/2-UL51 while the positive control was *staphalococcus* enterotoxin B (SEB). FIG. 9 shows that the negative control showed minimal responses to all antigen stimulations but responded to the positive control agent *staphalococcus* enterotoxin B (SEB) as expected. All ten vaccinated monkeys from both groups responded to HCMV-specific antigens with similar magnitude and patterns. The geometric mean values to each antigen were computed for all ten monkeys. All monkeys showed comparable CD8+ (FIG. 9A) and CD4+ (FIG. 9B) T-cell responses when their PBMCs were stimulated with CMV antigen peptide pools (i.e., pp65, IE1 and IE2) but preferentially showed CD4+ T-cell responses when stimulated with whole HCMV virions. This was not unexpected since whole virions are protein antigens and are likely processed as exogenous antigens and presented by MHC class II molecules to CD4+ T-cells. The double fusion virus IE1/2-UL51 can elicit T-cell responses of both CD4+ and CD8+ phenotypes, similar to those commonly seen in healthy subjects with HCMV infection.

Figure 10:
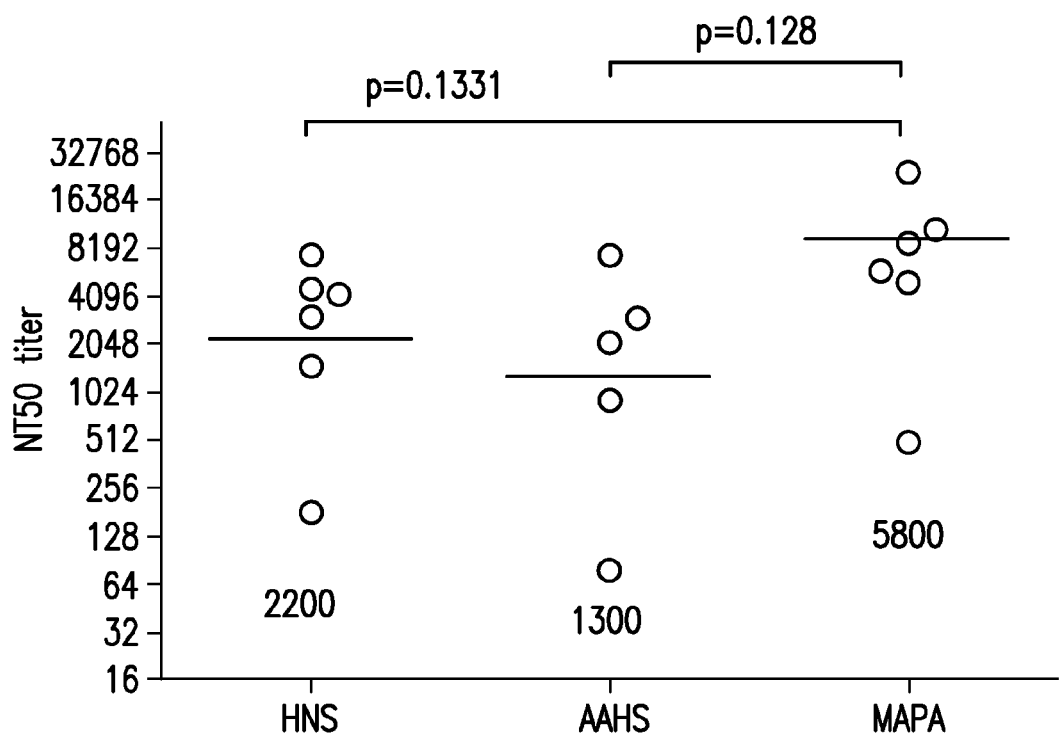
FIG. 10 shows Merck aluminum phosphate adjuvant (MAPA) can enhance neutralizing antibody titers in monkeys. Rhesus monkeys were immunized with a 30 µg dose of the double fusion virus vaccine formulated in HNS (base buffer), AAHS or MAPA at week 0 and 8. The serum samples were collected at week 12 and evaluated for neutralizing titers. The lines represent geometric means for the group.

Different formulations of the double fusion virus IE1/2-UL51 with aluminum salts were compared for their ability to generate neutralizing antibodies in rhesus macaques (FIG. 10). 30 µg/dose double fusion virus IE1/2-UL51 was formulated with either HNS (base buffer), amorphous aluminum hydroxylphosphate sulfate (AAHS) or Merck Aluminum Phosphate Adjuvant (MAPA) and administered at weeks 0 and 8. Serum samples collected at week 12 showed that although MAPA enhanced the neutralizing antibody induction, the enhancement was not statistically significant (two-tailed unpaired t-test).

Example 5

Identification of Buffers for Storage

The CMV virus in HBSS (Hank's Balanced Salt Solution) and stored at −70° C. until used was diluted ~10× with appropriate buffer. The residual components of the HBSS buffer in each sample included potassium chloride 0.533 mM, potassium phosphate monobasic 0.044 mM, sodium phosphate dibasic 0.034 mM, sodium chloride 13.79 mM, sodium bicarbonate 0.417 mM and glucose 0.1% w/v. The samples were then stored at room temperature or between 2° C.-8° C. temperatures for 4 days or freeze thawed. For freezing-thawing, the sample was stored at −70° C. for at least 1 hour and thawed at RT for 30 minutes for either one or three cycles. The stability of the samples was tested on day 4 using a viral entry assay. Briefly, the assay was performed using several different sample dilutions to obtain a response curve and EC50 (µg/mL) values were obtained from the viral entry assay results by non-linear curve fitting. Lower EC50 values represent better stability. EC50 values of the stability samples were compared against −70° C. frozen control sample.

Viral entry assay measures the ability of CMV to infect ARPE-19 cells and express IE1 (immediate early protein 1). The assay is performed in transparent 96-well plates. The IE1 specific primary antibodies and biotinylated secondary antibodies are used to detect target proteins in fixed cells and fluorescent signal from each well is quantified using an IR Dye 800CW Streptavidin together with Sapphire 700/DRAQ5 (for cell input normalization). The results were plotted as 800/700 Integrated Intensity Ratio (Integ. Ratio) vs. CMV concentration (total protein, µg/mL). EC50 values were also obtained from the infectivity assay results using non-linear curve fitting. Since viral infection of ARPE-19 cells relies on integrity of viral glycoprotein antigens, in particular the pentameric gH complex, the EC50 values reflect how well the viral particles are preserved under these conditions.

Figure 11A:
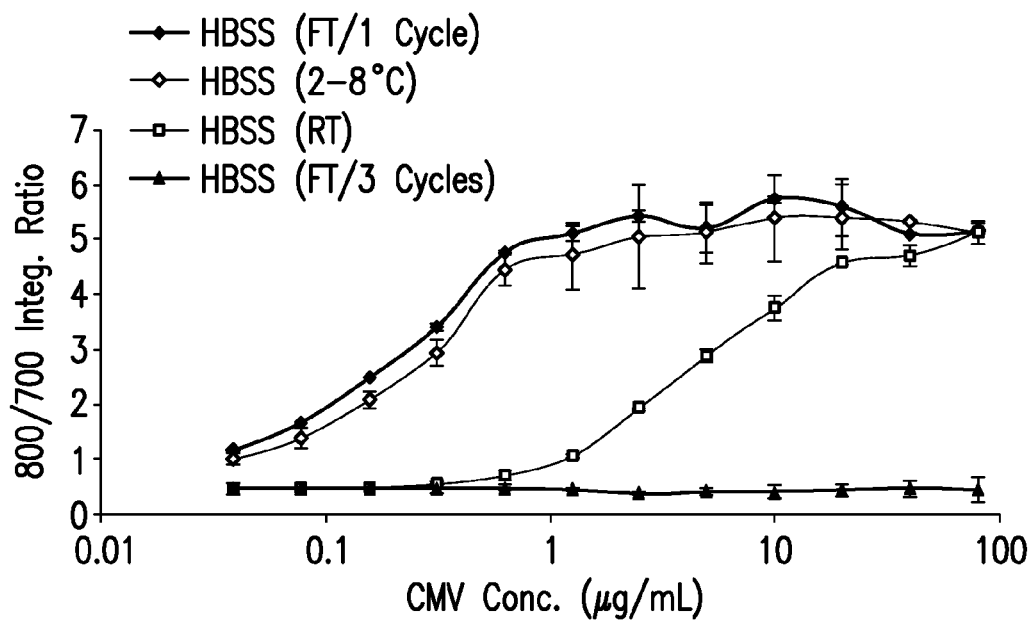
FIGS. 11A-11B show gH expressing CMV stability in Hank's balanced salt solution (HBSS) at different temperatures. (A) CMV samples in HBSS were stored at the indicated temperatures for 4 days before CMV virus stability was measured using a viral entry assay. (B) EC50 values were calculated for the samples using the viral entry assay results. * indicates that the EC50 could not be calculated due to complete loss of infectivity.
Figure 11B:
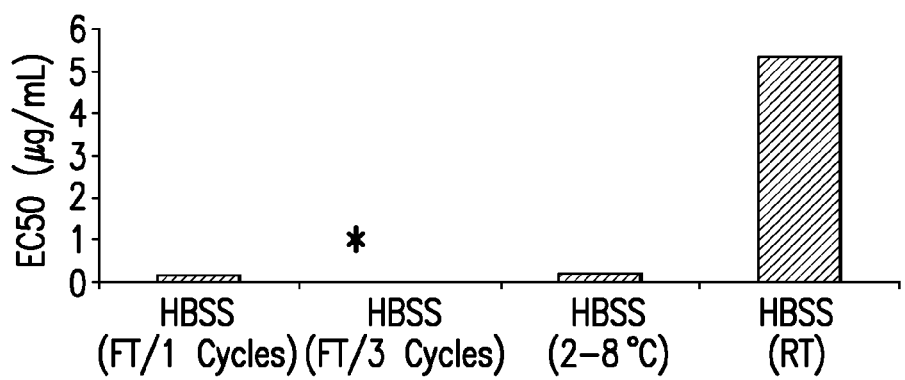

As shown in FIG. 11, the CMV loses infectivity when stored for four days in HBSS at RT. Moreover, 3 cycles of freezing-thawing in HBSS lead to complete loss of infectivity when assessed by viral entry assay. Thus, HBSS was not an optimal buffer for CMV storage.

The effect of pH on CMV stability at room temperature was examined using the pH range of 3 to 8. The following buffers were utilized: Citrate buffer (25 mM), pH 3.0; Acetate buffer (25 mM), pH 4; Acetate buffer (25 mM), pH 5; Histidine buffer (25 mM), pH 6; HEPES buffer (25 mM), pH 7; Hanks' Balanced Salt Solution (HBSS), pH 7.5 and Tris buffer (25 mM), pH 8.

The samples were prepared by dilution of the viral bulk 10 times with the appropriate buffer. The samples were stored at RT (25° C.) for 4 days. On day 4, the stability of the samples was measured by utilizing the viral entry assay. The CMV in HBSS stored frozen at −70° C. was treated as a control. The UV-Vis spectra for each of the samples were obtained at time 0 and on day 4 to examine the structural changes and aggregation that occurred during storage.

Figure 12A:
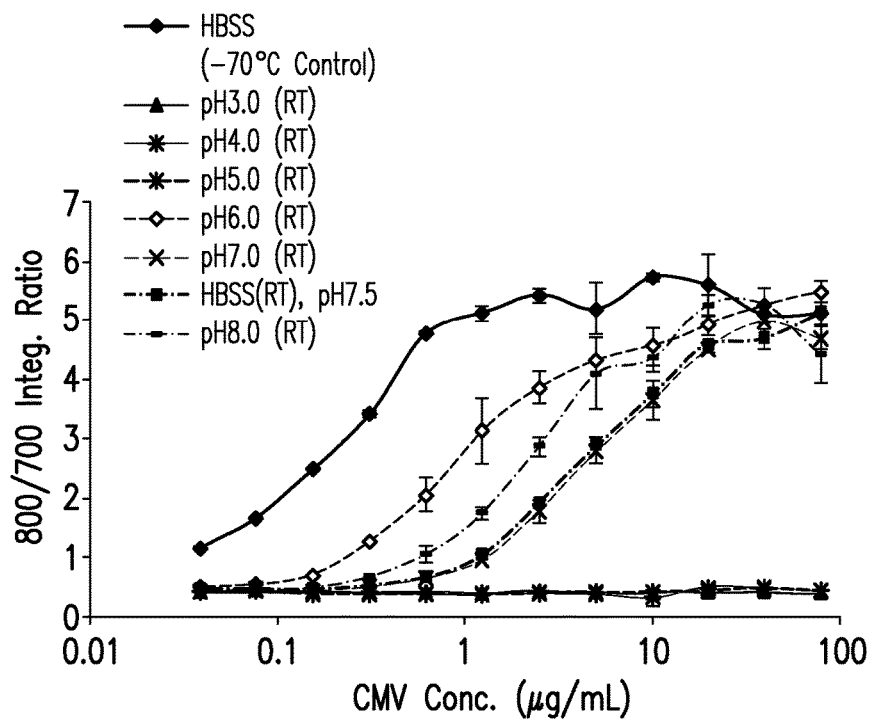
FIGS. 12A-12B show the effect of pH on the stability of gH expressing CMV at room temperature. (A) CMV samples in buffers with different pH were stored at room temperature for 4 days before CMV virus stability was measured using a viral entry assay. (B) EC50 values were calculated for the samples using the viral entry assay results.
Figure 12B:
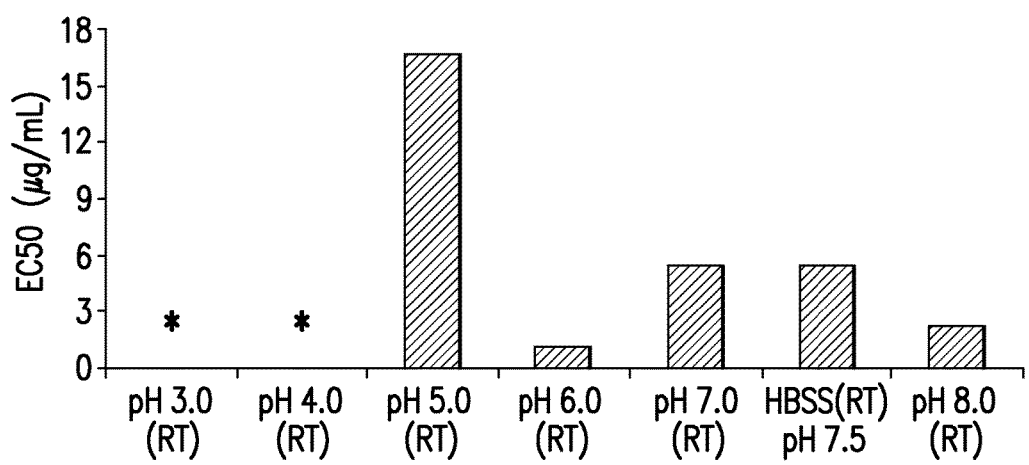

As shown in FIG. 12, 25 mM Histidine buffer at pH 6 provided better stability for CMV by retaining higher infectivity at RT compared to other pH tested. The second derivative of the UV-spectra indicated similar structural profile of the virus at all pHs (data not shown). No significant aggregation was observed at any of the pH tested as measured by optical density at 350 nm (data not shown).

Figure 13A:
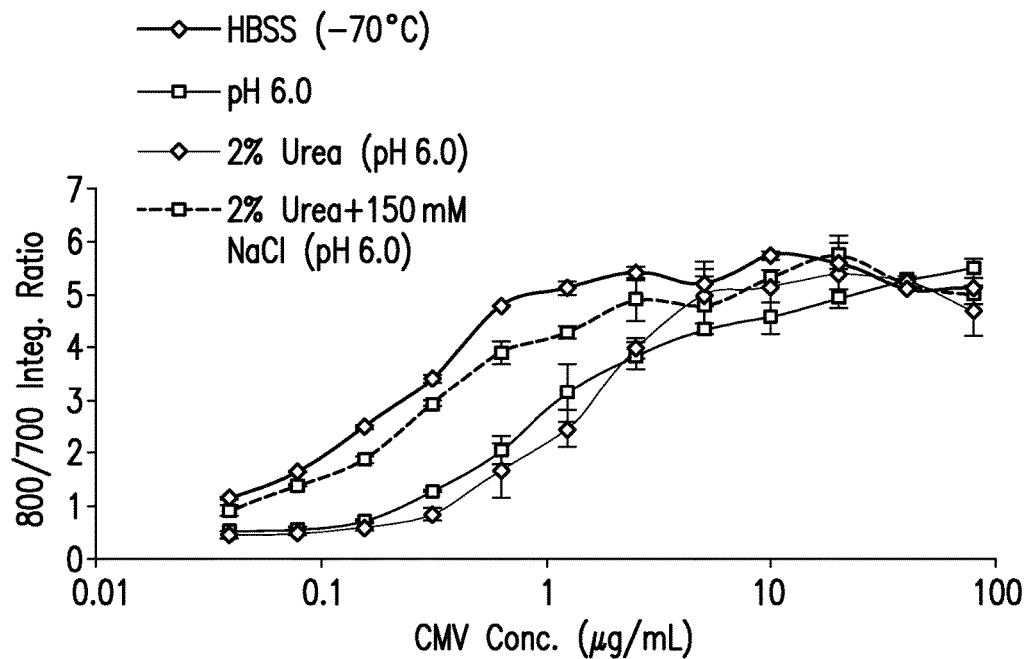
FIGS. 13A-13B show the effect of urea alone or in combination with sodium chloride on gH expressing CMV virus stability. (A) 2% urea alone or in combination with 150 mM NaCl was added to CMV in 25 mM histidine buffer, pH 6 at room temperature for 4 days before CMV virus stability was measured using a viral entry assay. (B) EC50 values were calculated for the samples using the viral entry assay results.
Figure 13B:
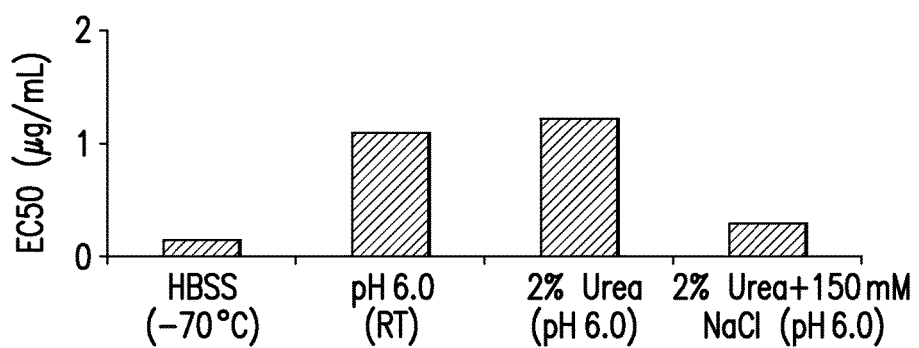

The effect of urea alone or in combination with sodium chloride on CMV virus stability was tested in 25 mM Histidine buffer, pH 6. Addition of 2% urea alone did not have an effect on CMV stability. However, 2% urea in combination with 150 mM NaCl improved the stability of CMV at RT (FIG. 13).

Figure 14A:
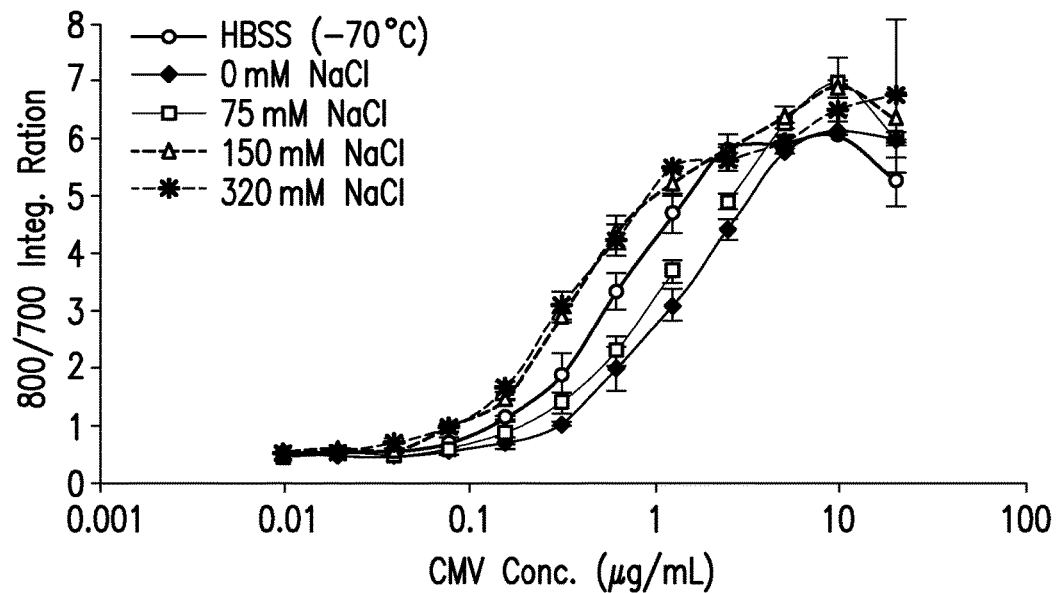
FIGS. 14A-14B show the effect of ionic strength on gH expressing CMV virus stability. (A) Increasing concentrations of NaCl (0 mM, 75 mM, 150 mM and 320 mM NaCl) was added to CMV in 25 mM histidine buffer, pH 6 at room temperature for 4 days before CMV virus stability was measured using a viral entry assay. (B) EC50 values were calculated for the samples using the viral entry assay results.
Figure 14B:
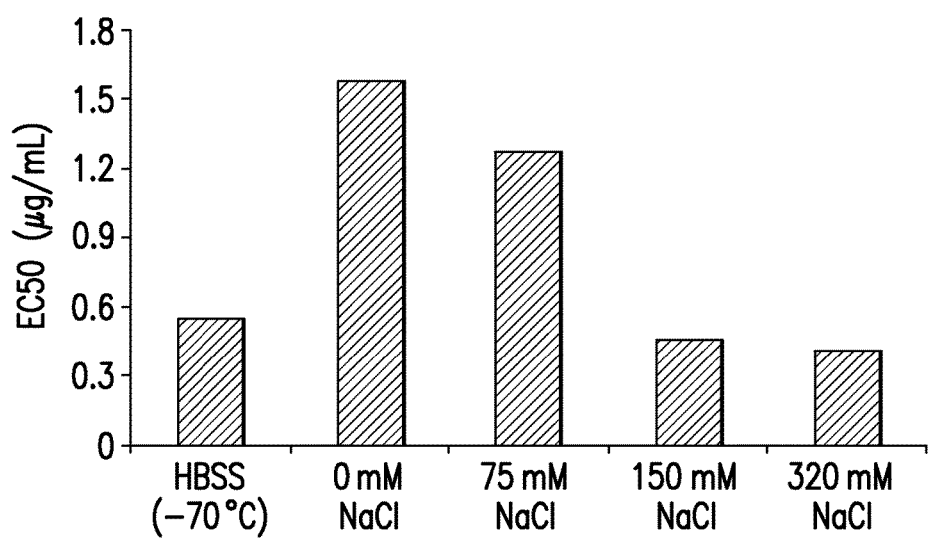
Figure 15:
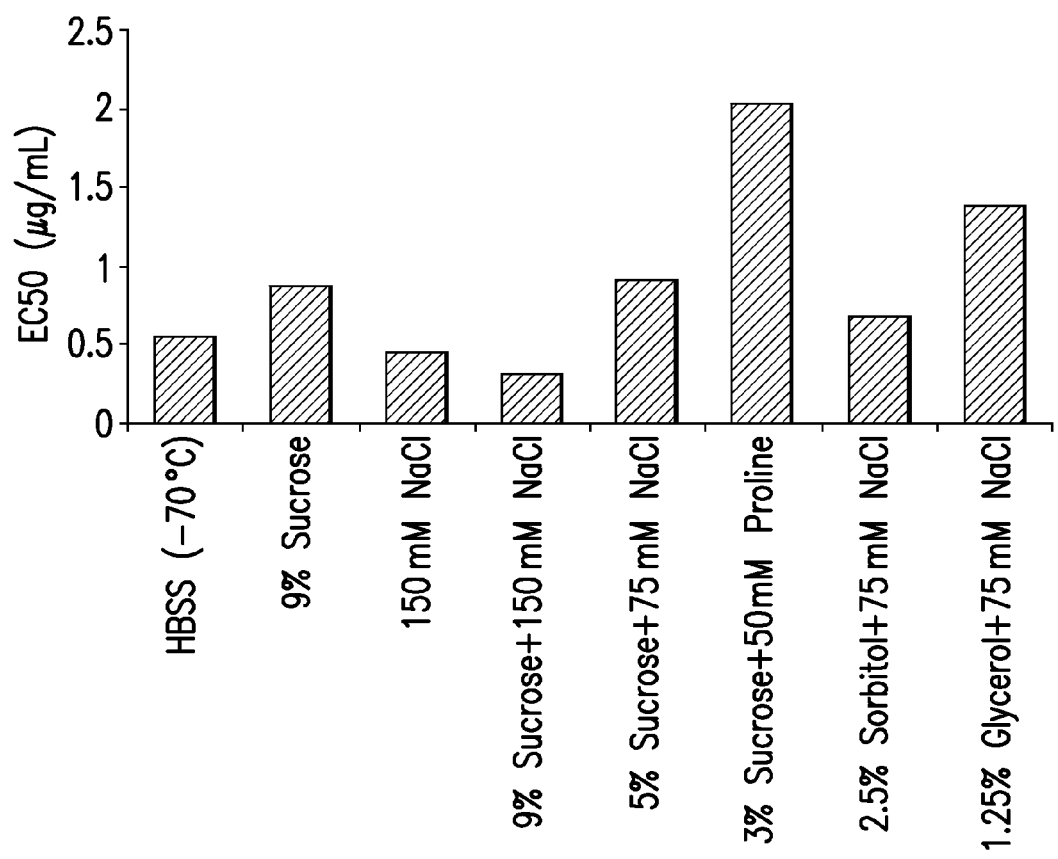
FIG. 15 shows the effect of cryoprotectants on gH expressing CMV stability against freezing-thawing cycles. The indicated cryoprotectants were added to CMV in 25 mM histidine buffer, pH 6 and subjected to three freeze-thaw cycles before CMV virus stability was measured using a viral entry assay. EC50 values were calculated for the samples using the viral entry assay results.
Figure 16A:
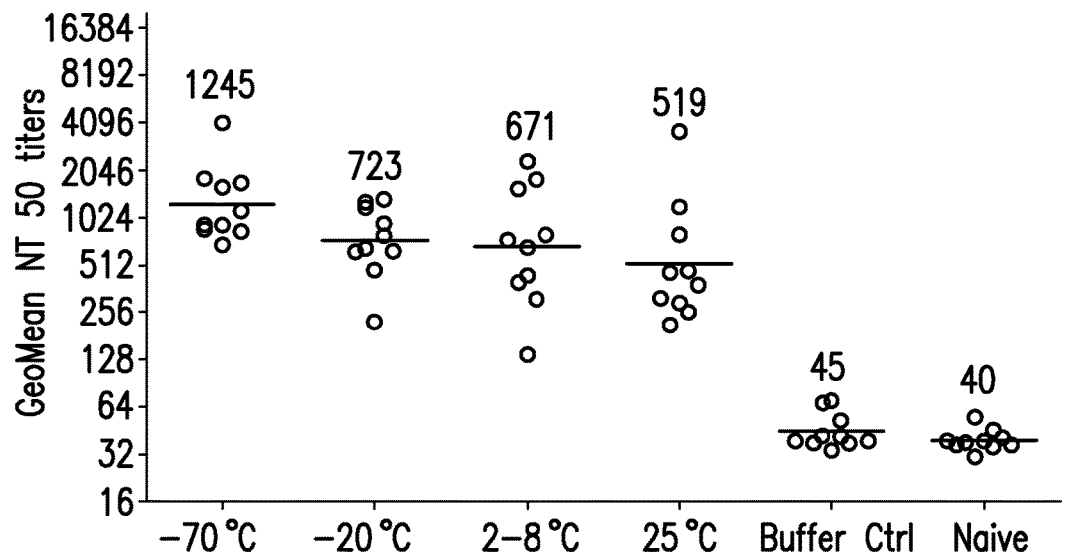
FIGS. 16A-16B show the effect of storage temperature on inducing CMV neutralizing antibodies in a mouse immunogenicity study. Mice were immunized on day 0 and boosted on day 21 followed by bleeding on day 28. The mouse serum was tested for neutralizing antibodies against a gH expressing CMV using ARPE-19 cells. NT50 titers were obtained by non-linear curve fitting. (A) The CMV samples were stored at different temperatures for 3 months prior to the immunogenicity study. (B) The CMV samples were stored at different temperatures for 8 hours following thawing and prior to the immunogenicity study.
Figure 16B:
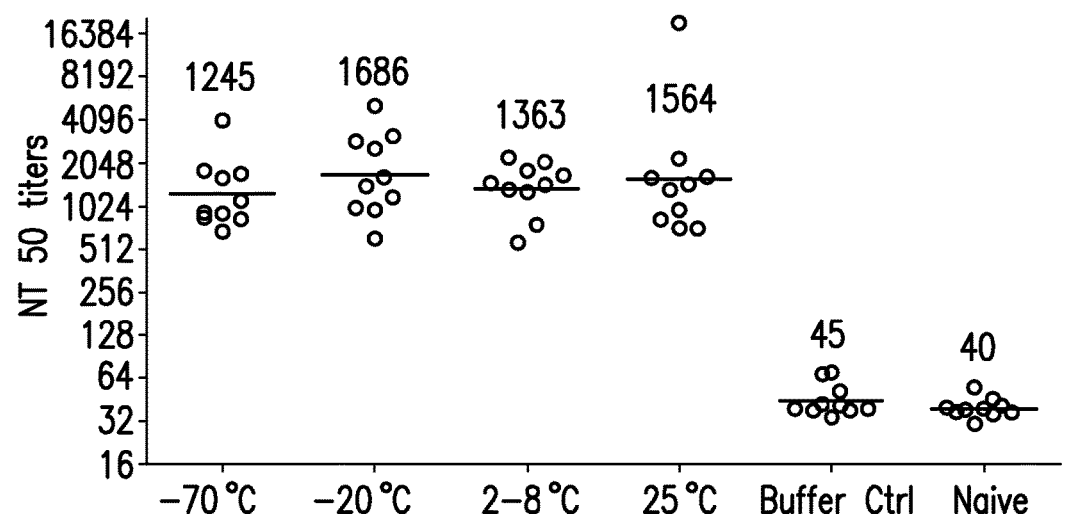

The effect of ionic strength on CMV stability was examined at pH 6. Increasing concentrations of NaCl (0 mM, 75 mM, 150 mM and 320 mM NaCl) were added to 25 mM Histidine buffer at pH 6. The CMV stability was dependent on ionic strength where higher ionic strength led to better stability (FIG. 14). Presence of urea had no or minimal effect on CMV stability (data not shown).

Additionally, several other excipients (sucrose, sorbitol, glycerol, and proline) were screened for their effect on gH expressing CMV stability at room temperature. Exipients to be tested were added to CMV in 25 mm Histidine buffer, pH 6 at room temperature for 4 days before CMV virus stability was measured using a viral entry assay. $EC_{50}$ values were calculated for the samples. Among all the excipients tested, 150 mM NaCl alone or in combination with 9% w/v sucrose provided better stability at pH 6 (data not shown). Therefore, the recommended buffer for CMV storage at RT is 25 mM Histidine (pH 6) with 150 mM NaCl with or without 9% w/v sucrose.

The effect of cryoprotectants on CMV stability during freezing-thawing was investigated. As indicated previously (FIG. 11), CMV in HBSS completely lost its infectivity when subjected to three freezing-thawing cycles. Several cryoprotectants (including sucrose, sorbitol, glycerol) were screened for the ability to diminish the freeze-thaw stress on CMV. For each freeze-thawing cycle, the samples were frozen at −70° C. for at least 1 hour and thawed at RT for 30 minutes. The addition of cryoprotectants led to increased stability of the virus. Moreover, 9% w/v sucrose in combination with 150 mM sodium chloride led to significantly enhanced stability of the virus when compared to other cryoprotectants tested (FIG. 15). Therefore, the recommended buffer composition for CMV storage at −70° C. or up to 3 freezing-thawing cycles is 25 mM Histidine, 150 mM NaCl and 9% sucrose (HNS buffer).

HNS buffer was compared with HBSS buffer for protection of CMV stability during three freeze-thaw cycles, refrigeration (2-8° C.) and RT (25° C.). The HNS buffer provided better stability for CMV live virus at all the storage conditions tested (data not shown).

Example 6

CMV Stability in HNS Buffer

The double fusion IE1/2-UL51 CMV virus stock was supplied in HNS buffer and stored at −70° C. until used. The stability study was performed at a concentration of 100 μg/mL (based on total protein content measured by Bradford assay). The bulk virus was diluted with HNS buffer to obtain the final virus concentration. The samples were then stored at appropriate temperatures and tested as described for up to 3 months. For freezing-thawing, the samples were frozen at −70° C. for at least 1 hour and thawed at room temperature for 30 minutes. The samples were pulled at different time points and kept stored frozen at −70° C. until analyzed.

Total protein content of the samples was measured using a Bradford assay. The total protein content of the samples did not change over the 3 month period (data not shown).

Particle size of the CMV in the samples over time was monitored by measuring the hydrodynamic diameter of the sample using DLS method. This method monitored any aggregation or disruption of the virus particles over time and at different storage temperatures. No real trending was observed with sporadic changes in the particle size of certain samples (data not shown). The results indicated that the virus particles were intact and not aggregated at elevated temperatures.

Example 7

Effect of Storage Conditions on Viral Entry and Immunogenicity

Significant changes in viral entry titers (EC50 values) were observed by subjecting the CMV samples to different storage temperatures (data not shown). Storage at −20° C. resulted in lower viral entry titers compared to 2-8° C. and 25° C. The titers of 2-8° C. samples were found to be lower viral entry titers compared to 25° C. storage. Based on the EC50 values the storage temperatures were ranked in the following order (from most stable to least stable): 25° C.>2-8° C.>−20° C. up to a 1 month time point. The viral entry titers were not detectable at the 3 month time point for the samples stored at −20° C., 2-8° C. and 25° C.

A mouse immunogenicity study was initiated at the end of the stability study to determine the effect of storage temperature on the ability of CMV to induce CMV neutralizing antibodies. The mice were immunized with 2.5 μg per dose vaccine i.m. on day 0 and boosted on day 21 followed by bleeding on day 28. The mouse serum was tested for neutralizing antibodies against a gH expressing CMV using ARPE 19 cells and NT50 titers were obtained by non-linear curve fitting.

The effect of storage at different temperatures for 3 months on the IE1/2-UL51 double fusion CMV immunogenicity was evaluated. The NT50 titers were dependent on the storage temperature, with higher temperatures resulting in decreased titers compared to −70° C. frozen control although not significantly ($p=0.2584$, one way ANOVA) (FIG. 16A). The NT50 titer for formulations stored at −20° C. was lower by less than 2-fold, but the viral entry assay titers for these samples were significantly affected compared to −70° C. frozen control. The trending of NT50 titers for −20° C., 2-8° C. and 25° C. stability samples follows the CMV mass ELISA titers obtained for these samples.

The effect of storage at different temperatures for 8 hours after thawing on the IE1/2-UL51 double fusion CMV immunogenicity was evaluated. The NT50 titers of the formulations were compared to a −70° C. frozen control. The NT50 titers were not affected ($p=0.5865$, one way ANOVA) by storing the samples for 8 hours at any of the temperatures tested (FIG. 16B).

The effect of the double fusion IE1/2-UL51 CMV storage at 25° C. for different time points after thawing the samples was evaluated in a mouse immunogenicity study. The NT50 titers of these formulations were compared to a −70° C. frozen control. The NT50 titers were not affected ($p=0.1848$, unpaired two-tailed t-test) by storing the samples at 25° C. for up to a week. At 3 months, the NT 50 titers dropped by a little over 2-fold indicating possible stability issues of the formulation at 25° C. for longer time (data not shown).

The effect of 3 cycles of freeze-thaw on the double fusion IE1/2-UL51 CMV formulated in HNS buffer was evaluated by mouse immunogenicity. Three cycles of freeze-thaw (F/T) of the double fusion CMV formulation did not affect the immunogenicity ($p=0.2103$, unpaired two tailed t-test) compared to a −70° C. frozen control (data not shown).

Other embodiments are within the following claims. While several embodiments have been shown and described, various modifications may be made without departing from the spirit and scope of the present invention.

What is claimed is:

1. An immunogenic composition comprising an immunologically effective amount of a conditional replication defective cytomegalovirus (CMV) and a pharmaceutically acceptable carrier, wherein the conditional replication defective CMV comprises:
   (a) a pentameric gH complex comprising UL128, UL130, UL131, gH and gL; and
   (b) a nucleic acid encoding a first fusion protein between IE1/2 and a destabilizing protein and a second fusion protein between UL51 and the destabilizing protein, wherein the destabilizing protein is FK506-binding protein (FKBP) derivative comprising amino acid substitutions F36V and L106P; wherein the wild type IE1/2 and UL51 are no longer present and wherein the CMV is an attenuated strain that has restored gH complex expression due to a repair of a mutation in the UL131 gene.

2. The immunogenic composition of claim 1, wherein
   (a) the first fusion protein is SEQ ID NO:1 or an amino acid sequence that is at least 95% identical to SEQ ID NO:1; and
   (b) the second fusion protein is SEQ ID NO:3 or an amino acid sequence that is at least 95% identical to SEQ ID NO:3.

3. The immunogenic composition of claim 2, wherein
   (a) the first fusion protein is encoded by SEQ ID NO:2 or a nucleic acid sequence that is at least 95% identical to SEQ ID NO:2; and
   (b) the second fusion protein is encoded by SEQ ID NO:4 or a nucleic acid sequence that is at least 95% identical to SEQ ID NO:4.

4. The immunogenic composition of claim 3, wherein the first fusion protein is encoded by SEQ ID NO:2 and the second fusion protein is encoded by SEQ ID NO:4.

5. The immunogenic composition of claim 1 further comprising an adjuvant.

6. The immunogenic composition of claim 1, wherein the CMV is AD169 that has restored gH complex expression due to a repair of a mutation in the UL131 gene.

7. The immunogenic composition of claim 6, further comprising an adjuvant.

8. An immunogenic composition comprising an immunologically effective amount of a conditional replication defective cytomegalovirus (CMV) and a pharmaceutically acceptable carrier, wherein the conditional replication defective CMV comprises:
   (a) a pentameric gH complex comprising UL128, UL130, UL131, gH and gL; and
   (b) a nucleic acid encoding a first fusion protein between an essential protein and a destabilizing protein and a second fusion protein between an essential protein and a destabilizing protein, wherein the first fusion protein comprises SEQ ID NO:1 and the second fusion protein comprises SEQ ID NO:3, wherein the wild type IE1/2 and UL51 are no longer present; and
wherein the CMV is an attenuated strain that has restored gH complex expression due to a repair of a mutation in the UL131 gene.

9. The immunogenic composition of claim 8, further comprising an adjuvant.

10. The immunogenic composition of claim 8, wherein the CMV is AD169 that has restored gH complex expression due to a repair of a mutation in the UL131 gene.

11. The immunogenic composition of claim 10, further comprising an adjuvant.

12. The immunogenic composition of claim 8, wherein the conditional replication defective CMV has a genome as shown in SEQ ID NO: 14.

* * * * *